United States Patent
Jacobson et al.

(10) Patent No.: US 12,037,333 B2
(45) Date of Patent: Jul. 16, 2024

(54) PYRIDOPYRAZINE AND PYRIDOTRIAZINE INHIBITORS OF INFLUENZA VIRUS REPLICATION

(71) Applicants: COCRYSTAL PHARMA, INC., Bothell, WA (US); MERCK SHARP & DOHME LLC, Rahway, NJ (US)

(72) Inventors: Irina C. Jacobson, Sammamish, WA (US); Biing Yuan Lin, Bellevue, WA (US); Emiliano J. Sanchez, Bothell, WA (US); Sam S K Lee, Edmonds, WA (US); Hong Xiao, Bothell, WA (US)

(73) Assignees: COCRYSTAL PHARMA, INC., Bothell, WA (US); MERCK SHARP & DOHME LLC, Rahway, NJ (US)

( * ) Notice: Subject to any disclaimer, the term of this patent is extended or adjusted under 35 U.S.C. 154(b) by 567 days.

(21) Appl. No.: 17/275,158

(22) PCT Filed: Sep. 10, 2019

(86) PCT No.: PCT/US2019/050400
§ 371 (c)(1),
(2) Date: Mar. 10, 2021

(87) PCT Pub. No.: WO2020/055858
PCT Pub. Date: Mar. 19, 2020

(65) Prior Publication Data
US 2022/0056024 A1 Feb. 24, 2022

Related U.S. Application Data

(60) Provisional application No. 62/729,190, filed on Sep. 10, 2018.

(51) Int. Cl.
| | |
|---|---|
| *C07D 471/04* | (2006.01) |
| *A61K 31/4985* | (2006.01) |
| *A61K 31/53* | (2006.01) |
| *A61P 31/16* | (2006.01) |

(52) U.S. Cl.
CPC ........ *C07D 471/04* (2013.01); *A61K 31/4985* (2013.01); *A61K 31/53* (2013.01); *A61P 31/16* (2018.01)

(58) Field of Classification Search
CPC .. C07D 471/04; A61K 31/4985; A61K 31/53; A61P 31/16
See application file for complete search history.

(56) References Cited

U.S. PATENT DOCUMENTS

| | | |
|---|---|---|
| 9,464,067 B2 | 10/2016 | Jung et al. |
| 10,208,045 B2 | 2/2019 | Hendricks et al. |
| 2020/0283454 A1 | 9/2020 | Tang et al. |

FOREIGN PATENT DOCUMENTS

| | | | |
|---|---|---|---|
| CN | 107531717 A | 1/2018 | |
| EP | 2444400 A1 * | 4/2012 | ............. A61K 31/53 |
| EP | 2444400 A1 | 4/2012 | |
| EP | 3290424 A1 | 3/2018 | |
| JP | 2014-523417 A | 9/2014 | |
| WO | 2015/038655 A1 | 3/2015 | |
| WO | 2017/072341 A1 | 5/2017 | |
| WO | 2019/052565 A1 | 3/2019 | |

OTHER PUBLICATIONS

International Search Report dated Dec. 3, 2019, in corresponding PCT/US2019/050400 (6 pages).

* cited by examiner

*Primary Examiner* — Matthew P Coughlin
*Assistant Examiner* — Ashli Ariana Chicks
(74) *Attorney, Agent, or Firm* — Venable LLC

(57) ABSTRACT

Provided herein are compounds that can inhibit the replication of influenza viruses, reduce the amount of influenza viruses, and/or treat influenza. (I)

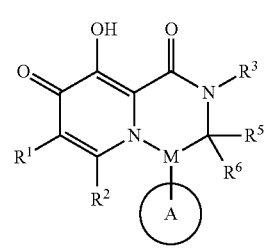

22 Claims, No Drawings

PYRIDOPYRAZINE AND PYRIDOTRIAZINE INHIBITORS OF INFLUENZA VIRUS REPLICATION

FIELD

This disclosure relates generally to inhibitors of influenza virus replication, and methods of treating or preventing an influenza infection by administering the inhibitors to a patient in need of treatment thereof.

BACKGROUND

Influenza spreads around the world in seasonal epidemics, resulting in the deaths of hundreds of thousands of people annually-millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogotovirus.

The Influenza virus A genus is responsible for seasonal flu and pandemic flu epidemics. It has one species, influenza A virus, and wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which presents a potential pandemic threat, H1N2 (endemic in humans and pigs), H9N2, H7N2, H7N3 and H10N7.

The Influenza virus B genus is responsible for seasonal flu, and has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza viruses are very similar in structure across serotypes and genera. The influenza virus genome consists of eight single-stranded RNAs packed into rod-like structures of varying size, known as the ribonucleoprotein complex (RNP). Each RNP contains a unique viral RNA, multiple copies of the scaffolding nucleoprotein, and a heterotrimeric viral polymerase consisting of the PA, PB1, and PB2 subunits, which catalyzes the transcription and replication of the viral genome. Recent biochemical and structural studies of influenza polymerase complex provide insight into the mechanistic understanding of cap-snatching and RNA synthesis by influenza polymerase. Briefly, the PB2 cap-binding domain first sequesters the host pre-mRNAs by binding to their 5' cap. PA, the endonuclease subunit, then cleaves the captured pre-mRNA 10-13 nucleotides downstream of the cap. The PB2 subunit subsequently rotates about 700 to direct the capped primer into the PB1 polymerase active site. The PB1 subunit directly interacts with both PB2 and PA subunits. These subunits contain highly conserved domains among different influenza strains, and have attracted as an attractive anti-influenza drug target. In addition to the polymerase complex, the influenza genome encodes its own neuraminidase (NA), hemagglutinin (HA), nucleoprotein (NP), matrix proteins, M1 and M2, and non-structural proteins, NS1 and NS2. NA is the target for the antiviral drugs oseltamivir (Tamiflu) and zanamivir (Relenza). These drugs are sialic acid analogues which inhibit the enzymatic activity of NA, thus slowing down the release of progeny virus from infected cells.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with NA inhibitors being particularly effective, but viruses can develop resistance to the approved NA antiviral drugs. Also, emergence of a multidrug-resistant pandemic influenza A viruses has been well documented. Drug-resistant pandemic influenza A becomes a substantial public health threat. In addition to the drug resistant influenza A viruses, the NA inhibitors are approved for the treatment early influenza infection (within 48 hours of influenza symptom onset).

Thus, there is still a need for drugs for treating influenza infections, such as for drugs with expanded treatment window, and/or reduced sensitivity to viral titer.

SUMMARY

The present disclosure generally relates to methods of treating influenza, to methods of inhibiting the replication of influenza viruses, to methods of reducing the amount of influenza viruses, to compounds and compositions that can be employed for such methods.

In one aspect, the disclosure provides compounds of Formula I and pharmaceutically acceptable salts thereof:

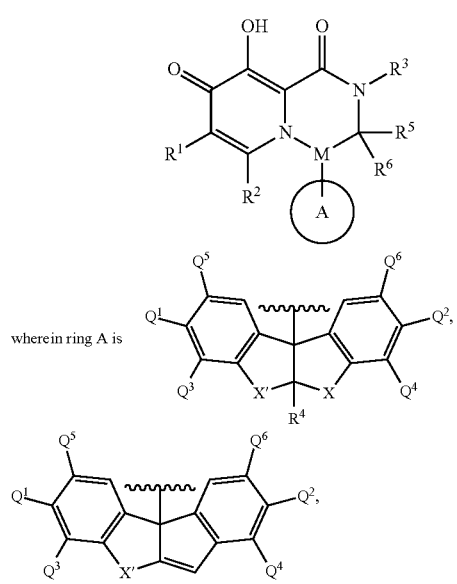

wherein ring A is

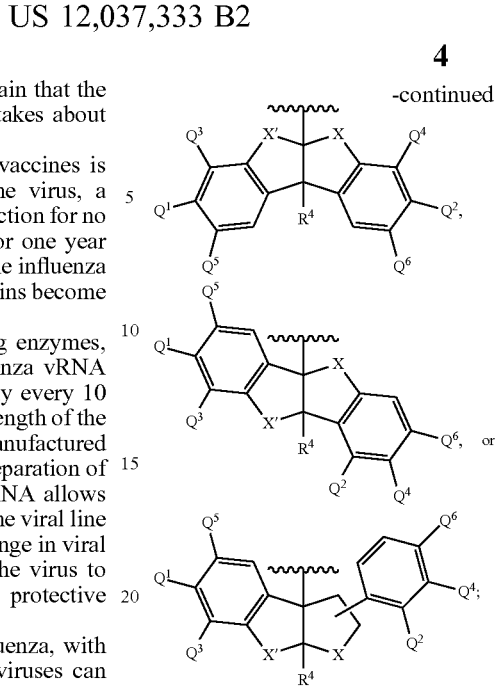

M is N or CH;

each of X and X' is independently $CH_2$, $CH_2CH_2$, $OCH_2$, or $CH_2O$;

each of $R^1$ and $R^2$ is independently H, halo, OH, $CO_2H$, CN, CHO, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{1-6}$ alkoxy optionally substituted by 1-3 of substituent group A, $C_{1-6}$alkyl-C(O)— optionally substituted by 1-3 of substituent group A, $C_{1-6}$alkyl-OC(O)— optionally substituted by 1-3 of substituent group A, $C_{3-10}$carbocyclyl-$C_{0-6}$ alkylene optionally substituted by 1-3 of substituent group A, $C_{3-10}$carbocyclyl-C(O)— optionally substituted by 1-3 of substituent group A, $C_{3-10}$carbocyclyl-O— optionally substituted by 1-3 of substituent group A, $C_{3-10}$carbocyclyl-OC(O)— optionally substituted by 1-3 of substituent group A, 3-7 membered heterocyclyl-$C_{0-6}$ alkylene optionally substituted by 1-3 of substituent group A, 3-7 membered heterocyclyl-C(O)— optionally substituted by 1-3 of substituent group A, 3-7 membered heterocyclyl-O-optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S;

$R^3$ is H, OH, $CO_2H$, CN, CHO, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{1-6}$alkoxy optionally substituted by 1-3 of substituent group A, $C_{1-6}$alkyl-C(O)— optionally substituted by 1-3 of substituent group A, $C_{1-6}$alkyl-OC (O)— optionally substituted by 1-3 of substituent group A, $C_{3-10}$carbocyclyl-$C_{0-6}$ alkylene optionally substituted by 1-3 of substituent group A, $C_{3-10}$carbocyclyl-O—$C_{1-6}$alkylene optionally substituted by 1-3 of substituent group A, $C_{3-10}$carbocyclyl-C(O)— optionally substituted by 1-3 of substituent group A, $C_{3-10}$ carbocyclyl-OC(O)— optionally substituted by 1-3 of substituent group A, 3-7 membered heterocyclyl- $C_{0-6}$alkylene optionally substituted by 1-3 of substituent group A, 3-7 membered heterocyclyl-C(O)— optionally substituted by 1-3 of substituent group A, 3-7 membered heterocyclyl-OC(O)— optionally substituted by 1-3 of substituent group A, wherein the heterocyclyl comprises 1-4 ring heteroatoms independently selected from N, O, and S, or $R^3$ and $R^5$ together with the atoms to which they are attached form a 5-7 heterocyclyl having 1-4 total ring heteroatoms selected from N, O, and S, and can be optionally substituted with 1-3 of substituent group A;

$R^4$, when present, is H, OH, $C_{1-3}$alkyl, $C_{1-3}$haloalkyl, or $C_{1-3}$alkoxy;

$R^5$ and $R^6$ are each independently H, OH, $CO_2H$, CN, CHO, $C_{1-6}$ alkyl optionally substituted by 1-3 of substituent group A, $C_{2-6}$ alkenyl optionally substituted by 1-3 of substituent group A, $C_{2-6}$ alkynyl optionally substituted by 1-3 of substituent group A, $C_{1-6}$alkyl carbonyl optionally substituted by 1-3 of substituent group A, $C_{1-6}$alkyl-O—C(O)— optionally substituted by 1-3 of substituent group A, $C_{3-8}$carbocyclyl$C_{1-6}$alkylene optionally substituted by 1-3 of substituent group A, $C_{3-8}$carbocyclyl-O—$C_{1-6}$alkylene optionally substituted by 1-3 of substituent group A, $C_{3-8}$carbocyclyl-C(O)— optionally substituted by 1-3 of substituent group A, $C_{3-8}$carbocyclyl-OC(O)— optionally substituted by 1-3 of substituent group A, 3-7 membered heterocyclyl-$C_{0-6}$alkylene optionally substituted by substituent group A, 3-7 membered heterocyclyl-O—$C_{1-6}$alkylene optionally substituted by 1-3 of substituent group A, 3-7 membered heterocyclyl-C(O)— optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S, or $R^5$ and $R^6$ together with the atom to which they are attached form a $C_{3-7}$carbocyclyl or 3-7 membered heterocyclyl having 1-3 ring heteroatoms selected N, O, and S, and is optionally substituted with 1-3 of substituent group A;

optionally one of $R^1$, $R^2$, $R^3$, $R^1$, and $R^6$ can be
—Z—N($R^N$)($R^N$)
—Z—N($R^N$)—$SO_2$—$R^{x2}$,
—Z—C(O)—N($R^N$)—$SO_2$—$R^{x2}$,
—Z—N($R^N$)—C(O)—$R^{x1}$,
—Z—C(O)—N($R^N$)($R^N$)
—Z—S(O)$_{0-2}$—$R^{x2}$
—Z—N($R^N$)—C(O)O—$R^{x1}$,
—Z—N($R^N$)—C(O)—N($R^N$)($R^N$),
—Z—C(O)—N($R^N$)—C(O)—N($R^N$)($R^N$), or
—Z—N($R^N$)—C(O)—C(O)—$R^{x1}$, in which:
each $R^N$ and $R^{x1}$ independently is hydrogen, $C_{1-6}$alkyl optionally substituted by 1-3 of substituent group A, $C_{2-6}$alkenyl optionally substituted by 1-3 of substituent group A, $C_{2-6}$ alkynyl optionally substituted by 1-3 of substituent group A, $C_{3-10}$carbocylyl-$C_{0-6}$alkylene optionally substituted by 1-3 of substituent group A, or 3-7 membered heterocyclyl-$C_{0-6}$ alkylene optionally substituted by 1-3 of substituent group A, and the heterocyclyl group comprises 1-4 ring heteroatoms independently selected from N, O, and S, or two $R^N$ attached to the same nitrogen atom can together with the nitrogen atom to which they are attached form a 3-8 membered heterocyclyl having 0-2 additional ring heteroatoms selected from N, O, and S;

each $R^{x2}$ is independently $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{3-10}$carbocylyl-$C_{0-6}$alkylene optionally substituted by 1-3 of substituent group A, or 3-7 membered heterocyclyl-$C_{0-6}$alkylene optionally substituted by 1-3 of substituent group A, and the heterocyclyl group comprises 1-4 ring heteroatoms independently selected from N, O, and S, and Z is a bond or $C_{1-6}$alkylene;

Substituent group A is halo, CN, OH, $CO_2H$, CHO, $NH_2$, oxo, $NO_2$, $C_{1-6}$alkyl, $C_{1-6}$ haloalkyl, $C_{1-6}$alkoxy, $C_{1-6}$alkylthio, $C_{1-6}$ alkyl-OH, $C_{3-10}$carbocyclyl, 3-7 membered heterocyclyl, $C_{6-10}$ aryl, $C_{3-10}$carbocyclyl-$C_{1-6}$ alkoxy, $C_{3-10}$carbocyclyl-O—$C_{1-6}$alkylene, $C_{3-10}$ carbocyclyl-$C_{1-6}$ alkoxy-$C_{1-6}$alkylene, 3-7 membered heterocyclyl-$C_{1-6}$ alkoxy, 3-7 membered heterocyclyl-O—$C_{1-6}$alkylene, 3-7 membered heterocyclyl-$C_{1-6}$ alkoxy-$C_{1-6}$alkylene, $C_{1-6}$haloalkoxy, $C_{1-6}$alkoxy-$C_{1-6}$alkylene, $C_{1-6}$alkoxy-$C_{1-6}$alkoxy, $C_{1-6}$alkyl-C(O)—, $C_{1-6}$alkyl-C(O)O—, $NHC_{1-6}$alkyl, $C_{1-6}$alkyl-C(O)NH—, $C_{1-6}$haloalkyl-C(O)NH, $C_{1-6}$alkyl-NHC(O)—, $C_{1-6}$alkyl-$SO_2$—, $C_{1-6}$alkyl-SO—, and $C_{1-6}$alkyl$SO_2$NH—; and each of $Q^1$, $Q^2$, $Q^3$, $Q^4$, $Q^5$, and $Q^6$ is independently H, halo, CN, OH, $CO_2H$, CHO, $NH_2$, $NO_2$, $C_{1-6}$alkyl, $C_{1-6}$haloalkyl, $C_{1-6}$alkoxy, $C_{1-6}$alkylthio, or $C_{1-6}$ alkyl-OH.

In some cases, the compounds are compounds of Formula (IIA) or (IB):

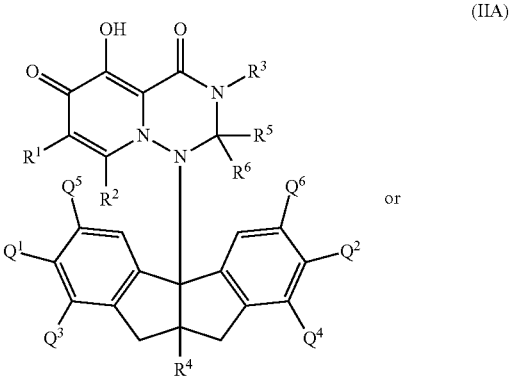

(IIA)

or

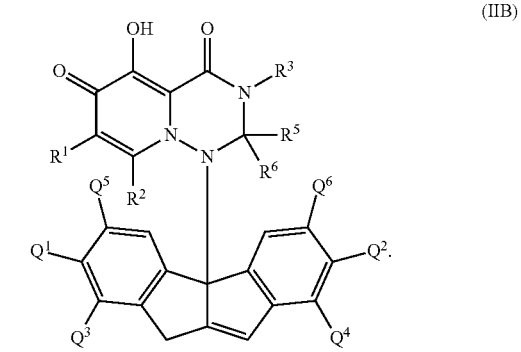

(IIB)

Further provided are methods of administering to a biological sample or patient a safe and effective amount of a compound as disclosed herein, e.g., as represented by Formulas I, IIA, or IIB.

Also provided are methods of endonuclease activity of influenza polymerase PA in an influenza A or B virus by contacting said virus with a safe and effective amount of a compound as disclosed herein, e.g., as represented by Formulas I, IIA, or IIB. In some cases, inhibiting endonuclease activity of influenza polymerase PA in an influenza A or B virus includes administering to a patient a safe and effective amount of a compound as disclosed herein e.g., as represented by Formulas I, IIA, or IIB.

Further provided are methods of reducing endonuclease activity of influenza polymerase PA in an influenza A or B virus in a host by administering a safe and effective amount of a compound as disclosed herein, e.g., as represented by Formulas I, IIA, or IIB.

Also provided herein are methods of reducing the amount of influenza viruses in a biological sample or in a patient by administering to said biological sample or patient a safe and effective amount of a compound as disclosed herein, e.g., as represented by any of Formulas I, IIA, or IIB.

Further provided are methods of treating or preventing an Influenza A or Influenza B infection in a patient, comprising administering to said patient a safe and effective amount of a compound as disclosed herein, e.g., as represented by Formulas I, IIA, or IIB.

Also provided are pharmaceutical compositions comprising a compound as disclosed herein, e.g., as represented by any of Formulas I, IIA, or IIB, or a pharmaceutically acceptable salt thereof, and a pharmaceutically acceptable excipient, carrier, adjuvant or vehicle.

Also provided are uses of a compound described herein for inhibiting or reducing the replication of influenza viruses in a biological sample or patient, for reducing the amount of influenza viruses in a biological sample or patient, or for treating influenza in a patient.

Further provided herein are uses of a compound described herein for the manufacture of a medicament for treating influenza in a patient, for reducing the amount of influenza viruses in a biological sample or in a patient, or for inhibiting the replication of influenza viruses in a biological sample or patient.

DETAILED DESCRIPTION

Disclosed herein are compounds, and uses of these compounds, in inhibiting influenza virus. One aspect of the present disclosure is generally related to the use of the compounds described herein or pharmaceutically acceptable salts, or pharmaceutically acceptable compositions comprising such a compound or a pharmaceutically acceptable salt thereof, for inhibiting the replication of influenza viruses in a biological sample or in a patient, for reducing the amount of influenza viruses (reducing viral titer) in a biological sample or in a patient, and for treating influenza in a patient.

Compounds of the Disclosure

The present disclosure provides compounds of Formula (I), or a pharmaceutically acceptable salt thereof:

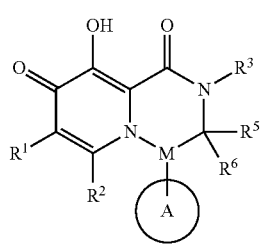

(I)

wherein ring A is

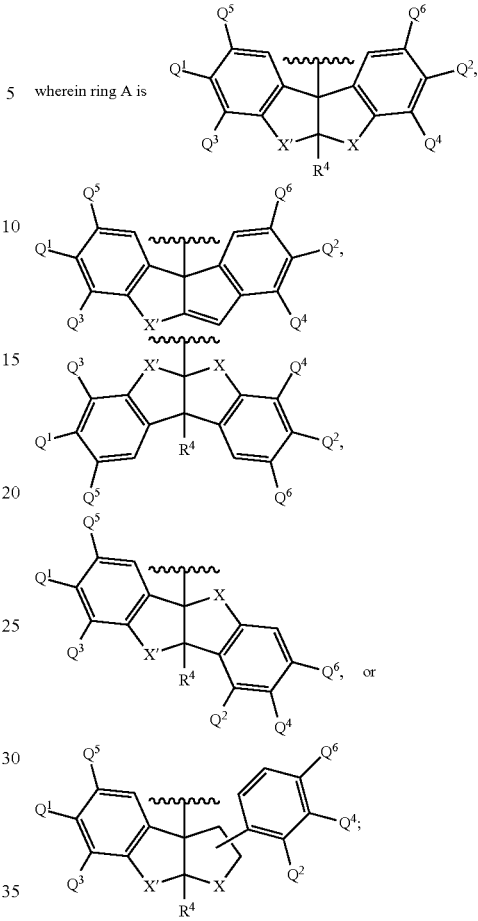

M is N or CH;

each of X and X is independently $CH_2$, $CH_2CH_2$, $OCH_2$, or $CH_2O$;

each of $R^1$ and $R^2$ is independently H, halo, OH, $CO_2H$, CN, CHO, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{1-6}$ alkoxy optionally substituted by 1-3 of substituent group A, $C_{1-6}$alkyl-C(O)— optionally substituted by 1-3 of substituent group A, $C_{1-6}$alkyl-OC(O)— optionally substituted by 1-3 of substituent group A, $C_{3-10}$carbocyclyl-$C_{0-6}$ alkylene optionally substituted by 1-3 of substituent group A, $C_{3-10}$carbocyclyl-C(O)— optionally substituted by 1-3 of substituent group A, $C_{3-10}$carbocyclyl-O— optionally substituted by 1-3 of substituent group A, $C_{3-10}$carbocyclyl-OC(O)— optionally substituted by 1-3 of substituent group A, 3-7 membered heterocyclyl-$C_{0-6}$ alkylene optionally substituted by 1-3 of substituent group A, 3-7 membered heterocyclyl-C(O)— optionally substituted by 1-3 of substituent group A, 3-7 membered heterocyclyl-O-optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S;

$R^3$ is H, OH, $CO_2H$, CN, CHO, $C_{1-6}$alkyl optionally substituted by 1-3 of substituent group A, $C_{2-6}$alkenyl optionally substituted by 1-3 of substituent group A, C$_{2-6}$alkynyl optionally substituted by 1-3 of substituent group A, C$_{1-6}$alkoxy optionally substituted by 1-3 of substituent group A, C$_{1-6}$alkyl-C(O)— optionally substituted by 1-3 of substituent group A, C$_{1-6}$alkyl-OC(O)— optionally substituted by 1-3 of substituent group A, C$_{3-10}$carbocyclyl-C$_{0-6}$ alkylene optionally substituted by 1-3 of substituent group A, C$_{3-10}$carbocyclyl-O—C$_{1-6}$alkylene optionally substituted by 1-3 of substituent group A, C$_{3-10}$carbocyclyl-C(O)— optionally substituted by 1-3 of substituent group A, C$_{3-10}$ carbocyclyl-OC(O)— optionally substituted by 1-3 of substituent group A, 3-7 membered heterocyclyl-C$_{0-6}$alkylene optionally substituted by 1-3 of substituent group A, 3-7 membered heterocyclyl-C(O)— optionally substituted by 1-3 of substituent group A, 3-7 membered heterocyclyl-OC(O)— optionally substituted by 1-3 of substituent group A, wherein the heterocyclyl comprises 1-4 ring heteroatoms independently selected from N, O, and S, or R$^3$ and R$^5$ together with the atoms to which they are attached form a 5-7 heterocyclyl having 1-4 total ring heteroatoms selected from N, O, and S, and can be optionally substituted with 1-3 of substituent group A;

R$^4$, when present, is H, OH, C$_{1-3}$alkyl, C$_{1-3}$haloalkyl, or C$_{1-3}$alkoxy;

R$^5$ and R$^6$ are each independently H, OH, CO$_2$H, CN, CHO, C$_{1-6}$ alkyl optionally substituted by 1-3 of substituent group A, C$_{2-6}$ alkenyl optionally substituted by 1-3 of substituent group A, C$_{2-6}$ alkynyl optionally substituted by 1-3 of substituent group A, C$_{1-6}$alkyl carbonyl optionally substituted by 1-3 of substituent group A, C$_{1-6}$alkyl-O—C(O)— optionally substituted by 1-3 of substituent group A, C$_{3-8}$carbocyclylC$_{1-6}$alkylene optionally substituted by 1-3 of substituent group A, C$_{3-8}$carbocyclyl-O—C$_{1-6}$alkylene optionally substituted by 1-3 of substituent group A, C$_{3-8}$carbocyclyl-C(O)— optionally substituted by 1-3 of substituent group A, C$_{3-8}$carbocyclyl-OC(O)— optionally substituted by 1-3 of substituent group A, 3-7 membered heterocyclyl-C$_{0-6}$alkylene optionally substituted by substituent group A, 3-7 membered heterocyclyl-O—C$_{1-6}$alkylene optionally substituted by 1-3 of substituent group A, 3-7 membered heterocyclyl-C(O)— optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S, or R$^5$ and R$^6$ together with the atom to which they are attached form a C$_3$carbocyclyl or 3-7 membered heterocyclyl having 1-3 ring heteroatoms selected N, O, and S, and is optionally substituted with 1-3 of substituent group A;

optionally one of R$^1$, R$^2$, R$^3$, R$^5$, and R$^6$ can be
—Z—N(R$^N$)(R$^N$),
—Z—N(R$^N$)—SO$_2$—R$^{x2}$
—Z—C(O)—N(R$^N$)—SO$_2$—R$^{x2}$
—Z—N(R$^N$)—C(O)—R$^{x1}$,
—Z—C(O)—N(R$^N$)(R$^N$)
—Z—S(O)$_{0-2}$—R$^{x2}$,
—Z—N(R$^N$)—C(O)O—R$^{x1}$,
—Z—N(R$^N$)—C(O)—N(R$^N$)(R$^N$)
—Z—C(O)—N(R$^N$)—C(O)—N(R$^N$)(R$^N$), or
—Z—N(R$^N$)—C(O)—C(O)—R$^{x1}$, wherein:
each R$^N$ and R$^{x1}$ independently is hydrogen, C$_{1-6}$alkyl optionally substituted by 1-3 of substituent group A, C$_2$-alkenyl optionally substituted by 1-3 of substituent group A, C$_{2-6}$ alkynyl optionally substituted by 1-3 of substituent group A, C$_{3-10}$carbocylyl-C$_{0-6}$alkylene optionally substituted by 1-3 of substituent group A, or 3-7 membered heterocyclyl-C$_{0-6}$ alkylene optionally substituted by 1-3 of substituent group A, and the heterocyclyl group comprises 1-4 ring heteroatoms independently selected from N, O, and S, or two R$^N$ attached to the same nitrogen atom can together with the nitrogen atom to which they are attached form a 3-8 membered heterocyclyl having 0-2 additional ring heteroatoms selected from N, O, and S;

each R$^{x2}$ is independently C$_{1-6}$alkyl optionally substituted by 1-3 of substituent group A, C$_{2-6}$alkenyl optionally substituted by 1-3 of substituent group A, C$_{2-6}$alkynyl optionally substituted by 1-3 of substituent group A, C$_{3-10}$carbocylyl-C$_{0-6}$alkylene optionally substituted by 1-3 of substituent group A, or 3-7 membered heterocyclyl-C$_{0-6}$alkylene optionally substituted by 1-3 of substituent group A, and the heterocyclyl group comprises 1-4 ring heteroatoms independently selected from N, O, and S, and Z is a bond or C$_{1-6}$alkylene;

Substituent group A is halo, CN, OH, CO$_2$H, CHO, NH$_2$, oxo, NO$_2$, C$_{1-6}$alkyl, C$_{1-6}$ haloalkyl, C$_{1-6}$alkoxy, C$_{1-6}$alkylthio, C$_{1-6}$ alkyl-OH, C$_{3-10}$carbocyclyl, 3-7 membered heterocyclyl, C$_{6-10}$ aryl, C$_{3-10}$carbocyclyl-C$_{1-6}$ alkoxy, C$_{3-10}$carbocyclyl-O—C$_{1-6}$alkylene, C$_{3-10}$ carbocyclyl-C$_{1-6}$ alkoxy-C$_{1-6}$alkylene, 3-7 membered heterocyclyl-C$_{1-6}$ alkoxy, 3-7 membered heterocyclyl-O—C$_{1-6}$alkylene, 3-7 membered heterocyclyl-C$_{1-6}$alkoxy-C$_{1-6}$alkylene, C$_{1-6}$haloalkoxy, C$_{1-6}$alkoxy-C$_{1-6}$alkylene, C$_{1-6}$alkoxy-C$_{1-6}$alkoxy, C$_{1-6}$alkyl-C(O)—, C$_{1-6}$alkyl-C(O)O—, NHC$_{1-6}$alkyl, C$_{1-6}$alkyl-C(O)NH—, C$_{1-6}$haloalkyl-C(O)NH, C$_{1-6}$alkyl-NHC(O)—, C$_{1-6}$alkyl-SO$_2$—, C$_{1-6}$alkyl-SO—, and C$_{1-6}$alkylSO$_2$NH—; and each of Q$^1$, Q$^2$, Q$^3$, Q$^4$, Q$^5$, and Q$^6$ is independently H, halo, CN, OH, CO$_2$H, CHO, NH$_2$, NO$_2$, C$_{1-6}$alkyl, C$_{1-6}$haloalkyl, C$_{1-6}$alkoxy, C$_{1-6}$alkylthio, or C$_{1-6}$alkyl-OH.

In some embodiments, M is N. In some embodiments, M is CH.

In some embodiments, X is CH$_2$ or CH$_2$CH$_2$. In some embodiments, X is OCH$_2$ or CH$_2$O. In some embodiments, X is CH$_2$. In some embodiments, X is CH$_2$CH$_2$. In some embodiments, X is OCH$_2$. In some embodiments, X is CH$_2$O.

In some embodiments, X' is CH$_2$ or CH$_2$CH$_2$. In some embodiments, X' is OCH$_2$ or CH$_2$O. In some embodiments, X' is CH$_2$. In some embodiments, X' is CH$_2$CH$_2$. In some embodiments, X' is OCH$_2$. In some embodiments, X' is CH$_2$O.

In some embodiments, ring A is

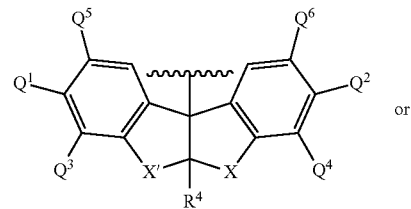 or

-continued

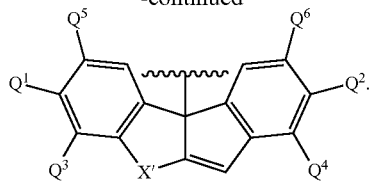

In some embodiments, Ring A is

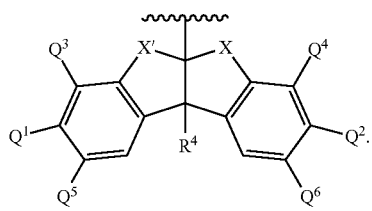

In some embodiments, Ring A is

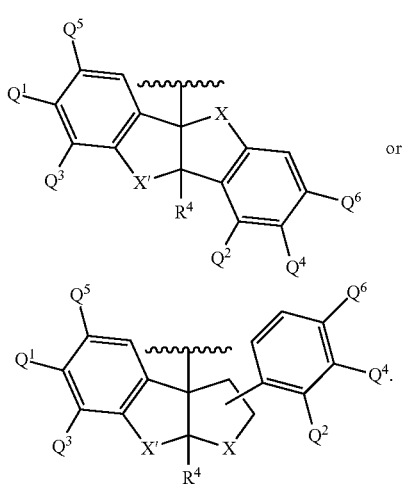

or

In some embodiments, ring A is

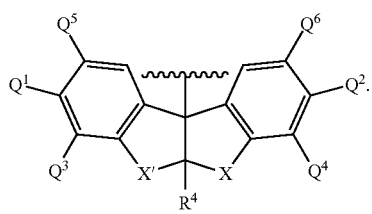

In some embodiments, ring A is

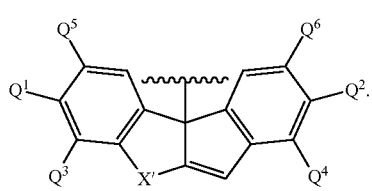

In some embodiments, ring A is

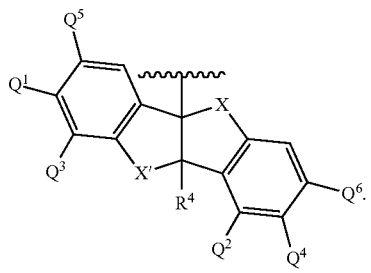

In some embodiments, ring A is

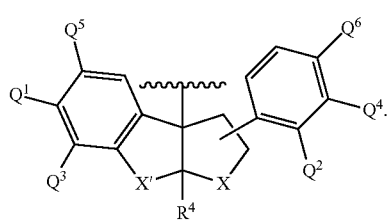

In some cases, the compound is one wherein ring A is

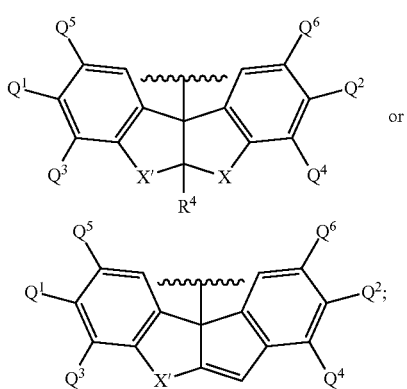

each of $R^1$, $R^2$, $R^4$, $R^5$, and $R^6$ is H;

M is N;

each of X and X' are $CH_2$;

$R^3$ is H, OH, $CO_2H$, CN, CHO, $C_{1-6}$alkyl optionally substituted by 1-3 of substituent group A, $C_{3-10}$carbocyclyl-$C_{0-6}$alkylene optionally substituted by 1-3 of substituent group A, $C_{3-10}$carbocyclyl-O—$C_{1-6}$alkylene optionally substituted by 1-3 of substituent group A, 3-7 membered heterocyclyl-$C_{0-6}$alkylene optionally substituted by 1-3 of substituent group A, 3-7 membered heterocyclyl-C(O)— optionally substituted by 1-3 of substituent group A wherein the heterocyclyl comprises 1-4 ring heteroatoms independently selected from N, O, and S;

substituent group A is halo; and each of $Q^1$, $Q^2$, $Q^3$, $Q^4$, $Q^5$, and $Q^6$ is H or halo, provided that at least two of $Q^1$, $Q^2$, $Q^3$, $Q^4$, $Q^5$, and $Q^6$ are H.

In some cases, the compound has a structure of Formula (IIA) or (IIB):

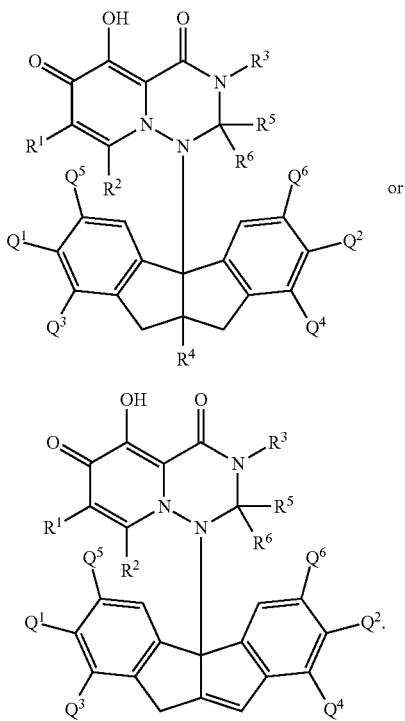

In some embodiments, at least one of $R^1$ and $R^2$ is H. In some embodiments, both of $R^1$ and $R^2$ are H. In some embodiments, $R^1$ is H. In some embodiments, $R^2$ is H.

In some embodiments, one of $R^1$ and $R^2$ is
—Z—N($R^N$)($R^N$)
—Z—N($R^N$)—SO$_2$—$R^{x2}$,
—Z—C(O)—N($R^N$)—SO$_2$—$R^{x2}$,
—Z—N($R^N$)—C(O)—$R^{x1}$,
—Z—C(O)—N($R^N$)($R^N$)
—Z—S(O)$_{0-2}$—$R^{x2}$,
—Z—N($R^N$)—C(O)O—$R^{x1}$,
—Z—N($R^N$)—C(O)—N($R^N$)($R^N$)
—Z—C(O)—N($R^N$)—C(O)—N($R^N$)($R^N$), or
—Z—N($R^N$)—C(O)—C(O)—$R^{x1}$.

In some embodiments, $R^4$, when present, is H, OH, $C_{1-3}$alkyl, or $C_{1-3}$alkoxy. In some embodiments, $R^4$ is H. In some embodiments, $R^4$ is OH or OMe. In some embodiments, $R^4$ is OH. In some embodiments, $R^4$ is OMe. In some embodiments, $R^4$ is CHF$_2$.

In some embodiments, at least one of $R^5$ and $R^6$ is H. In some embodiments, both of $R^5$ and $R^6$ are H. In some embodiments, $R^5$ is H. In some embodiments, $R^6$ is H.

In some embodiments, one of $R^5$ and $R^6$ is
—Z—N($R^N$)($R^N$)
—Z—N($R^N$)—SO$_2$—$R^{x2}$,
—Z—C(O)—N($R^N$)—SO$_2$—$R^{x2}$,
—Z—N($R^N$)—C(O)—$R^{x1}$,
—Z—C(O)—N($R^N$)($R^N$)
—Z—S(O)$_{0-2}$—$R^{x2}$,
—Z—N($R^N$)—C(O)O—$R^{x1}$,
—Z—N($R^N$)—C(O)—N($R^N$)($R^N$)
—Z—C(O)—N($R^N$)—C(O)—N($R^N$)($R^N$), or
—Z—N($R^N$)—C(O)—C(O)—$R^{x1}$.

In some embodiments, $R^5$ and $R^6$ together with the atom to which they are attached form a $C_{3-7}$carbocyclyl or 3-7 membered heterocyclyl having 1-3 ring heteroatoms selected N, O, and S, and is optionally substituted with 1-3 of substituent group A.

In some embodiments, $R^3$ and $R^5$ together with the atoms to which they are attached form a 5-7 membered heterocyclyl having 1-4 total ring heteroatoms selected N, O, and S, and can be optionally substituted with 1-3 of substituent group A.

In some embodiments, $R^3$ is
—Z—N($R^N$)($R^N$)
—Z—N($R^N$)—SO$_2$—$R^{x2}$,
—Z—C(O)—N($R^N$)—SO$_2$—$R^{x2}$,
—Z—N($R^N$)—C(O)—$R^{x1}$,
—Z—C(O)—N($R^N$)($R^N$)
—Z—S(O)$_{0-2}$—$R^{x2}$,
—Z—N($R^N$)—C(O)O—$R^{x1}$,
—Z—N($R^N$)—C(O)—N($R^N$)($R^N$)
—Z—C(O)—N($R^N$)—C(O)—N($R^N$)($R^N$), or
—Z—N($R^N$)—C(O)—C(O)—$R^{x1}$.

In some embodiments, $R^3$ is $C_{1-6}$alkyl, $C_{3-6}$carbocyclyl-$C_{1-6}$alkylene, $C_{3-6}$ carbocyclyl-O—$C_{1-6}$alkylene, or 3-7 membered heterocyclyl-$C_{1-6}$alkylene. In some embodiments, $R^3$ is ethyl, methyl, or $C_{1-3}$alkylene-cyclopropyl. In some embodiments, $R^3$ is $C_6$carbocyclyl-$C_{1-6}$alkylene or $C_6$carbocyclyl-O—$C_{1-6}$alkylene and the $C_6$carbocyclyl is phenyl, halophenyl, or dihalophenyl. In some embodiments, $R^3$ is 3-7 membered heterocyclyl-$C_{1-6}$alkylene and the heterocyclyl is tetrahydropyranyl.

In some embodiments, Substituent group A is halo, CN, OH, CO$_2$H, CHO, NH$_2$, oxo, NO$_2$, $C_{1-6}$alkyl, $C_{1-6}$haloalkyl, $C_{1-6}$alkoxy, $C_{1-6}$alkylthio, $C_{1-6}$ alkyl-OH, $C_{3-10}$carbocyclyl, 3-7 membered heterocyclyl, $C_{3-10}$carbocyclyl-$C_{1-6}$alkoxy, $C_{3-10}$carbocyclyl-O—$C_{1-6}$alkylene, $C_{3-10}$carbocyclyl-$C_{1-6}$ alkoxy-$C_{1-6}$alkylene, 3-7 membered heterocyclyl-$C_{1-6}$ alkoxy, 3-7 membered heterocyclyl-O—$C_{1-6}$alkylene, 3-7 membered heterocyclyl-$C_{1-6}$alkoxy-$C_{1-6}$alkylene, $C_{1-6}$haloalkoxy, $C_{1-6}$alkoxy-$C_{1-6}$alkylene, $C_{1-6}$alkoxy-$C_{1-6}$alkoxy, $C_{1-6}$alkyl-C(O)—, $C_{1-6}$alkyl-C(O)O—, NHC$_{1-6}$alkyl, $C_{1-6}$alkyl-C(O)NH—, $C_{1-6}$haloalkyl-C(O)NH, $C_{1-6}$alkyl-NHC(O)—, $C_{1-6}$alkyl-SO$_2$—, $C_{1-6}$alkyl-SO—, and $C_{1-6}$alkylSO$_2$NH—.

In some embodiments, one, two, three, four, five, or six of $Q^1$, $Q^2$, $Q^3$, $Q^4$, $Q^5$, and $Q^6$ are H. In some embodiments, at least two of $Q^1$, $Q^2$, $Q^3$, $Q^4$, $Q^5$, and $Q^6$ are H. In some embodiments, at least four of $Q^1$, $Q^2$, $Q^3$, $Q^4$, $Q^5$, and $Q^6$ are H. In some embodiments, each of $Q^1$, $Q^2$, $Q^3$, $Q^4$, $Q^5$, and $Q^6$ are H.

In some embodiments, one, two, three, four, five, or six of $Q^1$, $Q^2$, $Q^3$, $Q^4$, $Q^5$, and $Q^6$ are halo. In some embodiments, at least two of $Q^1$, $Q^2$, $Q^3$, $Q^4$, $Q^5$, and $Q^6$ are halo. In some embodiments, at least four of $Q^1$, $Q^2$, $Q^3$, $Q^4$, $Q^5$, and $Q^6$ are halo. In some embodiments, each of $Q^1$, $Q^2$, $Q^3$, $Q^4$, $Q^5$, and $Q^6$ are halo. In some embodiments, the halo is F.

It is understood that selections of values of each variable are those that result in the formation of stable or chemically feasible compounds.

Specific compounds contemplated include compounds in the following Tables. Compounds showing particular stereocenters indicate at least a relative stereoisomerism, and can refer to an absolute stereoisomerism. Compounds having a chiral center without indication of a particular stereoisomerism indicate a mixture of stereocenters at that chiral center.

The compound can be a compound as listed in Table A, or a pharmaceutically acceptable salt thereof.

TABLE A

| Compound No. | Structure |
| --- | --- |
| A1 | (structure) |
| A2 | (structure) |
| A3 | (structure) |
| A4 | (structure) |
| A5 | (structure) |
| A6 | (structure) |
| A7 | (structure) |
| A8 | (structure) |
| A9 | (structure) |
| A10 | (structure) |

TABLE A-continued

| Compound No. | Structure |
|---|---|
| A11 | (structure) |
| A12 | (structure) |
| A13 | (structure) |
| A14 | (structure) |
| A15 | (structure) |
| A16 | (structure) |
| A17 | (structure) |
| A18 | (structure) |
| A19 | (structure) |
| A20 | (structure) |

TABLE A-continued

| Compound No. | Structure |
|---|---|
| A21 | (structure) |
| A22 | (structure) |
| A23 | (structure) |
| A24 | (structure) |
| A25 | (structure) |
| A26 | (structure) |
| A27 | (structure) |
| A28 | (structure) |
| A29 | (structure) |

TABLE A-continued

| Compound No. | Structure |
|---|---|
| A30 | (structure) |
| A31 | (structure) |
| A32 | (structure) |
| A33 | (structure) |
| A34 | (structure) |
| A35 | (structure) |
| A36 | (structure) |
| A37 | (structure) |
| A38 | (structure) |

TABLE A-continued

| Compound No. | Structure |
|---|---|
| A39 | 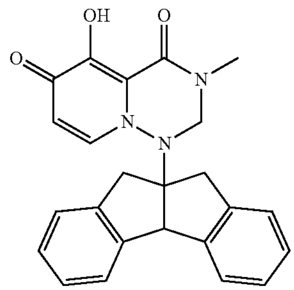 [SMILES: CN1CN(C23Cc4ccccc4C2c2ccccc2C3)n2ccc(=O)c(O)c2C1=O] |
| A40 | 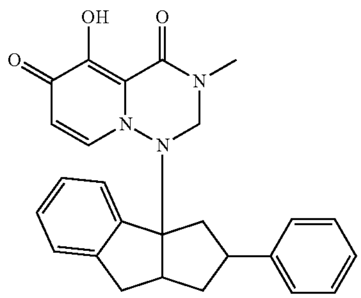 [SMILES: CN1CN(C23CC(c4ccccc4)CC2Cc2ccccc23)n2ccc(=O)c(O)c2C1=O] |
| A41 | 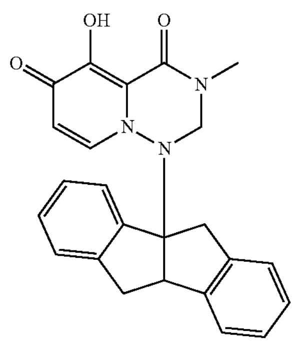 [SMILES: CN1CN(C23Cc4ccccc4C2Cc2ccccc23)n2ccc(=O)c(O)c2C1=O] |
| A42 | 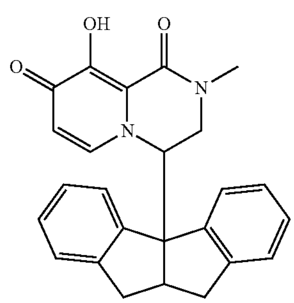 [SMILES: CN1CC(C23c4ccccc4CC2Cc2ccccc23)n2ccc(=O)c(O)c2C1=O] |
| A43 | 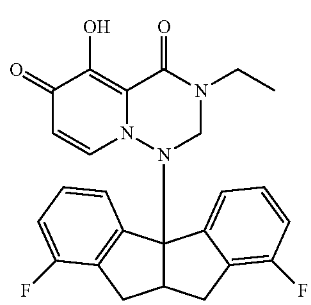 [SMILES: CCN1CN(C23c4cccc(F)c4CC2Cc2c(F)cccc23)n2ccc(=O)c(O)c2C1=O] |
| A106 | |
| A44 | |
| A107 | |
| A45 | |
| A108 | |

TABLE A-continued

| Compound No. | Structure |
|---|---|
| A46 | (structure) |
| A47 | (structure) |
| A110 | (structure) |
| A48 | (structure) |
| A111 | (structure) |
| A49 | (structure) |
| A112 | (structure) |
| A50 | (structure) |
| A113 | (structure) |
| A51 | (structure) |

TABLE A-continued

| Compound No. | Structure |
|---|---|
| A114 | (structure) |
| A52 | (structure) |
| A114 | (structure) |
| A52 | (structure) |
| A115 | (structure) |
| A53 | (structure) |
| A116 | (structure) |
| A54 | (structure) |
| A117 | (structure) |
| A55 | (structure) |

TABLE A-continued
| Compound No. | Structure |
|---|---|
| A118 | 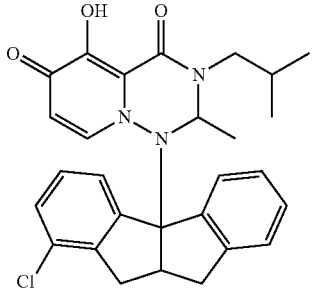 [SMILES: CC(C)CN1C(=O)c2c(O)c(=O)ccn2N(C23c4ccccc4CC2Cc2c(Cl)cccc23)C1C] |
| A56 | 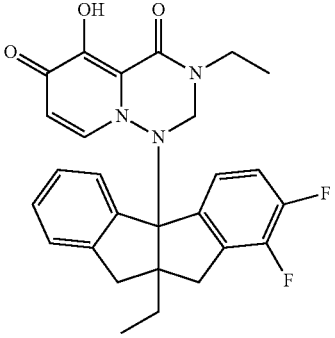 [SMILES: CCN1CN(C23c4ccccc4CC2(CC)Cc2c3ccc(F)c2F)n2ccc(=O)c(O)c2C1=O] |
| A57 | 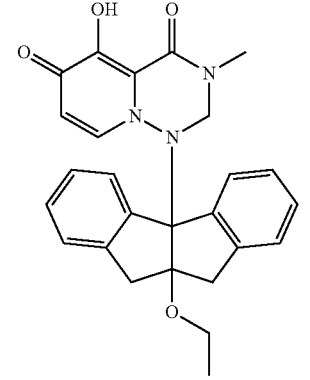 [SMILES: CCOC12Cc3ccccc3C1(N1CN(C)C(=O)c3c(O)c(=O)ccn31)c1ccccc1C2] |
| A58 | 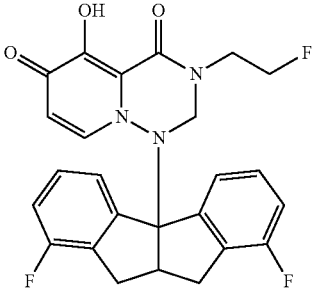 [SMILES: O=C1c2c(O)c(=O)ccn2N(C23c4cccc(F)c4CC2Cc2c(F)cccc23)CN1CCF] |
| A121 | 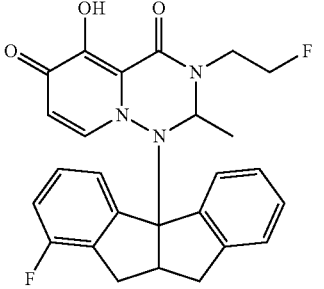 [SMILES: CC1N(CCF)C(=O)c2c(O)c(=O)ccn2N1C12c3ccccc3CC1Cc1c(F)cccc12] |
| A59 | 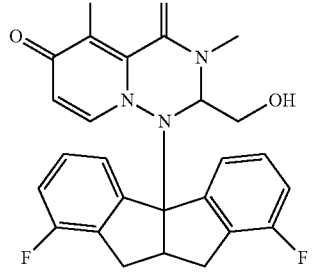 |
| A122 | 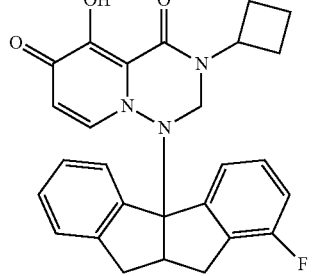 |
| A60 | 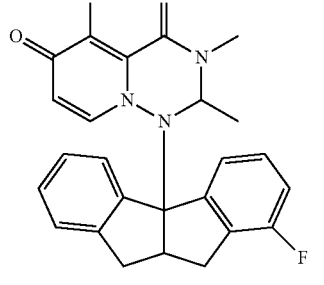 |
| A123 | 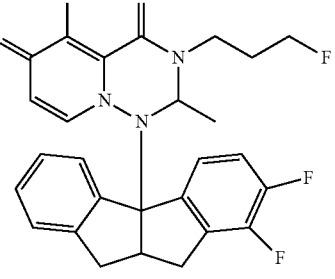 |

TABLE A-continued

| Compound No. | Structure |
|---|---|
| A61 | (structure) |
| A124 | (structure) |
| A62 | (structure) |
| A125 | (structure) |
| A63 | (structure) |
| A126 | (structure) |
| A64 | (structure) |
| A127 | (structure) |
| A65 | (structure) |
| A128 | (structure) |

TABLE A-continued

| Compound No. | Structure |
|---|---|
| A66 | 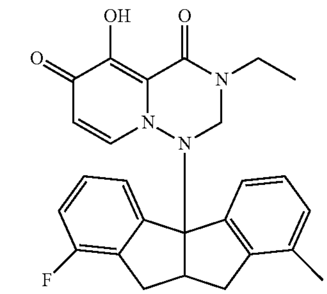 [SMILES: CCN1CN(C23c4cccc(C)c4CC2Cc2c(F)cccc23)n2ccc(=O)c(O)c2C1=O] |
| A129 | 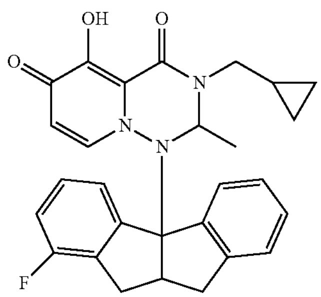 [SMILES: CC1N(CC2CC2)C(=O)c2c(O)c(=O)ccn2N1C12c3ccccc3CC1Cc1c(F)cccc12] |
| A67 | 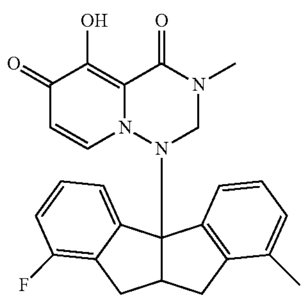 [SMILES: Cc1cccc2c1CC1Cc3c(F)cccc3C21N1CN(C)C(=O)c2c(O)c(=O)ccn21] |
| A130 | 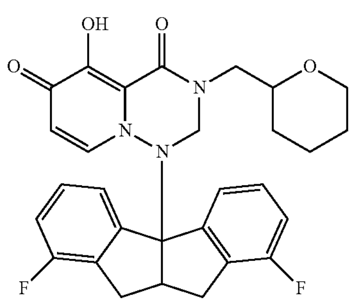 [SMILES: O=C1c2c(O)c(=O)ccn2N(C23c4cccc(F)c4CC2Cc2c(F)cccc23)CN1CC1CCCCO1] |
| A68 | 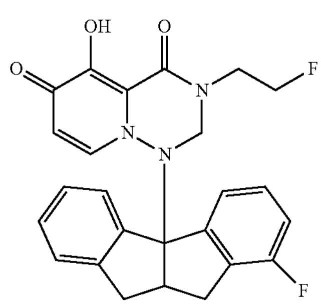 [SMILES: O=C1c2c(O)c(=O)ccn2N(C23c4ccccc4CC2Cc2c(F)cccc23)CN1CCF] |
| A131 | |
| A69 | |
| A132 | |
| A70 | |
| A133 | |

TABLE A-continued
| Compound No. | Structure |
|---|---|
| A71 | 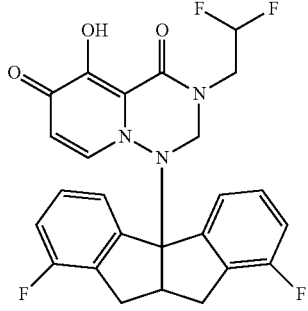 [SMILES: O=C1c2c(O)c(=O)ccn2N(C23c4cccc(F)c4CC2Cc2c(F)cccc23)CN1CC(F)F] |
| A72 | 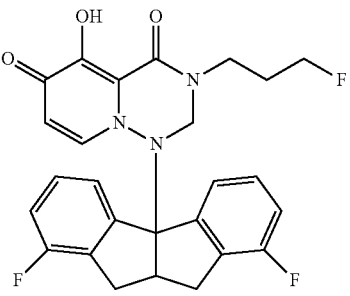 [SMILES: O=C1c2c(O)c(=O)ccn2N(C23c4cccc(F)c4CC2Cc2c(F)cccc23)CN1CCCF] |
| A73 | 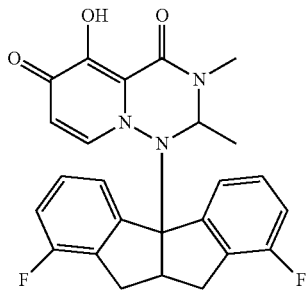 [SMILES: CC1N(C)C(=O)c2c(O)c(=O)ccn2N1C12c3cccc(F)c3CC1Cc1c(F)cccc12] |
| A136 | 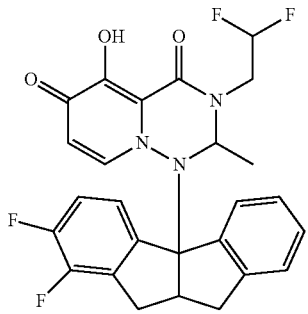 [SMILES: CC1N(CC(F)F)C(=O)c2c(O)c(=O)ccn2N1C12c3ccccc3CC1Cc1c2ccc(F)c1F] |
| A74 | 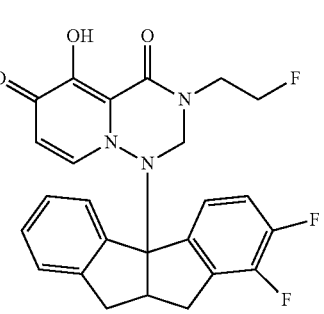 |
| A137 | 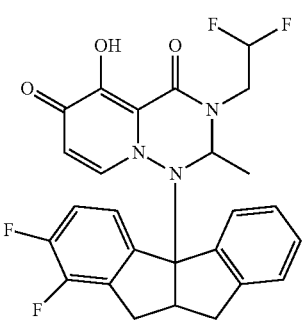 [SMILES: CC1N(CC(F)F)C(=O)c2c(O)c(=O)ccn2N1C12c3ccccc3CC1Cc1c2ccc(F)c1F] |
| A75 | 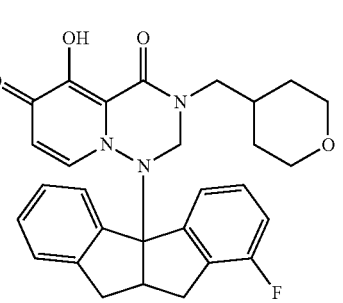 |
| A138 | 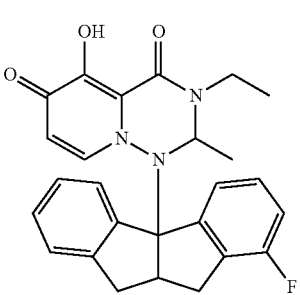 [SMILES: CCN1C(=O)c2c(O)c(=O)ccn2N(C23c4ccccc4CC2Cc2c(F)cccc23)C1C] |
| A76 | 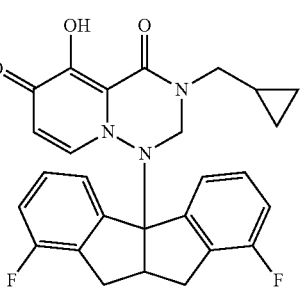 |
| A139 | 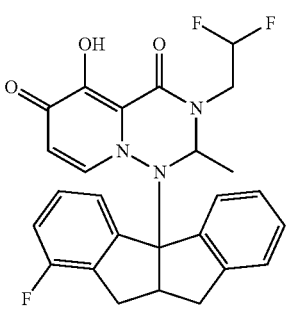 [SMILES: CC1N(CC(F)F)C(=O)c2c(O)c(=O)ccn2N1C12c3ccccc3CC1Cc1c(F)cccc12] |

TABLE A-continued

| Compound No. | Structure |
|---|---|
| A77 | (structure) |
| A140 | (structure) |
| A78 | (structure) |
| A141 | (structure) |
| A79 | (structure) |
| A142 | (structure) |
| A80 | (structure) |
| A144 | (structure) |
| A81 | (structure) |
| A145 | (structure) |

TABLE A-continued

| Compound No. | Structure |
|---|---|
| A82 | 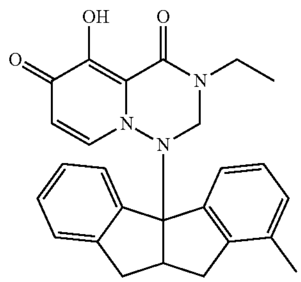 [SMILES: CCN1CN(C23c4ccccc4CC2Cc2c(C)cccc23)n2ccc(=O)c(O)c2C1=O] |
| A146 | 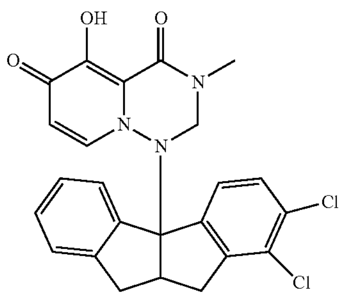 [SMILES: CN1CN(C23c4ccccc4CC2Cc2c3ccc(Cl)c2Cl)n2ccc(=O)c(O)c2C1=O] |
| A83 | 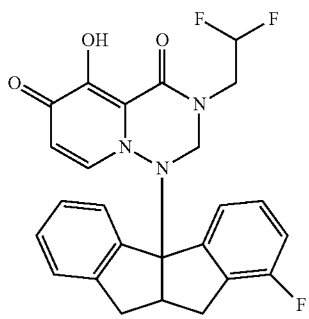 [SMILES: O=C1c2c(O)c(=O)ccn2N(C23c4ccccc4CC2Cc2c(F)cccc23)CN1CC(F)F] |
| A147 | 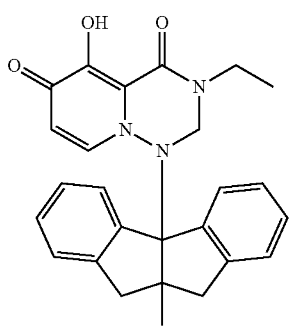 [SMILES: CCN1CN(C23c4ccccc4CC2(C)Cc2ccccc23)n2ccc(=O)c(O)c2C1=O] |
| A84 | 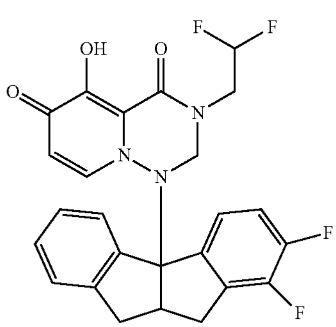 [SMILES: O=C1c2c(O)c(=O)ccn2N(C23c4ccccc4CC2Cc2c3ccc(F)c2F)CN1CC(F)F] |
| A148 | |
| A85 | |
| A149 | |
| A86 | |
| A150 | |

TABLE A-continued
| Compound No. | Structure |
|---|---|
| A87 | 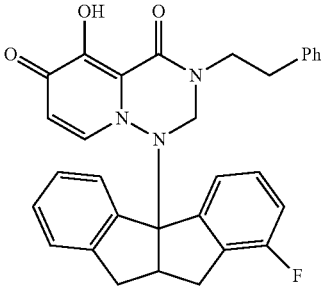 [SMILES: O=C1c2c(O)c(=O)ccn2N(C23c4ccccc4CC2Cc2c(F)cccc23)CN1CCc1ccccc1] |
| A151 | 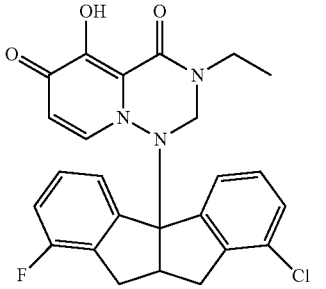 [SMILES: CCN1CN(C23c4cccc(F)c4CC2Cc2c(Cl)cccc23)n2ccc(=O)c(O)c2C1=O] |
| A88 | 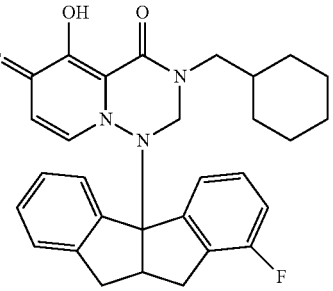 |
| A152 | 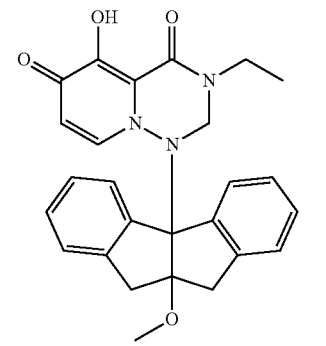 [SMILES: CCN1CN(C23c4ccccc4CC2(OC)Cc2ccccc23)n2ccc(=O)c(O)c2C1=O] |
| A89 | 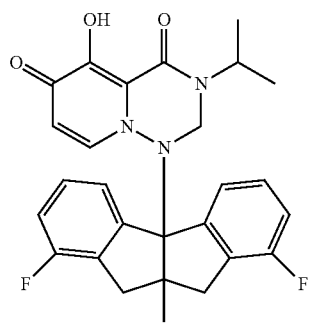 [SMILES: CC(C)N1CN(C23c4cccc(F)c4CC2(C)Cc2c(F)cccc23)n2ccc(=O)c(O)c2C1=O] |
| A153 | 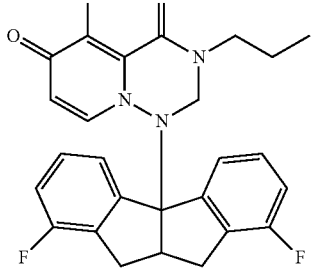 |
| A90 | 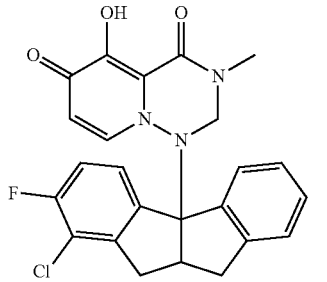 [SMILES: CN1CN(C23c4ccccc4CC2Cc2c3ccc(F)c2Cl)n2ccc(=O)c(O)c2C1=O] |
| A154 | 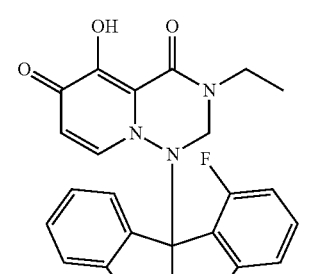 |
| A91 | 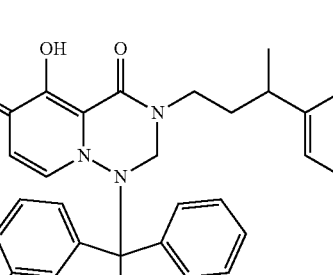 |
| A155 | 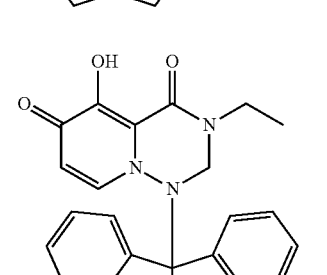 |

TABLE A-continued

| Compound No. | Structure |
|---|---|
| A92 | (structure) |
| A156 | (structure) |
| A93 | (structure) |
| A157 | (structure) |
| A94 | (structure) |
| A158 | (structure) |
| A95 | (structure) |
| A159 | (structure) |
| A96 | (structure) |
| A160 | (structure) |

TABLE A-continued

| Compound No. | Structure |
|---|---|
| A97 | (structure) |
| A161 | (structure) |
| A98 | (structure) |
| A162 | (structure) |
| A99 | (structure) |
| A163 | (structure) |
| A100 | (structure) |
| A164 | (structure) |
| A101 | (structure) |
| A165 | (structure) |

TABLE A-continued

| Compound No. | Structure |
|---|---|
| A102 | (structure) |
| A166 | (structure) |
| A103 | (structure) |
| A167 | (structure) |
| A104 | (structure) |
| A105 | (structure) |

Methods of Use

The compounds described herein or pharmaceutically acceptable salts thereof can be used to reduce viral titer in a biological sample (e.g. an infected cell culture) or in humans (e.g. lung viral titer in a patient).

The terms "influenza virus mediated condition", "influenza infection", or "Influenza", as used herein, are used interchangeably to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenza virus A, Influenza virus B, Influenza virus C, Isavirus and Thogotovirus. Influenza virus A genus has one species, influenza A virus which can be subdivided into different serotypes based on the antibody response to these viruses: H1N1, H2N2, H3N2, H5N1, H7N7, H1N2, H9N2, H7N2, H7N3 H7N9, and H10N7. Influenza virus B genus has one species, influenza B virus. Influenza B almost exclusively infects humans and is less common than influenza A. Influenza virus C genus has one species, influenza virus C virus, which infects humans and pigs and can cause severe illness and local epidemics. However, influenza virus C is less common than the other types and usually seems to cause mild disease in children.

In some embodiments, influenza or influenza viruses are associated with influenza virus A or B. In some embodiments, influenza or influenza viruses are associated with Influenza virus A. In some specific embodiments, influenza virus A is H1N1, H2N2, H3N2, H7N9, or H5N1.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness"). Usually, laboratory data is needed in order to confirm the diagnosis.

The terms, "disease", "disorder", and "condition" may be used interchangeably herein to refer to an influenza virus mediated medical or pathological condition.

As used herein, the terms "subject", "host", and "patient" are used interchangeably. The terms "subject", "host", and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, or mouse) and a primate (e.g., a monkey, chimpanzee, or human), and more specifically a human. In some embodiments, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses is inhibited by at least 50%, at least 65%, at least 75%, at least 85%, at least 90%, or at least 95%.

Influenza virus replication can be measured by any suitable method known in the art. For example, influenza viral titer in a biological sample (e.g. an infected cell culture) or in humans (e.g. lung viral titer in a patient) can be measured. More specifically, for cell-based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer" or "titer" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}, 10^{-2}, 10^{-3}, \ldots, 10^{-8}$. The lowest concentration of virus that still infects cells is the viral titer.

As used herein, the terms "treat", "treatment," and "treating" refer to both therapeutic and prophylactic treatments. For example, therapeutic treatments include the reduction or amelioration of the progression, severity and/or duration of influenza virus-mediated conditions, or the amelioration of one or more symptoms (specifically, one or more discernible symptoms) of influenza virus-mediated conditions, resulting from the administration of one or more therapies (e.g., one or more therapeutic agents such as a compound or composition described herein). In specific embodiments, the therapeutic treatment includes the amelioration of at least one measurable physical parameter of an influenza virus-mediated condition. In other embodiments, the therapeutic treatment includes the inhibition of the progression of an influenza virus-mediated condition, either physically by, e.g., stabilization of a discernible symptom, physiologically by, e.g., stabilization of a physical parameter, or both. In other embodiments, the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis", "prophylactic", "prophylactic use", and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes use in situations in which an outbreak has been detected to prevent contagion or spread of the infection in places where many people that are at high risk of serious influenza complications live in close contact with each other (e.g. in a hospital ward, daycare center, prison, nursing home, etc.). It also includes the use among populations who require protection from influenza but who do not get protection after vaccination (e.g. due to weak immune system), to whom the vaccine is unavailable, or who cannot receive the vaccine because of side effects. It also includes use during the two weeks following vaccination, or during any period after vaccination but before the vaccine is effective. Prophylactic use may also include treating a person who is not ill with the influenza or not considered at high risk for complications, in order to reduce the chances of getting infected with the influenza and passing it on to a high-risk person in close contact with him or her (for instance, healthcare workers, nursing home workers, etc.).

As used herein, and according to the United States Center for Disease Control (US CDC), an influenza "outbreak" is defined as a sudden increase of acute febrile respiratory illness (AFRI) occurring within a 48- to 72-hour period, in a group of people who are near each other (e.g. in the same area of an assisted living facility, in the same household, etc.) over the normal background rate or when any subject in the population being analyzed tests positive for influenza. One case of confirmed influenza by any testing method is considered an outbreak.

As used herein, the "index case", "primary case," or "patient zero" is the initial patient in the population sample of an epidemiological investigation. The index case is the first patient that indicates the existence of an outbreak. Earlier cases may be found and are labeled primary, secondary, tertiary, etc.

In some embodiments, the methods of the disclosure are a preventative or prophylactic measure to a patient, specifically a human, having a predisposition to complications resulting from infection by an influenza virus. The prophylactic methods described herein can be used in situations in which an index case or an outbreak has been confirmed, in order to prevent the spread of infection in the rest of the community or population group.

In some embodiments, the methods of the disclosure are applied as a prophylactic measure to members of a community or population group, specifically humans, in order to prevent the spread of infection.

As used herein, an "effective amount" refers to an amount sufficient to elicit the desired biological response. In the present disclosure the desired biological response is to inhibit the replication of influenza virus, to reduce the amount of influenza virus, or to reduce or ameliorate the severity, duration, progression, or onset of an influenza virus infection, prevent the advancement of an influenza virus infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other antiviral agents, e.g., when co-administered with an anti-influenza medication, an effective amount of the second agent will depend on the type of drug used. A safe amount is one with minimal side effects, as can readily be determined by those skilled in the art. Suitable dosages are known for approved agents and can be adjusted by the skilled artisan according to the condition of the subject, the type of condition(s) being treated and the amount of a compound described herein being used. In cases where no amount is expressly noted, a safe and effective amount should be assumed. For example, compounds described herein can be administered to a subject in a dosage range from between approximately 0.01 to 100 mg/kg body weight/day for therapeutic or prophylactic treatment.

As used herein, a "safe and effective amount" of a compound or composition described herein is an effective amount of the compound or composition which does not cause excessive or deleterious side effects in a patient.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe a safe and effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Combination Therapy

A compound described herein, or a pharmaceutically acceptable salt thereof, can be administered alone or in combination with an additional suitable therapeutic agent, for example, an antiviral agent or a vaccine. When combination therapy is employed, a safe and effective amount can be achieved using a first amount of a compound as disclosed herein, e.g., a compound of any one of Formulas I, IIA, or IIB, or a pharmaceutically acceptable salt thereof, and a second amount of an additional suitable therapeutic agent (e.g. an antiviral agent or vaccine). In some cases, the second antiviral agent is a pyrazinecarboxamide antiviral compound, an influenza neuraminidase inhibitor, an influenza PB1 polymerase domain inhibitor, or an influenza CAP-binding PB2 domain inhibitor.

In some embodiments of this disclosure, a compound described herein, or a pharmaceutically acceptable salt thereof, and the additional therapeutic agent, are each administered in a safe and effective amount (i.e., each in an amount which would be therapeutically effective if administered alone). In some embodiments, the compound and the additional therapeutic agent are each administered in an amount which alone does not provide a therapeutic effect (a sub-therapeutic dose). In some embodiments, the compound can be administered in a safe and effective amount, while the additional therapeutic agent is administered in a sub-therapeutic dose. In some embodiments, the compound can be administered in a sub-therapeutic dose, while the additional therapeutic agent, for example, a suitable cancer therapeutic agent, is administered in a safe and effective amount.

As used herein, the terms "combination therapy", "in combination", and "co-administration" or "coadministration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration can encompass administration of the first and second amounts of the compounds of the combination in an essentially simultaneous manner, such as in a single pharmaceutical composition, for example, capsule or tablet having a fixed ratio of first and second amounts, or in multiple, separate capsules or tablets for each. In addition, such coadministration can also encompass use of each compound of the combination in a sequential manner in either order.

In some embodiments, the present disclosure is directed to methods of combination therapy for inhibiting influenza virus replication in biological samples or patients, or for treating or preventing influenza virus infections in patients using the compounds or pharmaceutical compositions of the disclosure. Accordingly, pharmaceutical compositions described herein also include those comprising an inhibitor of influenza virus replication as described herein in combination with an anti-viral compound exhibiting anti-influenza virus activity.

Methods of use also include combination of chemotherapy with a compound described herein or with a combination of a compound disclosed herein with another anti-viral agent and vaccination with a flu vaccine.

When co-administration involves the separate administration of a first amount of a compound as described herein and a second amount of an additional therapeutic agent, the compound and agent are administered sufficiently close in time to have the desired therapeutic effect. For example, the period between each administration can range from minutes to hours and can be selected by taking into account the properties of each compound such as potency, solubility, bioavailability, plasma half-life, and kinetic profile, to result in the desired therapeutic effect. For example, a compound as described herein and a second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the disclosure) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional therapeutic agent (e.g., an anti-viral agent or flu vaccine) to a subject.

It is understood that the method of co-administration of a first amount of a compound as described herein and a second amount of an additional therapeutic agent can result in an enhanced or synergistic therapeutic effect, wherein the combined effect is greater than the additive effect that would result from separate administration of the first amount of the compound as described herein and the second amount of the additional therapeutic agent.

As used herein, the term "synergistic" refers to a combination of a compound of the disclosure and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using compounds of the present disclosure is in combination with a flu vaccine, both therapeutic agents can be administered so that the period between each administration can be longer (e.g. days, weeks or months).

The presence of a synergistic effect can be determined using suitable methods for assessing drug interaction. Suitable methods include, for example, the Sigmoid-Emax equation (Holford, N. H. G. and Scheiner, L. B., *Clin. Pharmacokinet.* 6: 429-453 (1981)), the equation of Loewe additivity (Loewe, S, and Muischnek, H., Arch. Exp. *Pathol. Pharmacol.* 114: 313-326 (1926)) and the median-effect equation (Chou, T. C. and Talalay, P., *Adv. Enzyme Regul.* 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Anti-Influenza Vaccines

The compounds described herein can be prophylactically administered in conjunction with anti-influenza vaccines. These vaccines can be administered, for example, via subcutaneous or intranasal administration. Vaccination via subcutaneous injection typically induces an IgG antibody having a neutralizing activity in the serum, and is highly effective for preventing progression of the condition into a more severe one such as pneumonia and the like. However, in the upper airway mucosa, which is the infection site, IgA is the main prophylactic component. Since IgA is not induced by subcutaneous administration, it can also be advantageous to administer vaccines via an intranasal route.

Antiviral Inhibitors

A variety of other compounds can be used, in combination with the compounds described herein, to treat or prevent an influenza infection. Approved compounds include neuraminidase (NA) inhibitors, ion channel (M2) inhibitors, polymerase (PB1) inhibitors, and other influenza antivirals.

There are three FDA-approved influenza antiviral drugs for use against influenza viruses, including Relenza® (zanamivir), Tamiflu® (oseltamivir phosphate), and Rapivab® (peramivir). Older drugs, such as Symmetrel® (amantadine) and Flumadine® (rimantadine), are approved for treating and preventing influenza A.

Neuraminidase (NA) inhibitors are a class of drugs which block the neuraminidase enzyme. They are commonly used as antiviral drugs because they block the function of viral neuraminidases of the influenza virus, by preventing its reproduction by budding from the host cell. Representative neuraminidase inhibitors include oseltamivir (Tamiflu®), zanamivir (Relenza®), Ianinamivir (Inavir®), and peramivir (Rapivab®).

M2 inhibitors can also be used. The Matrix-2 (M2) protein is a proton-selective ion channel protein, integral in the viral envelope of the influenza A virus.

The anti-influenza virus drug, amantadine, is a specific blocker of the M2 H+ channel. Aminoadamantanes, including amantadine and rimantadine have been widely abandoned due to virus resistance, but combination therapy can lessen the development of resistance to these agents, as virus which becomes resistant to one active agent can still be treated by the other agent(s) in the combination therapy.

Inhibitors of influenza RNA-dependent RNA polymerase (RdRp) include, for example, certain pyrazine carboxamide derivatives, such as favipiravir (T-705 or Avigan®) and compounds described in PCT WO 2013/138236. Additional compounds, disclosed in Muratore et al., *PNAS*, 109(16), 6247-6252 (April 2012), include the following:

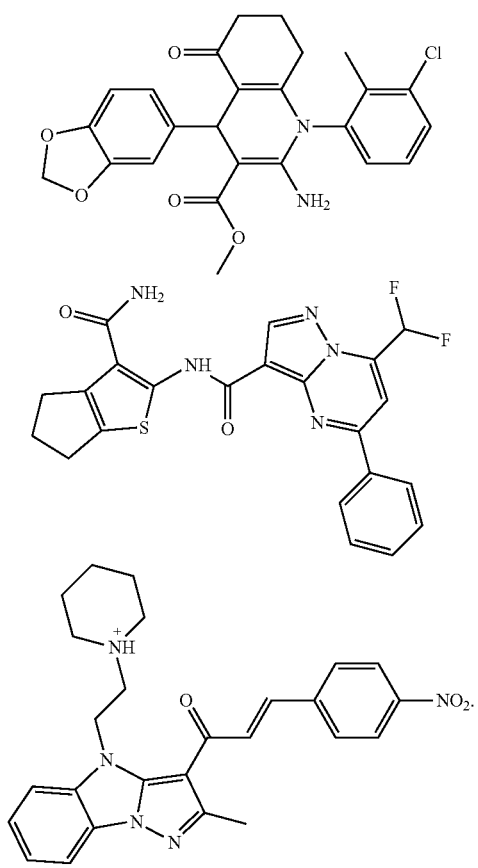

Specific examples that can be co-administered with a compound described herein include neuraminidase inhibitors, such as oseltamivir (Tamiflu®) and zanamivir (Relenza®), viral ion channel (M2 protein) blockers, such as amantadine (Symmetrel®) and rimantadine (Flumadine®), and antiviral drugs described in WO 2003/015798, including favipiravir (Avidan®). (See also Ruruta et al., *Antiviral Res.*, 82: 95-102 (2009)) In some embodiments, the compounds described herein can be co-administered with a traditional influenza vaccine.

Additional examples of compounds that can be co-administered with a compound described herein include pyrazinecarboxamide antiviral compounds, influenza PB1 polymerase domain inhibitors, influenza CAP-binding PB2 domain inhibitors, such as (3-(2-(5-chloro-1H-pyrrolo[2,3-b]pyridin-3-yl)-5-fluoro-7H-pyrrolo[2,3-d]pyrimidin-7-yl) bicyclo[2.2.2]octane-2-carboxylic acid).

The compounds described herein can be useful as inhibitors of influenza virus replication in biological samples or in a patient. These compounds can also be useful in reducing the amount of influenza virus (viral titer) in a biological sample or in a patient. They can also be useful for therapeutic and prophylactic treatment of infections caused by influenza viruses in a biological sample or in a patient.

The present disclosure also provides methods of preparing a compound described herein. In some embodiments, the methods are directed to prepare compounds represented by Formulas I, IIA, IIB, or pharmaceutically acceptable salts thereof.

Preparation of Compounds Disclosed Herein

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; and Greene, T. W., Wuts, P. G. M., *Protective Groups in Organic Synthesis,* $3^{rd}$ edition, John Wiley & Sons: New York, 1999, are useful and recognized reference textbooks of organic synthesis known to those in the art. For example, the compounds disclosed herein can be synthesized by solid phase synthesis techniques including those described in Merrifield, *J. Am. Chem. Soc.* 1963; 85:2149; Davis et al., *Biochem. Intl.* 1985; 10:394-414; Larsen et al., *J. Am. Chem. Soc.* 1993; 115: 6247; Smith et al., *J. Peptide Protein Res.* 1994; 44: 183; O'Donnell et al., *J. Am. Chem. Soc.* 1996; 118:6070; Stewart and Young, *Solid Phase Peptide Synthesis*, Freeman (1969); Finn et al., *The Proteins,* 3rd ed., vol. 2, pp. 105-253 (1976); and Erickson et al., *The Proteins,* 3rd ed., vol. 2, pp. 257-527 (1976). The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, ester or prodrug thereof.

In general, compounds of Formula (I) can be synthesized according to Scheme 1.

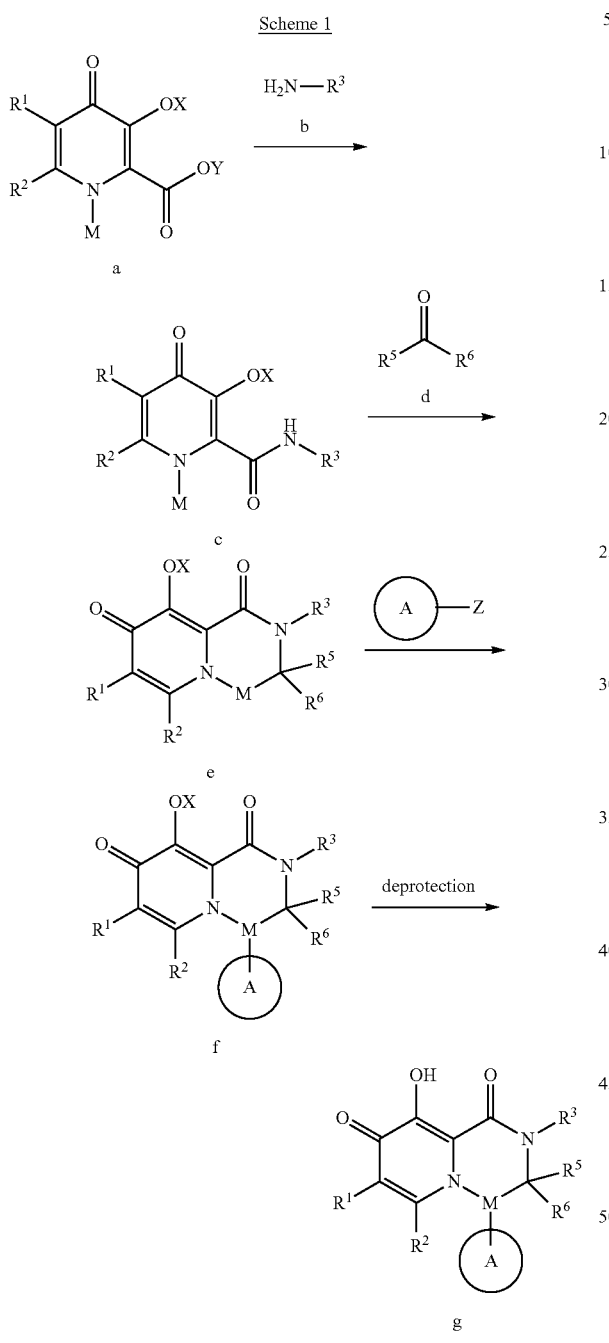

Y = alkyl X = protecting group

Compounds having structure g can be synthesized using the procedure shown in Scheme 1. Reaction of an O-protected, optionally substituted 4-oxo-1,4-dihydropyridine ester a with an optionally substituted amine compound b produces 4-oxo-1,4-dihydropyridine amides having structure c. Condensation with an appropriate carbonyl compound d, e.g., formaldehyde or other aldehyde or ketone, produces 3,4-dihydro-2H-pyrido[1,2-a]pyrazine-1,8-dione compounds having structure e. Addition of a Ring A moiety to form an intermediate f followed by deprotection gives compounds as described herein, i.e., compounds of Formula I having structure g.

The coupling of compounds a and b can be catalyzed by appropriate reagents selected based on the precise nature of compounds a and b. For example, the coupling of compounds a and b can be catalyzed by a base e.g., 1,8-Diazabicyclo[5.4.0]undec-7-ene (DBU). Occasionally, the coupling reaction may not require a catalyst.

Likewise, appropriate conditions for the condensation of compounds c and d can be selected based on the precise nature of compounds c and d. For example, M can be an amino moiety (i.e., —$NH_2$), and the coupling of compounds c and d can be performed in a solvent at elevated temperature. For example, the solvent can be a protic solvent such as an alcohol (e.g., ethanol), and the reaction can be heated via microwave irradiation.

Appropriate reaction conditions for the addition of a Ring A moiety to a compound having structure e can be selected based on the nature of M and reactive moiety Z of Ring A. For example, when M is an amino moiety, Z can be a leaving group (a nucleofuge) such as a halide, e.g., a chloro or iodo group, and the addition of Ring A to e can be performed using a base in a solvent, e.g., sodium hydride in DMF.

Compounds a, b, d, and Ring A can be purchased commercially or prepared by a variety of methods from commercially-available starting materials.

For example, a Ring A moiety having structure k can be prepared through a transition-metal catalyzed cyclization of an acyclic compound, as shown in Scheme 2.

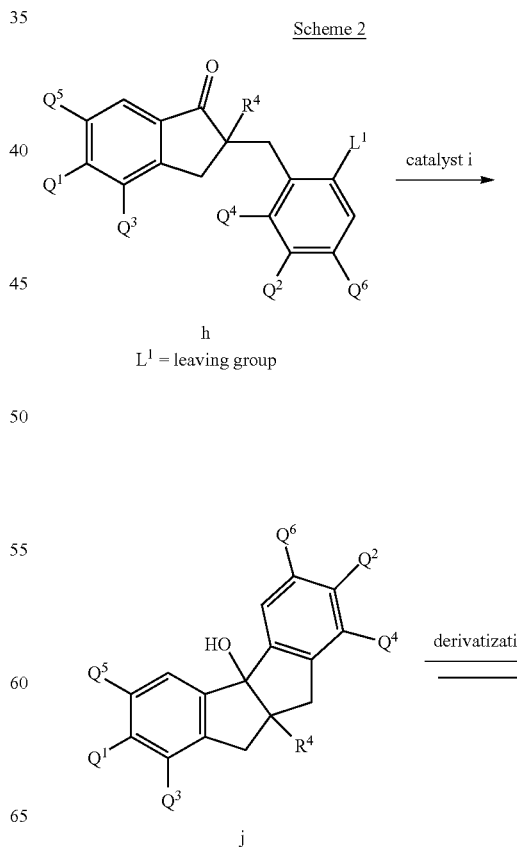

$L^1$ = leaving group

-continued

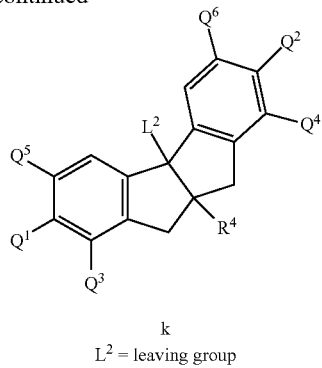

$L^2$ = leaving group

Compounds having structure h can be cyclized in the presence of an appropriate catalyst, such as a transition metal catalyst. For example, when $L^1$ is a halide leaving group, e.g., a bromo moiety, a chromium/nickel catalyst, e.g., $CrCl_2/NiCl_2$, can catalyze the cyclization of h to produce a compound having structure j. Further derivatization can produce a Ring A moiety having structure k with an appropriate leaving group moiety $L^2$ for addition to a compound having structure e, above. Derivatization reactions can be selected based on the desired identity of moiety $L^2$. For example, the OH moiety of structure j can be converted into a chloro group corresponding to $L^2$ in structure k by dehydration with phosphoric acid, followed by treatment with chlorine gas in the presence of acetic acid.

Chiral Separations

The compounds described herein can have asymmetric centers and occur as racemates, racemic mixtures, individual diastereomers or enantiomers, with all isomeric forms being included in the present disclosure. Compounds described herein having a chiral center can exist in and be isolated in optically active and racemic forms. Some compounds can exhibit polymorphism. The present disclosure encompasses racemic, optically-active, polymorphic, or stereoisomeric forms, or mixtures thereof, of a compound described herein, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.
  i) physical separation of crystals: a technique whereby macroscopic crystals of the individual enantiomers are manually separated. This technique can be used if crystals of the separate enantiomers exist, i.e., the material is a conglomerate, and the crystals are visually distinct;
  ii) simultaneous crystallization: a technique whereby the individual enantiomers are separately crystallized from a solution of the racemate, possible only if the latter is a conglomerate in the solid state;
  iii) enzymatic resolutions: a technique whereby partial or complete separation of a racemate by virtue of differing rates of reaction for the enantiomers with an enzyme;
  iv) enzymatic asymmetric synthesis: a synthetic technique whereby at least one step of the synthesis uses an enzymatic reaction to obtain an enantiomerically pure or enriched synthetic precursor of the desired enantiomer;
  v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;
  vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
  vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;
  viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;
  ix) enantiospecific synthesis from non-racemic precursors: a synthetic technique whereby the desired enantiomer is obtained from non-chiral starting materials and where the stereochemical integrity is not or is only minimally compromised over the course of the synthesis;
  x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;
  xi) chiral gas chromatography: a technique whereby the racemate is volatilized and enantiomers are separated by virtue of their differing interactions in the gaseous mobile phase with a column containing a fixed non-racemic chiral adsorbent phase;
  xii) extraction with chiral solvents: a technique whereby the enantiomers are separated by virtue of preferential dissolution of one enantiomer into a particular chiral solvent;
  xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in some embodiments. A wide variety of chiral stationary phases are commercially available.

In some embodiments, the disclosure provides compounds having a structure of Formula (I), or a pharmaceutically acceptable salt thereof:

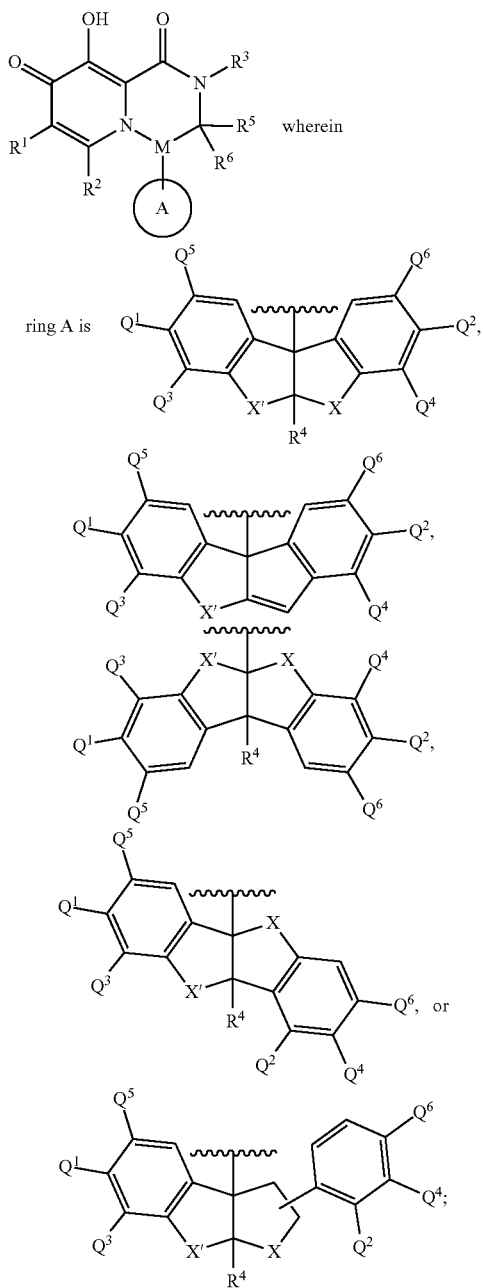

wherein

M is N or CH;
each of X and X' is independently $CH_2$, $CH_2CH_2$, $OCH_2$, or $CH_2O$;

each of $R^1$ and $R^2$ is independently H, halo, OH, $CO_2H$, CN, CHO, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{1-6}$alkoxy optionally substituted by 1-3 of substituent group A, $C_{1-6}$alkyl-C(O)— optionally substituted by 1-3 of substituent group A, $C_{1-6}$alkyl-OC(O)— optionally substituted by 1-3 of substituent group A, $C_{3-10}$carbocyclyl-$C_{0-6}$ alkylene optionally substituted by 1-3 of substituent group A, $C_{3-10}$carbocyclyl-C(O)— optionally substituted by 1-3 of substituent group A, $C_{3-10}$carbocyclyl-O— optionally substituted by 1-3 of substituent group A, $C_{3-10}$carbocyclyl-OC(O)— optionally substituted by 1-3 of substituent group A, 3-7 membered heterocyclyl-$C_{0-6}$ alkylene optionally substituted by 1-3 of substituent group A, 3-7 membered heterocyclyl-C(O)— optionally substituted by 1-3 of substituent group A, 3-7 membered heterocyclyl-O-optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S;

$R^3$ is H, OH, $CO_2H$, CN, CHO, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{1-6}$alkoxy optionally substituted by 1-3 of substituent group A, $C_{1-6}$alkyl-C(O)— optionally substituted by 1-3 of substituent group A, $C_{1-6}$alkyl-OC(O)— optionally substituted by 1-3 of substituent group A, $C_{3-10}$carbocyclyl-$C_{0-6}$ alkylene optionally substituted by 1-3 of substituent group A, $C_{3-10}$carbocyclyl-O—$C_{1-6}$alkylene optionally substituted by 1-3 of substituent group A, $C_{3-10}$carbocyclyl-C(O)— optionally substituted by 1-3 of substituent group A, $C_{3-10}$ carbocyclyl-OC(O)— optionally substituted by 1-3 of substituent group A, 3-7 membered heterocyclyl-$C_{0-6}$alkylene optionally substituted by 1-3 of substituent group A, 3-7 membered heterocyclyl-C(O)— optionally substituted by 1-3 of substituent group A, 3-7 membered heterocyclyl-OC(O)— optionally substituted by 1-3 of substituent group A, wherein the heterocyclyl comprises 1-4 ring heteroatoms independently selected from N, O, and S, or $R^3$ and $R^5$ together with the atoms to which they are attached form a 5-7 heterocyclyl having 1-4 total ring heteroatoms selected from N, O, and S, and can be optionally substituted with 1-3 of substituent group A;

$R^4$, when present, is H, OH, $C_{1-3}$alkyl, $C_{1-3}$haloalkyl, or $C_{1-3}$alkoxy;

$R^5$ and $R^6$ are each independently H, OH, $CO_2H$, CN, CHO, $C_{1-6}$ alkyl optionally substituted by 1-3 of substituent group A, $C_{2-6}$ alkenyl optionally substituted by 1-3 of substituent group A, $C_{2-6}$ alkynyl optionally substituted by 1-3 of substituent group A, $C_{1-6}$alkyl carbonyl optionally substituted by 1-3 of substituent group A, $C_{1-6}$ alkyl-O—C(O)— optionally substituted by 1-3 of substituent group A, $C_{3-8}$carbocyclyl$C_{1-6}$ alkylene optionally substituted by 1-3 of substituent group A, $C_{3-8}$carbocyclyl-O—$C_{1-6}$alkylene optionally substituted by 1-3 of substituent group A, $C_3$-carbocyclyl-C(O)— optionally substituted by 1-3 of substituent group A, $C_{3-8}$carbocyclyl-OC(O)— optionally substituted by 1-3 of substituent group A, 3-7 membered heterocyclyl-$C_{0-6}$alkylene optionally substituted by substituent group A, 3-7 membered heterocyclyl-O—C$_{1-6}$alkylene optionally substituted by 1-3 of substituent group A, 3-7 membered heterocyclyl-C(O)— optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S, or R$^5$ and R$^6$ together with the atom to which they are attached form a C$_3$-carbocyclyl or 3-7 membered heterocyclyl having 1-3 ring heteroatoms selected N, O, and S, and is optionally substituted with 1-3 of substituent group A;

optionally one of R$^1$, R$^2$, R$^3$, R$^5$, and R$^6$ can be
—Z—N(R$^N$)(R$^N$),
—Z—N(R$^N$)—SO$_2$—R$^{x2}$,
—Z—C(O)—N(R$^N$)—SO$_2$—R$^{x2}$,
—Z—N(R$^N$)—C(O)—R$^{x1}$,
—Z—C(O)—N(R$^N$)(R$^N$),
—Z—S(O)$_{0-2}$—R$^{x2}$,
—Z—N(R$^N$)—C(O)O—R$^{x1}$,
—Z—N(R$^N$)—C(O)—N(R$^N$)(R$^N$),
—Z—C(O)—N(R$^N$)—C(O)—N(R$^N$)(R$^N$), or
—Z—N(R$^N$)—C(O)—C(O)—R$^{x1}$, in which:
each R$^N$ and R$^{x1}$ independently is hydrogen, C$_{1-6}$alkyl optionally substituted by 1-3 of substituent group A, C$_{2-6}$alkenyl optionally substituted by 1-3 of substituent group A, C$_{2-6}$ alkynyl optionally substituted by 1-3 of substituent group A, C$_{3-10}$carbocylyl-C$_{0-6}$alkylene optionally substituted by 1-3 of substituent group A, or 3-7 membered heterocyclyl-C$_{0-6}$ alkylene optionally substituted by 1-3 of substituent group A, and the heterocyclyl group comprises 1-4 ring heteroatoms independently selected from N, O, and S, or two R$^N$ attached to the same nitrogen atom can together with the nitrogen atom to which they are attached form a 3-8 membered heterocyclyl having 0-2 additional ring heteroatoms selected from N, O, and S;

each R$^{x2}$ is independently C$_{1-6}$alkyl optionally substituted by 1-3 of substituent group A, C$_{2-6}$alkenyl optionally substituted by 1-3 of substituent group A, C$_{2-6}$alkynyl optionally substituted by 1-3 of substituent group A, C$_{3-10}$carbocylyl-C$_{0-6}$alkylene optionally substituted by 1-3 of substituent group A, or 3-7 membered heterocyclyl-C$_{0-6}$alkylene optionally substituted by 1-3 of substituent group A, and the heterocyclyl group comprises 1-4 ring heteroatoms independently selected from N, O, and S, and Z is a bond or C$_{1-6}$alkylene;

Substituent group A is halo, CN, OH, CO$_2$H, CHO, NH$_2$, oxo, NO$_2$, C$_{1-6}$alkyl, C$_{1-6}$ haloalkyl, C$_{1-6}$alkoxy, C$_{1-6}$alkylthio, C$_{1-6}$ alkyl-OH, C$_{3-10}$carbocyclyl, 3-7 membered heterocyclyl, C$_{6-10}$ aryl, C$_{3-10}$carbocylyl-C$_{1-6}$ alkoxy, C$_{3-10}$carbocylyl-O—C$_{1-6}$alkylene, C$_{3-10}$ carbocylyl-C$_{1-6}$ alkoxy-C$_{1-6}$alkylene, 3-7 membered heterocyclyl-C$_{1-6}$ alkoxy, 3-7 membered heterocyclyl-O—C$_{1-6}$alkylene, 3-7 membered heterocyclyl-C$_{1-6}$alkoxy-C$_{1-6}$alkylene, C$_{1-6}$haloalkoxy, C$_{1-6}$alkoxy-C$_{1-6}$alkylene, C$_{1-6}$alkoxy-C$_{1-6}$alkoxy, C$_{1-6}$alkyl-C(O)—, C$_{1-6}$alkyl-C(O)O—, NHC$_{1-6}$alkyl, C$_{1-6}$alkyl-C(O)NH—, C$_{1-6}$haloalkyl-C(O)NH, C$_{1-6}$alkyl-NHC(O)—, C$_{1-6}$alkyl-SO$_2$—, C$_{1-6}$alkyl-SO—, and C$_{1-6}$alkylSO$_2$NH—; and each of Q$^1$, Q$^2$, Q$^3$, Q$^4$, Q$^5$, and Q$^6$ is independently H, halo, CN, OH, CO$_2$H, CHO, NH$_2$, NO$_2$, C$_{1-6}$alkyl, C$_{1-6}$haloalkyl, C$_{1-6}$alkoxy, C$_{1-6}$alkylthio, or C$_{1-6}$ alkyl-OH. (Embodiment A)

Also described are embodiments of Embodiment A wherein M is N. (Embodiment B)

Also described are embodiments of Embodiment A wherein M is CH. (Embodiment C)

Also described are embodiments of Embodiments A-C wherein X is CH$_2$. (Embodiment D)

Also described are embodiments of Embodiments A-C wherein X is CH$_2$CH$_2$. (Embodiment E)

Also described are embodiments of Embodiments A-C wherein X is CH$_2$O or OCH$_2$. (Embodiment F)

Also described are embodiments of Embodiments A-F wherein X is CH$_2$. (Embodiment G)

Also described are embodiments of Embodiments A-F wherein X is CH$_2$CH$_2$. (Embodiment H)

Also described are embodiments of Embodiments A-F wherein X is CH$_2$O or OCH$_2$. (Embodiment I)

Also described are embodiments of Embodiments A-I wherein ring A is

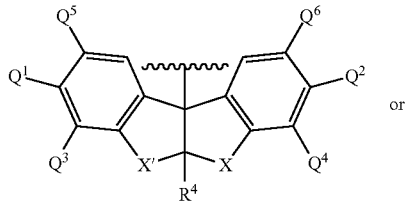 or

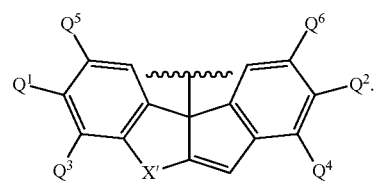

(Embodiment J)

Also described are embodiments of Embodiments A-I wherein ring A is

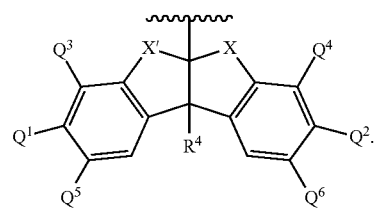

(Embodiment K)

Also described are embodiments of Embodiments A-I wherein ring A is

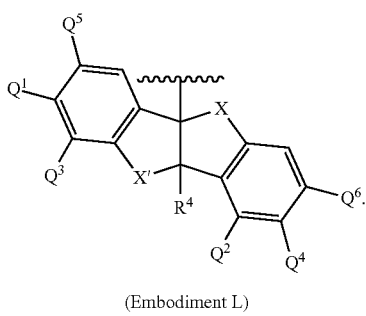

(Embodiment L)

Also described are embodiments of Embodiments A-I wherein ring A is

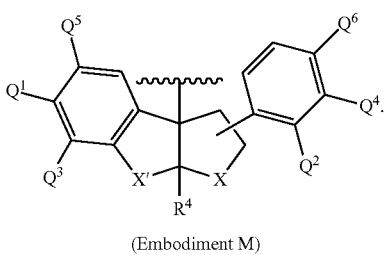

(Embodiment M)

Also described are embodiments of Embodiment A having a structure of Formula (IIA) or (IIB):

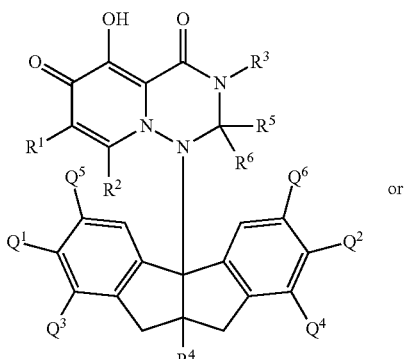

(IIA)

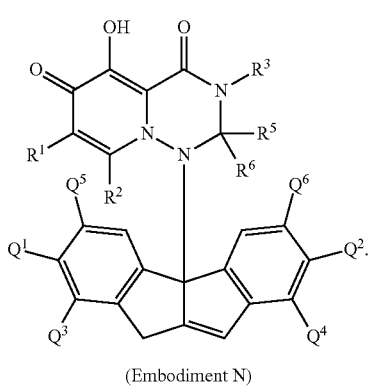

(IIB)

(Embodiment N)

Also described are embodiments of Embodiments A-N wherein at least one of $R^1$ and $R^2$ is H. (Embodiment O)

Also described are embodiments of Embodiments A-O wherein each of $R^1$ and $R^2$ is H. (Embodiment P)

Also described are embodiments of Embodiments A-P wherein $R^4$ is H. (Embodiment Q)

Also described are embodiments of Embodiments A-P wherein $R^4$ is OH or OMe. (Embodiment R)

Also described are embodiments of Embodiments A-R wherein at least one of $R^5$ and $R^6$ is H. (Embodiment S)

Also described are embodiments of Embodiment S wherein each of $R^5$ and $R^6$ is H. (Embodiment T)

Also described are embodiments of Embodiments A-R wherein $R^5$ and $R^6$ together with the atom to which they are attached form a $C_{3-7}$carbocyclyl or 3-7 membered heterocyclyl having 1-3 ring heteroatoms selected N, O, and S, and is optionally substituted with 1-3 of substituent group A. (Embodiment U)

Also described are embodiments of Embodiments A-S wherein $R^3$ and $R^5$ together with the atoms to which they are attached form a 5-7 membered heterocyclyl having 1-4 total ring heteroatoms selected N, O, and S, and can be optionally substituted with 1-3 of substituent group A. (Embodiment V)

Also described are embodiments of Embodiments A-V wherein $R^3$ is $C_{1-6}$alkyl, $C_{3-6}$ carbocyclyl-$C_{1-6}$alkylene, $C_{3-6}$carbocyclyl-O—$C_{1-6}$alkylene, or 3-7 membered heterocyclyl-$C_{1-6}$ alkylene. (Embodiment W)

Also described are embodiments of Embodiment W wherein $R^3$ is ethyl, methyl, or $C_{1-3}$alkylene-cyclopropyl. (Embodiment X)

Also described are embodiments of Embodiment X wherein $R^3$ is $C_6$carbocyclyl-$C_{1-6}$alkylene or $C_6$carbocyclyl-O—$C_{1-6}$alkylene and the $C_6$carbocyclyl is phenyl, halophenyl, or dihalophenyl. (Embodiment Y)

Also described are embodiments of Embodiment Y wherein $R^3$ is 3-7 membered heterocyclyl-$C_{1-6}$alkylene and the heterocyclyl is tetrahydropyranyl. (Embodiment Z)

Also described are embodiments of Embodiments A-U wherein $R^3$ is
—Z—N($R^N$)($R^N$)
—Z—N($R^N$)—SO$_2$—$R^{x2}$,
—Z—C(O)—N($R^N$)—SO$_2$—$R^{x2}$,
—Z—N($R^N$)-C(O)—$R^{x1}$,
—Z—C(O)—N($R^N$)($R^N$),
—Z—S(O)$_{0-2}$—$R^{x2}$,
—Z—N($R^N$)—C(O)O—$R^{x1}$,
—Z—N($R^N$)—C(O)—N($R^N$)($R^N$)
—Z—C(O)—N($R^N$)—C(O)—N($R^N$)($R^N$),
—Z—N(R)—C(O)—C(O)—$R^{x1}$. (Embodiment AA)

Also described are embodiments of Embodiments A-AA wherein at least two of $Q^1$, $Q^2$, $Q^3$, $Q^4$, $Q^5$, and $Q^6$ are H. (Embodiment BB)

Also described are embodiments of Embodiment BB wherein at least four of $Q^1$, $Q^2$, $Q^3$, $Q^4$, $Q^5$, and $Q^6$ are H. (Embodiment CC)

Also described are embodiments of Embodiment CC wherein each of $Q^1$, $Q^2$, $Q^3$, and $Q^4$, $Q^5$, and $Q^6$ is H. (Embodiment DD)

Also described are embodiments of Embodiments A-CC wherein at least two of $Q^1$, $Q^2$, $Q^3$, $Q^4$, $Q^5$, and $Q^6$ are halo. (Embodiment EE)

Also described are embodiments of Embodiments EE wherein at least four of $Q^1$, $Q^2$, $Q^3$, $Q^4$, $Q^5$, and $Q^6$ are halo. (Embodiment FF)

Also described are embodiments of Embodiment EE wherein two of $Q^1$, $Q^2$, $Q^3$, $Q^4$, $Q^5$, and $Q^6$ are halo and the others are H. (Embodiment GG)

Also described are embodiments of Embodiments EE-GG wherein the halo is F. (Embodiment HH)

Also described are embodiments of Embodiment A wherein ring A is

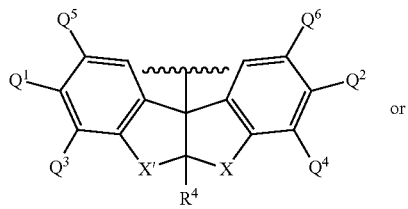

or

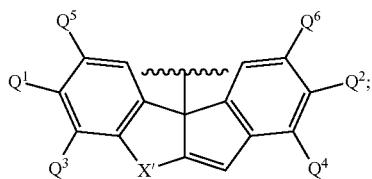

each of $R^1$, $R^2$, $R^4$, $R^5$, and $R^6$ is H;

M is N;

each of X and X' are $CH_2$;

$R^3$ is H, OH, $CO_2H$, CN, CHO, $C_{1-6}$alkyl optionally substituted by 1-3 of substituent group A, $C_{3-10}$carbocyclyl-$C_{0-6}$alkylene optionally substituted by 1-3 of substituent group A, $C_{3-10}$carbocyclyl-O—$C_{1-6}$alkylene optionally substituted by 1-3 of substituent group A, 3-7 membered heterocyclyl-$C_{0-6}$alkylene optionally substituted by 1-3 of substituent group A, 3-7 membered heterocyclyl-C(O)— optionally substituted by 1-3 of substituent group A wherein the heterocyclyl comprises 1-4 ring heteroatoms independently selected from N, O, and S;

substituent group A is halo; and each of $Q^1$, $Q^2$, $Q^3$, $Q^4$, $Q^5$, and $Q^6$ is iH or halo, provided that at least two of $Q^1$, $Q^2$, $Q^3$, $Q^4$, $Q^5$, and $Q^6$ are H. (Embodiment II)

Also described are embodiments of Embodiment A wherein the compound or salt has a structure of

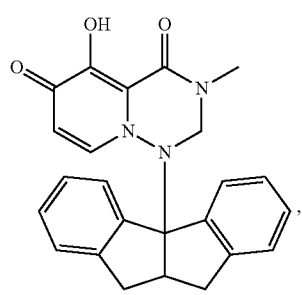

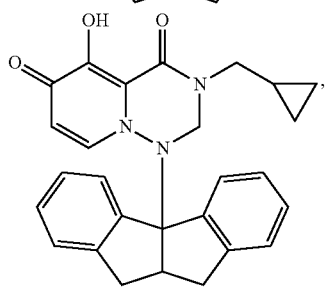

-continued

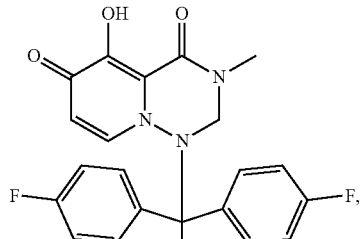

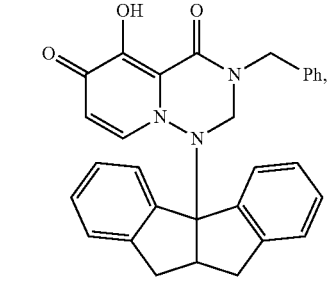

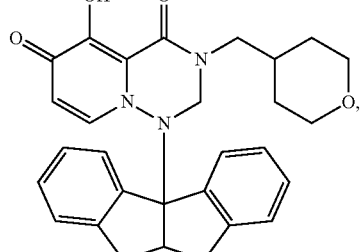

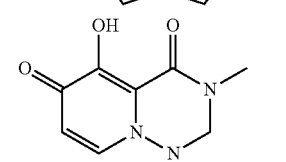

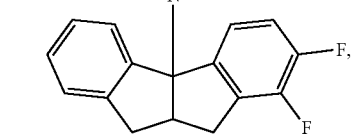

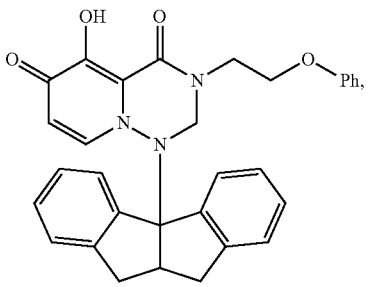

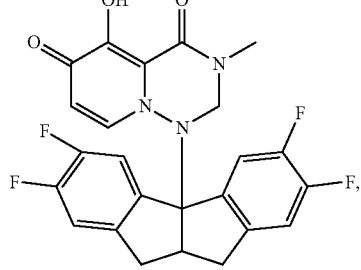

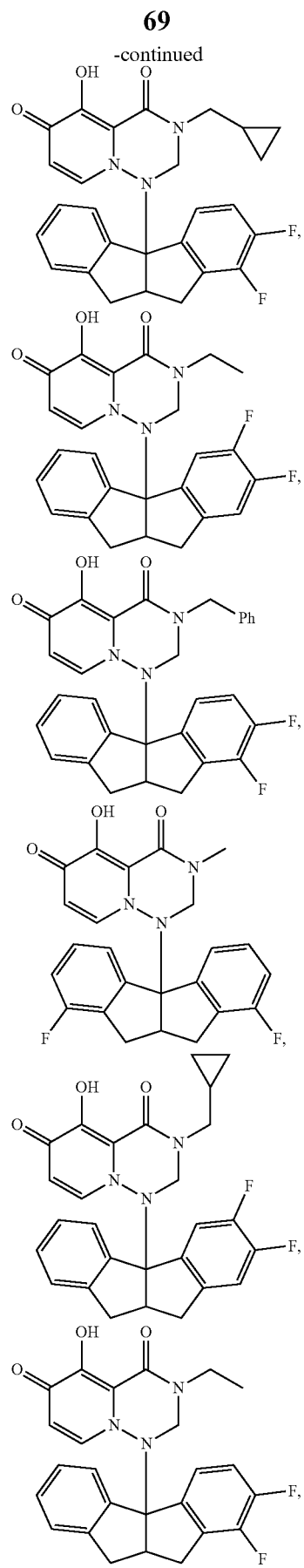
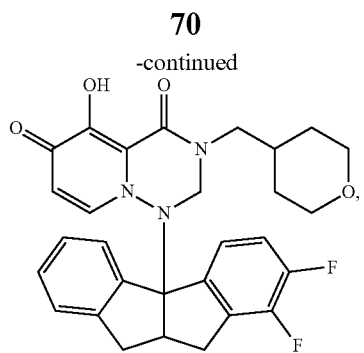
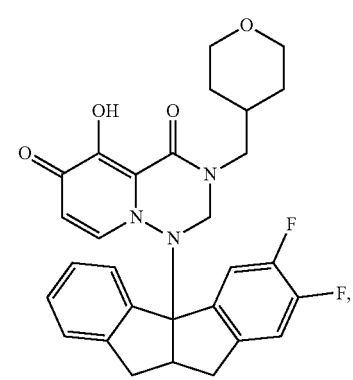
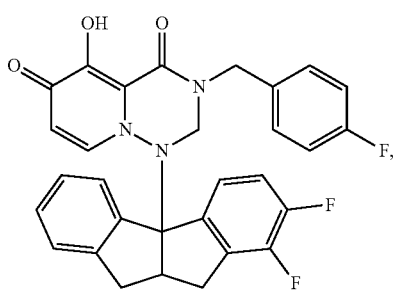
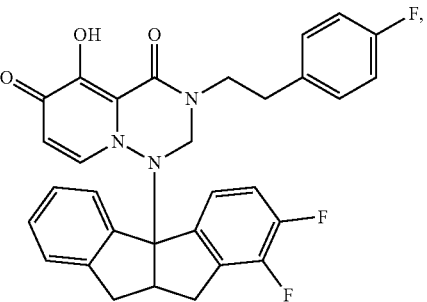
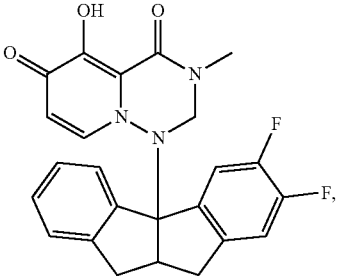

71
-continued
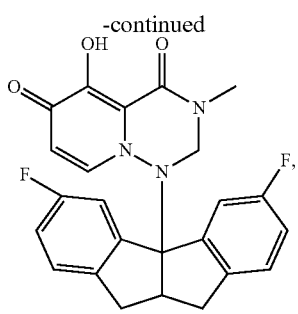
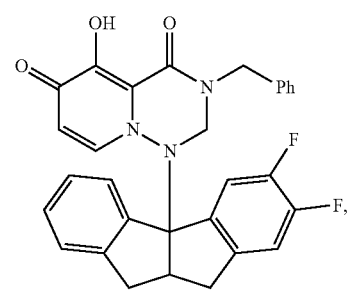
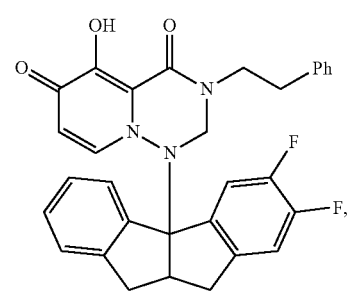
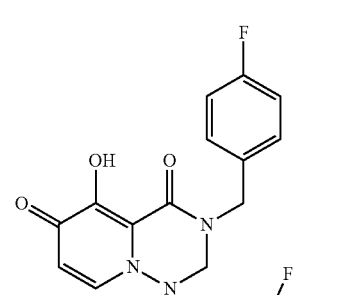
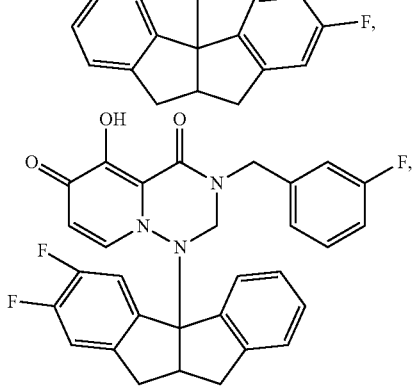
72
-continued
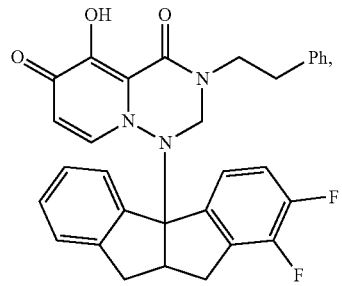
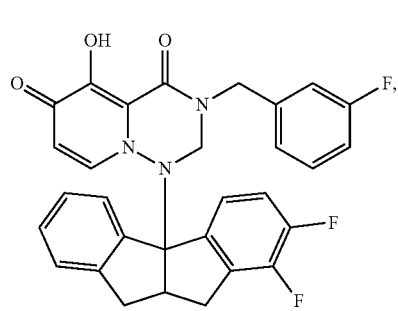
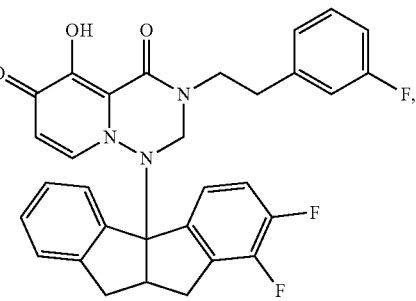
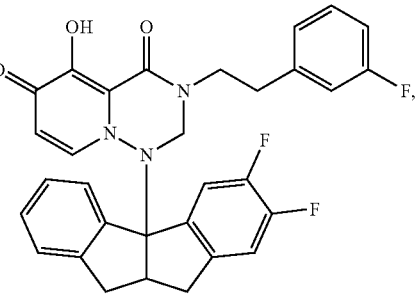
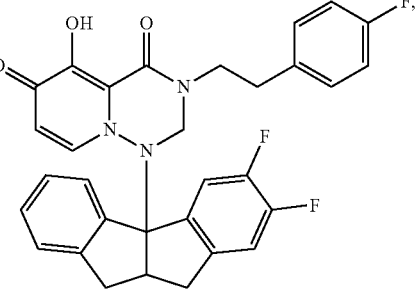

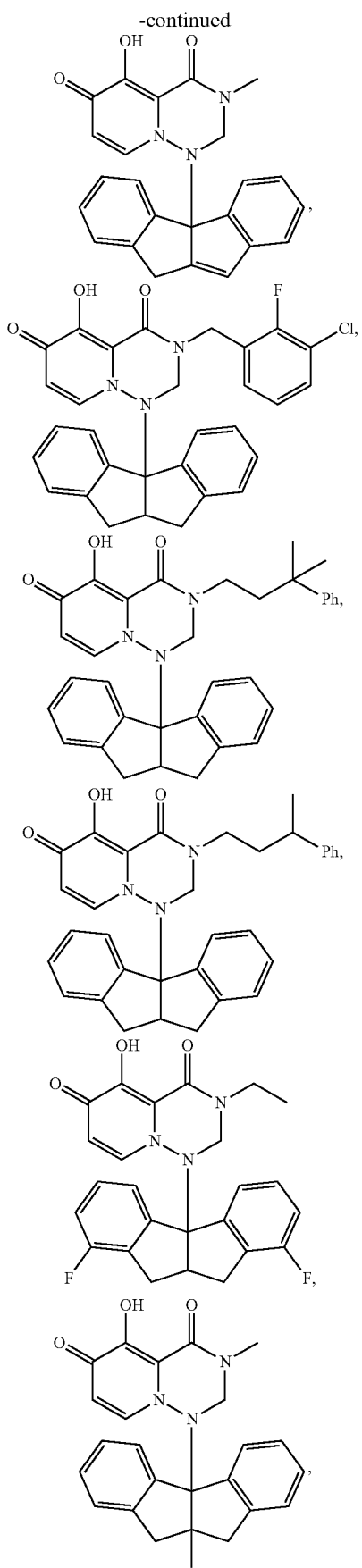
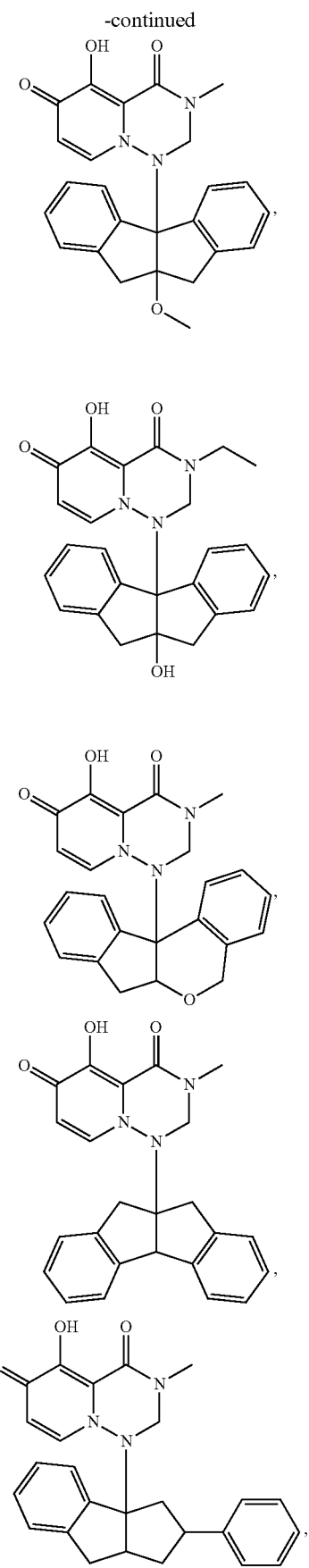

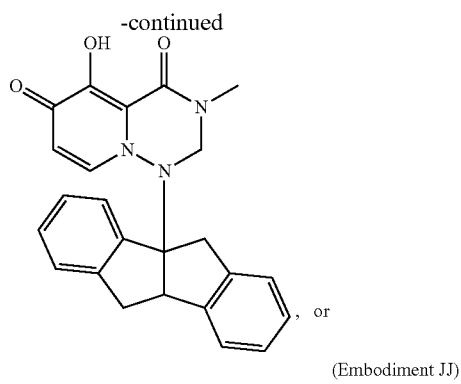

(Embodiment JJ)

(shown above, or structure below)

In some embodiments, the disclosure provides pharmaceutical formulations comprising the compound or salt of any of Embodiments A-JJ and a pharmaceutically acceptable excipient. (Embodiment KK)

In some embodiments, the disclosure provides methods of inhibiting endonuclease activity of influenza polymerase PA in an influenza A or B virus, comprising contacting the virus with the compound or salt of any of Embodiments A-JJ. (Embodiment LL)

In some embodiments, the disclosure provides methods for treating or preventing an Influenza A or Influenza B infection in a host, comprising administering to the host a therapeutic amount of the compound or salt of any of Embodiments A-JJ. (Embodiment MM)

In some embodiments, the disclosure provides methods for reducing endonuclease activity of influenza polymerase PA in an influenza A or B virus in a host, comprising administering to the host a therapeutic amount of the compound or salt of any of Embodiments A-JJ. (Embodiment NN)

In some embodiments, the disclosure provides methods for reducing influenza virus replication in a host, comprising administering to the host a therapeutic amount of the compound or salt of any of Embodiments A-JJ. (Embodiment OO)

Also described are embodiments of Embodiments LL-OO further comprising contacting the influenza virus with or administering to the host a therapeutically effective amount of a second antiviral agent. (Embodiment PP)

Also described are embodiments of Embodiment PP wherein the second antiviral agent is a pyrazinecarboxamide antiviral compound, an influenza neuraminidase inhibitor, an influenza PB1 polymerase domain inhibitor, or an influenza CAP-binding PB2 domain inhibitor. (Embodiment QQ)

Also described are embodiments of Embodiment QQ wherein the second antiviral agent is favipiravir, oseltamivir or 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid. (Embodiment RR)

Also described are embodiments of Embodiments LL-RR further comprising administering to the host an influenza vaccine before, after, or concurrently with the compound. (Embodiment SS)

In some embodiments, the disclosure provides uses of the compound or salt of any of Embodiments A-JJ in the a treatment for an Influenza A or Influenza B virus infection. (Embodiment TT)

In some embodiments, the disclosure provides uses of the compound or salt of any of Embodiments A-JJ in the manufacture of a medicament for the treatment of an Influenza A or Influenza B virus infection. (Embodiment UU)

Definitions and General Terminoloqy

For purposes of this disclosure, the chemical elements are identified in accordance with the Periodic Table of the Elements, CAS version, *Handbook of Chemistry and Physics,* 75th Ed. Additionally, general principles of organic chemistry are described in Organic Chemistry, Thomas Sorrell, University Science Books, Sausalito: 1999, and *March's Advanced Organic Chemistry,* 5th Ed., Ed.: Smith, M. B. and March, J., John Wiley & Sons, New York: 2001, the entire contents of which are hereby incorporated by reference.

As described herein, compounds described herein may optionally be substituted with one or more substituents, such as illustrated generally below, or as exemplified by particular classes, subclasses, and species described herein. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. In some cases, the substituent is selected from group A: halo, CN, OH, $CO_2H$, CHO, $NH_2$, oxo, $NO_2$, $C_{1-6}$alkyl, $C_{1-6}$haloalkyl, $C_{1-6}$alkoxy, $C_{1-6}$alkylthio, $C_{1-6}$ alkyl-OH, $C_{3-10}$carbocyclyl, 3-7 membered heterocyclyl, $C_{3-10}$carbocyclyl-$C_1$-alkoxy, $C_{3-10}$carbocyclyl-O—$C_{1-6}$alkylene, $C_{3-10}$carbocyclyl-$C_{1-6}$alkoxy-$C_{1-6}$alkylene, 3-7 membered heterocyclyl-$C_{1-6}$alkoxy, 3-7 membered heterocyclyl-O—$C_{1-6}$alkylene, 3-7 membered heterocyclyl-$C_1$-alkoxy-$C_{1-6}$alkylene, $C_{1-6}$haloalkoxy, $C_{1-6}$alkoxy-$C_{1-6}$alkylene, $C_{1-6}$alkoxy-$C_{1-6}$alkoxy, $C_{1-6}$alkyl-C(O)—, $C_{1-6}$alkyl-C(O)O—, $NHC_{1-6}$alkyl, $C_{1-6}$alkyl-C(O)NH—, $C_{1-6}$haloalkyl-C(O)NH, $C_{1-6}$alkyl-NHC(O)—, $C_{1-6}$alkyl-$SO_2$—, $C_{1-6}$alkyl-SO—, and $C_{1-6}$alkyl$SO_2$NH—.

Selection of substituents and combinations of substituents contemplated herein are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_1$-$C_{14}$ alkyl, $C_1$-$C_6$ alkyl or $C_1$-$C_4$ alkyl. In some embodiments, the "alkenyl" is $C_2$-$C_6$ alkenyl or $C_2$-$C_4$ alkenyl. In some embodiments, the "alkynyl" is $C_2$-$C_6$ alkynyl or $C_2$-$C_4$ alkynyl. The term "alkylene" refers to an alkyl group that is further substituted. For example, "carbocyclyl-alkylene" indicates an alkyl group that is the point of attachment to the rest of the compound and is also substituted with a carbocyclyl group. When an alkylene group is indicated as "$C_0$" that indicates the alkylene group is not present and the substituent also recited is directly attached to the rest of the compound—e.g., $C_{3-10}$carbocyclyl-$C_{0-6}$alkylene indicates both $C_{3-10}$carbocyclyl directly attached to the rest of the compound or through a $C_{1-6}$alkylene linker.

The term "carbocycle" or "carbocyclyl" refers to a carbon only containing ring system which can be saturated or contains one or more units of unsaturation or is aromatic (i.e., aryl), having three to fourteen ring carbon atoms. In some embodiments, the number of carbon atoms is 3 to 10 (i.e., $C_3$-$C_{10}$ carbocyclyl). In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more carbocyclic or heterocyclic rings, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of carbocycle groups include, but are not limited to, cycloalkyl (i.e., fully saturated carbocycle rings) and cycloalkenyl (i.e., carbocycle rings having one or more degrees of unsaturation but not aromatic) groups. Specific examples include, but are not limited to, cyclohexyl, cyclopropenyl, cyclobutyl, and cyclopropyl.

Aromatic carbocycle rings contemplated include monocyclic aromatic groups, such as phenyl. Unless otherwise indicated, an aryl group can have from 6 to 14 carbon atoms in the ring, such as 6 to 10 carbon atoms in the ring (i.e., $C_6$-$C_{10}$ aryl). Unless otherwise indicated, an aryl group can be unsubstituted or substituted with one or more, and in particular one to four groups, e.g., from substituent group A. Aryl groups can be isolated (e.g., phenyl) or fused to another aryl group (e.g., naphthyl, anthracenyl), a cycloalkyl group (e.g. tetrahydronaphthyl), a heterocycloalkyl group, and/or a heteroaryl group. Exemplary aryl groups include, but are not limited to, phenyl, halophenyl (e.g., chlorophenyl or fluorophenyl), dihalophenyl (e.g., dichlorophenyl or difluorophenyl), methylphenyl, methoxyphenyl, trifluoromethylphenyl, nitrophenyl, 2,4-methoxychlorophenyl, 1-naphthyl, 2-naphthyl, 1-anthracyl, 2-anthracyl, indanyl, phthalimidyl, naphthimidyl, phenanthridinyl, or tetrahydronaphthyl, and the like.

The term "heterocycle" or "heterocyclyl" as used herein refers to a non-aromatic ring system which can be saturated or contain one or more units of unsaturation or an aromatic ring system, the ring system having three to fourteen ring atoms in which one or more (e.g., 1-4) ring atoms is a heteroatom such as N, S, or O. In some embodiments, the ring system can include from 3 to 12 ring atoms (i.e., 3-12 membered heterocyclyl), 3 to 7 ring atoms (i.e., 3-7 membered heterocyclyl), or 5 to 7 ring atoms (i.e., 5-7 membered heterocyclyl). In some embodiments, heterocyclic rings comprise up to three heteroatoms selected from N, S and O within the ring. In other embodiments, heterocyclic rings comprise up to two ring heteroatoms selected from N, S and O. In yet other embodiments, heterocyclic rings comprise up to two ring heteroatoms selected from N and O. The term includes monocyclic, bicyclic or polycyclic fused, spiro or bridged heterocyclic ring systems. The term also includes polycyclic ring systems in which the heterocyclic ring can be fused to one or more carbocyclic or heterocyclic rings or combination thereof, wherein the radical or point of attachment is on the heterocyclic ring. Examples of heterocycles include, but are not limited to, piperidinyl, piperazinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydropyranyl, tetrahydrothiophenyl, morpholino (including, for example, 3-morpholino, 4-morpholino, 2-thiomorpholino, 3-thiomorpholino, 4-thiomorpholino), 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl. Examples of contemplated aromatic heterocyclyl rings include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "heteroatom," unless otherwise stated herein, means one or more of oxygen, sulfur, nitrogen, or phosphorus.

As used herein, a "carbonyl" refers to —C(O)—.

As used herein, an "oxo" refers to =O.

As used herein, the term "alkoxy", or "alkylthio", as used herein, refers to an alkyl group, as previously defined, attached to the molecule through an oxygen ("alkoxy" e.g., —O— alkyl) or sulfur ("alkylthio" e.g., —S-alkyl) atom.

As used herein, the terms "halogen" and "halo" mean F, Cl, Br, or I.

The terms "haloalkyl", and "haloalkoxy" mean alkyl, alkenyl, or alkoxy, as the case may be, substituted with one or more halogen atoms. This term includes perfluorinated alkyl groups, such as —$CF_3$ and —$CF_2CF_3$.

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "*Protective Groups in Organic Synthesis*", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "*Protective Groups in Organic Synthesis*", Third Edition, John Wiley & Sons, New York: 1999, the entire contents of which are hereby incorporated by reference.

As used herein, the term "leaving group" refers to a group that is subject to being displaced by nucleophilic attack by a nucleophile.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this disclosure, unless only one of the isomers is drawn specifically.

Therefore, single stereochemical isomers as well as enantiomeric, diastereomeric, cis/trans, conformational, and rotational mixtures of the present compounds are within the scope of the disclosure.

Unless otherwise indicated, all tautomeric forms of the compounds described herein are within the scope of the disclosure.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this disclosure. Such compounds are useful, for example, as analytical tools or probes in biological assays. Such compounds, especially deuterium analogs, can also be therapeutically useful.

The terms "a bond" and "absent" are used interchangeably to indicate that a group is absent.

The compounds described herein are defined herein by their chemical structures and/or chemical names. Where a compound is referred to by both a chemical structure and a chemical name, and the chemical structure and chemical name conflict, the chemical structure is determinative of the compound's identity.

Pharmaceutically Acceptable Salts

The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds described herein or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxylic acid group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this disclosure includes mixtures/combinations of different pharmaceutically acceptable salts and also mixtures/combinations of compounds in free form and pharmaceutically acceptable salts.

Pharmaceutical Compositions

The compounds described herein can be formulated into pharmaceutical compositions that further comprise a pharmaceutically acceptable carrier, diluent, adjuvant or vehicle. In some embodiments, the present disclosure relates to a pharmaceutical composition comprising a compound described herein, and a pharmaceutically acceptable carrier, diluent, adjuvant or vehicle. In some embodiments, the present disclosure includes a pharmaceutical composition comprising a safe and effective amount of a compound described herein or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient. The term "prophylactically effective amount" refers to an amount effective in preventing and/or substantially lessening the chances or the size of influenza virus infection outbreak.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this disclosure. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropyleneblock polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and anti-oxidants can also be present in the composition, according to the judgment of the formulator.

Formulations for Pulmonary Delivery

In some embodiments, the pharmaceutical compositions described herein are adapted to be administered to the lower respiratory tract (e.g., the lungs) directly through the airways by inhalation. Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminum foil for use in an inhaler or insufflators. Each capsule or cartridge may generally contain e.g., from about 10 mg to about 100 g of each active compound. Alternatively, the composition described herein may be presented without excipients.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360, and 5,590,645 (all illustrating the "Diskus®" device), or GB2178965, GB2129691, GB2169265, U.S. Pat. Nos. 4,778,054, 4,811,731 and 5,035,237 (which illustrate the "Diskhaler®" device), or EP 69715 ("Turbuhaler®" device), or GB 2064336 and U.S. Pat. No. 4,353,656 ("Rotahaler®" device).

Spray compositions for topical delivery to the lung by inhalation may be formulated as aqueous solutions or suspensions or as aerosols delivered from pressurized packs, such as a metered dose inhaler (MDI), with the use of a suitable liquefied propellant, including hydrofluoroalkanes such as dichlorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof. Aerosol compositions suitable for inhalation can be presented either as suspensions or as solutions.

Medicaments for administration by inhalation typically have a controlled particle size. The optimum particle size for inhalation into the bronchial system is usually about 1 to about 10 μm, and in some embodiments, from about 2 to about 5 μm. Particles having a size above about 20 μm are generally too large when inhaled to reach the small airways. To achieve these particle sizes the particles of the active ingredient may be subjected to a size reducing process such as micronization. The desired size fraction may be separated out by air classification or sieving. Preferably, the particles will be crystalline.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulization may be formulated with an aqueous vehicle with the addition of agents such as acid or alkali, buffer salts, isotonic adjusting agents or antimicrobial agents. They may be sterilized by filtration or heating in an autoclave, or presented as a non-sterile product. Nebulizers supply the aerosol as a mist created from an aqueous formulation.

In some embodiments, the pharmaceutical compositions described herein can be formulated with supplementary active ingredients.

In some embodiments, the pharmaceutical composition described herein is administered from a dry powder inhaler.

In other embodiments, the pharmaceutical composition described herein is administered by an aerosol dispensing device, optionally in conjunction with an inhalation chamber such as the "Volumatic"® inhalation chamber.

The carrier can be a solvent or dispersion medium containing, for example, water, ethanol, polyol (for example, glycerol, propylene glycol and liquid polyethylene glycol, and the like), suitable mixtures thereof, and/or vegetable oils. The proper fluidity can be maintained, for example, by the use of a coating such as, for example, lecithin, by the maintenance of the required particle size in the case of dispersion and by the use of surfactants. Preventing the action of microorganisms in the compositions described herein is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, a pharmaceutical composition described herein can be within a matrix which controls the release of the composition. In some embodiments, the matrix can comprise lipid, polyvinyl alcohol, polyvinyl acetate, polycaprolactone, poly(glycolic)acid, poly(lactic) acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly (ortho esters), sucrose acetate isobutyrate (SAIB), and combinations thereof and other polymers such as those disclosed, for example, in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. In these embodiments, the matrix sustainedly releases the drug.

Pharmaceutically acceptable carriers and/or diluents may also include any solvents, dispersion media, coatings, antibacterials and/or antifungals, isotonic and absorption delaying agents and the like. The use of such media and agents for pharmaceutically active substances is well known in the art. Except insofar as any conventional medium or agent is incompatible with the active ingredient, use thereof in the pharmaceutical compositions is contemplated.

The pharmaceutical compositions described herein can be formulated for administration in accordance with conventional techniques. See, e.g., Remington, The Science and Practice of Pharmacy (20th Ed. 2000). For example, the intranasal pharmaceutical compositions of the present disclosure can be formulated as an aerosol (this term includes both liquid and dry powder aerosols). Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles (e.g., lyophilized, freeze dried, etc.) can likewise be produced with any solid particulate medicament aerosol generator, by techniques known in the pharmaceutical art. As another example, the pharmaceutical compositions of the present disclosure can be formulated as an on-demand dissolvable form, which provides a lyophilized portion of the pharmaceutical composition and a dissolving solution portion of the pharmaceutical composition.

In some embodiments of the present disclosure, the pharmaceutical composition is in the form of an aqueous suspension, which can be prepared from solutions or suspensions. With respect to solutions or suspensions, dosage forms can be comprised of micelles of lipophilic substances, liposomes (phospholipid vesicles/membranes) and/or a fatty acid (e.g., palmitic acid). In particular embodiments, the pharmaceutical composition is a solution or suspension that is capable of dissolving in the fluid secreted by mucous membranes of the epithelium of the tissue to which it is administered, applied and/or delivered, which can advantageously enhance absorption.

The pharmaceutical composition can be an aqueous solution, a nonaqueous solution or a combination of an aqueous and nonaqueous solution.

Suitable aqueous solutions include, but are not limited to, aqueous gels, aqueous suspensions, aqueous microsphere suspensions, aqueous microsphere dispersions, aqueous liposomal dispersions, aqueous micelles of liposomes, aqueous microemulsions, and any combination of the foregoing, or any other aqueous solution that can dissolve in the fluid secreted by the mucosal membranes of the nasal cavity. Exemplary nonaqueous solutions include, but are not limited to, nonaqueous gels, nonaqueous suspensions, nonaqueous microsphere suspensions, nonaqueous microsphere dispersions, nonaqueous liposomal dispersions, nonaqueous emulsions, nonaqueous microemulsions, and any combination of the foregoing, or any other nonaqueous solution that can dissolve or mix in the fluid secreted by mucosal membranes.

Examples of powder formulations include, without limitation, simple powder mixtures, micronized powders, freeze dried powder, lyophilized powder, powder microspheres, coated powder microspheres, liposomal dispersions, and any combination of the foregoing. Powder microspheres can be formed from various polysaccharides and celluloses, which include without limitation starch, methylcellulose, xanthan gum, carboxymethylcellulose, hydroxypropyl cellulose, carbomer, alginate polyvinyl alcohol, acacia, chitosans, and any combination thereof.

In particular embodiments, the composition is one that is at least partially, or even substantially (e.g., at least 80%, 90%, 95% or more) soluble in the fluids that are secreted by mucosa so as to facilitate absorption. Alternatively or additionally, the composition can be formulated with a carrier and/or other substances that foster dissolution of the agent within secretions, including without limitation fatty acids (e.g., palmitic acid), gangliosides (e.g., GM-1), phospholipids (e.g., phosphatidylserine), and emulsifiers (e.g., polysorbate 80).

Those skilled in the art will appreciate that for intranasal administration or delivery, because the volume of the pharmaceutical composition administered is generally small, nasal secretions may alter the pH of the administered dose since the range of pH in the nasal cavity can be as wide as 5 to 8. Such alterations can affect the concentration of un-ionized drug available for absorption. Accordingly, in representative embodiments, the pharmaceutical composition further comprises a buffer to maintain or regulate pH in situ. Typical buffers include, but are not limited to, ascorbate, acetate, citrate, prolamine, carbonate, and phosphate buffers.

In embodiments of the disclosure, the pH of the pharmaceutical composition is selected so that the internal environment of the mucosal tissue after administration is on the acidic to neutral side, which (1) can provide the active compound in an un-ionized form for absorption, (2) prevents growth of pathogenic bacteria, which is more likely to occur in an alkaline environment, and (3) reduces the likelihood of irritation of the mucosa.

For liquid and powder sprays or aerosols, the pharmaceutical composition can be formulated to have any suitable and desired particle or droplet size. In illustrative embodiments, the majority and/or the mean size of the particles or droplets range from equal to or greater than about 1, 2.5, 5, 10, 15 or 20 microns and/or equal to or less than about 25, 30, 40, 45, 50, 60, 75, 100, 125, 150, 175, 200, 225, 250, 275, 300, 325, 350, 375, 400, or 425 microns (including all combinations of the foregoing). Representative examples of suitable ranges for the majority and/or mean particle or droplet size include, without limitation, from about 5 to 100 microns, from about 10 to 60 microns, from about 175 to 325 microns, and from about 220 to 300 microns which facilitate the deposition of a safe and effective amount of the active compound, for example, in the nasal cavity (e.g., in the upper third of the nasal cavity, the superior meatus, the olfactory region and/or the sinus region to target the olfactory neural pathway). In general, particles or droplets smaller than about 5 microns will be deposited in the trachea or even the lung, whereas particles or droplets that are about 50 microns or larger generally do not reach the nasal cavity and are deposited in the anterior nose.

International patent publication WO 2005/023335 (Kurve Technology, Inc.) describes particles and droplets having a diameter size suitable for the practice of representative embodiments of the present disclosure. In particular embodiments, the particles or droplets have a mean diameter of about 5 to 30 microns, about 10 to 20 microns, about 10 to 17 microns, about 10 to 15 microns, about 12 to 17 microns, about 10 to 15 microns or about 10 to 12 microns. The particles can "substantially" have a mean diameter or size as described herein, i.e., at least about 50%, 60%, 70%, 80%, 90% or 95 or more of the particles are of the indicated diameter or size range.

The pharmaceutical composition described herein can be delivered as a nebulized or atomized liquid having a droplet size as described above.

According to particular embodiments of this disclosure that comprise methods of intranasal delivery, it can be desirable to prolong the residence time of the pharmaceutical composition in the nasal cavity (e.g., in the upper third of the nasal cavity, the superior meatus, the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl), which are agents that enhance residence time in the nasal cavity. As a further approach, increasing the viscosity of the formulation can also provide a means of prolonging contact of the agent with the nasal epithelium. The pharmaceutical composition can be formulated as a nasal emulsion, ointment or gel, which offers advantages for local application because of their viscosity.

Moist and highly vascularized membranes can facilitate rapid absorption; consequently, the pharmaceutical composition can optionally comprise a humectant, particularly in the case of a gel-based composition so as to assure adequate intranasal moisture content. Examples of suitable humectants include but are not limited to glycerin or glycerol, mineral oil, vegetable oil, membrane conditioners, soothing agents, and/or sugar alcohols (e.g., xylitol, sorbitol; and/or mannitol). The concentration of the humectant in the pharmaceutical composition will vary depending upon the agent selected and the formulation.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g., EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol and benzalkonium chloride, and combinations of the foregoing. The concentration of the preservative will vary depending upon the preservative used, the compound being formulated, the formulation, and the like. In representative embodiments, the preservative is present in an amount of about 2% by weight or less.

The pharmaceutical compositions described herein can optionally contain an odorant, e.g., as described in EP 0 504 263 B1, to provide a sensation of odor, to aid in inhalation of the composition so as to promote delivery to the olfactory region and/or to trigger transport by the olfactory neurons.

As another option, the composition can comprise a flavoring agent, e.g., to enhance the taste and/or acceptability of the composition to the subject.

Porous Particles for Pulmonary Administration

In some embodiments, the particles are porous, so that they have an appropriate density to avoid deposition in the back of the throat when administered via an inhaler. The combination of relatively large particle size and relatively low density avoids phagocytosis in the lungs, provides appropriately targeted delivery, avoids systemic delivery of the components, and provides a high concentration of the components in the lung.

Representative methods for preparing such particles, and for delivering such particles, are described, for example, in U.S. Pat. Nos. 7,384,649, 7,182,961, 7,146,978, 7,048,908, 6,956,021, 6,766,799, and 6,732,732.

Additional patents disclosing such particles include U.S. Pat. Nos. 7,279,182, 7,252,840, 7,032,593, 7,008,644, 6,848,197, and 6,749,835.

U.S. Pat. No. 7,678,364, discloses methods for delivering particles to the pulmonary system comprising: administering to the respiratory tract of a patient in need of treatment, prophylaxis or diagnosis a safe and effective amount of a dry powder comprising: a) a multivalent metal cation which is complexed with a therapeutic, prophylactic or diagnostic agent; b) a pharmaceutically acceptable carrier; and c) a multivalent metal cation-containing component wherein the dry powder is spray-dried and has a total amount of multivalent metal cation which is about 10% w/w or more of the total weight of the agent, a tap density of about 0.4 g/cm$^3$ or less, a median geometric diameter of from about 5 micrometers to about 30 micrometers and an aerodynamic diameter of from about 1 to about 5 microns.

The amount of the compounds described herein, or salts thereof, present in the particles can range from about 0.1 weight % to about 95 weight %, though in some cases, can even be as high as 100%. For example, from about 1 to about 50%, such as from about 5 to about 30%. Particles in which the drug is distributed throughout a particle can be preferred.

In some embodiments, the particles include a surfactant other than the phospholipids described above. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to particles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles described herein include but are not limited to hexadecanol; fatty alcohols such as polyethylene glycol (PEG); polyoxyethylene-9-lauryl ether; a surface-active fatty acid, such as palmitic acid or oleic acid; glycocholate; surfactin; a poloxamer; a sorbitan fatty acid ester such as sorbitan trioleate (Span® 85); Tween® 80 and tyloxapol.

The surfactant can be present in the particles in an amount ranging from about 0 to about 5 weight %. Preferably, it can be present in the particles in an amount ranging from about 0.1 to about 1.0 weight %.

Particles that have a tap density less than about 0.4 g/cm$^3$, median diameters of at least about 5 μm, and an aerodynamic diameter of from about 1 μm to about 5 μm, or from about 1 μm to about 3 μm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

Liposomal Delivery

The compositions described herein are advantageously delivered to the lungs, so as to provide the compounds at the site of an actual or potential influenza infection. This can be accomplished by pulmonary delivery via metered-dose inhalers or other pulmonary delivery devices, and also by lodging particles in the capillary beds surrounding the alveoli in the lungs.

Nanocarriers, such as liposomes, including small unilamellar vesicles, show several advantages over other conventional approaches for delivering drugs to the lungs, including prolonged drug release and cell-specific targeted drug delivery. Nano-sized drug carriers can also be advantageous for delivering poorly water soluble drugs, and certain of the compounds described herein are poorly water-soluble. Additional advantages include their ability to provide controlled release, protection from metabolism and degradation, decreased drug toxicity and targeting capabilities.

The liposomes (preferably unilamellar vesicles) have a size less than 200 nm as measured by dynamic light scattering, and preferably characterized by being comprised of chemically pure synthetic phospholipids, most preferably having side chains of a length of at least 16 carbons, and containing one or more of the compounds described herein, or a pharmaceutically acceptable salt thereof, sufficient to preferentially deliver (i.e., target) a quantity of the compounds thereof to the capillary beds surrounding the alveoli. Vesicle diameter can be measured, for example, by dynamic light scattering using a helium-neon 100 mW NEC gas laser and a Malvern K7027 correlator, ideally with at least two or three measurements made for each for each size determination.

The expression "chemically pure phospholipids" is meant to define phospholipids which are essentially free of deleterious detergent moieties and impurities which cause aggregation of small unilamellar vesicles (SUVs) formed therefrom, and which are more than 97% pure. Preferably, the liposomes have a diameter predominantly of from about 50 to about 160 nm, are essentially neutral in charge, and incorporate phospholipids having a side chain length of from 16 to 18 carbon atoms. More preferably, the liposomes are prepared from distearoyl phosphatidylcholine (DSPC) and include cholesterol (most preferably in an amount of from 10 to 50% of total lipid) as a vesicle stabilizer.

It can also be advantageous that the liposomes have a melting point above body temperature (i.e., above 37° C.). For this reason, it can be advantageous to use pure phospholipids, preferably ones that are saturated, and have a carbon chain length of at least 16 carbons, preferably between 16 and 18 carbons. Distearoylphosphatidyl choline (DSPC) is a preferred phospholipid. Cholesterol helps to stabilize the liposomes, and is preferably added in a sufficient amount to provide liposome stability. Most preferably, the liposomes further comprise a pegylated phospholipid, such as DSPEPEG. The method involves introducing into a patient's bloodstream an amount of liposomes, of a size of less than 200 nm (preferably unilamellar vesicles) and preferably characterized by being comprised of chemically pure synthetic phospholipids, most preferably having side chains of a length of at least 16 carbons, and containing the compounds described herein, or a pharmaceutically acceptable salt or prodrug thereof, sufficient to preferentially deliver (i.e., target) a quantity of the compounds to the capillary beds in the lungs, surrounding the alveoli.

The compounds described herein can be combined with other anti-influenza agents, as also described herein. Such additional agents can also be present in the liposomes, can be present in different liposomes, or can be co-administered via a different route.

The liposomes include one or more of the compounds described herein, or a pharmaceutically acceptable salt thereof, and can optionally include other anti-influenza agents. The liposomes can be prepared by dissolving the phospholipid and cholesterol in an appropriate organic solvent, such as chloroform, and evaporating the solvent to form a lipid film. If an ionophore is employed to load the compounds described herein into the liposomes, the ionophore may be added to the lipid solution before evaporation. The dried lipid film is then rehydrated in an appropriate aqueous phase, such as phosphate-buffered saline or other physiologically appropriate solution. Water-soluble drugs or therapeutic agents may be contained in the hydrating solution, although if remote loading is desired a loading agent such as a chelating agent described above may be added to the hydrating solution to be encapsulated within the inner aqueous space of the liposome.

Upon the addition of the hydrating solution, liposomes of varying size spontaneously form and encapsulate a portion of the aqueous phase. Thereafter, the liposomes and suspending aqueous solution are subjected to a shear force such as extrusion, sonication, or processing through a homogenizer according to the method described in U.S. Pat. No. 4,753,788; to produce vesicles within the specified size.

The liposomes can then be processed to remove undesirable compounds from the suspending solution, for example, un-encapsulated drug, which may be accomplished through processes such as gel chromatography or ultrafiltration.

The use of liposomes in dry powder aerosols for targeted lung delivery is described, for example, in Willis et al., Lung, June 2012, 190(3):251-262. One advantage is that the phospholipids used to prepare the liposomes are similar to endogenous lung surfactant.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, to the pulmonary system, such as by using an inhaler, such as a metered dose inhaler (MDI), or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as polysorbates, sorbitan esters, and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds described herein include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzalkonium chloride. Alternatively, for ophthalmic uses, the pharmaceutical compositions may be formulated in an ointment such as petrolatum.

The compounds for use in the methods described herein can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

The disclosure will be more fully understood by reference to the examples described herein which detail exemplary embodiments. These examples should not, however, be construed as limiting the scope of the disclosure. All citations throughout the disclosure are hereby expressly incorporated by reference.

EXAMPLES

Example 1: 1-(9a, 10-dihydroindeno[1,2-a]inden-4b(9H)-yl)-5-hydroxy-3-methyl-2,3-dihydro-1H-pyrido[2,1-f][1,2,4]triazine-4,6-dione (A1)

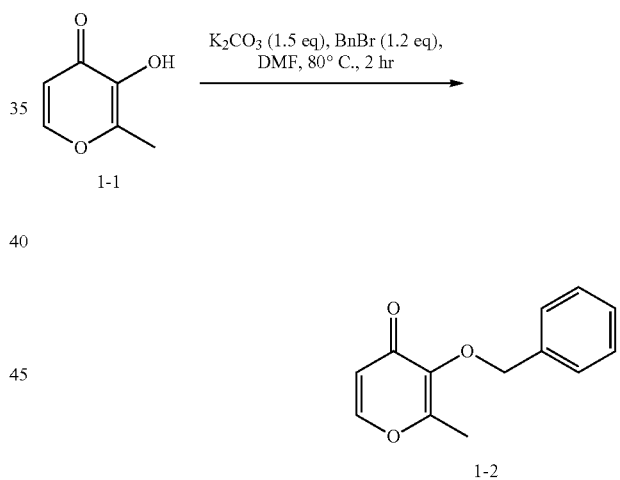

To a stirred solution of 3-hydroxy-2-methyl-4H-pyran-4-one 1-1 (100 g, 793 mmol) in N,N-dimethylformamide (DMF; 1 L) were added potassium carbonate (219 g, 1.59 mol) and benzyl bromide (188 mL, 1.59 mol) at room temperature (RT). The reaction mixture was stirred at 80° C. for 12 hours (hr). After consumption of starting material (as determined by TLC), the reaction mixture was quenched with ice-cold water (3 L), extracted with ethyl acetate (EtOAc) (5×1 L), dried over sodium sulfate (Na$_2$SO$_4$), and concentrated under reduced pressure. The residue was dissolved in diethyl ether (3 L), washed with 1 N HCl (5×1 L), ice-cold water (1 L), and saturated NaHCO$_3$ (2×1 L) solution, dried over Na$_2$SO$_4$ and concentrated under reduced pressure to afford 3-(benzyloxy)-2-methyl-4H-pyran-4-one 1-2. TLC: 40% EtOAc/petroleum ether; Rf: 0.4. LCMS (ESI): m/z 217.06 (M+H)$^+$.

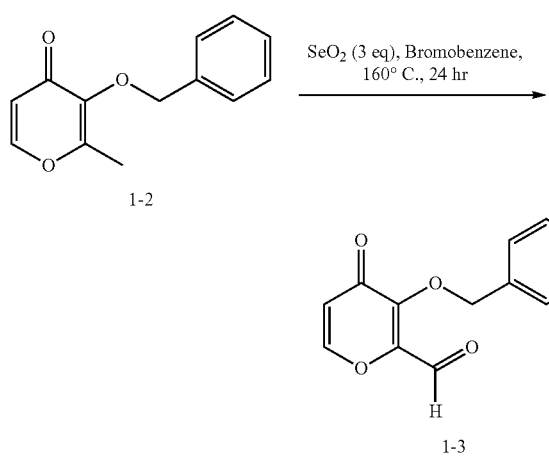

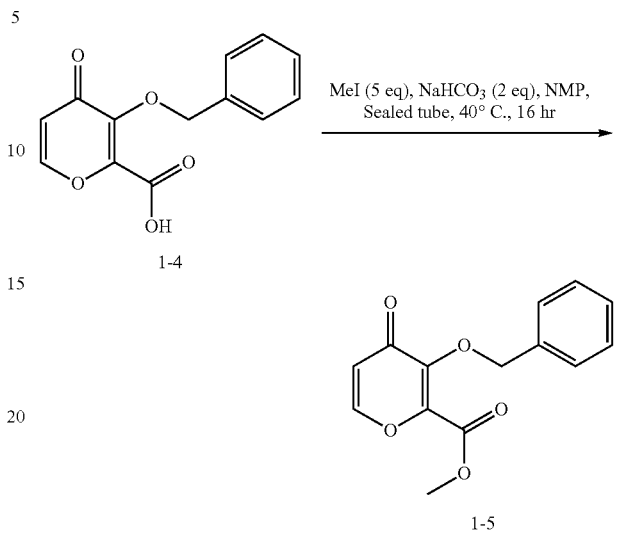

To a stirred solution of 3-(benzyloxy)-2-methyl-4H-pyran-4-one 1-2 (100 g, 463 mmol) in bromobenzene (1500 mL), was added selenium dioxide (154 g, 1.39 mol) at RT. The reaction mixture was stirred at 160° C. for 24 hr, progress of the reaction was monitored by TLC (~50% conversion), the reaction mixture was cooled to RT, excess of SeO₂ solid was filtered, and the solid quenched with ice-cold water and saturated NaOH solution. The filtrate was concentrated under reduced pressure and the crude compound was purified by silica gel (100-200 mesh) column chromatography and compound eluted with 40% of EtOAc/pet ether to afford 3-(benzyloxy)-4-oxo-4H-pyran-2-carbaldehyde 1-3. TLC: 40% EtOAc/pet ether; Rf=0.5.

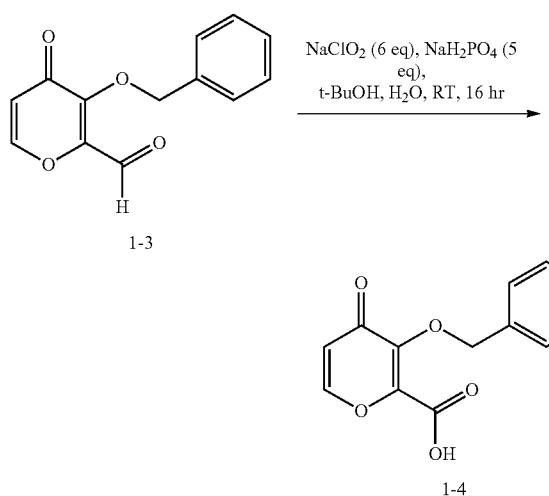

To a stirred solution of 3-(benzyloxy)-4-oxo-4H-pyran-2-carbaldehyde 1-3 (60 g, 261 mmol) in tert-butanol (1000 mL) and water (500 mL), were added sodium chlorite (140 g, 1565 mmol) and sodium dihydrogen phosphate (156 g, 1304 mmol) at 0° C. then stirred at RT for 16 Hr. After consumption of starting material (monitored by TLC), ~50% of reaction volume was removed by concentration, then water (1 L) was added, and the mixture was extracted with diethyl ether (2×500 mL), and the aqueous layer was acidified with citric acid and extracted with 10% MeOH (MeOH) in dichloromethane (DCM) (3×2 L), dried over Na₂SO₄ and concentrated under reduced pressure to afford 3-(benzyloxy)-4-oxo-4H-pyran-2-carboxylic acid 1-4 (25 g, 0.10 mol, 39% yield) as an off-white solid. TLC: 10% MeOH in DCM; Rf=0.1. LCMS: (ESI): m/z 246.99 (M+H)⁺.

To a stirred solution of 3-(benzyloxy)-4-oxo-4H-pyran-2-carboxylic acid 1-4 (10 g, 41 mmol) in N-methyl-2-pyrrolidone (100 mL), were added sodium bicarbonate (6.82 g, 81.30 mmol) and methyl iodide (MeI) (12.65 mL, 203 mmol) at RT. The reaction mixture was stirred at 50° C. for 16 hr. After consumption of starting material ad determined by TLC, the reaction mixture was cooled to RT and the reaction mixture was quenched with ice-cold water (300 mL), extracted with EtOAc (2×300 mL), dried over Na₂SO₄ and concentrated under reduced pressure. The crude compound was purified by silica gel (100-200 mesh) column chromatography by eluting with 40% of EtOAc/pet ether to afford methyl-3-(benzyloxy)-4-oxo-4H-pyran-2-carboxylate 1-5. TLC: 40% EtOAc in pet ether; Rf=0.4. LCMS: (ESI): m/z 261.20 (M+H)⁺.

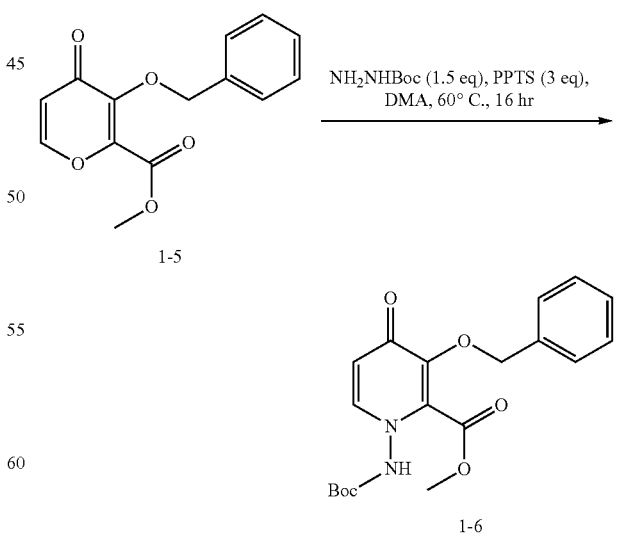

To a stirred solution of methyl-3-(benzyloxy)-4-oxo-4H-pyran-2-carboxylate 1-5 (15 g, 58 mmol) in dimethylacetamide (150 mL), were added pyridinium p-toluenesulfonate (43.44 g, 173 mmol) and tert-butyl carbazate (9.89 g, 75.0 mmol) at RT. The reaction mixture was stirred at 60° C. for 16 hr. The reaction mixture was cooled to RT and it was poured into crushed ice and the resultant solid was filtered to afford methyl-3-(benzyloxy)-1-(tert-butoxycarbonylamino)-4-oxo-1,4-dihydropyridine-2-carboxylate 1-6. TLC: 5% MeOH in DCM; Rf=0.2. LCMS: (ESI): m/z 375.32 (M+H)$^+$.

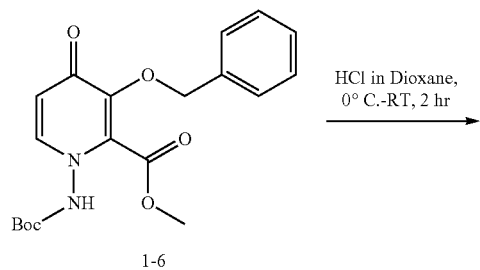

To a stirred solution of methyl-3-(benzyloxy)-1-(tert-butoxycarbonylamino)-4-oxo-1,4-dihydropyridine-2-carboxylate 1-6 (15 g, 40 mmol) in 1,4-dioxane (50 mL), was added 4N HCl in 1,4-dioxane (20 mL) at RT. The reaction mixture was stirred at RT for 4 hr. After completion of reaction (monitored by TLC), 1,4-dioxane solvent was distilled off, basified with sodium bicarbonate solution, extracted with EtOAc (2×200 mL). Organic layer was washed with brine solution (100 mL) and concentrated under reduced pressure to afford methyl-1-amino-3-(benzyloxy)-4-oxo-1,4-dihydropyridine-2-carboxylate INT-1. TLC: 10% MeOH in DCM; Rf=0.2. LCMS: (ESI): m/z 274.98 (M+H)$^+$.

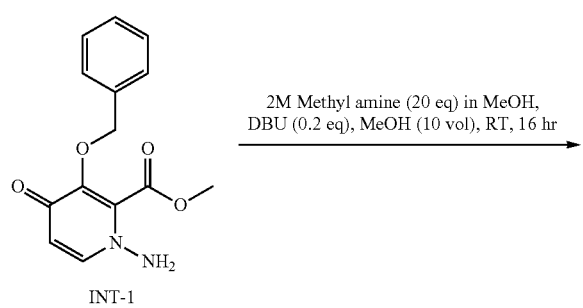

To a stirred solution of methyl-1-amino-3-(benzyloxy)-4-oxo-1,4-dihydropyridine-2-carboxylate INT-1 (3 g, 0.01 mmol) in MeOH (30 mL) in a sealed tube was added DBU (0.38 mg, 0.02 mmol) and methyl amine (2 M MeOH) (30 mL) then stirred at RT for 16 hr. Reaction mixture was completely distilled off under reduced pressure. Crude compound was purified over reverse phase chromatography by eluting with 38% acetonitrile (ACN) in 0.1% formic acid in water to afford 1-amino-3-(benzyloxy)-N-methyl-4-oxo-1,4-dihydropyridine-2-carboxamide 1-7. TLC: 10% MeOH in DCM; Rf: 0.4. LCMS (ESI): m/z 274.07 (M+H)$^+$.

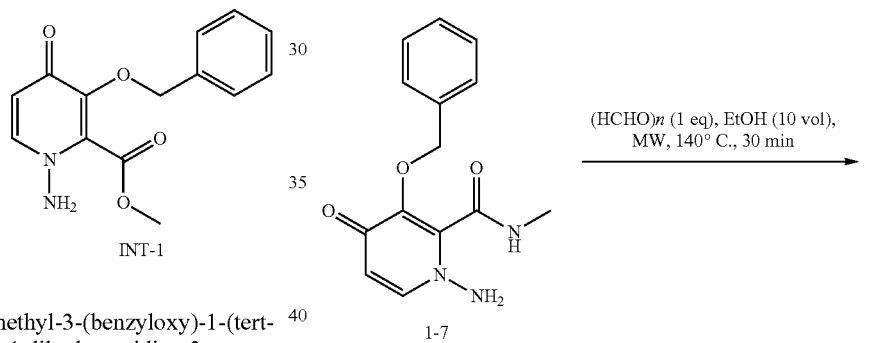

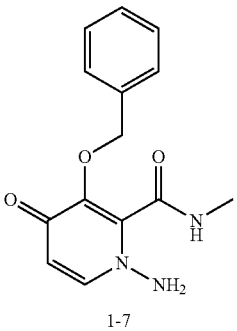

In a microwave vial, to a stirred solution of 1-amino-3-(benzyloxy)-N-methyl-4-oxo-1,4-dihydropyridine-2-carboxamide 1-7 (500 mg, 1.8 mmol) in ethanol (5 mL) was added paraformaldehyde (55 mg, 1.8 mmol), then kept under microwave irradiation at 140° C. for 30 minutes. After consumption of starting material, the reaction mixture was concentrated under reduced pressure. Crude compound was purified over reverse phase chromatography by eluting with 32% ACN in 0.1% formic acid in water to afford 5-(benzyloxy)-3-methyl-2,3-dihydro-1H-pyrido[2,1-f][1,2,4]triazine-4,6-dione INT-6. TLC: 10% MeOH in DCM; Rf=0.2. LCMS: (ESI): m/z 286.07 (M+H)$^+$.

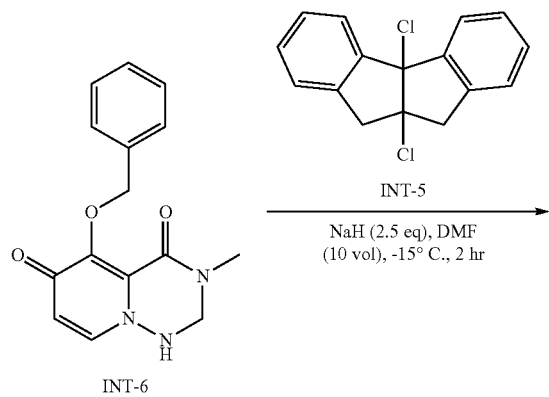

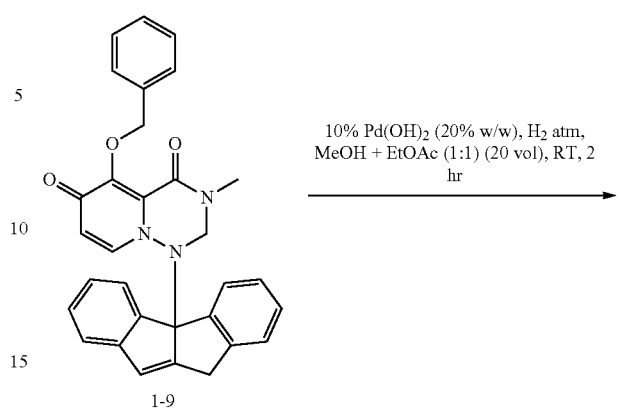

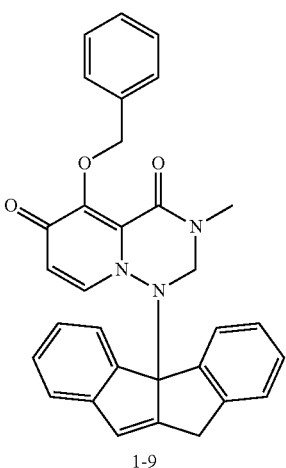

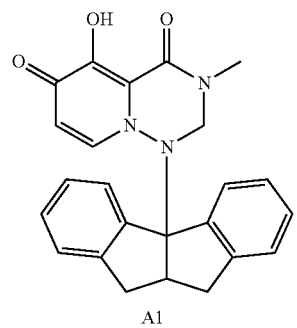

To a stirred solution of 5-(benzyloxy)-3-methyl-2,3-dihydro-1H-pyrido[2,1-f][1,2,4]triazine-4,6-dione INT-6 (80 mg, 0.280 mmol) in dry DMF (3 mL) was added 60% of NaH (23 mg, 1.751 mmol) at −15° C. and stirred for 15 minutes. Then added solution of 4b,9a-dichloro-4b,9,9a,10-tetrahydroindeno[1,2-a]indene INT-5 (115.3 mg, 0.421 mmol) (for preparation, see below) in dry DMF (1 mL) at −15° C. then stirred for 2 hr. Reaction mixture quenched with saturated NH$_4$Cl solution (10 mL) and extracted with EtOAc (2×20 mL). Combined organic layers were washed with brine solution (20 mL), dried over Na$_2$SO$_4$ and concentrated under reduced pressure. Crude compound was purified over reverse phase chromatography by eluting with 57% ACN in 0.1% formic acid in water to afford 5-benzyloxy-1-(9a,10-dihydro-9H-indeno[1,2-a]inden-4b-yl)-3-methyl-2,3-dihydro-1H-pyrido[2,1-f][1,2,4]triazine-4,6-dione 1-9. TLC: 10% MeOH in DCM; Rf=0.5. LCMS: (ESI): m/z 488.4 (M+H)$^+$.

To a stirred solution of 5-benzyloxy-1-(9a,10-dihydro-9H-indeno[1,2-a]inden-4b-yl)-3-methyl-2,3-dihydro-1H-pyrido[2,1-f][1,2,4]triazine-4,6-dione 1-9 (2×30 mg, 0.06 mmol) in MeOH (1 mL) and EtOAc (1 mL) was treated with 10% w/w of 20% Pd(OH)$_2$ on carbon (10 mg) and stirred under hydrogen balloon atmosphere for 1 hour. Reaction mixture filtered through Diatomaceous earth and washed the Diatomaceous earth pad with 10% MeOH in DCM (20 mL) and concentrated under reduced pressure. Crude compound was purified over Prep HPLC method to afford 1-(9a,10-dihydroindeno[1,2-a]inden-4b(9H)-yl)-5-hydroxy-3-methyl-2,3-dihydro-1H-pyrido[2,1-f][1,2,4]triazine-4,6-dione A1. TLC: 15% MeOH in DCM; Rf=0.1. LCMS: (ESI): m/z 400.42 (M+H)$^+$.

Preparation of INT-5

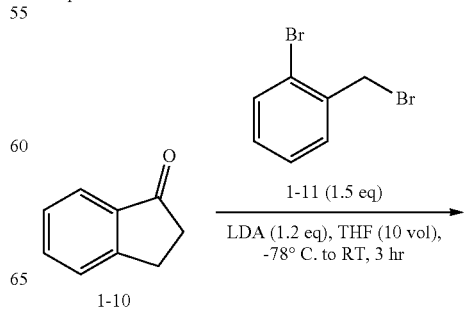

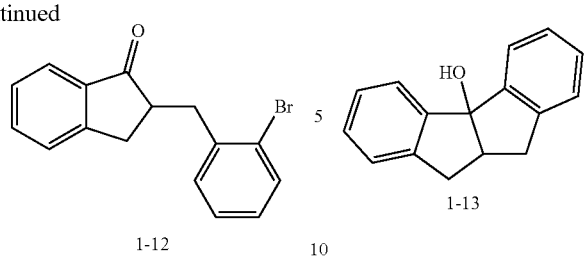

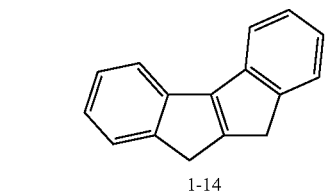

To a stirred solution of 2,3-dihydro-1H-inden-1-one 1-10 (50 g, 0.38 mol) in THF (500 mL) was added lithium diisopropylamide (LDA) (227 mL, 2.5 M in THF) drop wise at −78° C. and the reaction mixture was warmed to −20° C. for 2 hr and again cooled to −78° C. Now added 1-bromo-2-(bromomethyl)benzene 1-11 (93.5 g, 379 mmol) dissolved in 100 mL of THF) drop wise over a period of 1 hour and the reaction mixture was stirred at −78° C. for 1 hour. Then reaction mixture was warmed to RT and stirred for 2 hr. After completion of reaction as determined by TLC, the reaction mixture was poured into ice-cold sodium bicarbonate solution, and then extract with diethyl ether (400 mL×3), combined organic layer were dried over Na$_2$SO$_4$, and concentrated under reduced pressure. The resultant crude residue was purified by silica gel (100-200 mesh) column chromatography to obtain semi pure sample. It was re-purified through reverse phase chromatography by eluting with ACN and 0.1% formic acid in water to afford 2-(2-bromobenzyl)-2,3-dihydro-1H-inden-1-one 1-12. TLC: 20% EtOAc in pet ether; Rf=0.5. LCMS: (ESI): m/z 301.3 (M+H)$^+$.

To a stirred solution of 9a,10-dihydroindeno[1,2-a]inden-4b(9H)-ol 1-13 (1.2 g, 5.4 mmol) in DCM (12 mL) was added H$_3$PO$_4$ (14 mL) at 0° C. and stirred at RT for 12 hr. Reaction was monitored by TLC. Reaction mixture was poured into ice water (25 mL) and extracted with ether (2×100 mL). Combined organic layers were washed with brine solution (50 mL), dried over Na$_2$SO$_4$ and concentrated under reduced pressure. Crude compound was purified over chromatography to afford 9, 10-dihydroindeno [1, 2-a] indene 1-14. TLC: 5% EtOAc in pet ether; Rf=0.8. LCMS: (ESI): m/z 205 (M+H)+.

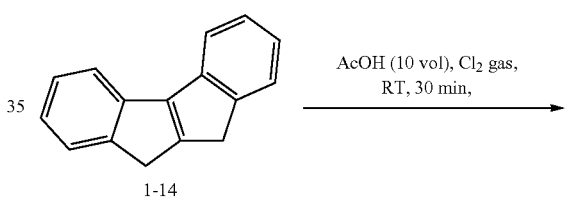

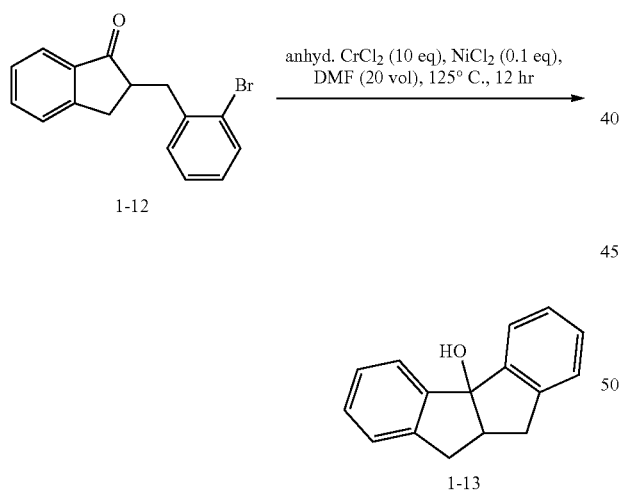

To a stirred solution of 2-(2-bromobenzyl)-2,3-dihydro-1H-inden-1-one 1-12 (100 mg, 0.333 mmol) in dry DMF (5 mL) was added NiCl$_2$ (4.29 mg, 0.033 mmol), and Cr$_2$Cl$_2$ (406 mg, 3.33 mmol) then stirred at 120° C. for 16 hr. After consumption of starting material, the reaction mixture was quenched with ice water extracted with ether (100 mL×2) the combined organic layer was dried over Na$_2$SO$_4$ and concentrated under reduced pressure. Crude compound was purified over combi-flash to afford 9a,10-dihydroindeno[1,2-a]inden-4b(9H)-ol 1-13. TLC: 10% EtOAc/pet ether; Rf=0.3. LCMS: (ESI): m/z 205 (M−H$_2$O).

To a stirred solution 9,10-dihydroindeno[1,2-a]indene 1-14 (60 mg, 0.27 mol) in AcOH (2 mL) purged the Cl$_2$ gas for 25 min. at RT. After consumption of starting material (checked by TLC), reaction mixture quenched with ice water (5 mL) and basified with sodium bicarbonate solution and extracted with ether (2×20 mL). Combined organic layers were washed with brine solution (20 mL), dried over Na$_2$SO$_4$ and concentrated under reduced pressure. Crude compound was purified over chromatography to afford 4b,9a-dichloro-4b,9,9a,10-tetrahydroindeno[1,2-a]indene INT-5. TLC: 5% EtOAc in pet ether; Rf=0.5. LCMS: (ESI): m/z 274 (M+H)$^+$.

Example 2: 1-(1,2-Difluoro-9a,10-dihydro-9H-indeno[1,2-a]inden-4b-yl)-5-hydroxy-3-methyl-2,3-dihydro-1H-pyrido[2,1-f][1,2,4]triazine-4,6-dione (A6)

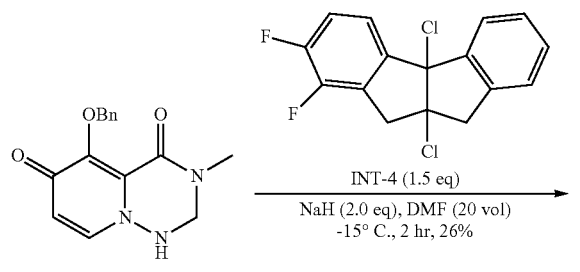

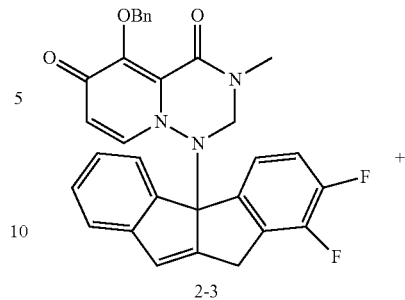

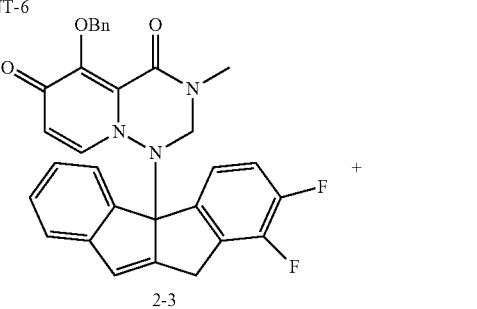

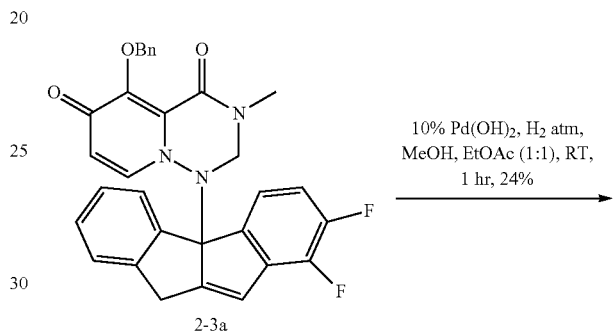

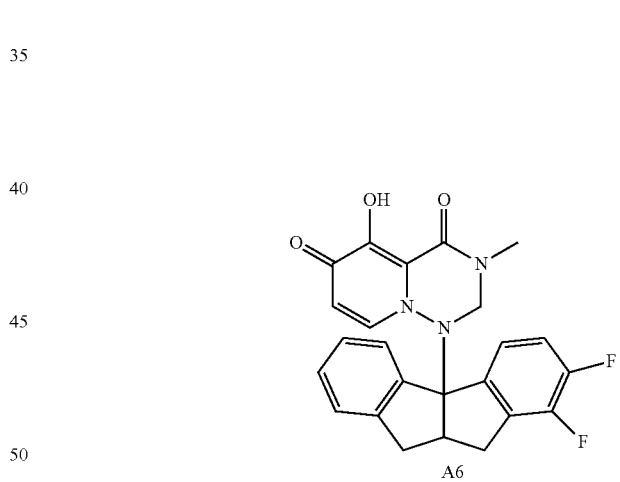

To a stirred solution of 5-(benzyloxy)-3-methyl-2,3-dihydro-1H-pyrido[2,1-f][1,2,4]triazine-4,6-dione INT-6 (250 mg, 0.877 mmol; Bn, as in the scheme above, means benzyl group) in DMF (15 mL) was added 60% of NaH (70 mg, 1.75 mmol) at −15° C. and stirred for 15 minutes, then added solution of 4b,9a-dichloro-1,2-difluoro-4b,9,9a,10-tetrahydroindeno[1,2-a]indene INT-4 (327 mg, 1.05 mmol) (see Example 14) in DMF (5 mL) at −15° C. then stirred 2 hr. Reaction mixture was quenched with saturated NH$_4$Cl solution (40 mL) and extracted with EtOAc (2×30 mL). Combined organic layers were washed with brine solution (30 mL), dried over Na$_2$SO$_4$ and concentrated under reduced pressure. Crude compound was purified through reverse phase chromatography by eluting with 70% ACN in 0.1% formic acid in water to afford isomeric mixture of 5-(benzyloxy)-1-(7,8-difluoroindeno[1,2-a]inden-4b(9H)-yl)-3-methyl-2,3-dihydro-1H-pyrido[2,1-f][1,2,4]triazine-4,6-dione 2-3 and 5-(benzyloxy)-1-(1,2-difluoroindeno[1,2-a]inden-4b(9H)-yl)-3-methyl-2,3-dihydro-1H-pyrido[2,1-f][1,2,4]triazine-4,6-dione 2-3a. TLC: 10% MeOH in MeCl; Rf=0.4. LCMS: (ESI): m/z 524.39 (M+H)$^+$.

To a stirred solution of 5-(benzyloxy)-1-(7,8-difluoroindeno[1,2-a]inden-4b(9H)-yl)-3-methyl-2,3-dihydro-1H-pyrido[2,1-f][1,2,4]triazine-4,6-dione 2-3 (50 mg, 0.096 mmol) in MeOH (5 mL) and EtOAc (5 mL) was treated with 10% w/w of 20% Pd(OH)$_2$ on carbon (10 mg) and stirred under balloon hydrogen atmosphere for 1 hour. Reaction mixture was filtered through Diatomaceous earth and washed the Diatomaceous earth bed with MeOH (20 mL) and concentrated under reduced pressure. Crude compound was purified by prep HPLC to afford 1-(1,2-difluoro-9a,10-dihydro-9H-indeno[1,2-a]inden-4b-yl)-5-hydroxy-3-methyl-2,3-dihydro-1H-pyrido[2,1-f][1,2,4]triazine-4,6-dione A6. TLC: 10% MeOH in DCM; Rf=0.3. LCMS: (ESI): m/z 436.34 (M+H)$^+$.

Example 3: 1-(2,7-Difluoro-9a,10-dihydro-9H-indeno[1,2-a]inden-4b-yl)-5-hydroxy-3-methyl-2,3-dihydro-1H-pyrido[2,1-f][1,2,4]triazine-4,6-dione (A3)

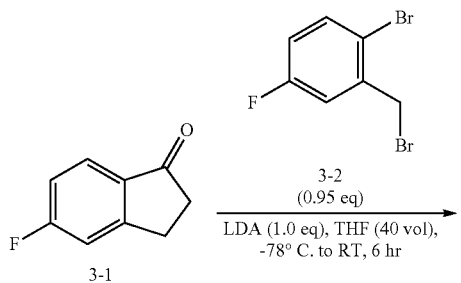

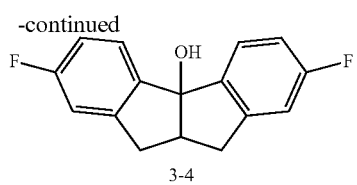

To a stirred solution of 2-(2-bromo-5-fluorobenzyl)-5-fluoro-2,3-dihydro-1H-inden-1-one 3-3 (1 g, 2.9 mmol) in dry DMF (30 mL) was added NiCl$_2$ (37 mg, 0.29 mmol), and anhydrous Cr$_2$Cl$_2$ (3.6 g, 29 mmol) then stirred at 110° C. for 16 hr. After consumption of starting material, the reaction mixture was quenched with ice water and extracted with ether (2×150 mL) the combined organic layer was dried over Na$_2$SO$_4$ and concentrated under reduced pressure. Crude compound was used to next step without purification to afford 2,7-difluoro-9a,10-dihydroindeno[1,2-a]inden-4b (9H)-ol 3-4. TLC: 10% EtOAc in pet ether; Rf=0.3. LCMS: (ESI): m/z 259.4.

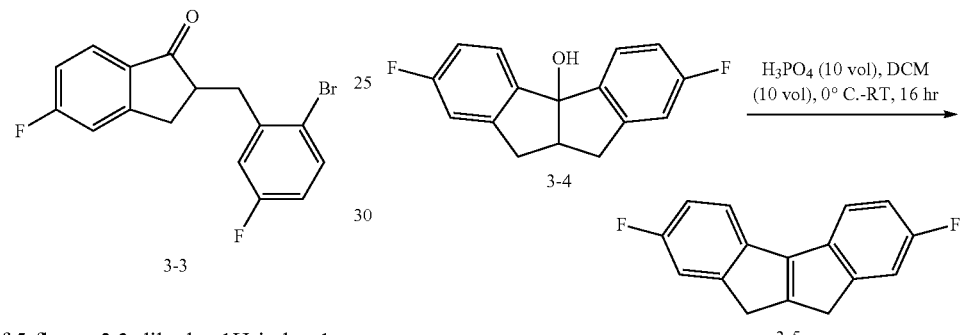

To a stirred solution of 5-fluoro-2,3-dihydro-1H-inden-1-one 3-1 (10 g, 66 mmol) in THF (300 mL) was added LDA (33 mL, 2.0 M in THF) drop wise at −78° C. and the reaction mixture was warmed to −20° C. for 2 hr and again cooled to −78° C. Now added 1-bromo-2-(bromomethyl)-4-fluorobenzene 3-2 (17 g, 63 mmol) in 100 mL of THF) dropwise over a period of 1 hour and the reaction mixture was stirred at −78° C. for 1 hour. Then reaction mixture was warmed to RT then stirred for 2 hr. After completion of reaction as determined by TLC, the reaction mixture was poured into ice-cold sodium bicarbonate solution, and then extract with diethyl ether (3×300 mL), combined organic layer was dried over Na$_2$SO$_4$, and concentrated under reduced pressure to provide crude compound. The resultant crude compound was purified by silica gel (100-200 mesh) column chromatography using 2% of EtOAc in pet ether to afford 2-(2-bromo-5-fluorobenzyl)-5-fluoro-2,3-dihydro-1H-inden-1-one 3-3. TLC: 10% EtOAc in pet ether; Rf=0.5. LCMS (ESI): m/z 338.93 (M+H)$^+$.

To a stirred solution of 2,7-difluoro-9a,10-dihydroindeno[1,2-a]inden-4b(9H)-ol 3-4 (200 mg, 0.77 mmol) in DCM (0.2 mL, 10 vol) was added H$_3$PO$_4$ (0.2 mL, 10 vol) at 0° C. and allowed to stir at RT for 16 hr. After consumption of starting material, reaction mixture was quenched with ice water (25 mL) and extracted with ether (2×50 mL). Combined organic layers were washed with brine solution (50 mL), dried over Na$_2$SO$_4$ and concentrated under reduced pressure. Crude compound was purified by silica gel (100-200 mesh) column chromatography to afford 2, 7-difluoro-9, 10-dihydroindeno [1, 2-a]indene 3-5. TLC: 5% EtOAc in pet ether; Rf=0.8. LCMS: (ESI): m/z 241.07 (M+H)+.

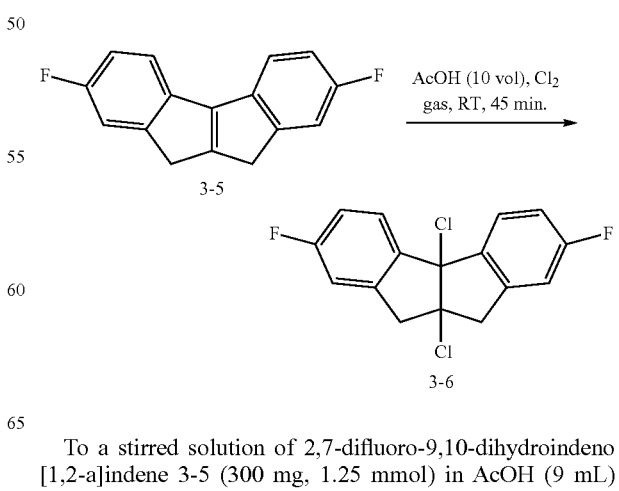

To a stirred solution of 2,7-difluoro-9,10-dihydroindeno[1,2-a]indene 3-5 (300 mg, 1.25 mmol) in AcOH (9 mL)

purge the Cl₂ gas for 45 min. at RT. After consumption of starting material, reaction mixture quenched with ice water (50 mL) and basified with sodium bicarbonate solution and extracted with ether (2×50 mL). Combined organic layers were washed with brine solution (50 mL), dried over Na₂SO₄ and concentrated under reduced pressure. Crude compound was purified by chromatography afford 4b,9a-dichloro-2,7-difluoro-4b,9,9a,10-tetrahydroindeno[1,2-a]indene 3-6. TLC: 5% EtOAc in pet ether; Rf=0.5. LCMS: (ESI): m/z 275 (M−H₂O).

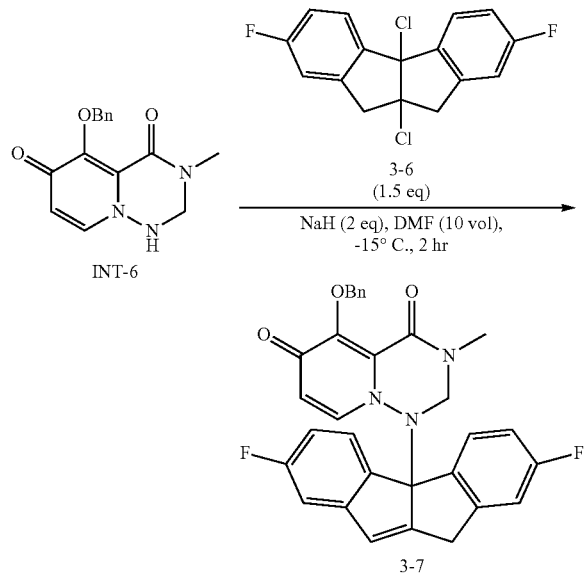

To a stirred solution of 5-(benzyloxy)-3-methyl-2,3-dihydro-1H-pyrido[2,1-f][1,2,4]triazine-4,6-dione INT-6 (200 mg, 0.67 mmol) (See Example 1) in dry DMF (1 mL) was added of NaH (60% in mineral oil) (56 mg, 1.0 mmol) at −15° C. and stirred for 15 minutes. Then added a solution of 4b,9a-dichloro-2,7-difluoro-4b,9,9a,10-tetrahydroindeno[1,2-a]indene 3-6 (326 mg, 1.0 mmol) in dry DMF (1 mL) at −15° C. then stirred 2 hr. Reaction mixture quenched with saturated NH₄Cl solution (20 mL) and extracted with EtOAc (2×20 mL). Combined organic layers were washed with brine solution (10 mL), dried over Na₂SO₄ and concentrated under reduced pressure. Crude compound was purified through reverse phase chromatography by eluting with 60% of ACN in 0.1% formic acid in water to afford 5-(benzyloxy)-1-(2,7-difluoroindeno[1,2-a]inden-4b(9H)-yl)-3-methyl-2,3-dihydro-1H-pyrido[2,1-f][1,2,4]triazine-4,6-dione 3-7. TLC: 10% MeOH in DCM; Rf=0.6. LCMS: (ESI): m/z 524.42 (M+H)⁺.

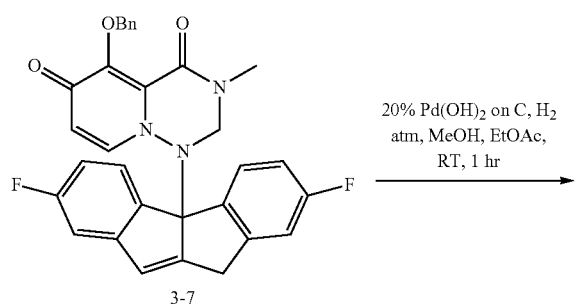

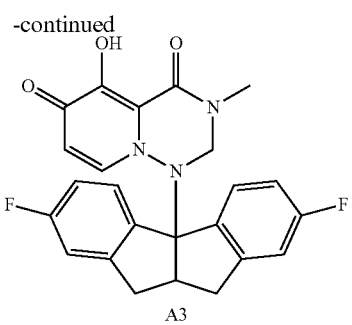

To a stirred solution of 5-(benzyloxy)-1-(2,7-difluoroindeno[1,2-a]inden-4b(9H)-yl)-3-methyl-2,3-dihydro-1H-pyrido[2,1-f][1,2,4]triazine-4,6-dione 3-7 (110 mg, 0.21 mmol) in MeOH (2 mL) and EtOAc (2 mL) was treated with 10% w/w of 20% Pd(OH)₂ on carbon (10 mg) and stirred under hydrogen balloon atmosphere for 1 hour. Reaction mixture was filtered through Diatomaceous earth and the Diatomaceous earth pad washed with 10% MeOH in DCM (20 mL), and the wash concentrated under reduced pressure. Crude compound was purified by Prep HPLC method to afford 1-(2,7-difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione A3. TLC: 10% MeOH in DCM; Rf=0.3. LCMS: (ESI): m/z 436.37 (M+H)⁺.

Example 4: 1-(1,8-Difluoro-9a,10-dihydro-9H-indeno[1,2-a]inden-4b-yl)-5-hydroxy-3-methyl-2,3-dihydro-1H-pyrido[2,1-f][1,2,4]triazine-4,6-dione (A12)

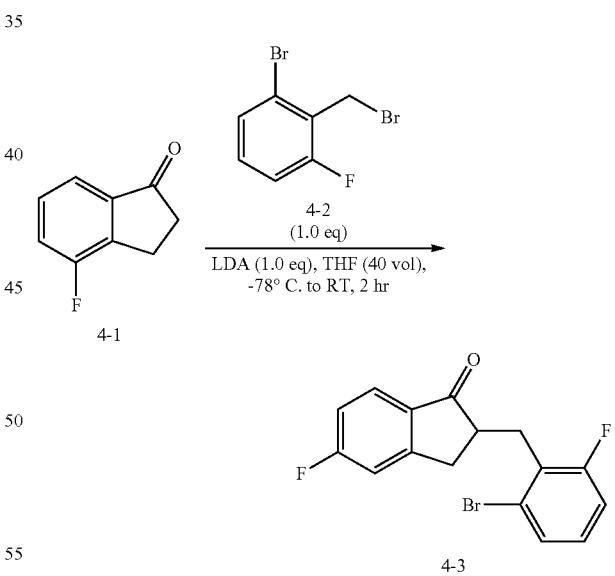

To a stirred solution of 4-fluoro-2,3-dihydro-1H-inden-1-one 4-1 (2.5 g, 17 mmol) in THF (100 mL) was added LDA (12.5 mL, 2.0 M in THF) drop-wise at −78° C. and the reaction mixture was warmed to −20° C. for 2 hr, and again cooled to −78° C. 1-Bromo-2-(bromomethyl)-3-fluorobenzene 4-2 (4.4 g, 17 mmol) in 25 mL of THF) was added drop-wise over 1 hour and the reaction mixture was stirred at −78° C. for 1 hour. The reaction mixture was warmed to RT, then stirred it for 2 hr. After completion of reaction (as determined by TLC), the reaction mixture was poured into ice-cold NaHCO₃ solution, and then extracted with diethyl ether (3×300 mL). The combined organic layer was dried over Na₂SO₄ and concentrated under reduced pressure to provide crude compound. The resultant crude compound was purified by silica gel (100-200 mesh) column chromatography using 2% of EtOAc/pet ether to afford 2-(2-bromo-6-fluorobenzyl)-5-fluoro-2,3-dihydro-1H-inden-1-one 4-3. TLC: 10% EtOAc in pet ether; Rf=0.5. LCMS: (ESI): m/z 337.15 (M+H)⁺.

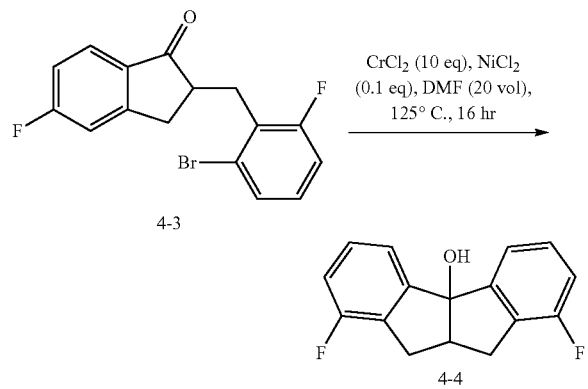

To a stirred solution of 2-(2-bromo-6-fluorobenzyl)-5-fluoro-2,3-dihydro-1H-inden-1-one 4-3 (2 g, 5.9 mmol) in dry DMF (20 mL) was added NiCl₂ (76 mg, 0.59 mmol), followed by anhydrous CrCl₂ (7.2 g, 59 mmol), and the mixture was stirred at 110° C. for 16 hr. After consumption of starting material, the reaction mixture was quenched with ice water and extracted with ether (2×150 mL). The combined organic layer was dried over Na₂SO₄ and concentrated under reduced pressure. Crude compound was used to next step without purification to afford 1,8-difluoro-9a,10-dihydroindeno[1,2-a]inden-4b(9H)-ol] 4-4. TLC: 10% EtOAc in pet ether; Rf=0.3. LCMS: (ESI): m/z 241.18 (M-OH).

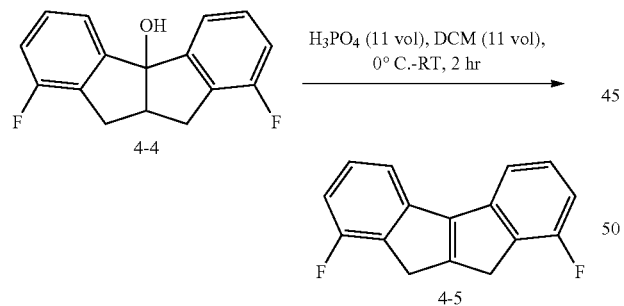

To a stirred solution of 1,8-difluoro-9a,10-dihydroindeno[1,2-a]inden-4b(9H)-ol 4-4 (1.8 g, 6.97 mmol) in DCM (20 mL, 11 vol) was added H₃PO₄ (20 mL, 11 vol) at 0° C., and the mixture was allowed to stir at RT for 2 hr. After consumption of starting material, reaction mixture was quenched with ice water (100 mL) and extracted with ether (3×75 mL). Combined organic layers were washed with brine solution (100 mL), dried over Na₂SO₄, and concentrated under reduced pressure. Crude compound was purified by silica gel (100-200 mesh) column chromatography to afford 1,8-difluoro-9,10-dihydroindeno[1,2-a]indene 4-5. TLC: 5% EtOAc in pet ether; Rf=0.7. LCMS: (ESI): m/z 241.25 (M+H)⁺.

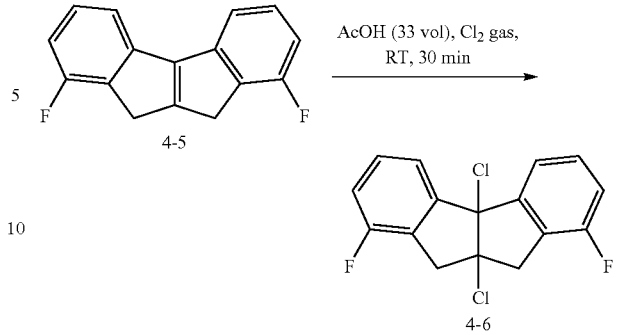

To a stirred solution of 1,8-difluoro-9,10-dihydroindeno[1,2-a]indene 4-5 (600 mg, 2.5 mmol) in AcOH (20 mL) purged the Cl₂ gas for 30 min. at RT. After consumption of starting material, reaction mixture was quenched with ice water (100 mL) and basified with sodium bicarbonate solution and extracted with ether (2×75 mL). Combined organic layers were washed with brine solution (50 mL), dried over Na₂SO₄ and concentrated under reduced pressure to afford 650 mg of 4b,9a-dichloro-1,8-difluoro-4b,9,9a,10 tetrahydroindeno[1,2a]indene 4-6. TLC: 5% EtOAc/pet ether; Rf=0.5. LCMS (ESI): m/z 274.88 (M-Cl).

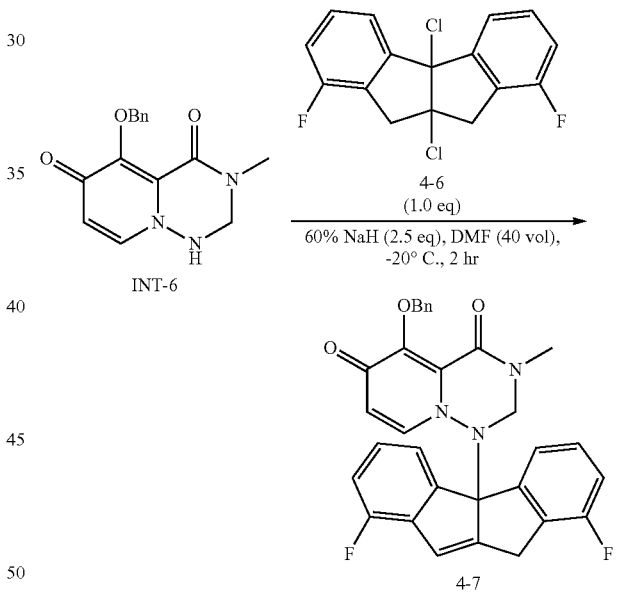

To a stirred solution of 5-(benzyloxy)-3-methyl-2,3-dihydro-1H-pyrido[2,1-f][1,2,4]triazine-4,6-dione INT-6 (500 mg, 1.7 mmol) (see Example 1) in dry DMF (10 mL) was added of NaH (60% in mineral oil) (175 mg, 4.0 mmol) at −20° C. and stirred for 20 minutes. Then added a solution of 4b,9a-dichloro-1,8-difluoro-4b,9,9a,10 tetrahydroindeno[1,2a]indene 4-6 (543 mg, 1.0 mmol) in dry DMF (1 mL) at −15° C. then stirred for 15 minutes. Reaction mixture was quenched with saturated NH₄Cl solution (10 mL) and extracted with EtOAc (2×50 mL). Combined organic layers were washed with brine solution (50 mL), dried over Na₂SO₄ and concentrated under reduced pressure. Crude compound was purified through reverse phase chromatography by eluting with 80% ACN in 0.1% formic acid in water to afford 5-(benzyloxy)-1-(1,8-difluoroindeno[1,2-a]

inden-4b(9H)-yl)-3-methyl-2,3-dihydro-1H-pyrido[2,1-f][1,2,4]triazine-4,6-dione 4-7. TLC: 10% MeOH in DCM; Rf=0.6. LCMS: (ESI): m/z 524.39 (M+H)⁺.

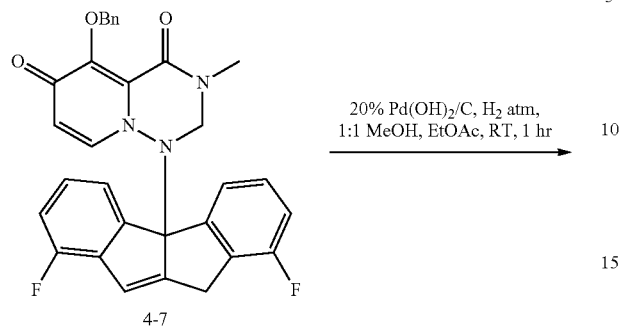

To a stirred solution of 5-(benzyloxy)-1-(1,8-difluoroindeno[1,2-a]inden-4b(9H)-yl)-3-methyl-2,3-dihydro-1H-pyrido[2,1-][1,2,4]triazine-4,6-dione 4-7 (80 mg, 0.15 mmol) in MeOH (3 mL) and EtOAc (3 mL) was added 10% w/w of 20% Pd(OH)₂ on carbon (10 mg), and the mixture was stirred under H₂ balloon atmosphere for 2 hr. The reaction mixture was filtered through Diatomaceous earth, the Diatomaceous earth pad washed with 10% MeOH in DCM (20 mL), and the wash concentrated under reduced pressure. Crude compound was purified by Prep HPLC to afford 1-(1,8-difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione A12. TLC: 10% MeOH in DCM; Rf=0.3. LCMS: (ESI): m/z 436.13 (M+H)⁺.

Example 5: 5-Hydroxy-3-methyl-1-(2,3,6,7-tetrafluoro-9a,10-dihydro-9H-indeno[1,2-a]inden-4b-yl)-2,3-dihydro-1H-pyrido[2,1-f][1,2,4]triazine-4,6-dione (A8)

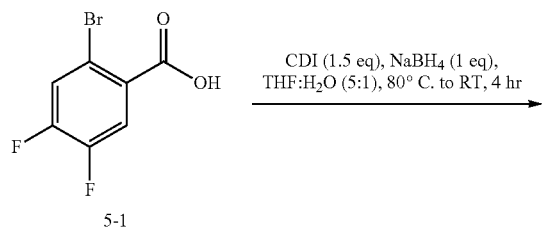

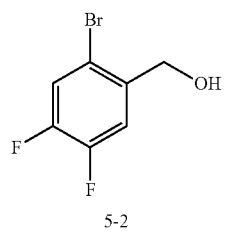

To a stirred solution of 2-bromo-4,5-difluorobenzoic acid 5-1 (12 g, 50.6 mmol) in THF (120 mL) was added CDI (12.3 g, 75.9 mmol) at 0° C. The reaction mixture was heated to 80° C. for 4 hr. After consumption of starting material, the reaction mixture cooled to 0° C. then added NaBH₄ (1.87 g, 50.6 mmol) in water (10 mL) slowly drop wise for 10 minutes, Then the reaction mixture was stirred for 30 minutes at RT. After consumption of starting material, the reaction mixture was poured in ice water and extracted with EtOAc (2×50 mL) and separated Organic layer was washed with brine solution, dried with Na₂SO₄ and concentrated to get crude. Crude compound was purified by column chromatography to afford (2-bromo-4, 5-difluorophenyl)methanol 5-2. TLC: 20% EtOAc in hexane; Rf=0.5. ¹H NMR: Consistent (DMSO).

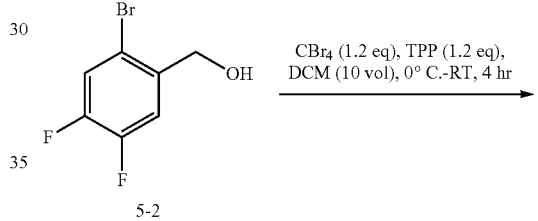

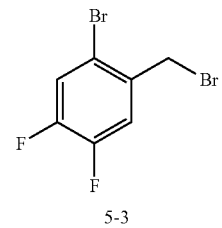

To a stirred solution of (2-bromo-4, 5-difluorophenyl) methanol 5-2 (9 g, 41 mmol) in DCM (100 mL) was added Tri phenyl phosphine (12.68 g, 48.43 mmol) and CBr₄ (16 g, 48 mmol) and at 0° C. Then the reaction mixture was stirred at RT for 16 hr. After consumption of starting material, the reaction mixture was quenched with water and extracted with DCM (2×30 mL) and separated Organic layer was washed with brine solution, dried with Na₂SO₄ and concentrated to get crude. Crude compound was purified by column chromatography to afford 1-bromo-2-(bromomethyl)-4, 5-difluorobenzene 5-3. TLC: 5% EtOAc in hexane; Rf=0.8. ¹H NMR: Consistent (CDCl₃).

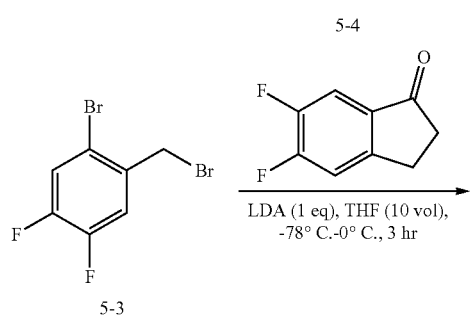

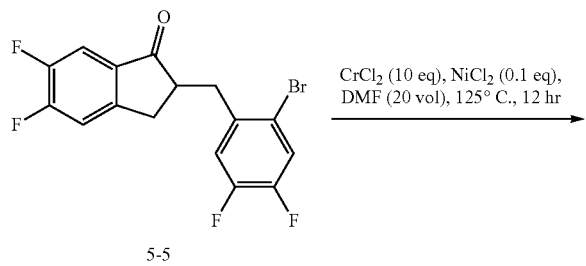

To a stirred solution of 5,6-difluoro-2,3-dihydro-1H-inden-1-one 5-4 (2 g, 12 mmol) in THF (20 mL) was added LDA (4.7 mL, 2.5 M in THF, 1.2 eq.) drop wise at −70° C. and the reaction mixture was warmed to −20° C. for 2 hr and again cooled to −78° C. To that was added 1-bromo-2-(bromomethyl)-4,5-difluorobenzene 5-3 (3.4 g, 12 mmol, dissolved in 100 mL of THF) drop-wise over a period of 1 hour and the reaction mixture was stirred at −78° C. for 1 hour. The reaction mixture was warmed to RT then stirred for 2 hr. After completion of reaction (as determined by TLC), the reaction mixture was poured into ice-cold NaHCO₃ solution, and then extracted with diethyl ether (40 mL×3), and the combined organic layer was dried over Na₂SO₄, and concentrated under reduced pressure to give crude product. The resultant crude was purified by silica gel column chromatography to afforded 2-(2-bromo-4, 5-difluorobenzyl)-5, 6-difluoro-2, 3-dihydro-1H-inden-1-one 5-5. TLC: 10% EtOAc in pet ether; Rf=0.5. LCMS: (ESI): m/z 375.19 (M+2)+.

To a stirred solution of 2-(2-bromo-4, 5-difluorobenzyl)-5, 6-difluoro-2, 3-dihydro-1H-inden-1-one 5-5 (900 mg, 2.43 mmol) in dry DMF (10 mL) was added NiCl₂ (31 mg, 0.24 mmol), and Cr₂Cl₂ (2.94 g, 24.1 mmol), then stirred at 120° C. for 12 hr. After consumption of starting material, the reaction mixture was quenched with ice water extracted with ether (100 mL×2), and the combined organic layer was dried over with Na₂SO₄ and concentrated under reduced pressure to afford 2, 3,6,7-tetrafluoro-4b,9,9a,10-tetrahydroindeno[1,2-a]inden-4b-ol 5-6. Crude compound was used for the next step without any purification. TLC: 15% EtOAc in pet ether; Rf=0.3. LCMS: (ESI): m/z 277.31 (M−H₂O).

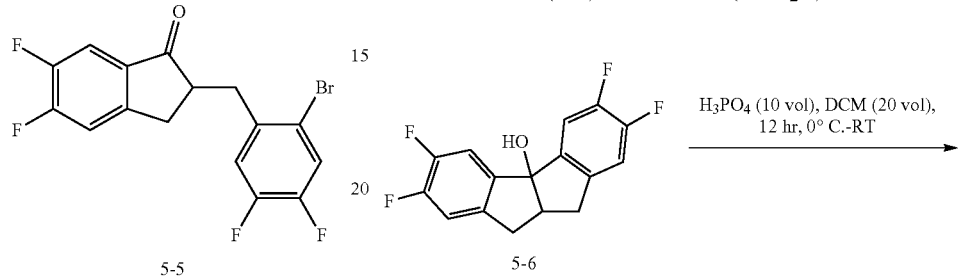

To a stirred solution of 2,3,6,7-tetrafluoro-4b,9,9a,10-tetrahydroindeno[1,2-a]inden-4b-ol 5-6 (1 g crude 3.4013 mmol) in DCM (20 mL, 20 vol) was added H₃PO₄ (10 mL, 10 vol) at 0° C. and allowed to come to RT, then stirred for 12 hr. After consumption of starting material (as determined by TLC) reaction mixture was quenched with ice water (25 mL) and extracted with DCM (2×100 mL). Combined organic layers were washed with brine solution (50 mL), dried over Na₂SO₄ and concentrated under reduced pressure. Crude compound was purified through chromatography to afford 2,3,6,7-tetrafluoro-9,10-dihydroindeno[1,2-a]indene 5-7. TLC: 5% EtOAc in pet ether; Rf=0.8. LCMS: (ESI): m/z 275.54 (M−H)⁻.

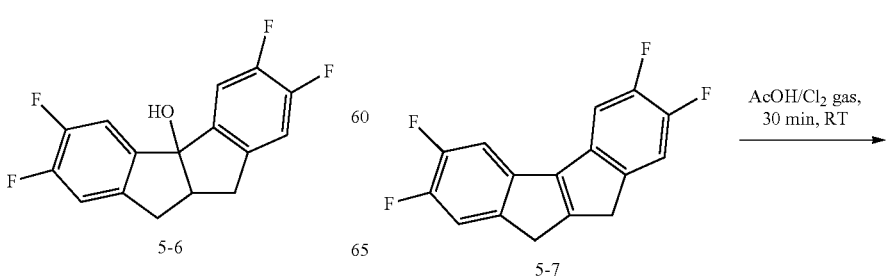

-continued

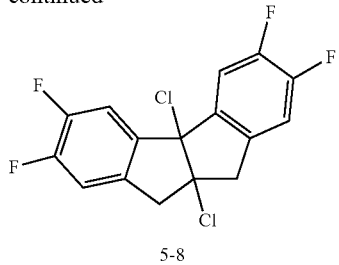
5-8

To a stirred solution of 2,3,6,7-tetrafluoro-9,10-dihydroindeno[1,2-a]indene 5-7 (350 mg, 1.268 mmol) in AcOH (3 mL) purge the Cl₂ gas for 25 min at RT. After consumption of starting material (monitored by TLC) Reaction mixture quenched with Ice water (10 mL) and basified with sodium bicarbonate solution and extracted with ether (2×20 mL). Combined organic layers were washed with brine solution (20 mL), dried over Na₂SO₄ and concentrated under reduced pressure. Crude compound was purified through chromatography afford 4b,9a-dichloro-2,3,6,7-tetrafluoro-4b,9,9a,10-tetrahydroindeno[1,2-a]indene 5-8. TLC: 5% EtOAc in pet ether; Rf=0.5. LCMS: (ESI): m/z 363.53 (M−HCl)⁺.

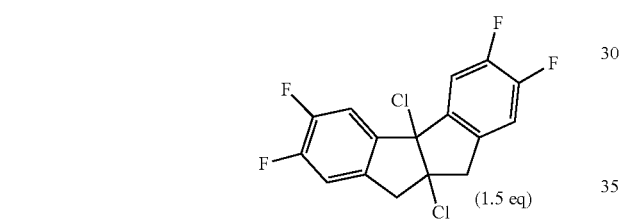

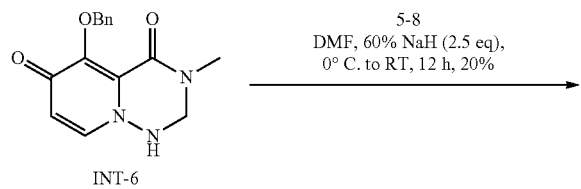
5-9

To a stirred solution of 5-(benzyloxy)-3-methyl-2,3-dihydro-1H-pyrido[2,1-f][1,2,4]triazine-4,6-dione INT-6 (300 mg, 1.05 mmol) in DMF (10 mL) was added 60% of NaH (105 mg, 2.63 mmol) at −15° C. and stirred for 15 minutes. A solution of 4b,9a-dichloro-2,3,6,7-tetrafluoro-4b,9,9a,10-tetrahydroindeno[1,2-a]indene 5-8 (365 mg, 1.05 mmol) in DMF (5 mL) was added at −15° C. then stirred 2 hr. The reaction mixture was quenched with saturated NH₄Cl solution (40 mL) and extracted with EtOAc (2×30 mL). Combined organic layers were washed with brine solution (30 mL), dried over Na₂SO₄ and concentrated under reduced pressure. Crude compound was purified through reverse phase chromatography by eluting with 65% ACN in 0.1% formic acid in water to afford 5-(benzyloxy)-3-methyl-1-(2,3,6,7-tetrafluoroindeno[1,2-a]inden-4b(9H)-yl)-2,3-dihydro-1H-pyrido[2,1-f][1,2,4]triazine-4,6-dione 5-9. TLC: 10% MeOH in DCM; Rf=0.4. LCMS: (ESI): m/z 560.37 (M+H⁺).

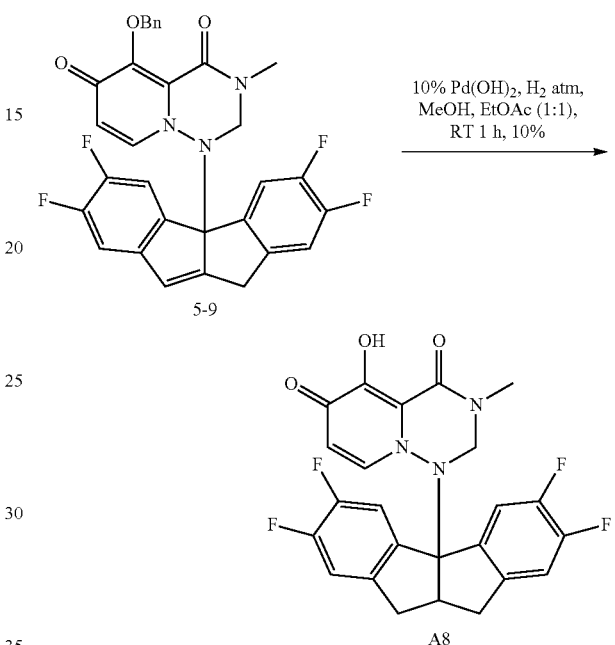

To a stirred solution of 5-(benzyloxy)-3-methyl-1-(2,3,6,7-tetrafluoroindeno[1,2-a]inden-4b(9H)-yl)-2,3-dihydro-1H-pyrido[2,1-f][1,2,4]triazine-4,6-dione 5-9 (120 mg, 0.214 mmol) in MeOH (5 mL) and EtOAc (5 mL) was treated with 10% w/w of 20% Pd(OH)₂ on carbon (20 mg) and stirred under balloon hydrogen atmosphere for 1 hour. Reaction mixture filtered through Diatomaceous earth and washed the Diatomaceous earth bed with 10% MeOH in DCM (20 mL) and concentrated under reduced pressure. Crude compound was purified through Prep HPLC to afford 5-hydroxy-3-methyl-1-(2,3,6,7-tetrafluoro-9a,10-dihydroindeno[1,2-a]inden-4b(9H)-yl)-2,3-dihydro-1H-pyrido[2,1-f][1,2,4]triazine-4,6-dione A8. TLC: 10% MeOH in DCM; Rf=0.3. LCMS: (ESI): m/z 472.03 (M+H)⁺.

Example 6: 3-Benzyl-1-(9a,10-dihydro-9H-indeno[1,2-a]inden-4b-yl)-5-hydroxy-2,3-dihydro-1H-pyrido[2,1-f][1,2,4]triazine-4,6-dione (A4)

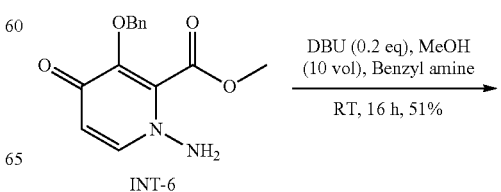
INT-6

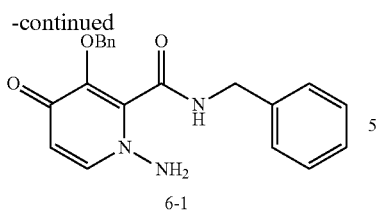

To a stirred solution of methyl-1-amino-3-(benzyloxy)-4-oxo-1,4-dihydropyridine-2-carboxylate INT-6 (200 mg, 0.72 mmol) (see Example 1) in MeOH (4 mL) was added DBU (0.027 mL, 0.18 mmol) and benzyl amine (1.56 g, 14.6 mmol) then stirred at RT for 16 hr. Volatiles were removed under reduced pressure and the crude compound was purified over reverse phase chromatography by eluting with 43% ACN in 0.1% formic acid in water to afford 1-amino-N-benzyl-3-(benzyloxy)-4-oxo-1,4-dihydropyridine-2-carboxamide 6-1. TLC: 10% MeOH in DCM; Rf=0.3. LCMS: (ESI): m/z 350.10 (M+H)⁺.

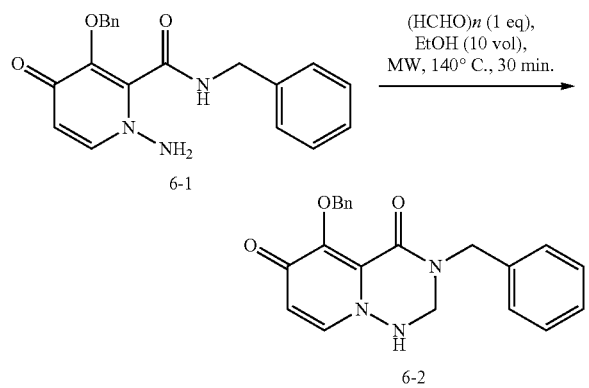

In a microwave vial, to a stirred solution of 1-amino-N-benzyl-3-(benzyloxy)-4-oxo-1,4-dihydropyridine-2-carboxamide 6-1 (500 mg, 1.43 mmol) in ethanol (5 mL) was added paraformaldehyde (47 mg, 1.57 mmol), then irradiated at 140° C. in microwave for 30 minutes. After consumption of starting material, the reaction mixture was concentrated under reduced pressure. Crude compound was purified through reverse phase chromatography by eluting with 43% ACN in 0.1% formic acid in water to afford 3-benzyl-5-(benzyloxy)-2,3-dihydro-1H-pyrido[2,1-f][1,2,4]triazine-4,6-dione 6-2. TLC: 10% MeOH in DCM; Rf=0.7. LCMS: (ESI): m/z 362.11 (M+H)⁺.

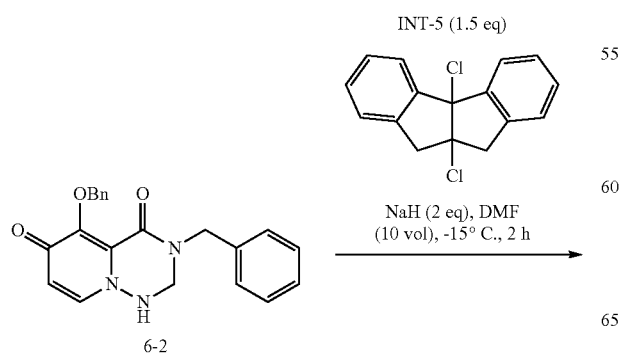

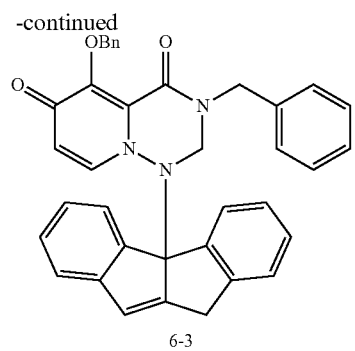

To a stirred solution of 3-benzyl-5-(benzyloxy)-2,3-dihydro-1H-pyrido[2,1-f][1,2,4]triazine-4,6-dione 6-2 (150 mg, 0.4155 mmol) in dry DMF (1 mL) was added 60% NaH (41 mg, 1.0 mmol) at −15° C. and stirred for 15 minutes. Then added solution of 4b,9a-dichloro-4b,9,9a,10-tetrahydroindeno[1,2-a]indene INT-5 (171 mg, 0.623 mmol) (see Example 1) in dry DMF (1 mL) at −15° C. then stirred 2 hr. Reaction mixture quenched with saturated NH₄Cl solution (20 mL) and extracted with EtOAc (2×20 mL). Combined organic layers were washed with brine solution (10 mL), dried over Na₂SO₄ and concentrated under reduced pressure. Crude compound was purified over reverse phase chromatography by eluting with 62% ACN in 0.1% formic acid in water to afford 3-benzyl-5-(benzyloxy)-1-(indeno[1,2-a]inden-4b(9H)-yl)-2,3-dihydro-1H-pyrido[2,1-f][1,2,4]triazine-4,6-dione 6-3. TLC: 10% MeOH in DCM; Rf=0.6. LCMS: (ESI): m/z 564.2 (M+H)⁺.

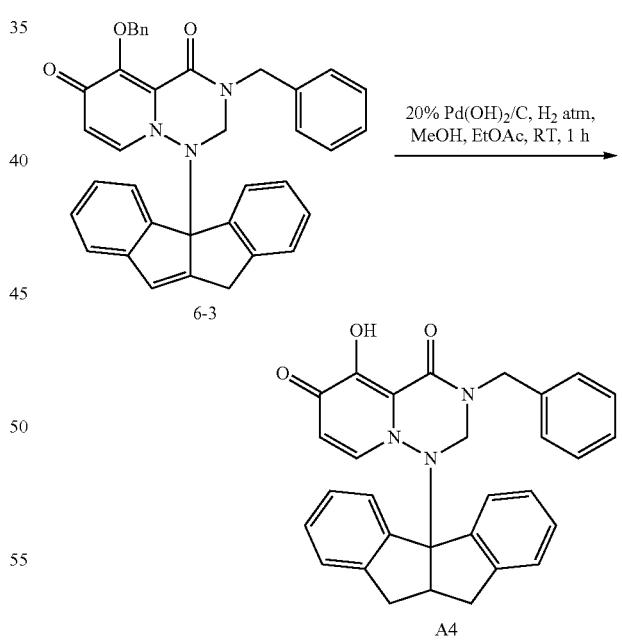

To a stirred solution of 3-benzyl-5-(benzyloxy)-1-(indeno[1,2-a]inden-4b(9H)-yl)-2,3-dihydro-1H-pyrido[2,1-f][1,2,4]triazine-4,6-dione 6-3 (45 mg, 0.07 mmol) in MeOH (1.5 mL) and EtOAc (1.5 mL) was treated with 10% w/w of 20% Pd(OH)₂ on carbon (10 mg) and kept under hydrogen balloon pressure for 1 hour. Reaction mixture was filtered through Diatomaceous earth pad and washed with 10% MeOH in DCM (20 mL) and concentrated under reduced pressure. Crude compound was purified by Prep HPLC to afford 3-benzyl-1-(9a,10-dihydroindeno[1,2-a]inden-4b(9H)-yl)-5-hydroxy-2,3-dihydro-1H-pyrido[2,1-f][1,2,4]triazine-4,6-dione A4. TLC: 10% MeOH in DCM; Rf=0.3. LCMS: (ESI): m/z 476.42 (M+H)+.

Example 7: 3-Cyclopropylmethyl-1-(9a,10-dihydro-9H-indeno[1,2-a]inden-4b-yl)-5-hydroxy-2,3-dihydro-1H-pyrido[2,1-f][1,2,4]triazine-4,6-dione (A2)

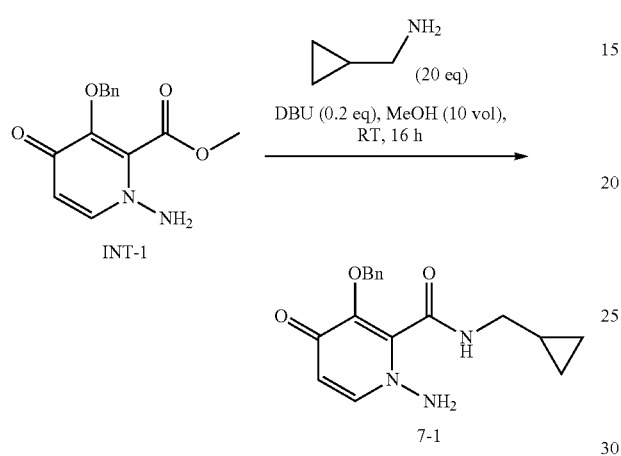

To a stirred solution of methyl-1-amino-3-(benzyloxy)-4-oxo-1,4-dihydropyridine-2-carboxylate INT-1 (750 mg, 2.73 mmol) (see Example 1) in MeOH (15 mL) was added DBU (109 mg, 0.68 mmol) and cyclopropylmethanamine (3.89 g, 54.7 mmol) then stirred at RT for 16 hr. Reaction mixture was distilled off under reduced pressure. Crude compound was purified over reverse phase chromatography by eluting with 43% of ACN in 0.1% formic acid in water to afford 1-amino-3-(benzyloxy)-N-(cyclopropylmethyl)-4-oxo-1,4-dihydropyridine-2-carboxamide 7-1. TLC: 10% MeOH in DCM; Rf=0.4. LCMS: (ESI): m/z 314.03 (M+H)+.

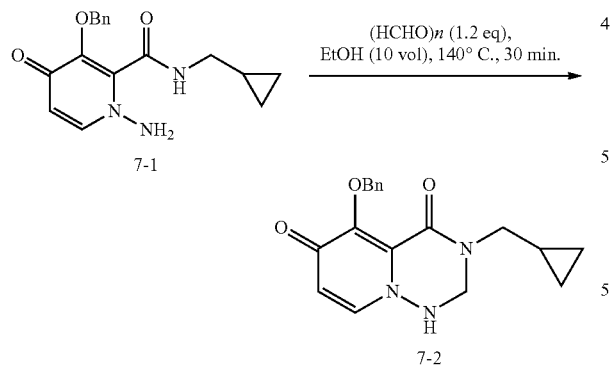

In a microwave vial, to a stirred solution of 1-amino-3-(benzyloxy)-N-(cyclopropylmethyl)-4-oxo-1,4-dihydropyridine-2-carboxamide 7-1 (400 mg, 1.28 mmol) in ethanol (4 mL) was added paraformaldehyde (42 mg, 1.4 mmol), then stirred in microwave at 140° C. for 30 minutes. After consumption of starting material, the reaction mixture was concentrated under reduced pressure. Crude compound was purified through reverse phase chromatography by eluting with 32% ACN in 0.1% formic acid in water to afford 5-(benzyloxy)-3-(cyclopropylmethyl)-2,3-dihydro-1H-pyrido[2,1-f][1,2,4]triazine-4,6-dione 7-2. TLC: 10% MeOH in DCM; Rf=0.6. LCMS: (ESI): m/z 326.49 (M+H)+.

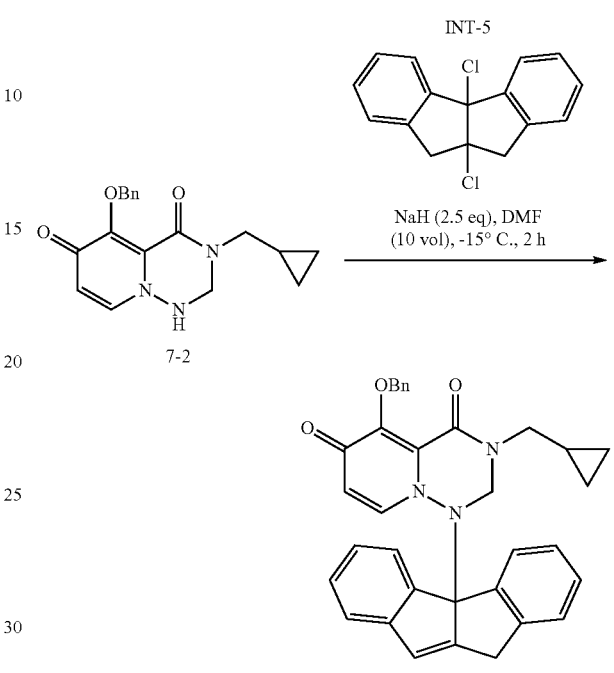

To a stirred solution of 5-(benzyloxy)-3-(cyclopropylmethyl)-2,3-dihydro-1H-pyrido[2,1-f][1,2,4]triazine-4,6-dione 7-2 (250 mg, 0.769 mmol) in dry DMF (2 mL) was added 60% of NaH (77 mg, 1.9 mmol) at −15° C. and stirred for 15 minutes. Then added solution of 4b,9a-dichloro-4b,9,9a,10-tetrahydroindeno[1,2-a]indene INT-5 (316 mg, 1.15 mmol) (see Example 1) in dry DMF (1 mL) at −15° C. then stirred for 2 hr. Reaction mixture quenched with saturated NH4Cl solution (20 mL) and extracted with EtOAc (2×20 mL). Combined organic layers were washed with brine solution (20 mL), dried over Na2SO4 and concentrated under reduced pressure. Crude compound was purified over reverse phase chromatography by eluting with 57% ACN in 0.1% formic acid in water to afford 5-(benzyloxy)-3-(cyclopropylmethyl)-1-(indeno[1,2-a]inden-4b(9H)-yl)-2,3-dihydro-1H-pyrido[2,1-f][1,2,4]triazine-4,6-dione 7-3. TLC: 10% MeOH in DCM; Rf=0.6. LCMS: (ESI): m/z 528.45 (M+H)+.

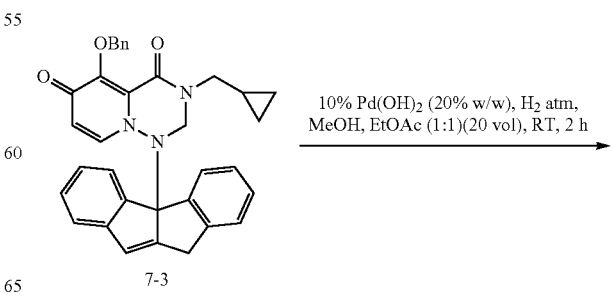

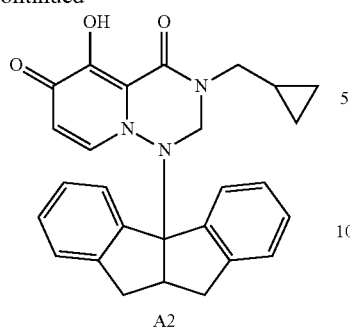

A2

To a stirred solution of 5-(benzyloxy)-3-(cyclopropylmethyl)-1-(indeno[1,2-a]inden-4b(9H)-yl)-2,3-dihydro-1H-pyrido[2,1-f][1,2,4]triazine-4,6-dione 7-3 (50 mg, 0.094 mmol) in MeOH (1 mL) and EtOAc (1 mL) was treated with 10% w/w of 20% Pd(OH)$_2$ on carbon (10 mg) and kept under hydrogen balloon atmosphere for 1 hour. Reaction mixture filtered through Diatomaceous earth and washed with 10% MeOH in DCM (20 mL) and concentrated under reduced pressure. Crude compound was purified through Prep HPLC method to afford 3-(cyclopropylmethyl)-1-(9a,10-dihydroindeno[1,2-a]inden-4b(9H)-yl)-5-hydroxy-2,3-dihydro-1H-pyrido[2,1-f][1,2,4]triazine-4,6-dione A2. TLC: 10% MeOH in DCM; Rf=0.5. LCMS: (ESI): m/z 440.16 (M+H)$^+$.

Example 8: 1-(9a,10-Dihydro-9H-indeno[1,2-a]inden-4b-yl)-5-hydroxy-3-(tetrahydro-pyran-4-ylmethyl)-2,3-dihydro-1H-pyrido[2,1-t][1,2,4]triazine-4,6-dione (A5)

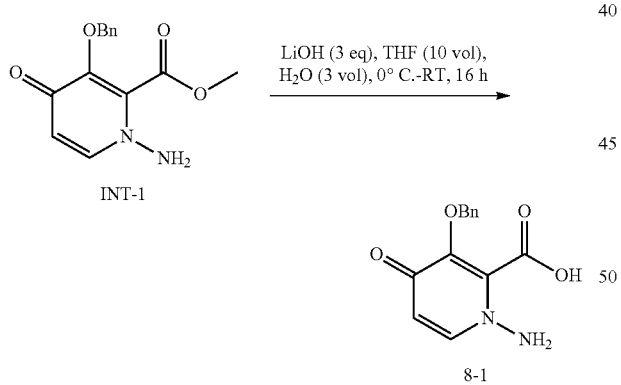

To a stirred solution of methyl-1-amino-3-(benzyloxy)-4-oxo-1-4-dihydropyridine-2-carboxylate INT-1 (1 g, 3.64 mmol) (see Example 1) in tetrahydrofuran (10 mL) and water (3 mL) was added lithium hydroxide (0.25 g, 10.94 mmol) then stirred at RT for 16 hr. Reaction mixture was distilled off under reduced pressure, to the crude added water (25 mL) then acidified up to ~pH 2 with 1 N aq. HCl and the resultant solid was collected by filtration to afford 1-amino-3-(benzyloxy)-4-oxo-1,4-dihydropyridine-2-carboxylic acid 8-1. TLC: 15% MeOH in DCM and 1 drop of acetic acid; Rf=0.5. LCMS: (ESI): m/z 314.03 (M+H)$^+$.

To a stirred solution of 1-amino-3-(benzyloxy)-4-oxo-1,4-dihydropyridine-2-carboxylic acid 8-1 (50 mg, 0.19 mmol) in DMF (2 mL) was added HATU (109 mg, 0.288 mmol), diisopropylethylamine (0.08 mL, 0.48 mmol) and (tetrahydro-2H-pyran-4-yl)methanamine (110.7 mg, 0.962 mmol) then stirred at RT for 16 hr. Reaction mixture completely distilled off under reduced pressure. Crude compound was purified over reverse phase chromatography by eluting with 38% of ACN in 0.1% formic acid in water to afford 1-amino-3-(benzyloxy)-4-oxo-N-((tetrahydro-2H-pyran-4-yl)methyl)-1,4-dihydropyridine-2-carboxamide 8-2. TLC: 15% MeOH in DCM and 1 drop Aq.NH$_3$; Rf=0.5. LCMS: (ESI): m/z 358.16 (M+H)$^+$.

In a microwave vial, to a stirred solution of 1-amino-3-(benzyloxy)-4-oxo-N-((tetrahydro-2H-pyran-4-yl)methyl)-1,4-dihydropyridine-2-carboxamide 8-2 (500 mg, 1.40 mmol) in ethanol (5 mL) was added paraformaldehyde (42 mg, 1.40 mmol), then stirred at 140° C. in microwave for 30 minutes. After consumption of starting material, the reaction mixture was concentrated under reduced pressure. Crude compound was purified by reverse phase chromatography by eluting with 43% of ACN in 0.1% formic acid in water to afford 5-(benzyloxy)-3-((tetrahydro-2H-pyran-4-yl)methyl)-2,3-dihydro-1H-pyrido[2,1-f][1,2,4]triazine-4,6-dione 8-3. TLC: 10% MeOH in DCM; Rf=0.4. LCMS: (ESI): m/z 370.5 (M+H)$^+$.

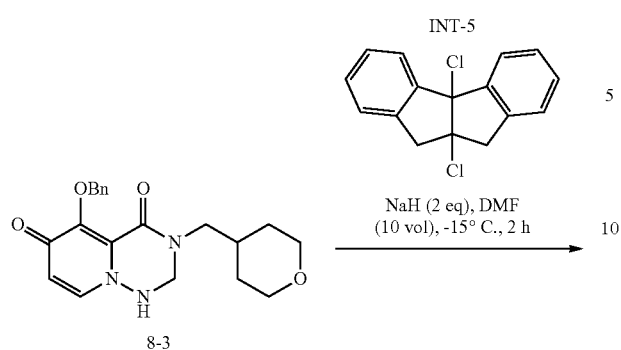
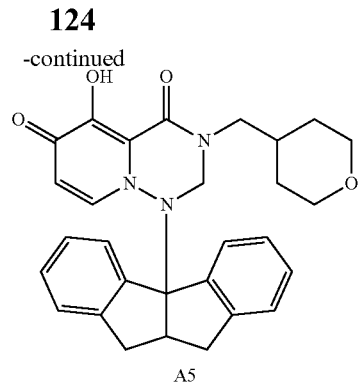

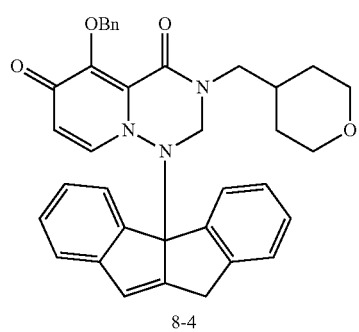

To a stirred solution of 5-(benzyloxy)-3-((tetrahydro-2H-pyran-4-yl)methyl)-2,3-dihydro-1H-pyrido[2,1-f][1,2,4]triazine-4,6-dione 8-3 (225 mg, 0.609 mmol) in dry DMF (2 mL) was added NaH (60% in mineral oil) (61 mg, 1.5 mmol) at −15° C. and stirred for 15 minutes. Then added solution of 4b,9a-dichloro-4b,9,9a,10-tetrahydroindeno[1,2-a]indene INT-5 (250 mg, 0.914 mmol) (see Example 1) in dry DMF (1 mL) at −15° C. then stirred at same temperature for 2 hr. Reaction mixture was quenched with saturated NH₄Cl solution (20 mL) and extracted with EtOAc (2×20 mL). Combined organic layers were washed with brine solution (20 mL), dried over Na₂SO₄ and concentrated under reduced pressure. Crude compound was purified by 100-200 silica gel column chromatography by eluting with 2% MeOH in DCM to afford 5-(benzyloxy)-1-(indeno[1,2-a]inden-4b (9H)-yl)-3-((tetrahydro-2H-pyran-4-yl)methyl)-2,3-dihydro-1H-pyrido[2,1-f][1,2,4]triazine-4,6-dione 8-4. TLC: 10% MeOH in DCM; Rf=0.5. LCMS: (ESI): m/z 572.5 (M+H)⁺.

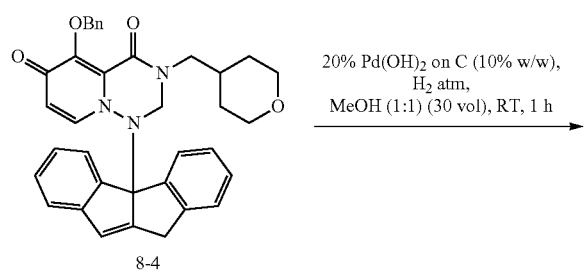

To a stirred solution of 5-(benzyloxy)-1-(4b,9-dihydroindeno[1,2-a]inden-4b-yl)-3-((tetrahydro-2H-pyran-4-yl)methyl)-2,3-dihydro-1H-pyrido[1,2-f][1,2,4]triazine-4,6-dione 8-4 (140 mg, 0.245 mmol) in MeOH and EtOAc (1:1) (30 mL) was treated with 10% w/w of 20% Pd(OH)₂ on carbon (20 mg) and stirred under H₂ balloon atmosphere for 1 hour. Reaction mixture was filtered through Diatomaceous earth; the Diatomaceous earth pad was washed with 10% MeOH in DCM (20 mL) and the wash was concentrated under reduced pressure. Crude compound was purified by Prep HPLC method to afford 1-(9a,10-dihydroindeno[1,2-a]inden-4b(9H)-yl)-5-hydroxy-3-((tetrahydro-2H-pyran-4-yl)methyl)-2,3-dihydro-1H-pyrido[2,1-f][1,2,4]triazine-4,6-dione A5. TLC: 10% MeOH in DCM; Rf=0.3. LCMS: (ESI): m/z 484.45 (M+H)⁺.

Example 9: 1-(9a,10-Dihydro-9H-indeno[1,2-a]inden-4b-yl)-5-hydroxy-3-(2-phenoxy-ethyl)-2,3-dihydro-1H-pyrido[2,1-t][1,2,4]triazine-4,6-dione (A7)

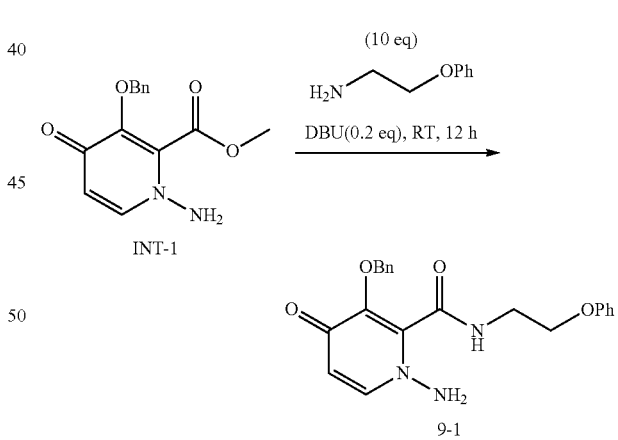

To a stirred solution of methyl 1-amino-3-(benzyloxy)-4-oxo-1,4-dihydropyridine-2-carboxylate INT-1 (200 mg, 0.729 mmol) (see Example 1) was added DBU (22 mg, 0.145 mmol) and 2-phenoxyethan-1-amine (1 g, 7.29 mmol) then stirred at RT for 12 hr. Reaction mixture was distilled off under reduced pressure. Crude compound was purified by reverse phase chromatography by eluting with 10% of ACN in 0.1% formic acid in water to afford pure 1-amino-3-(benzyloxy)-4-oxo-N-(2-phenoxyethyl)-1,4-dihydropyridine-2-carboxamide 9-1. TLC: 5% MeOH in DCM; Rf=0.4. LCMS: (ESI): m/z 380.49 (M+H)⁺.

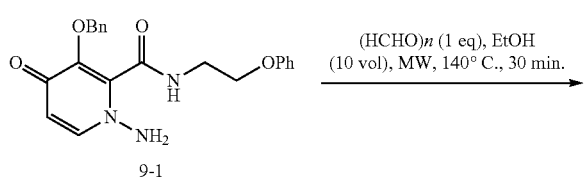

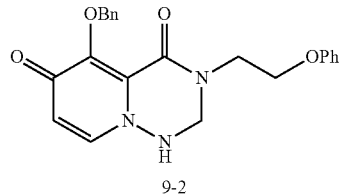

In a microwave vial, to a stirred solution of 1-amino-3-(benzyloxy)-4-oxo-N-(2-phenoxyethyl)-1,4-dihydropyridine-2-carboxamide 9-1 (500 mg, 1.32 mmol) in ethanol (2.5 mL) was added paraformaldehyde (4.3 mg, 1.45 mmol), then irradiated under microwave conditions at 140° C. for 30 minutes. After consumption of starting material, the reaction mixture was concentrated under reduced pressure. Crude compound was purified by reverse phase chromatography by eluting with 50% of ACN in 0.1% formic acid in water to afford 5-(benzyloxy)-3-(2-phenoxyethyl)-2,3-dihydro-1H-pyrido[2,1-f][1,2,4]triazine-4,6-dione 9-2. TLC: 10% MeOH in DCM; Rf=0.5. LCMS: (ESI): m/z 392.3 (M+H)+.

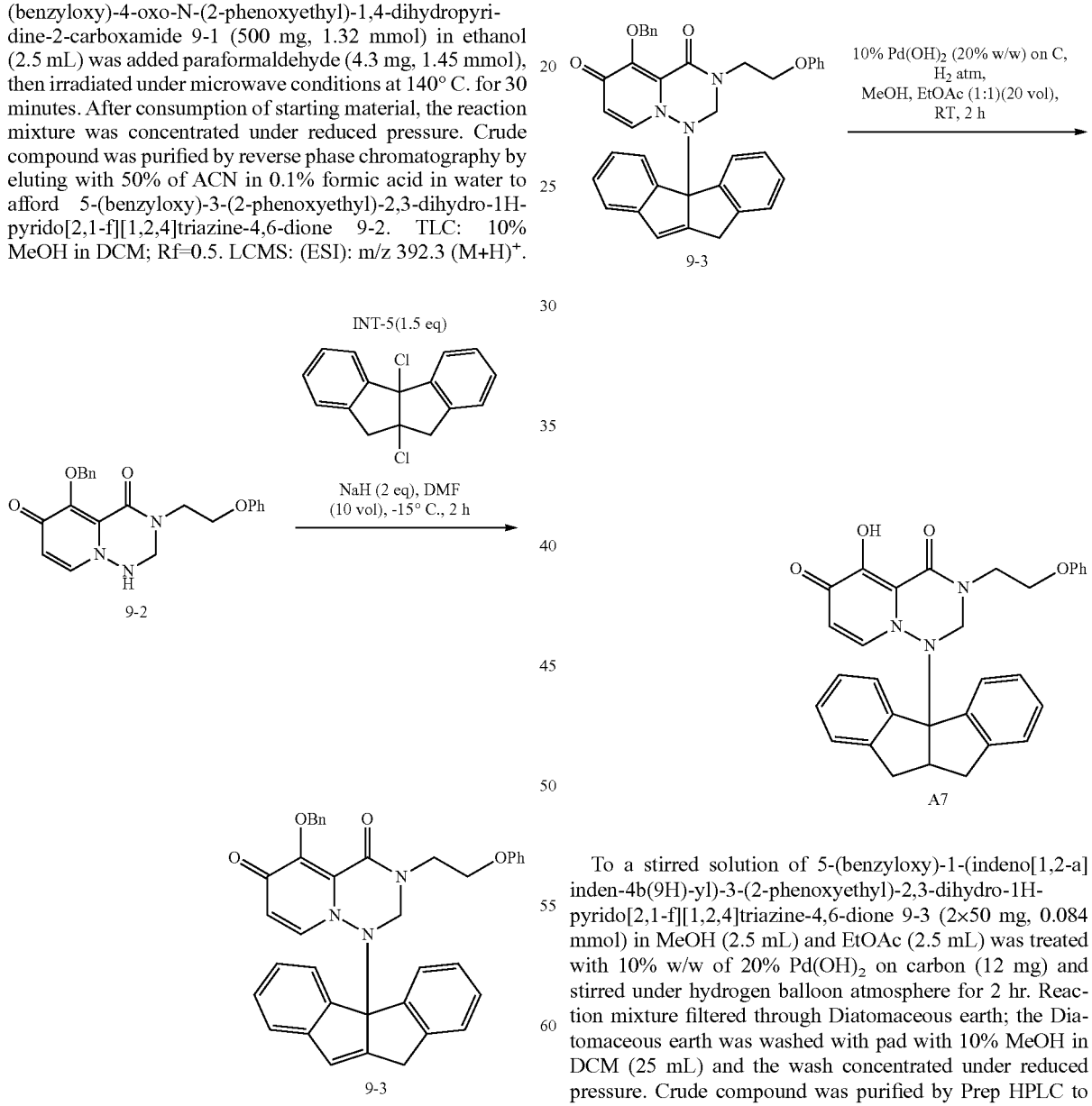

To a stirred solution of 5-(benzyloxy)-3-(2-phenoxyethyl)-2,3-dihydro-1H-pyrido[2,1-f][1,2,4]triazine-4,6-dione 9-2 (150 mg, 0.383 mmol) in dry DMF (5 mL) was added NaH (60% in mineral oil) (30.6 g, 1.28 mmol) at −15° C. and stirred for 10 minutes. Then added solution of 4b,9a-dichloro-4b,9,9a,10-tetrahydroindeno[1,2-a]indene INT-5 (157 mg, 0.575 mmol) (see Example 1) in dry DMF (2 mL) at −15° C. then stirred 2 hr. Reaction mixture quenched with saturated NH4Cl solution (10 mL) and extracted with EtOAc (2×20 mL). Combined organic layers were washed with brine solution (25 mL), dried over Na2SO4 and concentrated under reduced pressure. Crude compound was purified by reverse phase chromatography by eluting with 70% of ACN in 0.1% formic acid in water to afford 5-(benzyloxy)-1-(indeno[1,2-a]inden-4b(9H)-yl)-3-(2-phenoxyethyl)-2,3-dihydro-1H-pyrido[2,1-f][1,2,4]triazine-4,6-dione 9-3. TLC: 10% MeOH in DCM; Rf=0.3. LCMS: (ESI): m/z 594.4 (M+H)+.

To a stirred solution of 5-(benzyloxy)-1-(indeno[1,2-a]inden-4b(9H)-yl)-3-(2-phenoxyethyl)-2,3-dihydro-1H-pyrido[2,1-f][1,2,4]triazine-4,6-dione 9-3 (2×50 mg, 0.084 mmol) in MeOH (2.5 mL) and EtOAc (2.5 mL) was treated with 10% w/w of 20% Pd(OH)2 on carbon (12 mg) and stirred under hydrogen balloon atmosphere for 2 hr. Reaction mixture filtered through Diatomaceous earth; the Diatomaceous earth was washed with pad with 10% MeOH in DCM (25 mL) and the wash concentrated under reduced pressure. Crude compound was purified by Prep HPLC to afford 1-(9a,10-dihydroindeno[1,2-a]inden-4b(9H)-7yl)-5-hydroxy-3-(2-phenoxyethyl)-2,3-dihydro-1H-pyrido[2,1-f][1,2,4]triazine-4,6-dione A7. TLC: 10% MeOH in DCM; Rf=0.2. LCMS: (ESI): m/z 506.42 (M+H)+.

Example 10: 3-Cyclopropylmethyl-1-(1,2-difluoro-9a,10-dihydro-9H-indeno[1,2-a]inden-4b-yl)-5-hydroxy-2,3-dihydro-1H-pyrido[2,1-f][1,2,4]triazine-4,6-dione (A9)

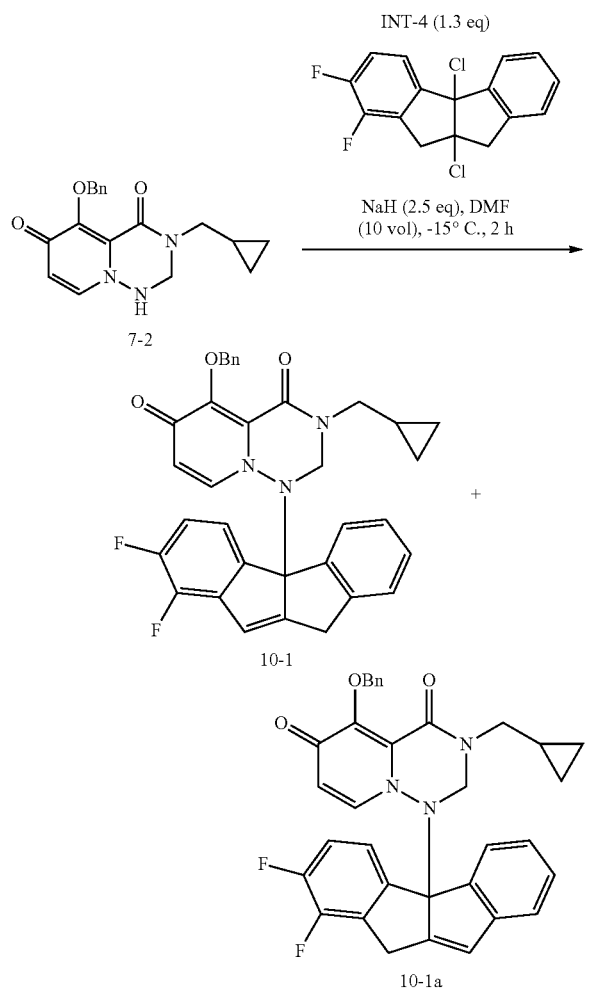

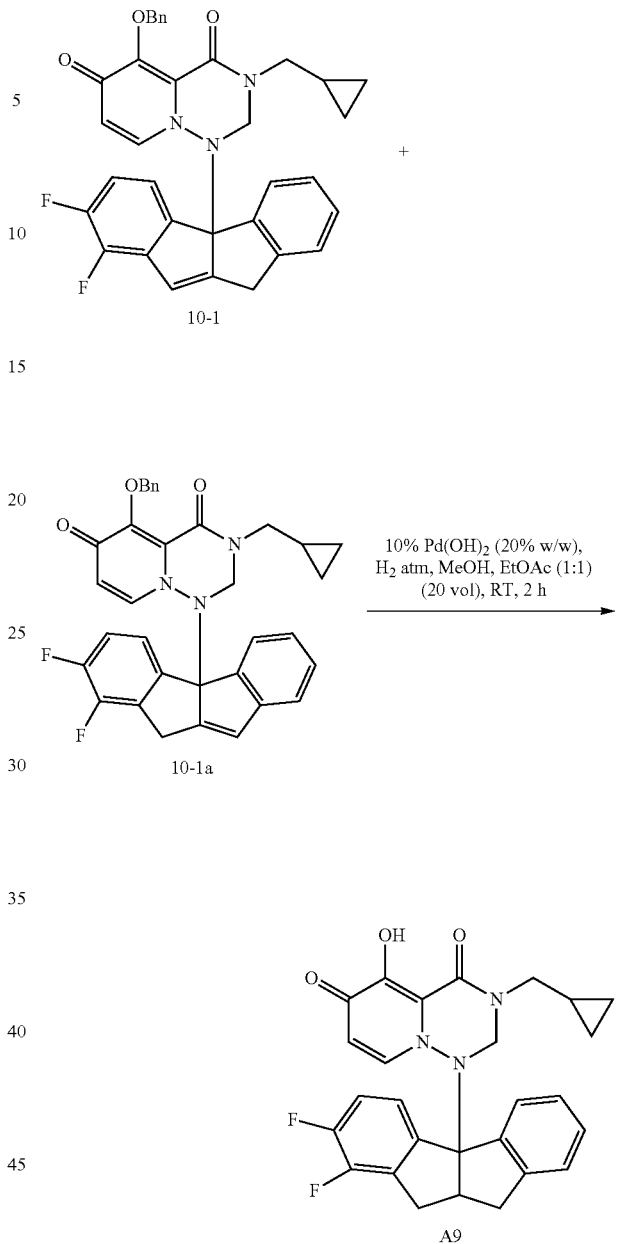

To a stirred solution of 5-(benzyloxy)-3-(cyclopropylmethyl)-2,3-dihydro-1H-pyrido[2,1-f][1,2,4]triazine-4,6-dione 7-2 (200 mg, 0.6153 mmol) in DMF (3 mL) was added 60% of NaH (61 mg, 1.5 mmol) at −15° C. and stirred for 15 minutes. Then added solution of 4b,9a-dichloro-1,2-difluoro-4b,9,9a,10-tetrahydroindeno[1,2-a]indene INT-4 (247 mg, 0.800 mmol) (see Example 14) in DMF (1 mL) at −15° C. then stirred for 2 hr. Reaction mixture quenched with saturated NH$_4$Cl solution (20 mL) and extracted with EtOAc (2×20 mL). Combined organic layers were washed with brine solution (20 mL), dried over Na$_2$SO$_4$ and concentrated under reduced pressure. Crude compound was purified through reverse phase chromatography by eluting with 58% ACN in 0.1% formic acid in water to afford isomeric mixture of 5-(benzyloxy)-3-(cyclopropylmethyl)-1-(1,2-difluoro-4b,9-dihydroindeno[1,2-a]inden-4b-yl)-2,3-dihydro-1H-pyrido[1,2-f][1,2,4]triazine-4,6-dione 10-1 and 5-(benzyloxy)-3-(cyclopropylmethyl)-1-(7,8-difluoroindeno[1,2-a]inden-4b(9H)-yl)-2,3-dihydro-1H-pyrido[2,1-f][1,2,4]triazine-4,6-dione 10-1a. TLC: 10% MeOH in DCM; Rf=0.6. LCMS: (ESI): m/z 564.60 (M+H)$^+$.

To a stirred solution of 5-(benzyloxy)-3-(cyclopropylmethyl)-1-(1,2-difluoro-4b,9-dihydroindeno[1,2-a]inden-4b-yl)-2,3-dihydro-1H-pyrido[1,2-f][1,2,4]triazine-4,6-dione 10-1 and 5-(benzyloxy)-3-(cyclopropylmethyl)-1-(7,8-difluoroindeno[1,2-a]inden-4b(9H)-yl)-2,3-dihydro-1H-pyrido[2,1-f][1,2,4]triazine-4,6-dione 10-1a (50 mg, 0.089 mmol) in MeOH (1 mL) and EtOAc (1 mL) was treated with 10% w/w of 20% Pd(OH)$_2$ on carbon (20 mg) and stirred under balloon hydrogen atmosphere for 1 hour. Reaction mixture was filtered through Diatomaceous earth and washed the Diatomaceous earth bed with 10% MeOH in DCM (20 mL) and concentrated under reduced pressure. Crude compound was purified through Prep HPLC method to afford 3-(cyclopropylmethyl)-1-(1,2-difluoro-4b,9,9a,10-tetrahydroindeno[1,2-a]inden-4b-yl)-5-hydroxy-2,3-dihydro-1H-pyrido[1,2-f][1,2,4]triazine-4,6-dione A9. TLC: 10% MeOH in DCM; Rf=0.5. LCMS: (ESI): m/z 476.38 (M+H)$^+$.

Example 11: 3-Cyclopropylmethyl-1-(2,3-difluoro-9a,10-dihydro-9H-indeno[1,2-a]inden-4b-yl)-5-hydroxy-2,3-dihydro-1H-pyrido[2,1-f][1,2,4]triazine-4,6-dione (A13)

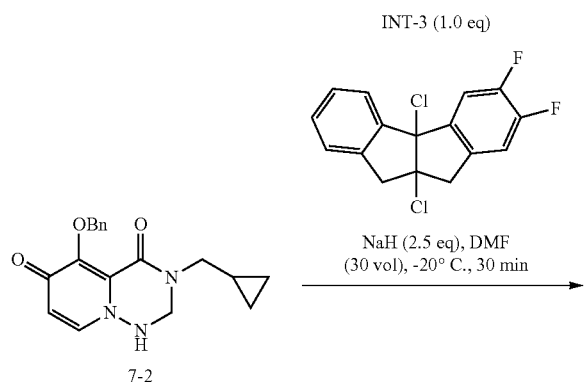

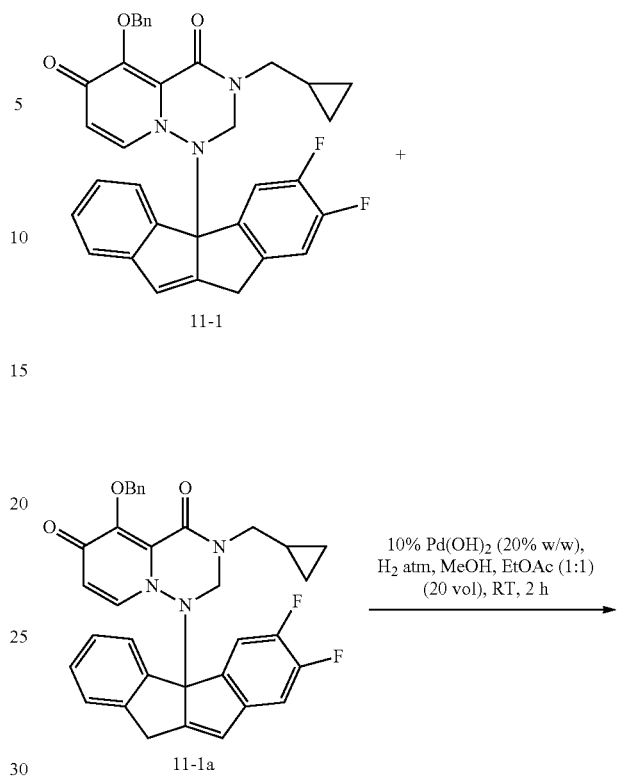

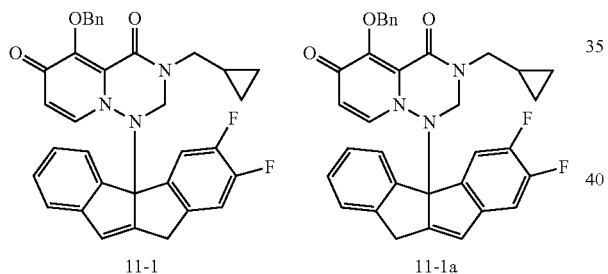

To a stirred solution of 5-(benzyloxy)-3-(cyclopropylmethyl)-2,3-dihydro-1H-pyrido[2,1-f][1,2,4]triazine-4,6-dione 7-2 (300 mg, 0.9 mmol) in DMF (6 mL) was added 60% of NaH (92 mg, 2.3 mmol) at −15° C. and stirred for 20 minutes. Then added solution of 4b,9a-dichloro-1,2-difluoro-4b,9,9a,10-tetrahydroindeno[1,2-a]indene INT-3 (286 mg, 0.9 mmol) (see Example 13) in DMF (3 mL) at −20° C. then stirred for 30 minutes. Reaction mixture was quenched with saturated NH$_4$Cl solution (20 mL) and extracted with EtOAc (2×20 mL). Combined organic layers were washed with brine solution (20 mL), dried over Na$_2$SO$_4$ and concentrated under reduced pressure. Crude compound was purified through reverse phase chromatography by eluting with 76% ACN in 0.1% formic acid in water to afford isomeric mixture of 5-(benzyloxy)-3-(cyclopropylmethyl)-1-(6,7-difluoroindeno[1,2-a]inden-4b(9H)-yl)-2,3-dihydro-1H-pyrido[2,1-f][1,2,4]triazine-4,6-dione 11-1 and 5-(benzyloxy)-3-(cyclopropylmethyl)-1-(2,3-difluoroindeno[1,2-a]inden-4b(9H)-yl)-2,3-dihydro-1H-pyrido[2,1-f][1,2,4]triazine-4,6-dione 11-1a. TLC: 10% MeOH in DCM; Rf=0.6. LCMS: (ESI): m/z 564.44 (M+H)$^+$.

To a stirred solution of 5-(benzyloxy)-3-(cyclopropylmethyl)-1-(6,7-difluoroindeno[1,2-a]inden-4b(9H)-yl)-2,3-dihydro-1H-pyrido[2,1-f][1,2,4]triazine-4,6-dione 11-1 & 5-(benzyloxy)-3-(cyclopropylmethyl)-1-(2,3-difluoroindeno[1,2-a]inden-4b(9H)-yl)-2,3-dihydro-1H-pyrido[2,1-f][1,2,4]triazine-4,6-dione 11-1a (50 mg, 0.089 mmol) in MeOH (3 mL) and EtOAc (3 mL) was treated with 10% w/w of 20% Pd(OH)$_2$ on carbon (10 mg) and stirred under balloon H$_2$ atmosphere for 2 hr. Reaction mixture was filtered through Diatomaceous earth and washed the Diatomaceous earth bed with 10% MeOH in DCM (20 mL) and concentrated under reduced pressure. Crude compound was purified through Prep HPLC method to afford 3-(cyclopropylmethyl)-1-(2,3-difluoro-9a,10-dihydroindeno[1,2-a]inden-4b(9H)-yl)-5-hydroxy-2,3-dihydro-1H-pyrido[2,1-f][1,2,4]triazine-4,6-dione A13. TLC: 10% MeOH in DCM; Rf=0.5. LCMS: (ESI): m/z 476.13 (M+H)$^+$.

Example 12: 1-(1,2-Difluoro-9a,10-dihydro-9H-indeno[1,2-a]inden-4b-yl)-3-ethyl-5-hydroxy-2,3-dihydro-1H-pyrido[2,1-f][1,2,4]triazine-4,6-dione (A14)

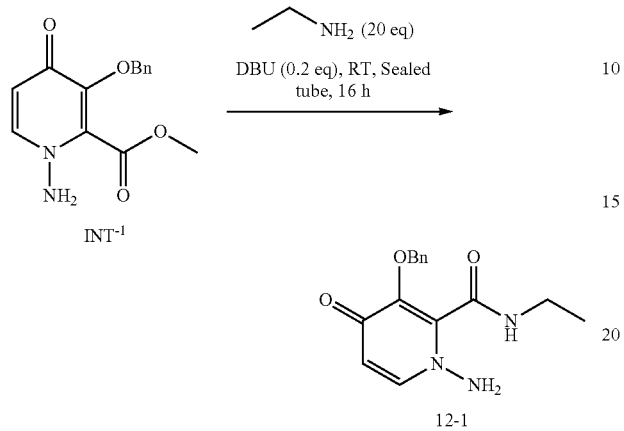

To a stirred solution of methyl 1-amino-3-(benzyloxy)-4-oxo-1,4-dihydropyridine-2-carboxylate INT-1 (2.0 g, 7.3 mmol) in DBU (0.227 mL, 1.46 mmol) was added ethyl amine (30 mL, 15 Vol) and then stirred at RT for 16 hr. Reaction progress was monitored by TLC. Reaction mixture was completely distilled off under reduced pressure. Crude compound was purified through reverse phase chromatography by eluting with 40% ACN in 0.1% formic acid in water to afford 1-amino-3-(benzyloxy)-N-ethyl-4-oxo-1,4-dihydropyridine-2-carboxamide 12-1. TLC: 10% MeOH in DCM; Rf=0.2. LCMS: (ESI): m/z 288.43 (M+H).

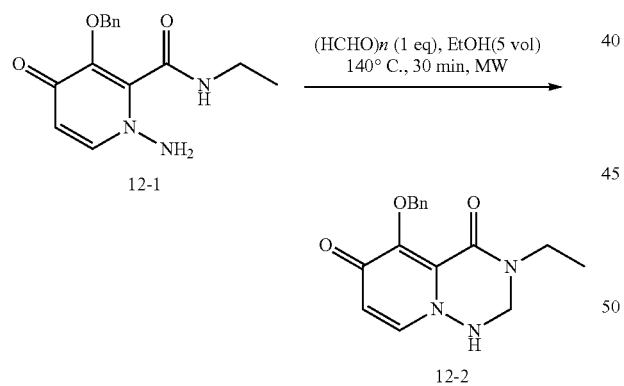

In a microwave vial, 1-amino-3-(benzyloxy)-N-ethyl-4-oxo-1,4-dihydropyridine-2-carboxamide 12-1 (500 mg, 1.74 mmol) was added in ethanol (15 mL) and followed by paraformaldehyde (52 mg, 1.7 mmol), then irradiated at 140° C. under microwave reactor for 30 minutes. After consumption of starting material, the reaction mixture was concentrated under reduced pressure. Crude compound was purified through reverse phase chromatography by eluting with 30% ACN in 0.1% formic acid in water to afford 5-(benzyloxy)-3-ethyl-2,3-dihydro-1H-pyrido[1,2-f][1,2,4]triazine-4,6-dione 12-2. TLC: 10% MeOH in DCM; Rf=0.3. LCMS: (ESI): m/z 300.42 (M+H)+.

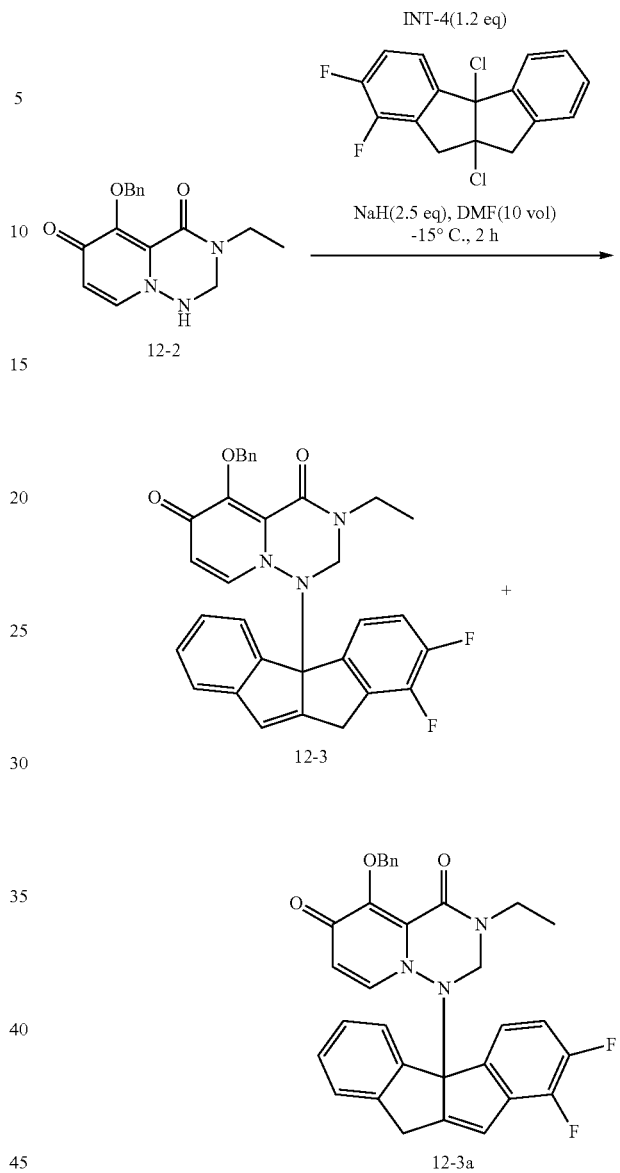

To a stirred solution of 5-(benzyloxy)-3-ethyl-2,3-dihydro-1H-pyrido[1,2-f][1,2,4]triazine-4,6-dione 12-2 (400 mg, 1.34 mmol) in DMF (15 mL) was added 60% of NaH (133 mg, 3.34 mmol) at −15° C. and stirred for 15 minutes. Then added solution of 4b,9a-dichloro-1,2-difluoro-4b,9,9a,10-tetrahydroindeno[1,2-a]indene INT-4 (497 mg, 1.61 mmol) (see Example 14) in DMF (5 mL) at −15° C. then stirred for 2 hr. Reaction mixture was quenched with saturated NH4Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 65% ACN in 0.1% formic acid in water to afford isomeric mixture of 5-(benzyloxy)-1-(7,8-difluoroindeno[1,2-a]inden-4b(9H)-yl)-3-ethyl-2,3-dihydro-1H-pyrido[2,1-f][1,2,4]triazine-4,6-dione 12-3 and 5-(benzyloxy)-1-(1,2-difluoroindeno[1,2-a]inden-4b(9H)-yl)-3-ethyl-2,3-dihydro-1H-pyrido[2,1-f][1,2,4]triazine-4,6-dione 12-3a. TLC: 10% MeOH in DCM; Rf=0.4. LCMS: (ESI): m/z 538.43 (M+H)+.

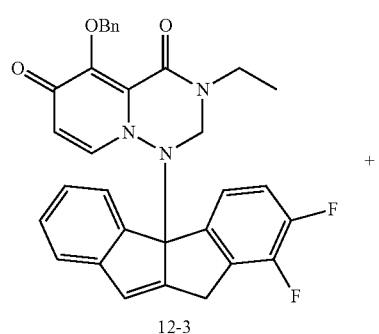

12-3

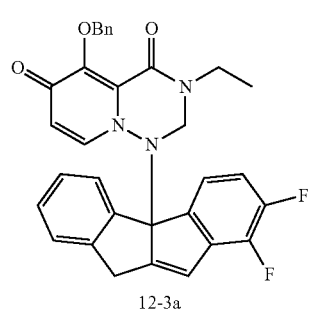

12-3a

10% Pd(OH)₂, H₂ atm,
MeOH, EtOAc (1:1), RT. 1 h
→

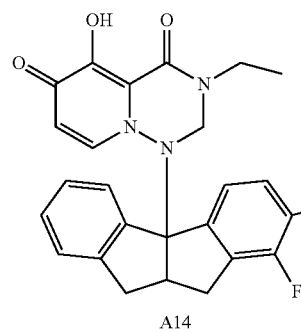

A14

To a stirred solution of 5-(benzyloxy)-1-(7,8-difluoroindeno[1,2-a]inden-4b(9H)-yl)-3-ethyl-2,3-dihydro-1H-pyrido[2,1-f][1,2,4]triazine-4,6-dione 12-3 and 5-(benzyloxy)-1-(1,2-difluoroindeno[1,2-a]inden-4b(9H)-yl)-3-ethyl-2,3-dihydro-1H-pyrido[2,1-f][1,2,4]triazine-4,6-dione 12-3a (60 mg, 0.11 mmol) in MeOH (2 mL) and EtOAc (2 mL) was treated with 10% w/w of 20% Pd(OH)₂ on carbon (10 mg) and stirred under hydrogen balloon pressure for 1 hour. Reaction mixture was filtered through Diatomaceous earth and washed the Diatomaceous earth bed with MeOH (20 mL) and filtrate was concentrated under reduced pressure. Crude compound was purified by prep-HPLC to afford compound 1-(1,2-difluoro-9a,10-dihydroindeno[1,2-a]inden-4b(9H)-yl)-3-ethyl-5-hydroxy-2,3-dihydro-1H-pyrido[2,1-f][1,2,4]triazine-4,6-dione A14. TLC: 10% MeOH in DCM; Rf=0.3. LCMS: (ESI): m/z 450.09 (M+H)⁺.

Example 13: 1-(2,3-Difluoro-9a,10-dihydro-9H-indeno[1,2-a]inden-4b-yl)-3-ethyl-5-hydroxy-2,3-dihydro-1H-pyrido[2,1-f][1,2,4]triazine-4,6-dione (A10)

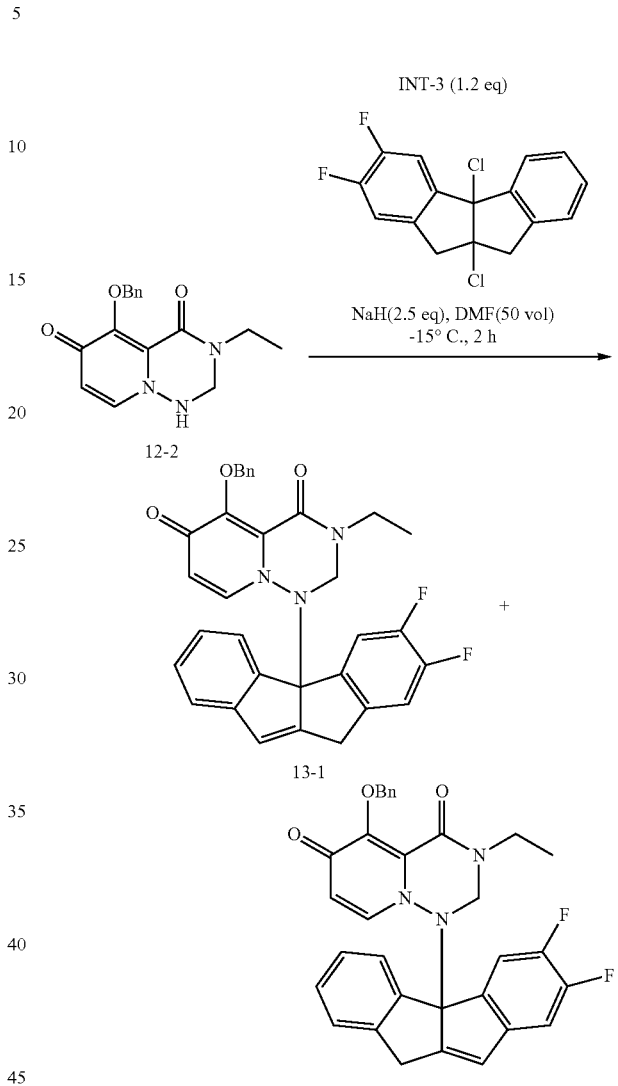

To a stirred solution of 5-(benzyloxy)-3-ethyl-2,3-dihydro-1H-pyrido[1,2-f][1,2,4]triazine-4,6-dione 12-2(320 mg, 1.07 mmol) in DMF (15 mL) was added 60% of NaH (107 mg, 2.68 mmol) at −15° C. and stirred for 15 minutes. Then added solution of 4b,9a-dichloro-2,3-difluoro-4b,9,9a,10-tetrahydroindeno[1,2-a]indene INT-3 (398 mg, 1.28 mmol) in dry DMF (5 mL) at −15° C. then stirred 2 hr. Reaction mixture quenched with saturated NH₄Cl solution (40 mL) and extracted with EtOAc (2×30 mL). Combined organic layers were washed with brine solution (30 mL), dried over Na₂SO₄ and concentrated under reduced pressure. Crude compound was purified through reverse phase chromatography by eluting with 65% ACN in 0.1% formic acid in water to afford 5-(benzyloxy)-1-(6,7-difluoro-4b,9-dihydroindeno[1,2-a]inden-4b-yl)-3-ethyl-2,3-dihydro-1H-pyrido[1,2-f][1,2,4]triazine-4,6-dione 13-1 and 5-(benzyloxy)-1-(2,3-difluoroindeno[1,2-a]inden-4b(9H)-yl)-3-ethyl-2,3-dihydro-1H-pyrido[2,1-f][1,2,4]triazine-4,6-dione 13-1a. TLC: 10% MeOH in DCM; Rf=0.4. LCMS: (ESI): m/z 538.14 (M+H)⁺.

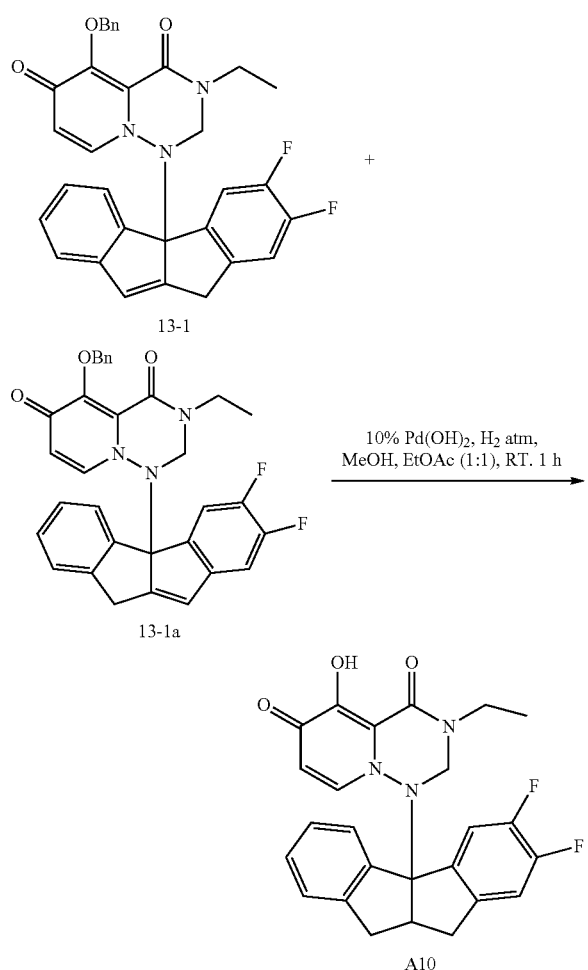

To a stirred solution of 5-(benzyloxy)-1-(6,7-difluoro-4b,9-dihydroindeno[1,2-a]inden-4b-yl)-3-ethyl-2,3-dihydro-1H-pyrido[1,2-f][1,2,4]triazine-4,6-dione 13-1 and 5-(benzyloxy)-1-(2,3-difluoroindeno[1,2-a]inden-4b(9H)-yl)-3-ethyl-2,3-dihydro-1H-pyrido[2,1-f][1,2,4]triazine-4,6-dione 13-1a (70 mg, 0.13 mmol) in MeOH (5 mL) and EtOAc (5 mL) was treated with 10% w/w of 20% Pd(OH)₂ on carbon (20 mg) and stirred under balloon H₂ atmosphere for 1 hour. Reaction mixture filtered through Diatomaceous earth and washed the Diatomaceous earth bed with MeOH (20 mL) and concentrated under reduced pressure. Crude compound was triturated with diethyl ether to afford 1-(2,3-difluoro-4b,9,9a,10-tetrahydroindeno[1,2-a]inden-4b-yl)-3-ethyl-5-hydroxy-2,3-dihydro-1H-pyrido[1,2-f][1,2,4]triazine-4,6-dione A10. TLC: 10% MeOH in DCM; Rf=0.3. LCMS: (ESI): m/z 450.09 (M+H)⁺.

INT-3 preparation

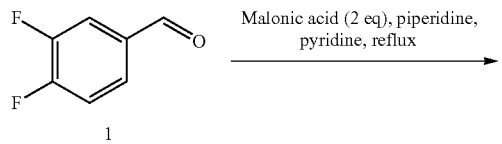

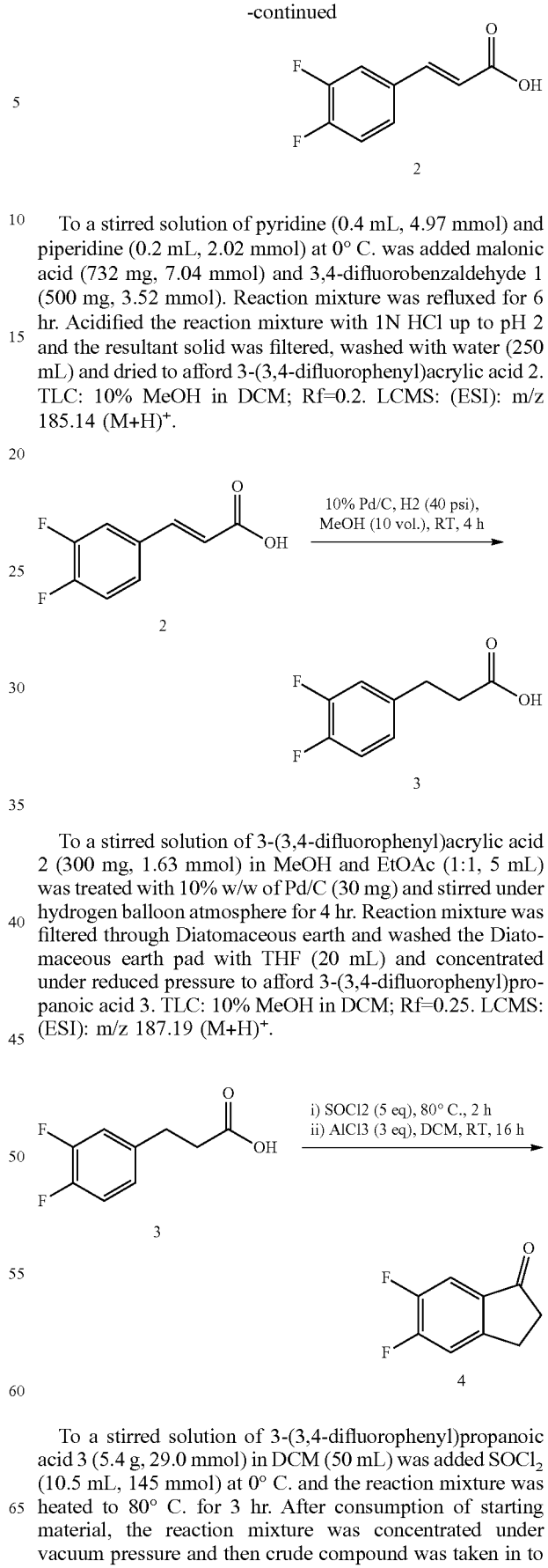

To a stirred solution of pyridine (0.4 mL, 4.97 mmol) and piperidine (0.2 mL, 2.02 mmol) at 0° C. was added malonic acid (732 mg, 7.04 mmol) and 3,4-difluorobenzaldehyde 1 (500 mg, 3.52 mmol). Reaction mixture was refluxed for 6 hr. Acidified the reaction mixture with 1N HCl up to pH 2 and the resultant solid was filtered, washed with water (250 mL) and dried to afford 3-(3,4-difluorophenyl)acrylic acid 2. TLC: 10% MeOH in DCM; Rf=0.2. LCMS: (ESI): m/z 185.14 (M+H)⁺.

To a stirred solution of 3-(3,4-difluorophenyl)acrylic acid 2 (300 mg, 1.63 mmol) in MeOH and EtOAc (1:1, 5 mL) was treated with 10% w/w of Pd/C (30 mg) and stirred under hydrogen balloon atmosphere for 4 hr. Reaction mixture was filtered through Diatomaceous earth and washed the Diatomaceous earth pad with THF (20 mL) and concentrated under reduced pressure to afford 3-(3,4-difluorophenyl)propanoic acid 3. TLC: 10% MeOH in DCM; Rf=0.25. LCMS: (ESI): m/z 187.19 (M+H)⁺.

To a stirred solution of 3-(3,4-difluorophenyl)propanoic acid 3 (5.4 g, 29.0 mmol) in DCM (50 mL) was added SOCl₂ (10.5 mL, 145 mmol) at 0° C. and the reaction mixture was heated to 80° C. for 3 hr. After consumption of starting material, the reaction mixture was concentrated under vacuum pressure and then crude compound was taken in to DCM and cooled to 0° C. then added AlCl₃ (4.63 g, 34.8 mmol) portion wise at 0° C. to the reaction mixture and stirred at RT for 16 hr. After consumption of starting material, the reaction mixture was poured in ice water and extracted with DCM. Organic layer was washed with brine solution, dried with Na₂SO₄ and concentrated to get crude. Crude compound was purified by column chromatography to afford 5,6-difluoro-2,3-dihydro-1H-inden-1-one 4. TLC: 20% EtOAc in pet ether; Rf=0.5. LCMS: (ESI): m/z 169.1 (M+H)⁺.

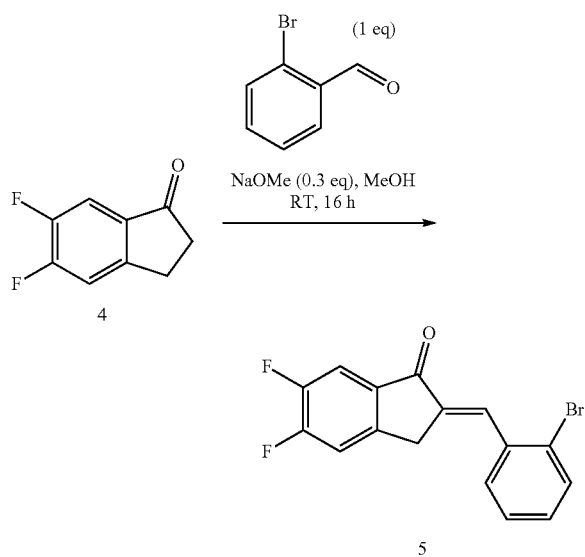

To a stirred solution of 5,6-difluoro-2,3-dihydro-1H-inden-1-one 4 (1 g, 6 mmol) in MeOH (25 mL) was added sodium methoxide (96 mg, 1.8 mmol) and 2-bromobenzaldehyde (1.14 g, 6.24 mmol) in MeOH (20 mL) drop-wise slowly at 0° C. to RT for 16 hr. The reaction mixture was acidified with 1 N HCl (5 mL) to pH 3-4, and precipitated solid was filtered and dried to afford (E)-2-(2-bromobenzylidene)-5,6-difluoro-2,3-dihydro-1H-inden-1-one 5. TLC: 20% EtOAc in pet ether; Rf=0.6. LCMS: (ESI): m/z 335.17 (M+H)⁺.

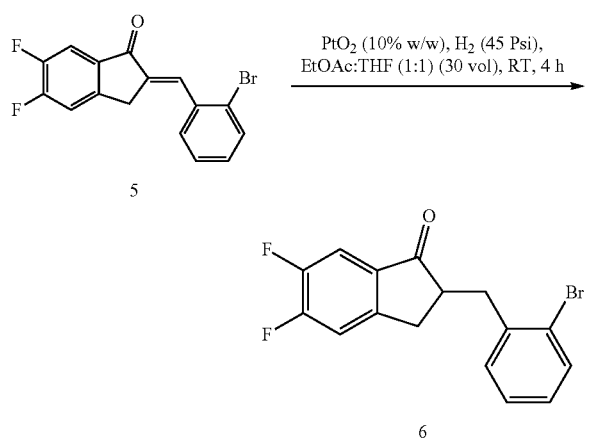

To a stirred solution of (E)-2-(2-bromobenzylidene)-5,6-difluoro-2,3-dihydro-1H-inden-1-one 5 (1 g, 3 mmol) in THF and EtOAc (1:1, 50 mL) was treated with PtO₂ (100 mg) and stirred under balloon hydrogen atmosphere for 3 hr. Reaction mixture filtered through Diatomaceous earth and washed the Diatomaceous earth bed with THF (30 mL) and concentrated under reduced pressure and the crude was purified by silica column to afford 2-(2-bromobenzyl)-5,6-difluoro-2,3-dihydro-1H-inden-1-one 6. TLC: 20% EtOAc in pet ether Rf: 0.65. LCMS: (ESI): m/z 336.9 (M+H)⁺.

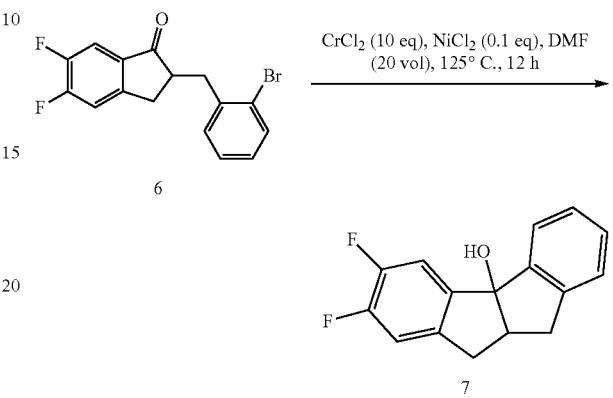

To a stirred solution of 2-(2-bromobenzyl)-5,6-difluoro-2,3-dihydro-1H-inden-1-one 6 (4.5 g, 13 mmol) in dry DMF (60 mL) was added NiCl₂ (172.7 mg, 1.339 mmol), and Cr₂Cl₂ (16.3 g, 134 mmol) then stirred at 120° C. for 12 hr. After consumption of starting material, the reaction mixture was quenched with ice water extracted with ether (2×200 mL). Organic layer washed with ice-cold water (2×100 mL), brine solution and dried over Na₂SO₄ and concentrated under reduced pressure to afford crude 2,3-difluoro-9a,10-dihydroindeno[1,2-a]inden-4b(9H)-ol 7. TLC: 20% EtOAc in pet ether; Rf=0.2. LCMS: (ESI): m/z 241.21 (M-OH)*.

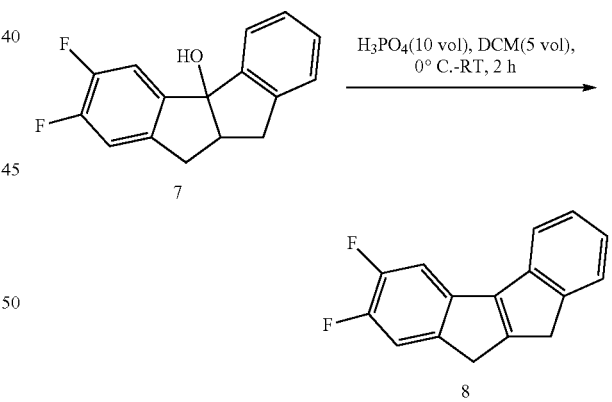

To a stirred solution of 2,3-difluoro-9a,10-dihydroindeno[1,2-a]inden-4b(9H)-ol 7 (crude) (6 g, 23 mmol) in DCM (60 mL) was added H₃PO₄ (60 mL) at 0° C. and stirred for 2 hr. After consumption of starting material (as determined by TLC) the reaction mixture was quenched with ice water (200 mL) and extracted with EtOAc (2×300 mL). Combined organic layers were washed with brine solution (100 mL), dried over Na₂SO₄ and concentrated under reduced pressure. Crude compound was purified silica by eluting with 2% EtOAc/pet ether to afford 2,3-difluoro-9,10-dihydroindeno[1,2-a]indene 8. TLC: 5% EtOAc in pet ether; Rf=0.4. LCMS: (ESI): m/z 241.21 (M+H)⁺.

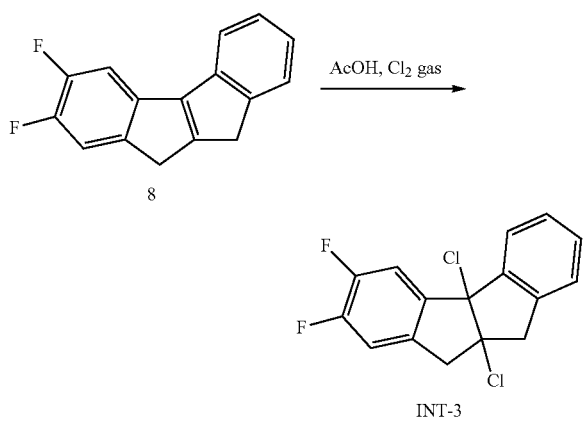

To a stirred solution of 2,3-difluoro-9,10-dihydroindeno[1,2-a]indene 8 (3.6 g, 15 mmol) in AcOH (28 mL) purged the Cl₂ gas for 25 min. at RT (Chlorine gas was generated in situ using NaClO₄ and conc. HCl). After consumption of starting material (as determined by TLC) the reaction mixture was quenched with ice water (100 mL) and basified with sodium bicarbonate solution and extracted with ether (2×200 mL). Combined organic layers were washed with brine solution (60 mL), dried over Na₂SO₄ and concentrated under reduced pressure. Crude compound was purified through chromatography to afford 4b,9a-dichloro-2,3-difluoro-4b,9,9a,10-tetrahydroindeno[1,2-a]indene INT-3. TLC: 100% Pet ether; Rf=0.3.

Example 14: 3-Benzyl-1-(1,2-difluoro-9a,10-dihydro-9H-indeno[1,2-a]inden-4b-yl)-5-hydroxy-2,3-dihydro-1H-pyrido[2,1-t][1,2,4]triazine-4,6-dione (A11)

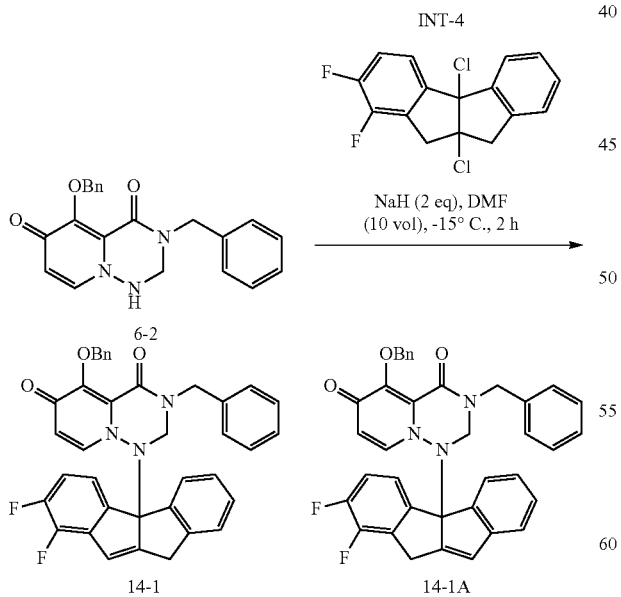

To a stirred solution of 3-benzyl-5-(benzyloxy)-2,3-dihydro-1H-pyrido[2,1-f][1,2,4]triazine-4,6-dione 6-2 (400 mg, 1.11 mmol) in DMF (4 mL) was added 60% of NaH (110 mg, 2.77 mmol) at −15° C. and stirred for 15 minutes.

Then added solution of 4b,9a-dichloro-1,2-difluoro-4b,9,9a,10-tetrahydroindeno[1,2-a]indene INT-4 (446 mg, 1.44 mmol) (see below) in DMF (4 mL) at −15° C. then stirred for 2 hr. Reaction mixture was quenched with saturated NH₄Cl solution (20 mL) and extracted with EtOAc (2×50 mL). Combined organic layers were washed with brine solution (10 mL), dried over Na₂SO₄ and concentrated under reduced pressure. Crude compound was purified through reverse phase chromatography by eluting with 80% ACN in 0.1% formic acid in water to afford 3-benzyl-5-(benzyloxy)-1-(1,2-difluoro-4b,9-dihydroindeno[1,2-a]inden-4b-yl)-2,3-dihydro-1H-pyrido[1,2-f][1,2,4]triazine-4,6-dione 14-1 and 3-benzyl-5-(benzyloxy)-1-(7,8-difluoroindeno[1,2-a]inden-4b(9H)-yl)-2,3-dihydro-1H-pyrido[2,1-f][1,2,4]triazine-4,6-dione 14-1a. TLC: 5% MeOH in DCM; Rf=0.4. LCMS: (ESI): m/z 600.38 (M+H)⁺.

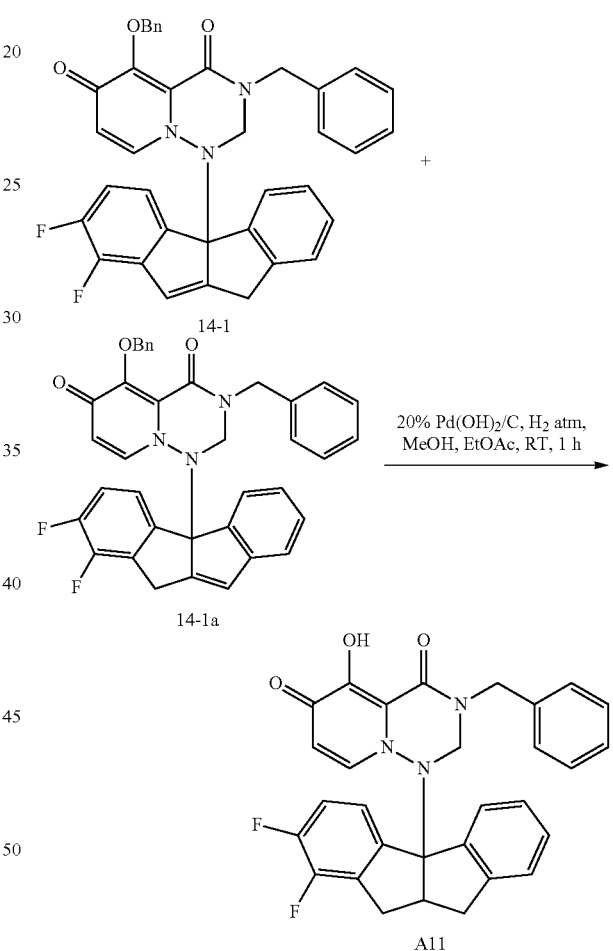

To a stirred solution of 3-benzyl-5-(benzyloxy)-1-(1,2-difluoro-4b,9-dihydroindeno[1,2-a]inden-4b-yl)-2,3-dihydro-1H-pyrido[1,2-f][1,2,4]triazine-4,6-dione 14-1 and 3-benzyl-5-(benzyloxy)-1-(7,8-difluoroindeno[1,2-a]inden-4b(9H)-yl)-2,3-dihydro-1H-pyrido[2,1-f][1,2,4]triazine-4,6-dione 14-1a (80 mg, 0.13 mmol) in MeOH (5 mL) and EtOAc (5 mL) was treated with 10% w/w of 20% Pd(OH)₂ on carbon (10 mg) and stirred under balloon hydrogen atmosphere for 1 hour. Reaction mixture was filtered through Diatomaceous earth and the Diatomaceous earth bed washed with 10% MeOH in DCM (20 mL), and the wash was concentrated under reduced pressure. Crude compound was purified through Prep HPLC method to afford 3-benzyl-1-(1,2-difluoro-4b,9,9a,10-tetrahydroindeno[1,2-a]inden-4b-yl)-5-hydroxy-2,3-dihydro-1H-pyrido[1,2-f][1,2,4]triazine-4,6-dione A11. TLC: 10% MeOH in DCM; Rf=0.3. LCMS: (ESI): m/z 512.08 (M+H)⁺.

Synthesis of INT-4

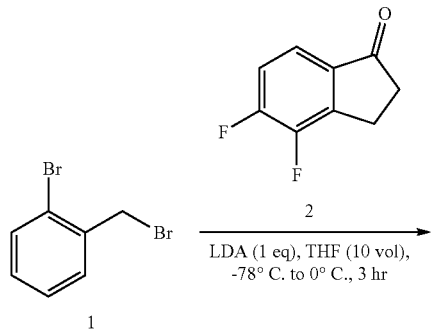

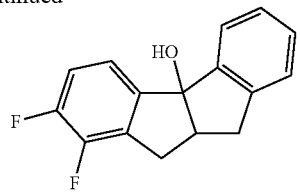

To a stirred solution of 2-(2-bromobenzyl)-4,5-difluoro-2,3 dihydro-1H-inden-1-one 3 (1.3 g, 3.9 mmol) in dry DMF (10 mL) was added $NiCl_2$ (49 mg, 0.39 mmol) and $CrCl_2$ (4.7 g, 39 mmol) then stirred at 120° C. for 12 hr. After consumption of starting material, the reaction mixture was quenched with ice water extracted with ether (2×200 mL). The combined organic layer was dried over $Na_2SO_4$ and concentrated under reduced pressure. The resultant crude was purified by silica gel column chromatography to afford 1,2-difluoro-4b,9,9a,10-tetrahydroindeno[1,2-a]inden-4b-ol 4. TLC: 5% EtOAc in pet ether; Rf=0.1. LCMS: (ESI): m/z 241.31 (M-OH).

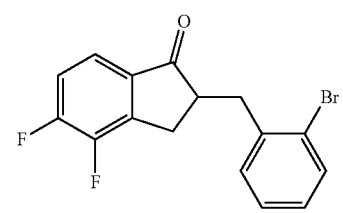

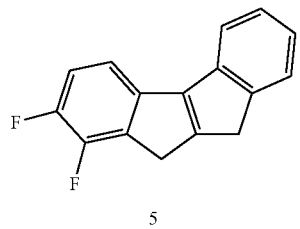

To a stirred solution of 4,5-difluoro-2,3-dihydro-1H-inden-1-one 2 (3.75 g, 22.3 mmol) in THF (110 mL) was added LDA (16.7 mL, 2 M in THF, 1.5 eq.) drop wise at −78° C. and the reaction mixture was warmed to −20° C. for 2 hr and again cooled to −78° C. To that added 1-bromo-2-(bromomethyl)benzene 1 (5.57 g, 22.3 mmol) dissolved in 100 mL of THF drop wise over a period of 1 hour and the reaction mixture was stirred at −78° C. for 1 hour. Then reaction mixture was warmed to RT and stirred for 2 hr. After completion of reaction as determined by TLC, the reaction mixture was poured into ice-cold sodium bicarbonate solution, and then extracted with diethyl ether (100 mL×3), combined organic layer was dried over $Na_2SO_4$, and concentrated under reduced pressure to give crude product. The resultant crude was purified by silica gel column chromatography to afford 2-(2-bromobenzyl)-4,5-difluoro-2,3 dihydro-1H-inden-1-one 3. TLC: 5% EtOAc in pet ether; Rf=0.5. LCMS: (ESI): m/z 339.30 (M+2)⁺.

To a stirred solution 1,2-difluoro-4b,9,9a,10-tetrahydroindeno[1,2-a]inden-4b-ol 4 (500 mg, 1.94 mmol) in DCM (10 mL) was added $H_3PO_4$ (10 mL, 10 vol) at 0° C., allowed to come to RT and stirred for 12 hr. After consumption of starting material, reaction mixture was quenched with ice water (25 mL) and extracted with DCM (2×100 mL). Combined organic layers were washed with brine solution (50 mL), dried over $Na_2SO_4$ and concentrated under reduced pressure to afford 1,2-difluoro-9,10-dihydroindeno[1,2-a]indene 5. TLC: 5% EtOAc in pet ether; Rf=0.7. LCMS: (ESI): m/z 241.34 (M+H)⁺.

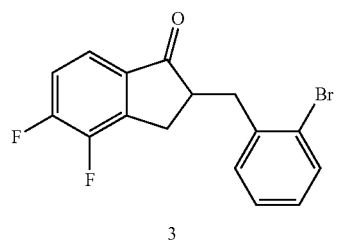

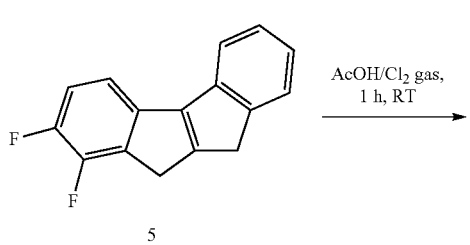

-continued

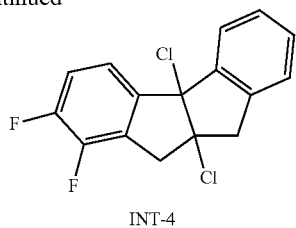

INT-4

To a stirred solution 1,2-difluoro-9,10-dihydroindeno[1,2-a]indene 5 (850 mg, 3.54 mmol) in AcOH (15 mL) Cl₂ gas was purged for 25 min at RT. After consumption of starting material (as determined by TLC) the reaction mixture was quenched with ice water (10 mL), basified with NaHCO₃ solution and extracted with ether (2×100 mL). Combined organic layers were washed with brine solution (50 mL), dried over Na₂SO₄ and concentrated under reduced pressure to afford 4b,9a-dichloro-1,2-difluoro-4b,9,9a,10-tetrahydroindeno[1,2-a]indene (INT-4). TLC: 5% EtOAc in pet ether; Rf=0.5. LCMS: (ESI): m/z 275.33 (M-Cl)⁺.

Example 15: 1-(1,2-Difluoro-9a,10-dihydro-9H-indeno[1,2-a]inden-4b-yl)-5-hydroxy-3-(tetrahydro-pyran-4-ylmethyl)-2,3-dihydro-1H-pyrido[2,1-f][1,2,4]triazine-4,6-dione (A15)

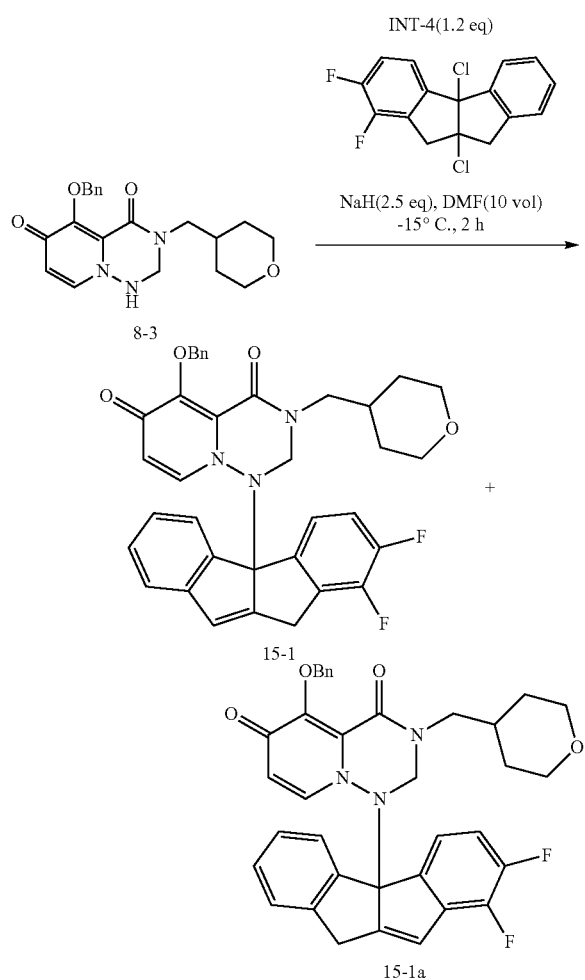

To a stirred solution of 5-(benzyloxy)-3-((tetrahydro-2H-pyran-4-yl)methyl)-2,3-dihydro-1H-pyrido[2,1-f][1,2,4]triazine-4,6-dione 8-3 (600 mg, 1.63 mmol) in DMF (15 mL) was added 60% of NaH (162 mg, 4.07 mmol) at −15° C. and stirred for 15 minutes. Then added solution of 4b,9a-dichloro-1,2-difluoro-4b,9,9a,10-tetrahydroindeno[1,2-a]indene INT-4 (605 mg, 1.95 mmol) (see Example 14) in DMF (5 mL) at −15° C. then stirred 2 hr. Reaction mixture was quenched with saturated NH₄Cl solution (40 mL) and extracted with EtOAc (2×30 mL). Combined organic layers were washed with brine solution (30 mL), dried over Na₂SO₄ and concentrated under reduced pressure. Crude compound was purified through reverse phase chromatography by eluting with 65% ACN in 0.1% formic acid in water to afford isomeric mixture of 5-(benzyloxy)-1-(7,8-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 15-1 and 5-(benzyloxy)-1-(1,2-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 15-1a. TLC: 10% MeOH in DCM; Rf=0.4. LCMS: (ESI): m/z 608.14 (M+H)⁺.

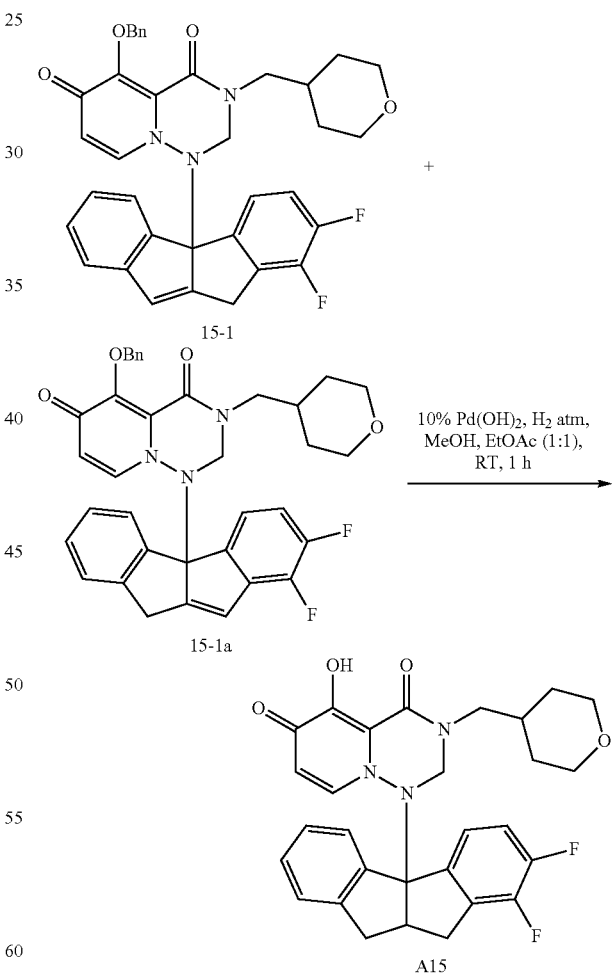

To a stirred solution of 5-(benzyloxy)-1-(7,8-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 15-1 and 5-(benzyloxy)-1-(1,2-difluoroindeno[1,2-a]inden-4b(9H)-yl)-3-((tetrahydro-2H-pyran-4-yl)methyl)-2, 3-dihydro-1H-pyrido[2,1-f][1,2,4]triazine-4,6-dione 15-1a (80 mg, 0.13 mmol) in MeOH (2 mL) and EtOAc (2 mL) was treated with 10% w/w of 20% Pd(OH)$_2$ on carbon (10 mg) and stirred under hydrogen atmosphere (balloon pressure) for 1 hour. Reaction mixture was filtered through Diatomaceous earth and washed the Diatomaceous earth bed with MeOH (20 mL) and concentrated under reduced pressure. Crude compound purified by prep-HPLC to afford compound 1-(1,2-difluoro-9a,10-dihydroindeno[1,2-a]inden-4b(9H)-yl)-5-hydroxy-3-(tetrahydro-2H-pyran-4-yl)methyl)-2,3-dihydro-1H-pyrido[2,1-f][1,2,4]triazine-4,6-dione A15. TLC: 10% MeOH in DCM; Rf=0.3. LCMS: (ESI): m/z 520.13 (M+H)$^+$.

Example 16: 1-(2,3-Difluoro-9a,10-dihydro-9H-indeno[1,2-a]inden-4b-yl)-5-hydroxy-3-(tetrahydro-pyran-4-ylmethyl)-2,3-dihydro-1H-pyrido[2,1-f][1,2,4]triazine-4,6-dione (A16)

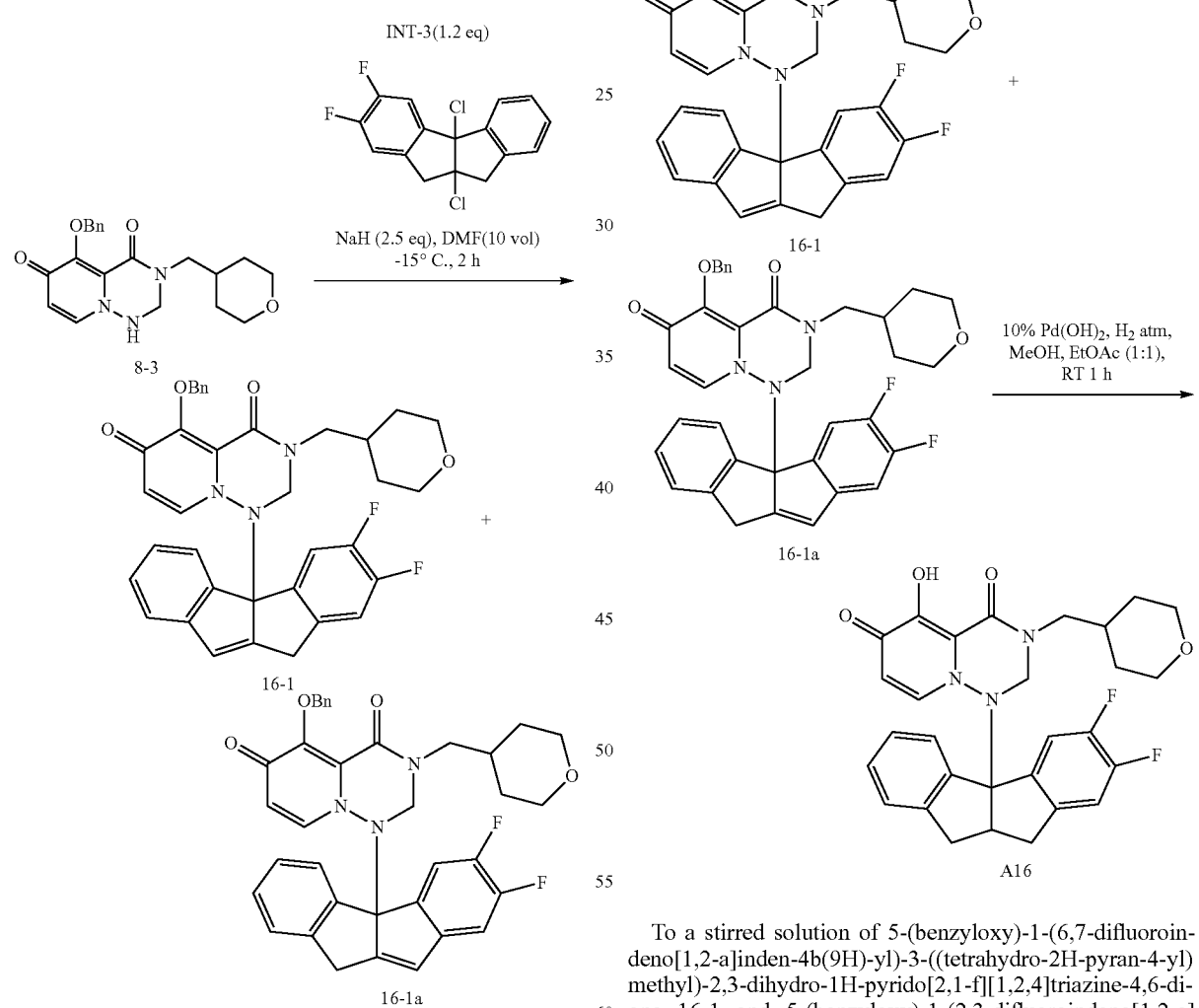

To a stirred solution of 5-(benzyloxy)-3-((tetrahydro-2H-pyran-4-yl)methyl)-2,3-dihydro-1H-pyrido[2,1-f][1,2,4]triazine-4,6-dione 8-3 (600 mg, 1.626 mmol) in DMF (15 mL) was added 60% of NaH (162 mg, 4.07 mmol) at −15° C. and stirred for 15 minutes. Then added solution of 4b,9a-dichloro-2,3-difluoro-4b,9,9a,10-tetrahydroindeno[1,2-a]indene INT-3 (605 mg, 1.95 mmol) (see Example 13) in DMF (5 mL) at −15° C. then stirred 2 hr. Reaction mixture was quenched with saturated NH$_4$Cl solution (40 mL) and extracted with EtOAc (2×30 mL). Combined organic layers were washed with brine solution (30 mL), dried over Na$_2$SO$_4$ and concentrated under reduced pressure. Crude compound was purified through reverse phase chromatography by eluting with 65% ACN in 0.1% formic acid in water to afford isomeric mixture of 5-(benzyloxy)-1-(6,7-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 16-1 and 5-(benzyloxy)-1-(2,3-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 16-1a. TLC: 10% MeOH in DCM; Rf=0.4. LCMS: (ESI): m/z 608.52 (M+H)$^+$.

To a stirred solution of 5-(benzyloxy)-1-(6,7-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 16-1 and 5-(benzyloxy)-1-(2,3-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 16-1a (60 mg, 0.099 mmol) in MeOH (2 mL) and EtOAc (2 mL) was treated with 10% w/w of 20% Pd(OH)$_2$ on carbon (10 mg) and stirred under hydrogen atmosphere (balloon pressure) for 1 hour. Reaction mixture was filtered through Diatomaceous earth and washed the Diatomaceous earth bed with MeOH (20 mL) and concentrated under reduced pressure. Crude compound purified by prep-HPLC to afford compound 1-(2,3-difluoro-9a,10-dihydroindeno[1,2-a]inden-4b(9H)-yl)-5-hydroxy-3-(tetrahydro-2H-pyran-4-yl)methyl)-2,3-dihydro-1H-pyrido[2,1-f][1,2,4]triazine-4,6-dione A16. TLC: 10% MeOH in DCM; Rf=0.3. LCMS: (ESI): m/z 520.13 (M+H)$^+$.

Example 17: 1-(1,2-Difluoro-9a,10-dihydro-9H-indeno[1,2-a]inden-4b-yl)-3-(4-fluoro-benzyl)-5-hydroxy-2,3-dihydro-1H-pyrido[2,1-f][1,2,4]triazine-4,6-dione (A17)

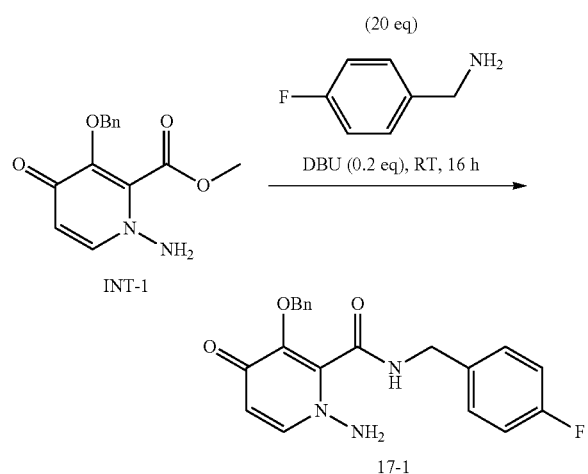

To a stirred mixture of methyl 1-amino-3-(benzyloxy)-4-oxo-1,4-dihydropyridine-2-carboxylate INT-1 (3.5 g, 13 mmol) (see Example 1 and (4-fluorophenyl)methanamine (8 g, 63.8686 mmol) was added DBU (1 mL), then stirred at RT for 16 hr. Reaction mixture was directly purified through reverse phase chromatography by eluting with 70% ACN in 0.1% formic acid in water to afford 1-amino-3-(benzyloxy)-N-(4-fluorobenzyl)-4-oxo-1,4-dihydropyridine-2-carboxamide 17-1. TLC: 10% MeOH in DCM; Rf=0.5. LCMS: (ESI): m/z 368.38 (M+H)$^+$.

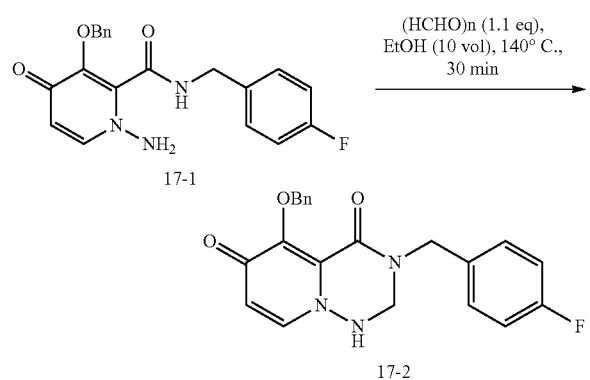

In a microwave vial, to a stirred solution of 1-amino-3-(benzyloxy)-N-(4-fluorobenzyl)-4-oxo-1,4-dihydropyridine-2-carboxamide 17-1 (500 mg, 1.36 mmol) in ethanol (10 mL) was added paraformaldehyde (45 mg, 1.5 mmol), then stirred in microwave at 140° C. for 30 minutes. After consumption of starting material, the reaction mixture was concentrated under reduced pressure. Crude compound was purified through reverse phase chromatography by eluting with 55% ACN in 0.1% formic acid in water to afford 5-(benzyloxy)-3-(4-fluorobenzyl)-2,3-dihydro-1H-pyrido[2,1-f][1,2,4]triazine-4,6-dione 17-2. TLC: 10% MeOH in DCM; Rf=0.5. LCMS: (ESI): m/z 380.08 (M+H)$^+$.

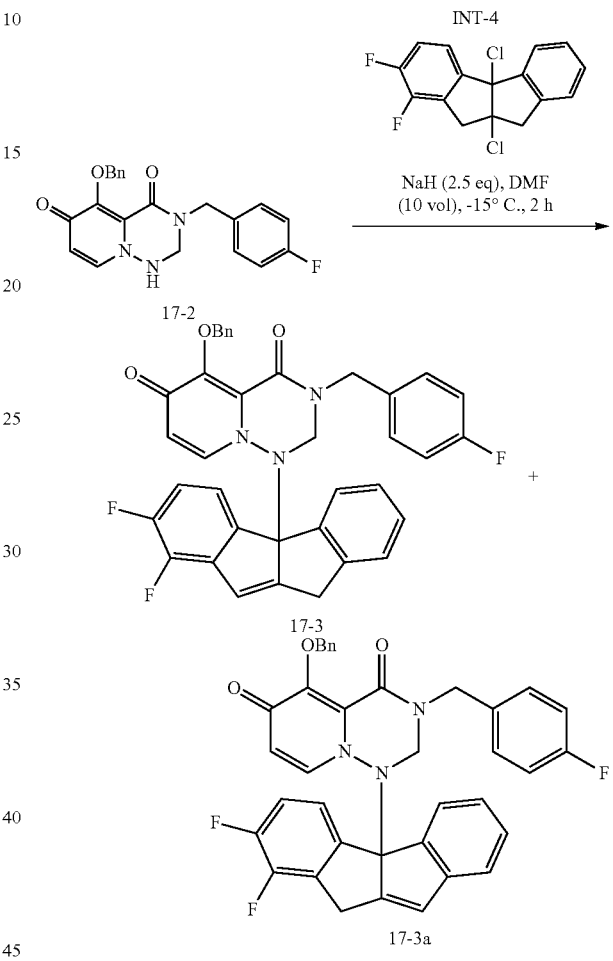

To a stirred solution of 5-(benzyloxy)-3-(4-fluorobenzyl)-2,3-dihydro-1H-pyrido[2,1-f][1,2,4]triazine-4,6-dione 17-2 (400 mg, 1.055 mmol) in DMF (5 mL) was added 60% of NaH (126 mg, 3.17 mmol) at −15° C. and stirred for 15 minutes. Then added solution of 4b,9a-dichloro-1,2-difluoro-4b,9,9a,10-tetrahydroindeno[1,2-a]indene INT-4 (425 mg, 1.37 mmol) (see Example 14) in DMF (5 mL) at −15° C. then stirred for 2 hr. Reaction mixture was quenched with saturated NH$_4$Cl solution (100 mL) and extracted with EtOAc (2×60 mL). Combined organic layers were washed with brine solution (50 mL), dried over Na$_2$SO$_4$ and concentrated under reduced pressure. Crude compound was purified through reverse phase chromatography by eluting with 82% ACN in 0.1% formic acid in water to afford compound with impurity. Again purified crude compound through 60-120 silica gel column chromatography by eluting with 1% MeOH in DCM to afford isomeric mixture of 5-(benzyloxy)-1-(1,2-difluoroindeno[1,2-a]inden-4b(9H)-yl)-3-(4-fluorobenzyl)-2,3-dihydro-1H-pyrido[2,1-f][1,2,4]triazine-4,6-dione 17-3 and 5-(benzyloxy)-1-(7,8-difluoroindeno[1,2-a]inden-4b(9H)-yl)-3-(4-fluorobenzyl)-2,3- dihydro-1H-pyrido[2,1-f][1,2,4]triazine-4,6-dione 17-3a. TLC: 10% MeOH in DCM; Rf=0.65. LCMS: (ESI): m/z 618.14 (M+H)+.

Example 18: 1-(2,3-Difluoro-9a,10-dihydro-9H-indeno[1,2-a]inden-4b-yl)-3-(4-fluoro-benzyl)-5-hydroxy-2,3-dihydro-1H-pyrido[2,1-f][1,2,4]triazine-4,6-dione (A23)

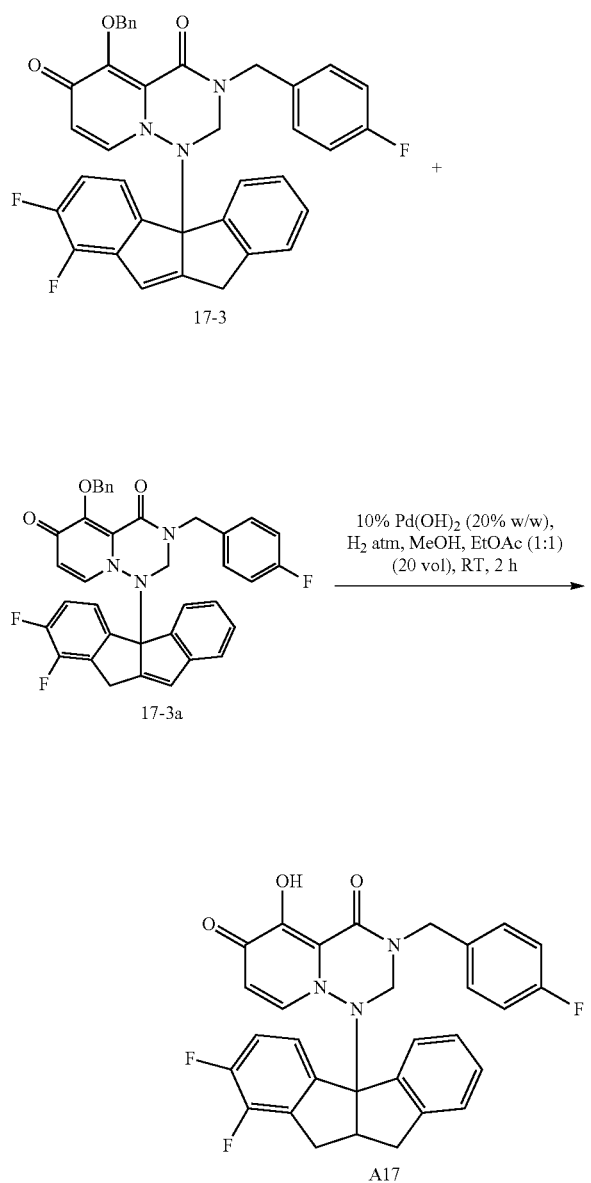

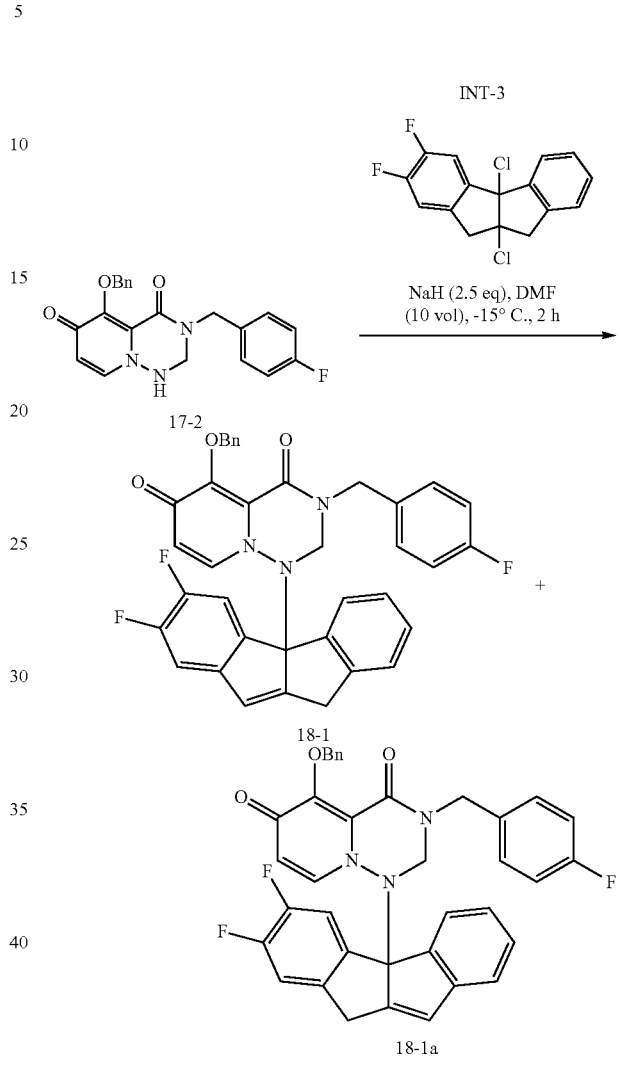

To a stirred solution of 5-(benzyloxy)-1-(1,2-difluoroindeno[1,2-a]inden-4b(9H)-yl)-3-(4-fluorobenzyl)-2,3-dihydro-1H-pyrido[2,1-f][1,2,4]triazine-4,6-dione 17-3 and 5-(benzyloxy)-1-(7,8-difluoroindeno[1,2-a]inden-4b(9H)-yl)-3-(4-fluorobenzyl)-2,3-dihydro-1H-pyrido[2,1-f][1,2,4]triazine-4,6-dione 17-3a (60 mg, 0.097 mmol) in MeOH (2 mL) and EtOAc (2 mL) was treated with 10% w/w of 20% Pd(OH)2 on carbon (12 mg) and stirred under H2 atmosphere (balloon pressure) for 1 hour. Reaction mixture was filtered through Diatomaceous earth and washed the Diatomaceous earth bed with 10% MeOH in DCM (20 mL) and concentrated under reduced pressure. Crude compound was purified through Prep HPLC method to afford 1-(1,2-difluoro-9a,10-dihydroindeno[1,2-a]inden-4b(9H)-yl)-3-(4-fluorobenzyl)-5-hydroxy-2,3-dihydro-1H-pyrido[2,1-f][1,2,4]triazine-4,6-dione A17. TLC: 5% MeOH in DCM; Rf=0.1. LCMS: (ESI): m/z 530.09 (M+H)+.

To a stirred solution of 5-(benzyloxy)-3-(4-fluorobenzyl)-2,3-dihydro-1H-pyrido[2,1-f][1,2,4]triazine-4,6-dione 17-2 (500 mg, 1.319 mmol) in DMF (5 mL) was added 60% of NaH (160 mg, 3.96 mmol) at −25° C. and stirred for 15 minutes. Then added solution of 4b,9a-dichloro-2,3-difluoro-4b,9,9a,10-tetrahydroindeno[1,2-a]indene INT-3 (613 mg, 1.98 mmol) (see Example 13) in DMF (5 mL) at −25° C. then stirred for 2 hr. Reaction mixture quenched with saturated NH4Cl solution (100 mL) and extracted with EtOAc (2×60 mL). Combined organic layers were washed with brine solution (50 mL), dried over Na2SO4 and concentrated under reduced pressure. Crude compound was purified through reverse phase chromatography by eluting with 82% ACN in 0.1% formic acid in water to afford compound with impurity. Again the crude compound was purified through 60-120 silica gel column chromatography by eluting with 1% MeOH in dichloromethane to afford isomeric mixture of 5-(benzyloxy)-1-(2,3-difluoroindeno[1,2-a]inden-4b(9H)-yl)-3-(4-fluorobenzyl)-2,3-dihydro-1H-pyrido[2,1-f][1,2,4]triazine-4,6-dione 18-1 and 5-(benzyloxy)-1-(6,7-difluoroindeno[1,2-a]inden-4b(9H)-yl)-3-(4- fluorobenzyl)-2,3-dihydro-1H-pyrido[2,1-f][1,2,4]triazine-4,6-dione 18-1a. TLC: 10% MeOH in DCM; Rf=0.5. LCMS: (ESI): m/z 618.42 (M+H)$^+$.

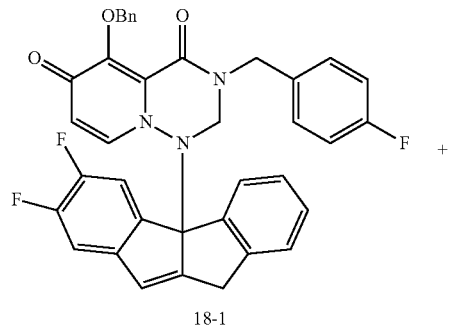

18-1

+

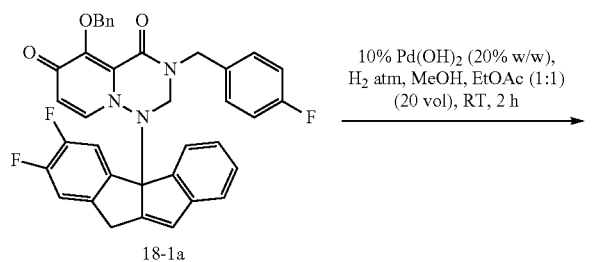

18-1a

10% Pd(OH)$_2$ (20% w/w), H$_2$ atm, MeOH, EtOAc (1:1) (20 vol), RT, 2 h

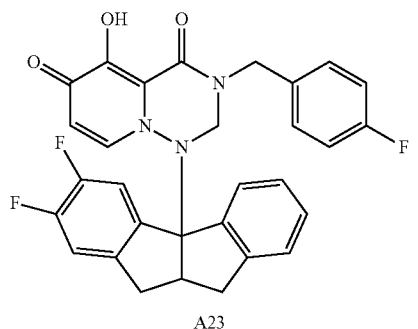

A23

To a stirred solution of 5-(benzyloxy)-1-(2,3-difluoroindeno[1,2-a]inden-4b(9H)-yl)-3-(4-fluorobenzyl)-2,3-dihydro-1H-pyrido[2,1-f][1,2,4]triazine-4,6-dione 18-1 and 5-(benzyloxy)-1-(6,7-difluoroindeno[1,2-a]inden-4b(9H)-yl)-3-(4-fluorobenzyl)-2,3-dihydro-1H-pyrido[2,1-f][1,2,4]triazine-4,6-dione 18-1a (130 mg, 0.210 mmol) in MeOH (5 mL) and EtOAc (5 mL) was treated with 10% w/w of 20% Pd(OH)$_2$ on carbon (20 mg) and stirred under balloon hydrogen atmosphere for 1 hour. Reaction mixture filtered through Diatomaceous earth and washed the Diatomaceous earth bed with 10% MeOH in DCM (20 mL) and concentrated under reduced pressure. Crude compound was purified through Prep HPLC method to afford 1-(2,3-difluoro-9a,10-dihydroindeno[1,2-a]inden-4b(9H)-yl)-3-(4-fluorobenzyl)-5-hydroxy-2,3-dihydro-1H-pyrido[2,1-f][1,2,4]triazine-4,6-dione A23. TLC: 5% MeOH in DCM; Rf=0.2. LCMS: (ESI): m/z 530.09 (M+H)$^+$.

Example 19: 1-(1,2-Difluoro-9a,10-dihydro-9H-indeno[1,2-a]inden-4b-yl)-3-[2-(4-fluoro-phenyl)-ethyl]-5-hydroxy-2,3-dihydro-1H-pyrido[2,1-t][1,2,4]triazine-4,6-dione (A18)

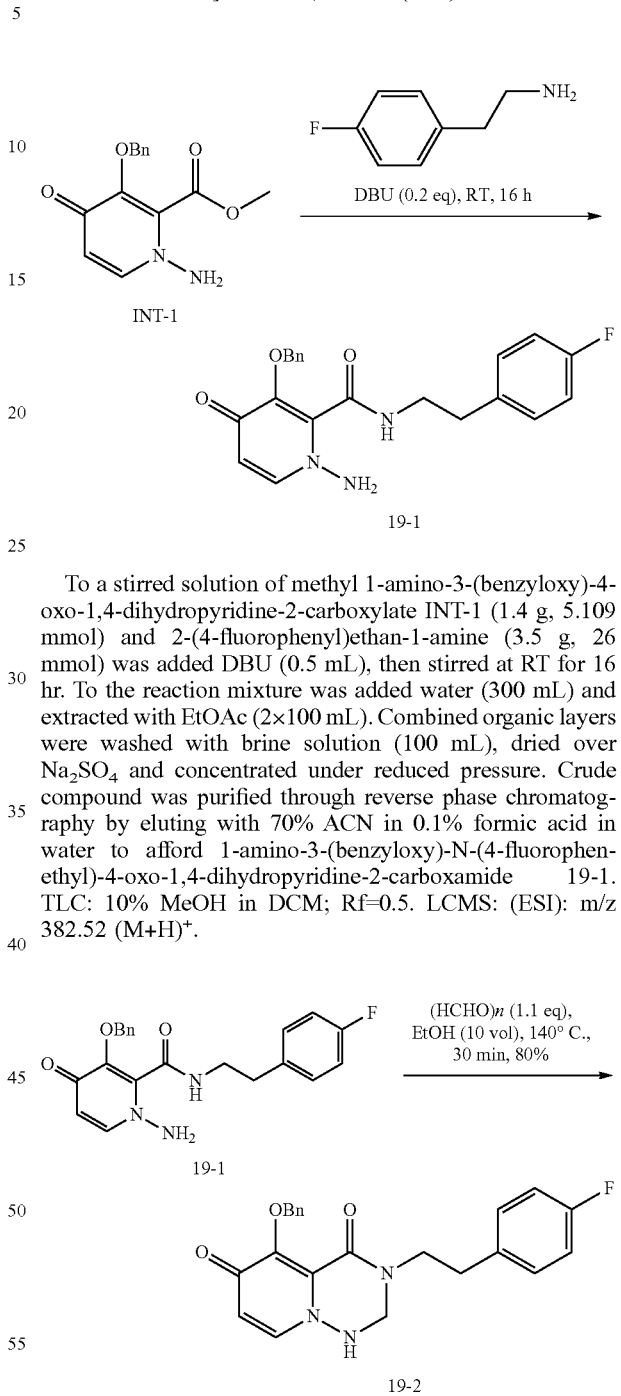

To a stirred solution of methyl 1-amino-3-(benzyloxy)-4-oxo-1,4-dihydropyridine-2-carboxylate INT-1 (1.4 g, 5.109 mmol) and 2-(4-fluorophenyl)ethan-1-amine (3.5 g, 26 mmol) was added DBU (0.5 mL), then stirred at RT for 16 hr. To the reaction mixture was added water (300 mL) and extracted with EtOAc (2×100 mL). Combined organic layers were washed with brine solution (100 mL), dried over Na$_2$SO$_4$ and concentrated under reduced pressure. Crude compound was purified through reverse phase chromatography by eluting with 70% ACN in 0.1% formic acid in water to afford 1-amino-3-(benzyloxy)-N-(4-fluorophenethyl)-4-oxo-1,4-dihydropyridine-2-carboxamide 19-1. TLC: 10% MeOH in DCM; Rf=0.5. LCMS: (ESI): m/z 382.52 (M+H)$^+$.

In a microwave vial, to a stirred solution of 1-amino-3-(benzyloxy)-N-(4-fluorophenethyl)-4-oxo-1,4-dihydropyridine-2-carboxamide 19-1 (480 mg, 1.26 mmol) in ethanol (5 mL) was added paraformaldehyde (42 mg, 1.4 mmol), then stirred in microwave at 140° C. for 30 minutes. After consumption of starting material, the reaction mixture was concentrated under reduced pressure. Crude compound was purified through reverse phase chromatography by eluting with 62% ACN in 0.1% formic acid in water to afford 5-(benzyloxy)-3-(4-fluorophenethyl)-2,3-dihydro-1H-pyrido[2,1-f][1,2,4]triazine-4,6-dione 19-2. TLC: 10% MeOH in DCM; Rf=0.5. LCMS: (ESI): m/z 394.38 (M+H)⁺.

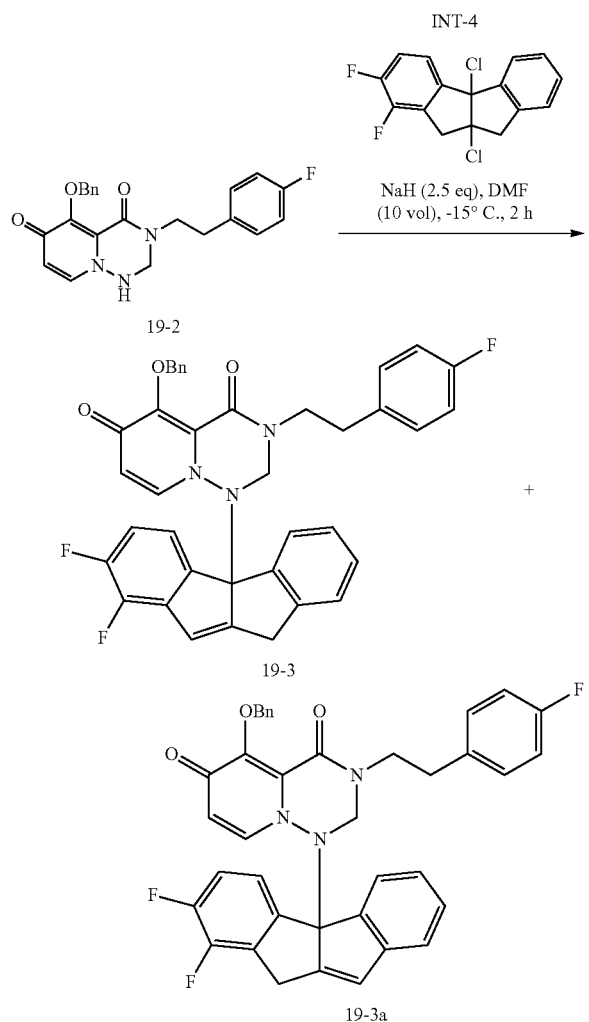

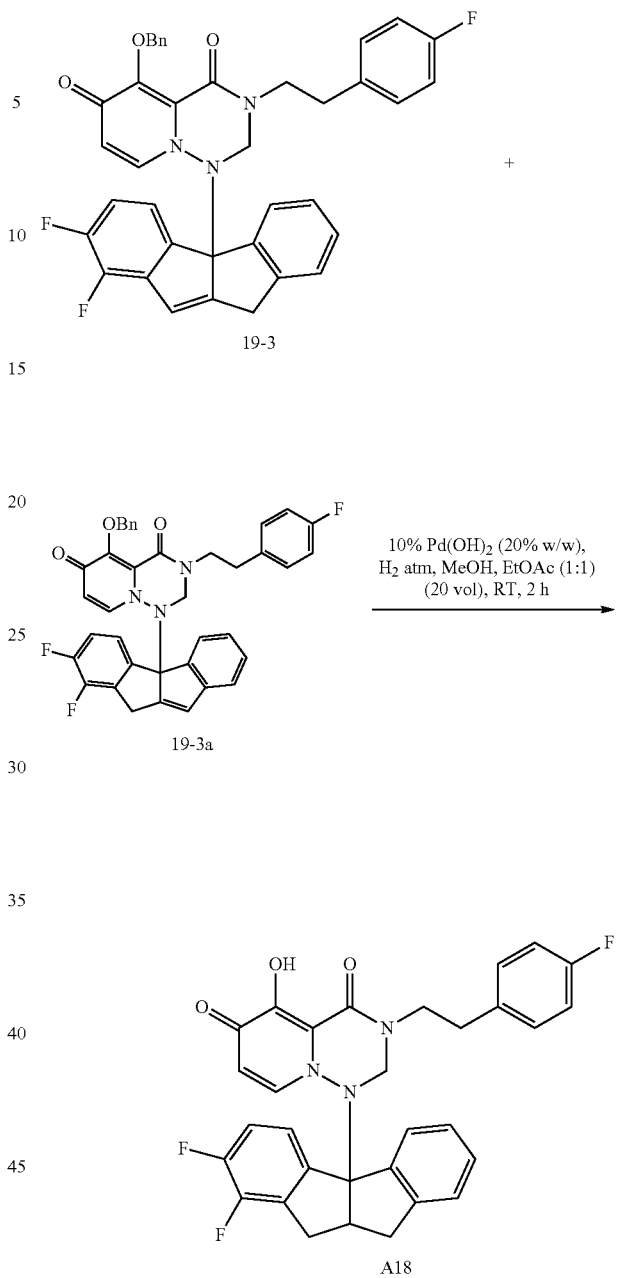

To a stirred solution of 5-(benzyloxy)-3-(4-fluorophenethyl)-2,3-dihydro-1H-pyrido[2,1-f][1,2,4]triazine-4,6-dione 19-2 (300 mg, 0.763 mmol) in DMF (3 mL) was added 60% of NaH (76 mg, 1.908 mmol) at −25° C. and stirred for 15 minutes. Then added a solution of 4b,9a-dichloro-1,2-difluoro-4b,9,9a,10-tetrahydroindeno[1,2-a]indene INT-4 (274 mg, 1.15 mmol) (see Example 14) in DMF (3 mL) at −25° C. then stirred for 2 hr. Reaction mixture was quenched with saturated NH₄Cl solution (50 mL) and extracted with EtOAc (2×30 mL). Combined organic layers were washed with brine solution (30 mL), dried over Na₂SO₄ and concentrated under reduced pressure. Crude compound was purified through reverse phase chromatography by eluting with 82% ACN in 0.1% formic acid in water to afford compound with impurity. Again crude was purified through 60-120 silica gel column chromatography by eluting with 1% MeOH in DCM to afford isomeric mixture of 5-(benzyloxy)-1-(1,2-difluoroindeno[1,2-a]inden-4b(9H)-yl)-3-(4-fluorophenethyl)-2,3-dihydro-1H-pyrido[2,1-f][1,2,4]triazine-4,6-dione 19-3 and 5-(benzyloxy)-1-(7,8-difluoroindeno[1,2-a]inden-4b(9H)-yl)-3-(4-fluorophenethyl)-2,3-dihydro-1H-pyrido[2,1-f][1,2,4]triazine-4,6-dione 19-3a. TLC: 10% MeOH in DCM; Rf=0.6. LCMS: (ESI): m/z 632.16 (M+H)⁺.

To a stirred solution of isomeric mixture of 5-(benzyloxy)-1-(1,2-difluoroindeno[1,2-a]inden-4b(9H)-yl)-3-(4-fluorophenethyl)-2,3-dihydro-1H-pyrido[2,1-f][1,2,4]triazine-4,6-dione 19-3 and 5-(benzyloxy)-1-(7,8-difluoroindeno[1,2-a]inden-4b(9H)-yl)-3-(4-fluorophenethyl)-2,3-dihydro-1H-pyrido[2,1-f][1,2,4]triazine-4,6-dione 19-3a (20 mg, 0.032 mmol) in MeOH (2 mL) and EtOAc (1 mL) was treated with 10% w/w of 20% Pd(OH)₂ on carbon (2 mg) and stirred under balloon H₂ atmosphere for 1 hour. Reaction mixture was filtered through Diatomaceous earth and washed the Diatomaceous earth bed with 10% MeOH in MeCl₂ (20 mL) and concentrated under reduced pressure. Crude compound was purified through Prep HPLC method to afford 1-(1,2-difluoro-9a,10-dihydroindeno[1,2-a]inden-4b(9H)-yl)-3-(4-fluorophenethyl)-5-hydroxy-2,3-dihydro-1H-pyrido[2,1-f][1,2,4]triazine-4,6-dione A18. TLC: 10% MeOH in DCM; Rr: 0.5. LCMS (ESI): m/z 544.14 (M+H)⁺.

Example 20: 1-(2,3-difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione (A19)

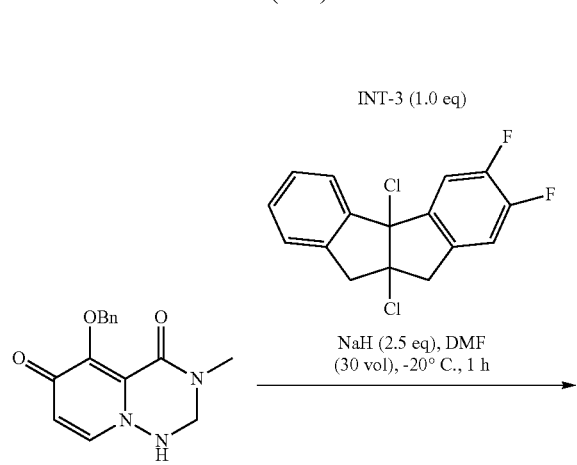

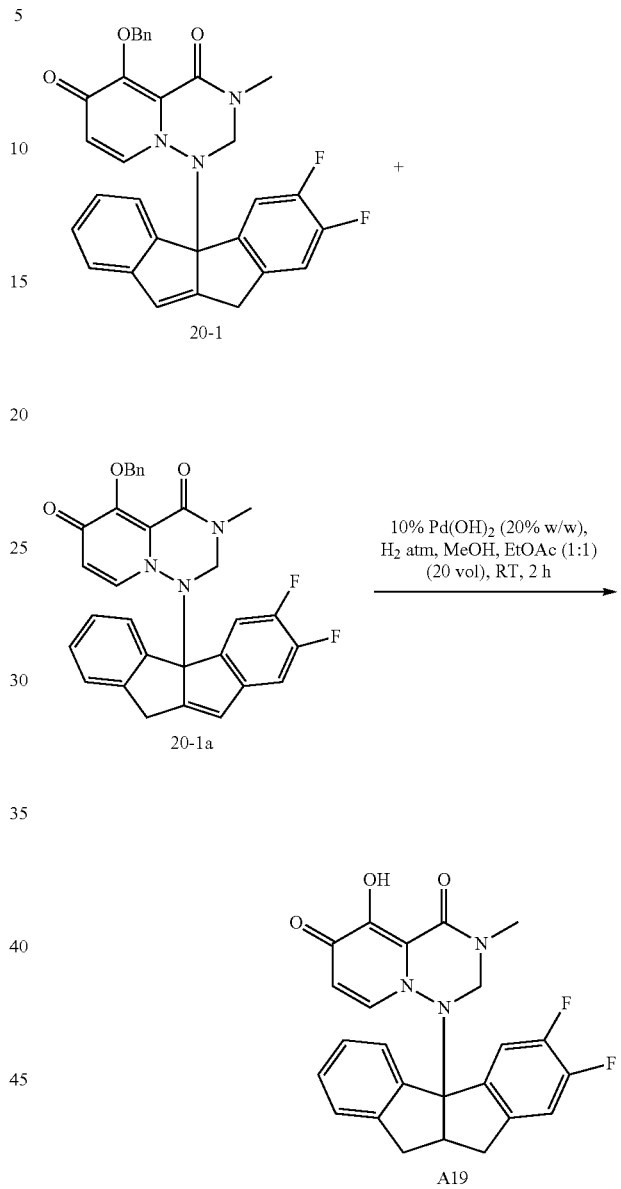

To a stirred solution of 5-(benzyloxy)-3-methyl-2,3-dihydro-1H-pyrido[2,1-f][1,2,4]triazine-4,6-dione INT-6 (500 mg, 1.7 mmol) in dry DMF (10 mL) was added NaH (60% in mineral oil) (175 mg, 4.0 mmol) at −20° C. and stirred for 20 minutes. Then added a solution of 4b,9a-dichloro-2,3-difluoro-4b,9,9a,10-tetrahydroindeno[1,2-a]indene INT-3 (543 mg, 1.0 mmol) in dry DMF (5 mL) at −20° C. and stirred for 1 hr. Reaction mixture was quenched with saturated NH4Cl solution (10 mL) and extracted with EtOAc (2×50 mL). Combined organic layers were washed with brine solution (50 mL), dried over Na2SO4 and concentrated under reduced pressure. Crude compound was purified through reverse phase chromatography by eluting with 82% of ACN in 0.1% formic acid in water to afford mixture of isomers 5-(benzyloxy)-1-(6,7-difluoroindeno[1,2-a]inden-4b(9H)-yl)-3-methyl-2,3-dihydro-1H-pyrido[2,1-f][1,2,4]triazine-4,6-dione (20-1) and 5-(benzyloxy)-1-(2,3-difluoroindeno[1,2-a]inden-4b(9H)-yl)-3-methyl-2,3-dihydro-1H-pyrido[2,1-f][1,2,4]triazine-4,6-dione (20-1a). TLC system: 10% MeOH in DCM Rf:0.5, LCMS (ESI): m/z 524.43 (M+H)+

To a stirred solution of 5-(benzyloxy)-1-(6,7-difluoroindeno[1,2-a]inden-4b(9H)-yl)-3-methyl-2,3-dihydro-1H-pyrido[2,1-f][1,2,4]triazine-4,6-dione (20-1) and 5-(benzyloxy)-1-(2,3-difluoroindeno[1,2-a]inden-4b(9H)-yl)-3-methyl-2,3-dihydro-1H-pyrido[2,1-f][1,2,4]triazine-4,6-dione (20-1A) (90 mg, 0.172 mmol) in MeOH (0.5 mL) and EtOAc (0.5 mL) was treated with 10% w/w of 20% Pd(OH)2 on carbon (18 mg) and stirred under balloon hydrogen atmosphere for 2 hr. Reaction mixture was filtered through Diatomaceous earth and washed the Diatomaceous earth bed with 10% MeOH in DCM (20 mL) and concentrated under reduced pressure. Crude compound was purified through Prep HPLC method to afford 1-(2,3-difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione A19. TLC system: 10% MeOH in DCM Rf: 0.5, LCMS (ESI): m/z 436.06 (M+H)+

Example 21: 1-(3,6-difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione (A20)

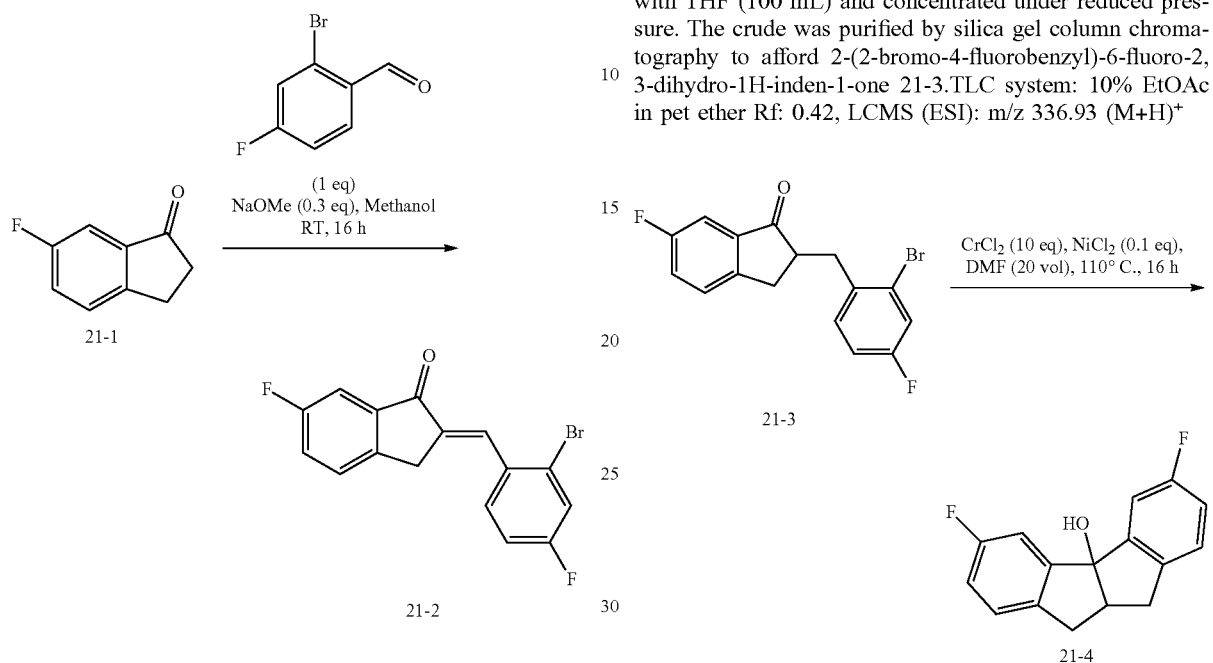

To a stirred solution of 6-fluoro-2,3-dihydro-1H-inden-1-one 21-1 (5 g, 33.3333 mmol) in MeOH (100 mL) was added sodium methoxide (540 mg, 9.999 mmol) and 2-bromo-4-fluorobenzaldehyde (7.03 g, 34.999 mmol) in MeOH (100 ml) drop wise slowly at 0° C. and stirred at RT for 16 hr. Reaction progress was monitored by TLC. The reaction mixture was acidified with 1N HCl (5 mL) to pH (3-4) and charged water (100 mL), filtered and dried to afford (E)-2-(2-bromo-4-fluorobenzylidene)-6-fluoro-2,3-dihydro-1H-inden-1-one 21-2.TLC system: 10% EtOAc in pet ether Rf: 0.4, LCMS (ESI): m/z 334.92 (M+H)+

To a stirred solution of (E)-2-(2-bromo-4-fluorobenzylidene)-6-fluoro-2,3-dihydro-1H-inden-1-one 21-2 (5 g, 14.97 mmol) in THE and EtOAc (1:1, 200 mL) was treated with PtO₂ (500 mg) and stirred under balloon hydrogen pressure for 6 hr. Reaction mixture was filtered through Diatomaceous earth and washed the Diatomaceous earth bed with THF (100 mL) and concentrated under reduced pressure. The crude was purified by silica gel column chromatography to afford 2-(2-bromo-4-fluorobenzyl)-6-fluoro-2,3-dihydro-1H-inden-1-one 21-3.TLC system: 10% EtOAc in pet ether Rf: 0.42, LCMS (ESI): m/z 336.93 (M+H)+

To a stirred solution of 2-(2-bromo-4-fluorobenzyl)-6-fluoro-2,3-dihydro-1H-inden-1-one 21-3 (2.5 g, 7.4404 mmol) in dry DMF (30 mL) was added NiCl₂ (95.98 mg, 0.744 mmol) and CrCl₂ (9.077 g, 74.404 mmol) then stirred at 120° C. for 12 hr. After consumption of starting material, the reaction mixture was quenched with ice water and extracted with ether (2×200 mL). Organic layer was washed with ice cold water (100 mL×2), brine solution and dried over sodium sulphate and concentrated under reduced pressure to afford crude 3,6-difluoro-9a,10-dihydroindeno[1,2-a]inden-4b(9H)-ol 21-4. TLC system: 30% EtOAc in pet ether Rf: 0.2· LCMS (ESI): m/z 241.21 (M-OH)

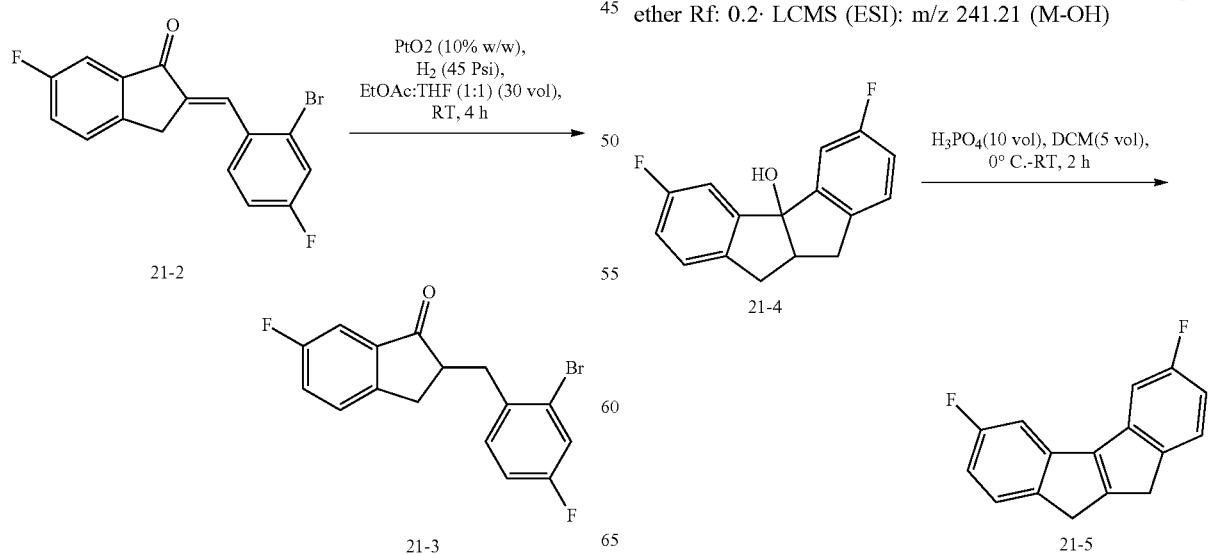

To a stirred solution of 3,6-difluoro-9a,10-dihydroindeno[1,2-a]inden-4b(9H)-ol 21-4 (crude) (1.7 g, 6.5891 mmol) in DCM (20 mL) was added H₃PO₄ (20 mL) at 0° C. and stirred for 2 hr. After consumption of starting material reaction mixture was quenched with ice water (100 mL) and extracted with DCM (2×100 mL). Combined organic layers were washed with brine solution (50 mL), dried over Na₂SO₄ and concentrated under reduced pressure. Crude compound was purified by silica gel column chromatography by eluting with 1% EtOAc in pet ether to afford 3,6-difluoro-9,10-dihydroindeno[1,2-a]indene 21-5. TLC system: 5% EtOAc in pet ether Rf: 0.7, LCMS (ESI): m/z 241.25 (M+H)⁺

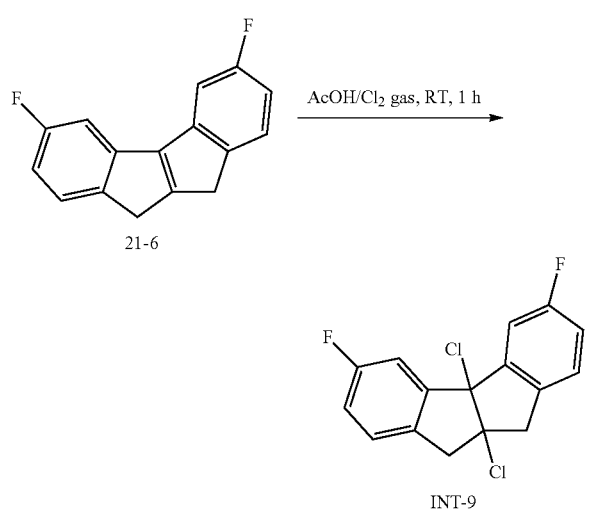

To a stirred solution 3,6-difluoro-9,10-dihydroindeno[1,2-a]indene 21-6 (900 mg, 3.75 mmol in AcOH (8 mL) purged the Cl₂ gas for 25 min. at RT (Chlorine gas was generated in situ using NaClO₄ and con. HCl). After consumption of starting material, Reaction mixture was quenched with ice water (500 mL) and basified with sodium bicarbonate solution and extracted with ether (2×50 mL). Combined organic layers were washed with brine solution (30 mL), dried over Na2SO4 and concentrated under reduced pressure. Crude compound was purified through chromatography to afford 4b,9a-dichloro-3,6-difluoro-4b,9,9a,10-tetrahydroindeno[1,2-a]indene INT-9. TLC system: 100% Pet ether Rf: 0.3, LCMS (ESI): m/z 275.25 (M-Cl)⁺

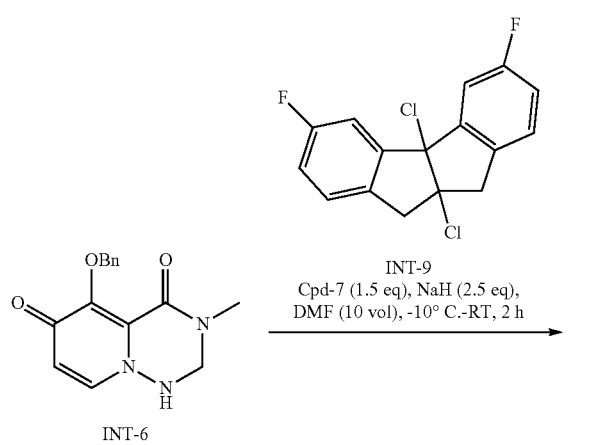

To a stirred solution of 5-(benzyloxy)-3-methyl-2,3-dihydro-1H-pyrido[2,1-f][1,2,4]triazine-4,6-dione INT-6 (500 mg, 1.7543 mmol) in DMF (4 mL) was added 60% of NaH (175 mg, 4.3859 mmol) at −15° C. and stirred for 15 minutes. Then added solution 4b,9a-dichloro-3,6-difluoro-4b,9,9a,10-tetrahydroindeno[1,2-a]indene INT-9 (815.7 mg, 2.6315 mmol) in DMF (4 mL) at −15° C. then stirred 2 hr. Reaction mixture quenched with saturated NH₄Cl solution (20 mL) and extracted with EtOAc (2×50 mL). Combined organic layers were washed with brine solution (10 mL), dried over Na2SO4 and concentrated under reduced pressure to afford 5-(benzyloxy)-1-(6-fluoroindeno[1,2-a]inden-4b(9H)-yl)-3-methyl-2,3-dihydro-1H-pyrido[2,1-f][1,2,4]triazine-4,6-dione 21-7. TLC system: 5% MeOH in DCM Rf: 0.4, LCMS (ESI): m/z 524.09 (M+H)⁺

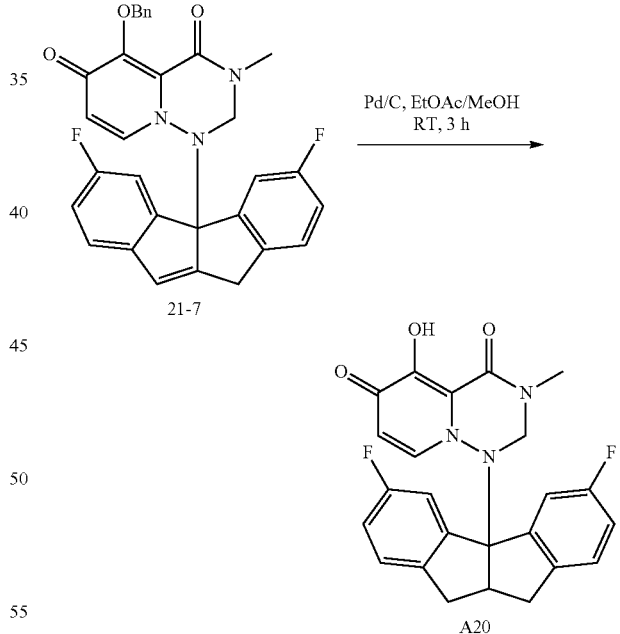

5-(benzyloxy)-1-(6-fluoroindeno[1,2-a]inden-4b(9H)-yl)-3-methyl-2,3-dihydro-1H-pyrido[2,1-f][1,2,4]triazine-4,6-dione 21-7 (150 mg, 0.2868 mmol) in MeOH (5 mL) and EtOAc (5 mL) was treated with 10% w/w of 20% Pd(OH)₂ on carbon (15 mg) and stirred under balloon hydrogen atmosphere for 1 hr. Reaction mixture filtered through Diatomaceous earth and washed the Diatomaceous earth bed with 10% MeOH in DCM (20 mL) and concentrated under reduced pressure. Crude compound was purified by reverse phase using 0.05% formic acid in ACN to afford 1-(3,6- difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione A20. TLC system: 10% MeOH in DCM Rf: 0.3, LCMS (ESI): m/z 436.10 (M+H)$^+$ Example 22: 3-(3-chloro-2-fluorobenzyl)-1-(9a,10-dihydroindeno[1,2-a]inden-4b(9H)-yl)-5-hydroxy-2,3-dihydro-1H-pyrido[2,1-f][1,2,4]triazine-4,6-dione (A31)

ethanol (40 mL) was added paraformaldehyde (60 mg, 2.00 mmol) then irradiated at 140° C. under microwave reactor for 30 minutes. After consumption of starting material, the reaction mixture was concentrated under reduced pressure. Crude compound was purified through reverse phase chromatography by eluting with 35% ACN in 0.1% formic acid in water to afford 5-(benzyloxy)-3-(3-chloro-2-fluorobenzyl)-2,3-dihydro-1H-pyrido[2,1-f][1,2,4]triazine-4,6-dione 22-2. TLC system: 10% MeOH in DCM Rf: 0.4, LCMS (ESI): m/z 414.07 (M+H)$^+$

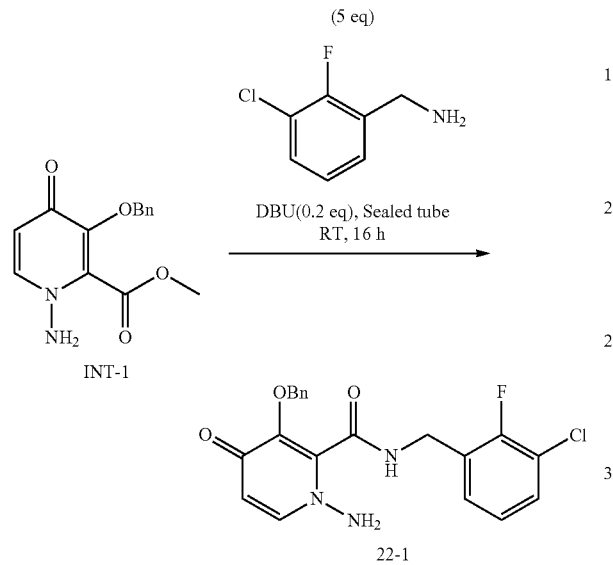

To a stirred solution of methyl 1-amino-3-(benzyloxy)-4-oxo-1,4-dihydropyridine-2-carboxylate INT-1 (1.0 g, 3.64 mmol) was added 2-fluoro-3-chloro benzyl amine (2.3 mL, 18.248 mmol) and DBU (0.15 mL, 0.72 mmol) under sealed tube then stirred at RT for 16 hr. Reaction mixture was completely distilled off under reduced pressure. Crude compound was purified through reverse phase chromatography by eluting with 45% ACN in 0.1% formic acid in water to afford 1-amino-3-(benzyloxy)-N-(3-chloro-2-fluorobenzyl)-4-oxo-1,4-dihydropyridine-2-carboxamide 22-1. TLC system: 10% MeOH in DCM Rf: 0.1, LCMS (ESI): m/z 402.02 (M+H)$^+$

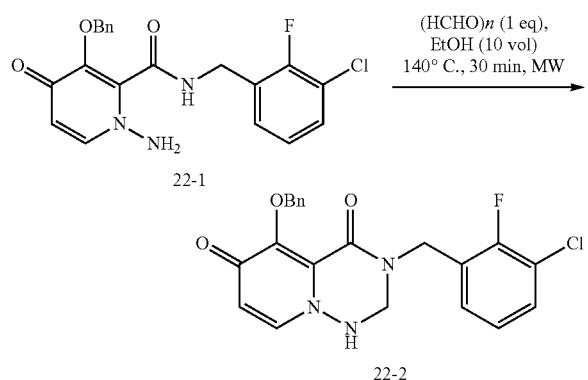

In a microwave vial, to a stirred solution of 1-amino-3-(benzyloxy)-N-(3-chloro-2-fluorobenzyl)-4-oxo-1,4-dihydropyridine-2-carboxamide 22-1 (800 mg, 1.99 mmol) in

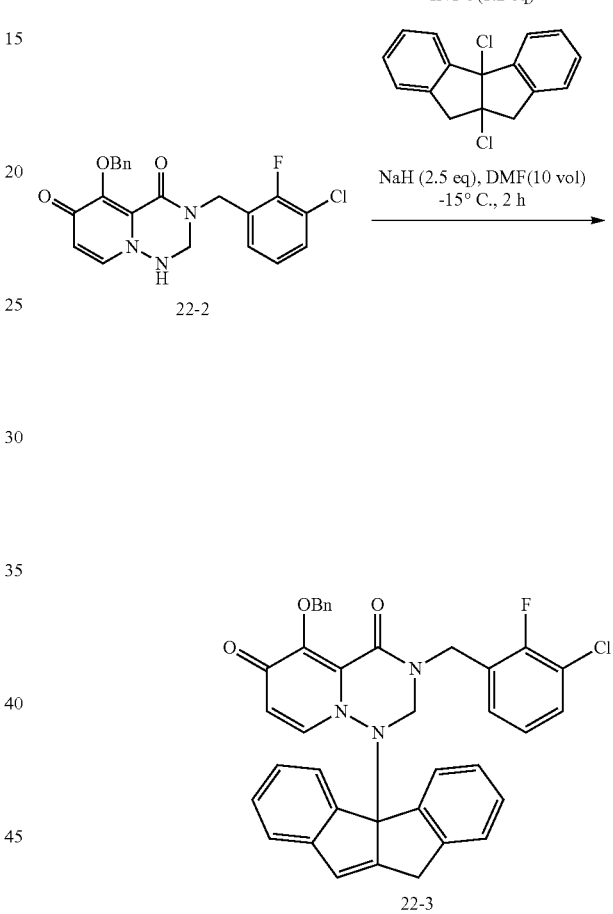

To a stirred solution of 5-(benzyloxy)-3-(3-chloro-2-fluorobenzyl)-2,3-dihydro-1H-pyrido[2,1-f][1,2,4]triazine-4,6-dione 22-2 (250 mg, 0.605 mmol) in DMF (10 mL) was added 60% of NaH (72 mg, 1.815 mmol) at −15° C. and stirred for 15 minutes. Then added solution of 4b,9a-dichloro-4b,9,9a,10-tetrahydroindeno[1,2-a]indene INT-5 (199 mg, 0.726 mmol) in dry DMF (5 mL) at −15° C. then stirred for 2 hr. Reaction mixture was quenched with saturated NH$_4$Cl solution (40 mL) and extracted with EtOAc (2×30 mL). Combined organic layers were washed with brine solution (30 mL), dried over Na$_2$SO$_4$ and concentrated under reduced pressure to afford 5-(benzyloxy)-3-(3-chloro-2-fluorobenzyl)-1-(indeno[1,2-a]inden-4b(9H)-yl)-2,3-dihydro-1H-pyrido[2,1-f][1,2,4]triazine-4,6-dione 22-3. This crude was used for next step without any purification. TLC system: 10% MeOH in DCM Rf: 0.3, LCMS (ESI): m/z 616.40 (M+H)$^+$

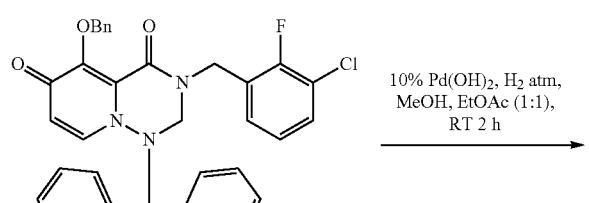

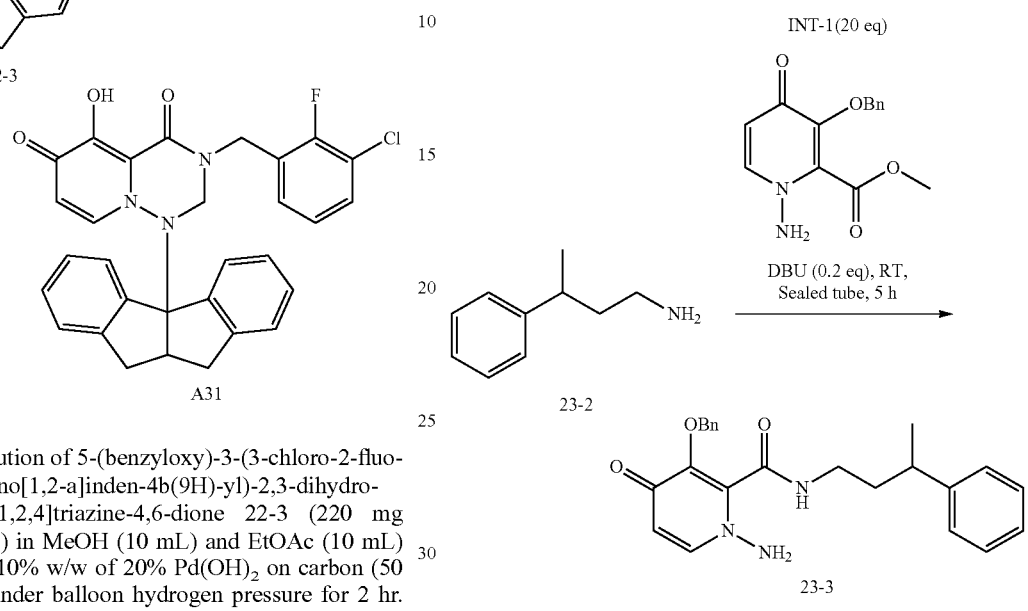

To a stirred solution of 5-(benzyloxy)-3-(3-chloro-2-fluorobenzyl)-1-(indeno[1,2-a]inden-4b(9H)-yl)-2,3-dihydro-1H-pyrido[2,1-f][1,2,4]triazine-4,6-dione 22-3 (220 mg crude, 0.35 mmol) in MeOH (10 mL) and EtOAc (10 mL) was treated with 10% w/w of 20% Pd(OH)$_2$ on carbon (50 mg) and stirred under balloon hydrogen pressure for 2 hr. Reaction mixture was filtered through Diatomaceous earth bed and washed with MeOH (20 mL) and concentrated under reduced pressure. Crude compound was purified by prep-HPLC to afford 3-(3-chloro-2-fluorobenzyl)-1-(9a,10-dihydroindeno[1,2-a]inden-4b(9H)-yl)-5-hydroxy-2,3-dihydro-1H-pyrido[2,1-f][1,2,4]triazine-4,6-dione A31. TLC system: 10% MeOH in DCM Rf: 0.2, LCMS (ESI): m/z 528.04 (M+H)$^+$ Example 23: 1-(9a,10-dihydroindeno[1,2-a]inden-4b (9H)-yl)-5-hydroxy-3-(3-phenylbutyl)-2,3-dihydro-1H-pyrido[2,1-f][1,2,4]triazine-4,6-dione (A32)

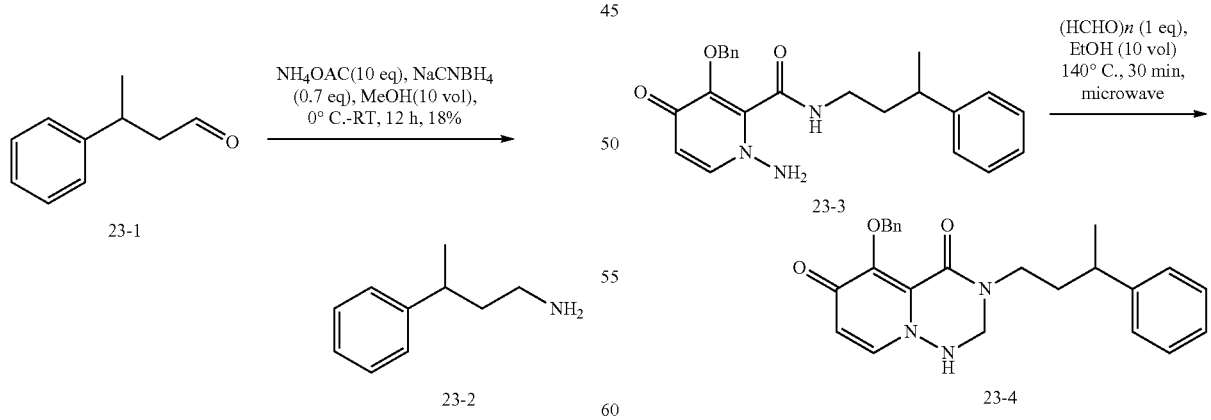

To a stirred solution of 3-phenylbutanal 23-1 (5 g, 33.783 mmol) in MeOH (50 mL) was added ammonium acetate (25 g, 337.8 mmol) and stirred for 30 minutes. Then added sodiumcyanoborohydride (1.48 g, 23.64 mmol) at 0° C. and stirred at RT for 16 hr. Organic solvents were distilled off and to the crude was added water and slowly acidified with conc. HCl at 0° C. to pH 3. Aqueous layer extracted with DCM (500 mL) and then basified with solid NaOH pellets at 0° C. to pH 12. Then extracted with DCM (500 mL) and the organic layer was washed with brine solution (200 mL) and dried over Na2SO4 and concentrated under reduced pressure to afford 3-phenylbutan-1-amine 23-2. TLC system: 40% EtOAc in pet ether Rf: 0.3

To a stirred solution of methyl 1-amino-3-(benzyloxy)-4-oxo-1,4-dihydropyridine-2-carboxylate INT-1 (1 g, 3.649 mmol) and 3-phenylbutan-1-amine 23-2 (2.7 g, 18.248 mmol) was added DBU (0.2 mL), then stirred at RT for 16 hr. Reaction mixture was directly purified through reverse phase chromatography by eluting with 72% ACN in 0.1% formic acid in water to afford 1-amino-3-(benzyloxy)-4-oxo-N-(3-phenylbutyl)-1,4-dihydropyridine-2-carboxamide 23-3. TLC system: 10% MeOH in DCM Rf: 0.3, LCMS (ESI): m/z 392.16 (M+H)$^+$ In a microwave vial, to a stirred solution of 1-amino-3-(benzyloxy)-4-oxo-N-(3-phenylbutyl)-1,4-dihydropyridine-2-carboxamide 23-3 (500 mg, 1.278 mmol) in ethanol (10 mL) was added paraformaldehyde (42 mg, 1.406 mmol), then stirred in microwave at 140° C. for 30 minutes. After consumption of starting material, the reaction mixture was concentrated under reduced pressure. Crude compound was purified through reverse phase chromatography by eluting with 56% ACN in 0.1% formic acid in water to afford 5-(benzyloxy)-3-(3-phenylbutyl)-2,3-dihydro-1H-pyrido[2,1-f][1,2,4]triazine-4,6-dione 23-4. TLC system: 10% MeOH in DCM R$_f$: 0.45, LCMS (ESI): m/z 404.16 (M+H)$^+$

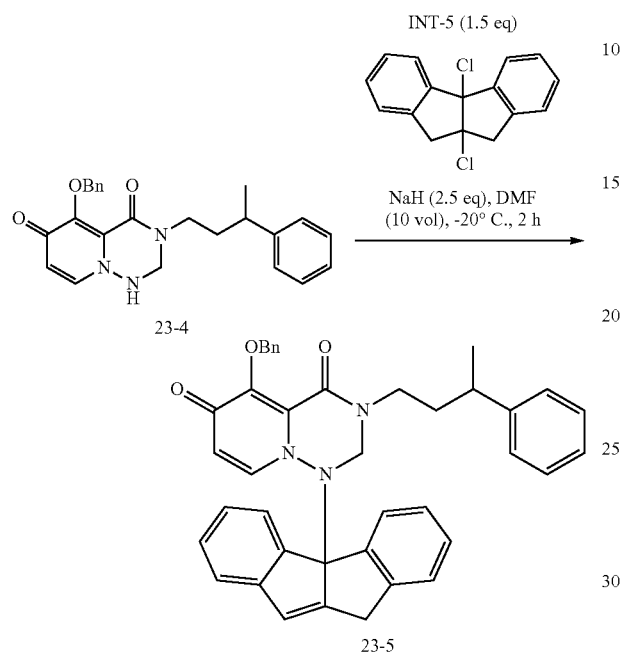

To a stirred solution of 5-(benzyloxy)-3-(3-phenylbutyl)-2,3-dihydro-1H-pyrido[2,1-f][1,2,4]triazine-4,6-dione 23-4 (500 mg, 1.240 mmol) in DMF (5 mL) was added 60% of NaH (124 mg, 3.101 mmol) at −25° C. and stirred for 30 minutes. Then added solution of 4b,9a-dichloro-4b,9,9a,10-tetrahydroindeno[1,2-a]indene INT-5 (680 mg, 2.481 mmol) in DMF (5 mL) at −25° C. then stirred for 2 hr. Reaction mixture was quenched with saturated NH$_4$Cl solution (100 mL) and extracted with EtOAc (2×50 mL). Combined organic layers were washed with brine solution (50 mL), dried over Na2SO4 and concentrated under reduced pressure. Crude compound was purified through reverse phase chromatography by eluting with 82% ACN in 0.1% formic acid in water to afford compound with impurity. Again crude was purified through 100-200 silica gel column chromatography by eluting with 1% MeOH in DCM to afford 5-(benzyloxy)-1-(indeno[1,2-a]inden-4b(9H)-yl)-3-(3-phenylbutyl)-2,3-dihydro-1H-pyrido[2,1-f][1,2,4]triazine-4,6-dione 23-5. TLC system: 10% MeOH in DCM Rr: 0.3, LCMS (ESI): m/z 606.57 (M+H)$^+$

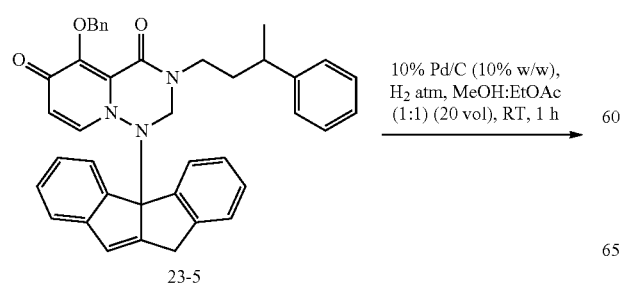

To a stirred solution of 5-(benzyloxy)-1-(indeno[1,2-a]inden-4b(9H)-yl)-3-(3-phenylbutyl)-2,3-dihydro-1H-pyrido[2,1-f][1,2,4]triazine-4,6-dione 23-5 (60 mg, 0.099 mmol) in MeOH (8 mL) and EtOAc (2 mL) was treated with 15% w/w of 20% Pd(OH)$_2$ on carbon (10 mg) and stirred under balloon hydrogen pressure for 1 hr. Reaction mixture was filtered through Diatomaceous earth and washed the Diatomaceous earth bed with 10% MeOH in DCM (20 mL) and concentrated under reduced pressure. Crude compound was purified through Prep HPLC method to afford 1-(1,2-difluoro-9a,10-dihydroindeno[1,2-a]inden-4b(9H)-yl)-3-(4-fluorophenethyl)-5-hydroxy-2,3-dihydro-1H-pyrido[2,1-f][1,2,4]triazine-4,6-dione A32. TLC system: 10% MeOH in DCM Rf:0.2, LCMS (ESI): m/z 518.17 (M+H)$^+$ Example 24: 3-(cyclopropylmethyl)-1-(1,2-difluoro-4b,9,9a,10-tetrahydroindeno[1,2-a]inden-4b-yl)-5-hydroxy-2,3-dihydro-1H-pyrido[1,2-f][1,2,4]triazine-4,6-dione (A9)

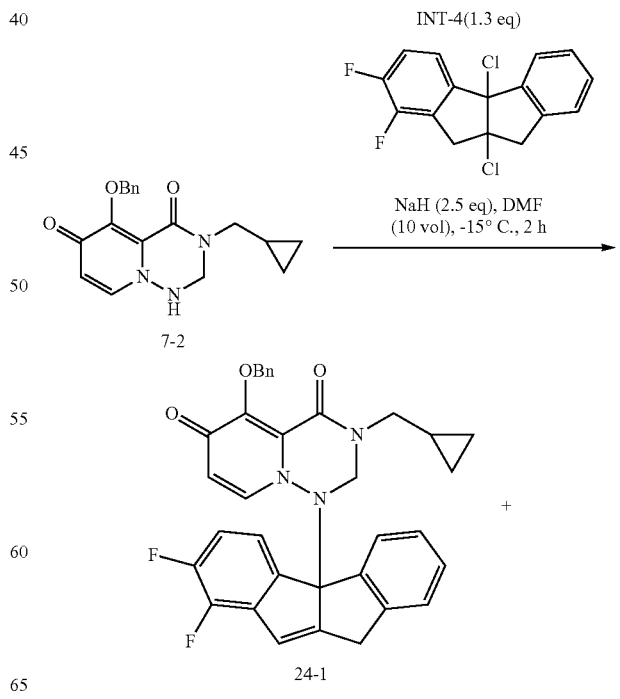

-continued

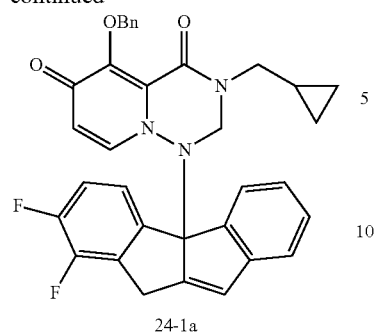

24-1a

A stirred solution of 5-(benzyloxy)-3-(cyclopropylmethyl)-2,3-dihydro-1H-pyrido[2,1-f][1,2,4]triazine-4,6-dione 7-2 (200 mg, 0.6153 mmol) in DMF (3 mL) was treated with 60% of NaH (61 mg, 1.5384 mmol) at −15° C. and stirred for 15 minutes. Then added solution of 4b,9a-dichloro-1,2-difluoro-4b,9,9a,10-tetrahydroindeno[1,2-a]indene INT-4 (247 mg, 0.7999 mmol) in DMF (1 mL) at −15° C. then stirred for 2 hr. Reaction mixture quenched with saturated NH₄Cl solution (20 mL) and extracted with EtOAc (2×20 mL). Combined organic layers were washed with brine solution (20 mL), dried over Na2SO4 and concentrated under reduced pressure. Crude compound was purified through reverse phase chromatography by eluting with 58% ACN in 0.1% formic acid in water to afford 5-(benzyloxy)-3-(cyclopropylmethyl)-1-(1,2-difluoro-4b,9-dihydroindeno[1,2-a]inden-4b-yl)-2,3-dihydro-1H-pyrido[1,2-f][1,2,4]triazine-4,6-dione 24-1 and 5-(benzyloxy)-3-(cyclopropylmethyl)-1-(7,8-difluoroindeno[1,2-a]inden-4b(9H)-yl)-2,3-dihydro-1H-pyrido[2,1-f][1,2,4]triazine-4,6-dione 24-1a. TLC system: 10% MeOH in DCM Rf: 0.6, LCMS (ESI): m/z 564.60 (M+H)⁺

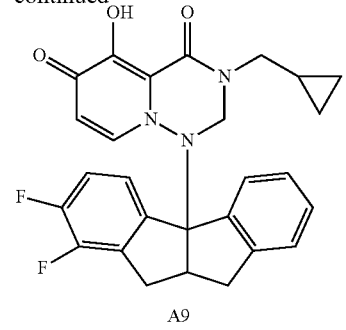

A9

To a stirred solution of 5-(benzyloxy)-3-(cyclopropylmethyl)-1-(1,2-difluoro-4b,9-dihydroindeno[1,2-a]inden-4b-yl)-2,3-dihydro-1H-pyrido[1,2-f][1,2,4]triazine-4,6-dione 24-1 and 5-(benzyloxy)-3-(cyclopropylmethyl)-1-(7,8-difluoroindeno[1,2-a]inden-4b(9H)-yl)-2,3-dihydro-1H-pyrido[2,1-f][1,2,4]triazine-4,6-dione 24-1a (50 mg, 0.0888 mmol) in MeOH (1 mL) and EtOAc (1 mL) was treated with 10% w/w of 20% Pd(OH)₂ on carbon (20 mg) and stirred under balloon hydrogen atmosphere for 1 hr. Reaction mixture was filtered through Diatomaceous earth and washed the Diatomaceous earth bed with 10% MeOH in DCM (20 mL) and concentrated under reduced pressure. Crude compound was purified through Prep HPLC method to afford 3-(cyclopropylmethyl)-1-(1,2-difluoro-4b,9,9a,10-tetrahydroindeno[1,2-a]inden-4b-yl)-5-hydroxy-2,3-dihydro-1H-pyrido[1,2-f][1,2,4]triazine-4,6-dione A9. TLC system: 10% MeOH in DCM Rf: 0.5, LCMS (ESI): m/z 476.38 (M+H)⁺

Example 25: 3-(cyclopropylmethyl)-1-(2,3-difluoro-9a,10-dihydroindeno[1,2-a]inden-4b(9H)-yl)-5-hydroxy-2,3-dihydro-1H-pyrido[2,1-f][1,2,4]triazine-4,6-dione (A13)

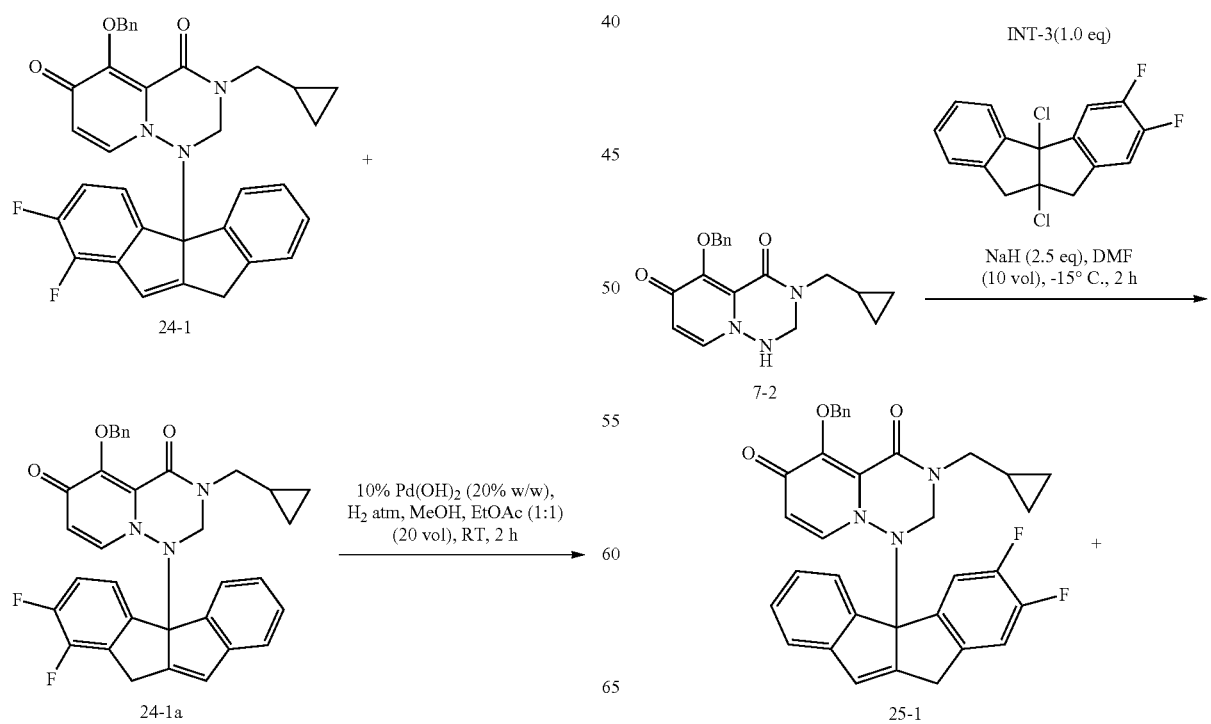

-continued

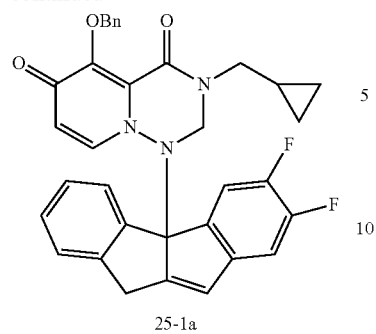

25-1a

-continued

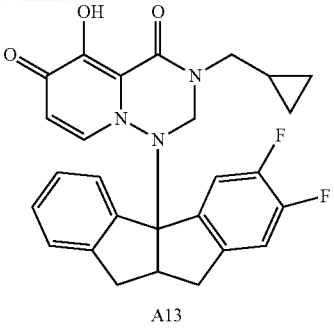

A13

To a stirred solution of 5-(benzyloxy)-3-(cyclopropylmethyl)-2,3-dihydro-1H-pyrido[2,1-f][1,2,4]triazine-4,6-dione 7-2 (300 mg, 0.9 mmol) in DMF (6 mL) was treated with 60% of NaH (92 mg, 2.3 mmol) at −15° C. and stirred for 20 minutes. Then added solution of 4b,9a-dichloro-1,2-difluoro-4b,9,9a,10-tetrahydroindeno[1,2-a]indene INT-3 (286 mg, 0.9 mmol) in DMF (3 mL) at −15° C. then stirred for 30 minutes. Reaction mixture was quenched with saturated NH₄Cl solution (20 mL) and extracted with EtOAc (2×20 mL). Combined organic layers were washed with brine solution (20 mL), dried over Na2SO4 and concentrated under reduced pressure. Crude compound was purified through reverse phase chromatography by eluting with 76% ACN in 0.1% formic acid in water to afford 5-(benzyloxy)-3-(cyclopropylmethyl)-1-(6,7-difluoroindeno[1,2-a]inden-4b(9H)-yl)-2,3-dihydro-1H-pyrido[2,1-f][1,2,4]triazine-4,6-dione 25-1 and 5-(benzyloxy)-3-(cyclopropylmethyl)-1-(2,3-difluoroindeno[1,2-a]inden-4b(9H)-yl)-2,3-dihydro-1H-pyrido[2,1-f][1,2,4]triazine-4,6-dione 25-1a. TLC system: 10% MeOH in DCM Rf: 0.6, LCMS (ESI): m/z 564.44 (M+H)⁺

To a stirred solution of 5-(benzyloxy)-3-(cyclopropylmethyl)-1-(6,7-difluoroindeno[1,2-a]inden-4b(9H)-yl)-2,3-dihydro-1H-pyrido[2,1-f][1,2,4]triazine-4,6-dione 25-1 and 5-(benzyloxy)-3-(cyclopropylmethyl)-1-(2,3-difluoroindeno[1,2-a]inden-4b(9H)-yl)-2,3-dihydro-1H-pyrido[2,1-f][1,2,4]triazine-4,6-dione 25-1a (50 mg, 0.0888 mmol) in MeOH (3 mL) and EtOAc (3 mL) was treated with 10% w/w of 20% Pd(OH)₂ on carbon (10 mg) and stirred under balloon hydrogen atmosphere for 2 hr. Reaction mixture was filtered through Diatomaceous earth and washed the Diatomaceous earth bed with 10% MeOH in DCM (20 mL) and concentrated under reduced pressure. Crude compound was purified through Prep HPLC method to afford 3-(cyclopropylmethyl)-1-(2,3-difluoro-9a,10-dihydroindeno[1,2-a]inden-4b(9H)-yl)-5-hydroxy-2,3-dihydro-1H-pyrido[2,1-f][1,2,4]triazine-4,6-dione A13. TLC system: 10% MeOH in DCMRf: 0.5, LCMS (ESI): m/z 476.13 (M+H)⁺

Example 26: 1-(2,3-Difluoro-4b,9,9a,10-tetrahydroindeno[1,2-a]inden-4b-yl)-3-ethyl-5-hydroxy-2,3-dihydro-1H-pyrido[1,2-f][1,2,4]triazine-4,6-dione (A10)

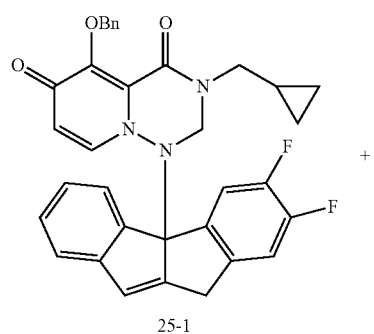

25-1

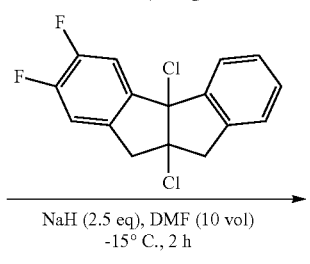

12-2

10% Pd(OH)₂ (20% w/w), H₂ atm, MeOH, EtOAc (1:1) (20 vol), RT, 2 h

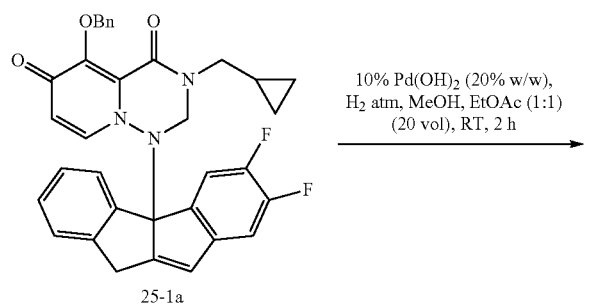

25-1a

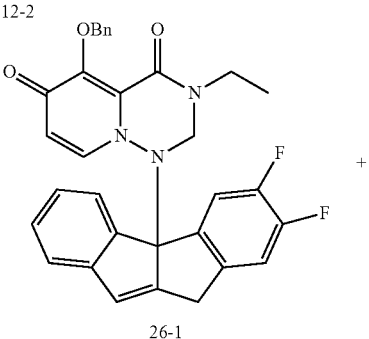

26-1

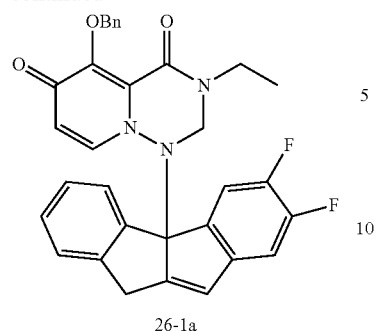

26-1a

To a stirred solution of 5-(benzyloxy)-3-ethyl-2,3-dihydro-1H-pyrido[1,2-f][1,2,4]triazine-4,6-dione 12-2 (320 mg, 1.0702 mmol) in DMF (15 mL) was added 60% of NaH (107 mg, 2.680 mmol) at −15° C. and stirred for 15 minutes. Then added solution of 4b,9a-dichloro-2,3-difluoro-4b,9,9a,10-tetrahydroindeno[1,2-a]indene INT-3 (398 mg, 1.284 mmol) in dry DMF (5 mL) at −15° C. then stirred 2 hr. Reaction mixture quenched with saturated $NH_4Cl$ solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 65% ACN in 0.1% formic acid in water to afford 5-(benzyloxy)-1-(6,7-difluoro-4b,9-dihydroindeno[1,2-a]inden-4b-yl)-3-ethyl-2,3-dihydro-1H-pyrido[1,2-f][1,2,4]triazine-4,6-dione 26-1 5-(benzyloxy)-1-(2,3-difluoroindeno[1,2-a]inden-4b(9H)-yl)-3-ethyl-2,3-dihydro-1H-pyrido[2,1-f][1,2,4]triazine-4,6-dione 26-1a. TLC system: 10% MeOH in DCM Rf: 0.4, LCMS (ESI): m/z 538.14 (M+H)$^+$ To a stirred solution of 5-(benzyloxy)-1-(6,7-difluoro-4b,9-dihydroindeno[1,2-a]inden-4b-yl)-3-ethyl-2,3-dihydro-1H-pyrido[1,2-f][1,2,4]triazine-4,6-dione 26-1 5-(benzyloxy)-1-(2,3-difluoroindeno[1,2-a]inden-4b(9H)-yl)-3-ethyl-2,3-dihydro-1H-pyrido[2,1-f][1,2,4]triazine-4,6-dione 26-1a (70 mg, 0.13 mmol) in MeOH (5 mL) and EtOAc (5 mL) was treated with 10% w/w of 20% $Pd(OH)_2$ on carbon (20 mg) and stirred under balloon hydrogen atmosphere for 1 hour. Reaction mixture filtered through Diatomaceous earth and washed the Diatomaceous earth bed with MeOH (20 mL) and concentrated under reduced pressure. Crude compound was triturated with diethyl ether to afford 1-(2,3-difluoro-4b,9,9a,10-tetrahydroindeno[1,2-a]inden-4b-yl)-3-ethyl-5-hydroxy-2,3-dihydro-1H-pyrido[1,2-f][1,2,4]triazine-4,6-dione A10. TLC system: 10% MeOH in DCM Rf: 0.3, LCMS (ESI): m/z 450.09 (M+H)$^+$ Example 27: 3-benzyl-1-(2,3-difluoro-9a,10-dihydroindeno[1,2-a]inden-4b(9H)-yl)-5-hydroxy-2,3-dihydro-1H-pyrido[2,1-f][1,2,4]triazine-4,6-dione (A21)

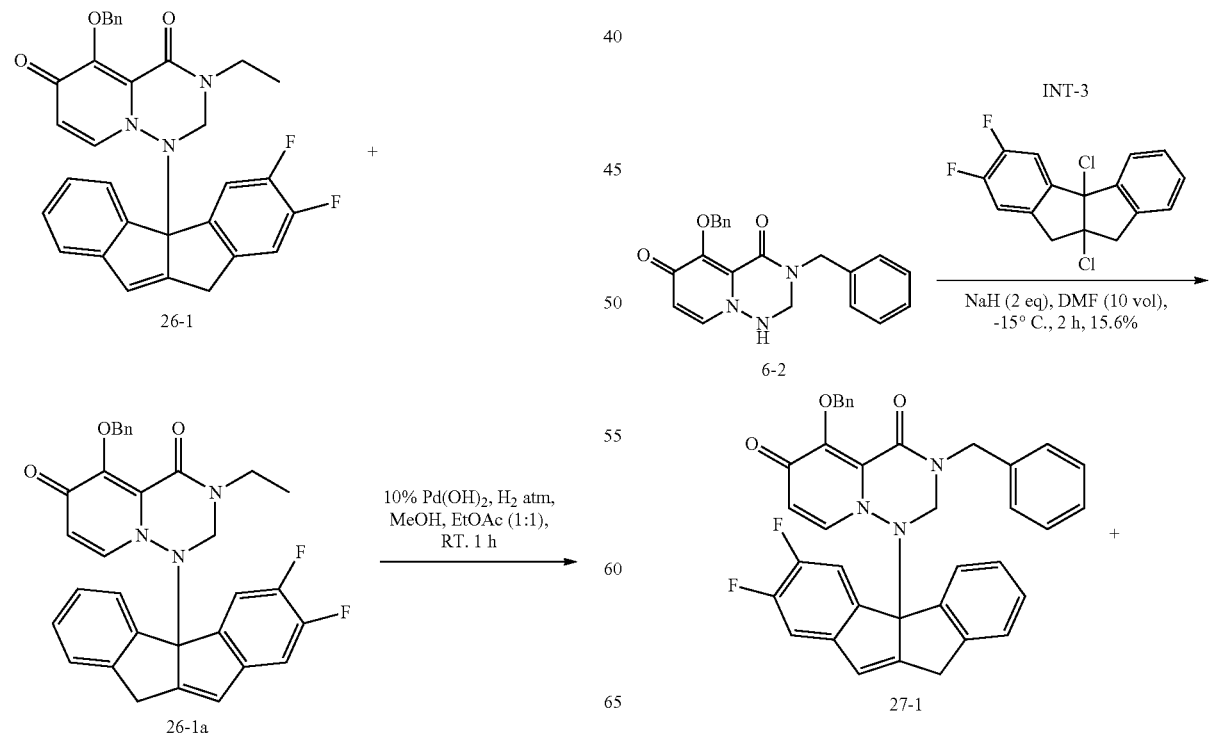

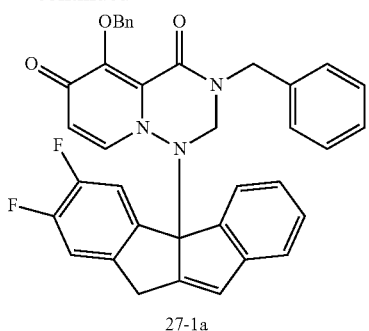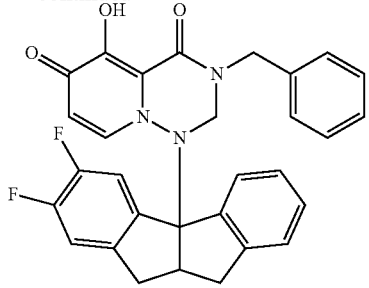

To a stirred solution of 3-benzyl-5-(benzyloxy)-2,3-dihydro-1H-pyrido[2,1-f][1,2,4]triazine-4,6-dione 6-2 (500 mg, 1.385 mmol) in DMF (15 mL) was added 60% of NaH (138 mg, 3.4625 mmol) at −15° C. and stirred for 15 minutes. Then added solution of 4b,9a-dichloro-2,3-difluoro-4b,9,9a,10-tetrahydroindeno[1,2-a]indene INT-3 (510 mg, 1.662 mmol) in DMF (5 mL) at −15° C. and stirred for 2 hr. Reaction mixture was quenched with saturated NH$_4$Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 80% ACN in 0.1% formic acid in water to afford isomeric mixture of 3-benzyl-5-(benzyloxy)-1-(2,3-difluoroindeno[1,2-a]inden-4b(9H)-yl)-2,3-dihydro-1H-pyrido[2,1-f][1,2,4]triazine-4,6-dione 27-1 and 3-benzyl-5-(benzyloxy)-1-(6,7-difluoroindeno[1,2-a]inden-4b(9H)-yl)-2,3-dihydro-1H-pyrido[2,1-f][1,2,4]triazine-4,6-dione 27-1a. TLC system: 10% MeOH in DCM Rf: 0.4, LCMS (ESI): m/z 600.38 (M+H)$^+$ To a stirred solution of 3-benzyl-5-(benzyloxy)-1-(2,3-difluoroindeno[1,2-a]inden-4b(9H)-yl)-2,3-dihydro-1H-pyrido[2,1-f][1,2,4]triazine-4,6-dione 27-1 3-benzyl-5-(benzyloxy)-1-(6,7-difluoroindeno[1,2-a]inden-4b(9H)-yl)-2,3-dihydro-1H-pyrido[2,1-f][1,2,4]triazine-4,6-dione 27-1a (120 mg, 0.2003 mmol) in MeOH (2 mL) and EtOAc (2 mL) was treated with 10% w/w of 20% Pd(OH)$_2$ on carbon (10 mg) and stirred under balloon hydrogen pressure for 1 hour. Reaction mixture was filtered through Diatomaceous earth and washed the Diatomaceous earth bed with MeOH (20 mL) and concentrated under reduced pressure. Crude compound was purified by prep-HPLC to afford 3-benzyl-1-(2,3-difluoro-9a,10-dihydroindeno[1,2-a]inden-4b(9H)-yl)-5-hydroxy-2,3-dihydro-1H-pyrido[2,1-f][1,2,4]triazine-4,6-dione A21. TLC system: 10% MeOH in DCM Rf: 0.3, LCMS (ESI): m/z 512.09 (M+H)$^+$ Example 28: 1-(1,2-difluoro-9a,10-dihydroindeno[1,2-a]inden-4b(9H)-yl)-5-hydroxy-3-phenethyl-2,3-dihydro-1H-pyrido[2,1-f][1,2,4]triazine-4,6-dione (A22)

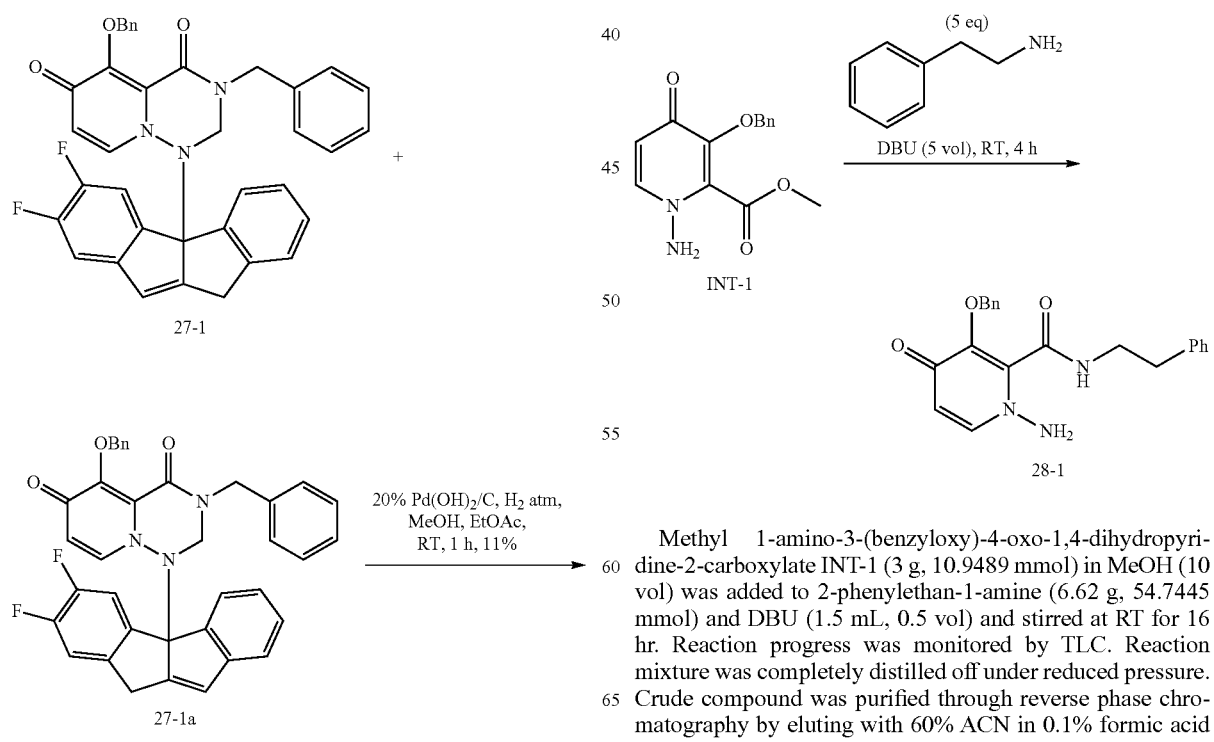

Methyl 1-amino-3-(benzyloxy)-4-oxo-1,4-dihydropyridine-2-carboxylate INT-1 (3 g, 10.9489 mmol) in MeOH (10 vol) was added to 2-phenylethan-1-amine (6.62 g, 54.7445 mmol) and DBU (1.5 mL, 0.5 vol) and stirred at RT for 16 hr. Reaction progress was monitored by TLC. Reaction mixture was completely distilled off under reduced pressure. Crude compound was purified through reverse phase chromatography by eluting with 60% ACN in 0.1% formic acid in water to afford 1-amino-3-(benzyloxy)-4-oxo-N-phenethyl-1,4-dihydropyridine-2-carboxamide 28-1. TLC system: 10% MeOH in DCM Rf: 0.4, LCMS (ESI): m/z 364.14 (M+H)+

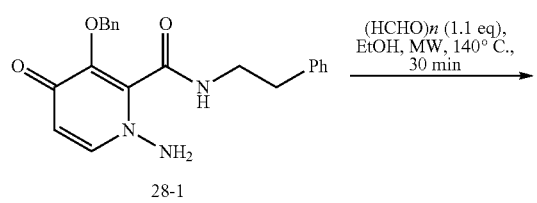

In a microwave vial, to a stirred solution of 1-amino-3-(benzyloxy)-4-oxo-N-phenethyl-1,4-dihydropyridine-2-carboxamide 28-1 (1.4 g, 3.856 mmol) in ethanol (20 mL) was added paraformaldehyde (127 mg, 4.2424 mmol), then irradiated at 140° C. under microwave reactor for 30 minutes. After consumption of starting material, the reaction mixture was concentrated under reduced pressure. Crude compound was purified through reverse phase chromatography by eluting with 30% ACN in 0.1% formic acid in water to afford 5-(benzyloxy)-3-phenethyl-2,3-dihydro-1H-pyrido[2,1-f][1,2,4]triazine-4,6-dione 28-2. TLC system: 10% MeOH in DCM Rf: 0.5, LCMS (ESI): m/z 376.34 (M+H)+

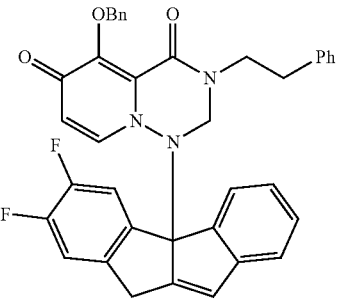

To a stirred solution of 5-(benzyloxy)-3-phenethyl-2,3-dihydro-1H-pyrido[2,1-f][1,2,4]triazine-4,6-dione 28-1 (350 mg, 0.9333 mmol) in DMF (5 mL) was added 60% of NaH (112 mg, 2.799 mmol) at −15° C. and stirred for 15 minutes. Then added solution of 4b,9a-dichloro-2,3-difluoro-4b,9,9a,10-tetrahydroindeno[1,2-a]indene INT-3 (318 mg, 1.066 mmol) in DMF (3 mL) at −15° C. and stirred for 2 hr. Reaction mixture was quenched with saturated NH4Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 75% ACN in 0.1% formic acid in water to afford isomeric mixture of 5-(benzyloxy)-1-(2,3-difluoroindeno[1,2-a]inden-4b(9H)-yl)-3-phenethyl-2,3-dihydro-1H-pyrido [2,1-f][1,2,4]triazine-4,6-dione 28-2 5-(benzyloxy)-1-(6,7-difluoroindeno[1,2-a]inden-4b(9H)-yl)-3-phenethyl-2,3-dihydro-1H-pyrido[2,1-f][1,2,4]triazine-4,6-dione 28-2a. TLC system: 10% MeOH in DCM Rf: 0.6, LCMS (ESI): m/z 614.42 (M+H)+

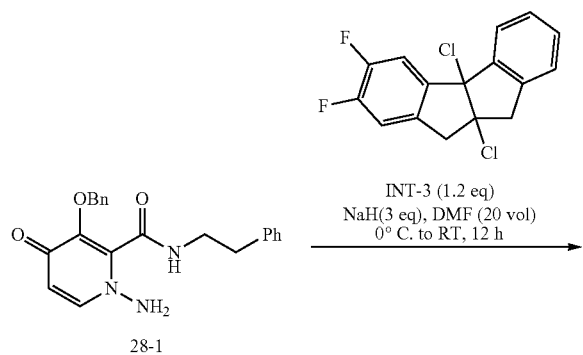

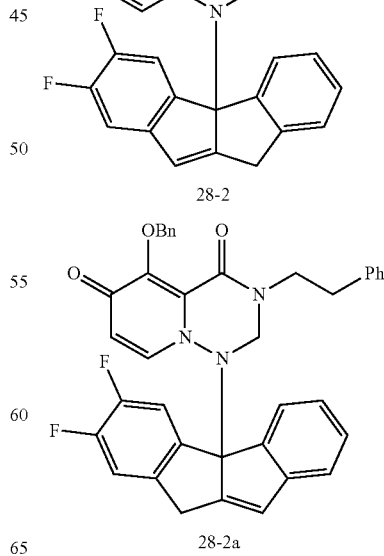

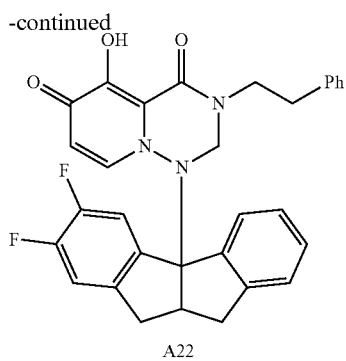

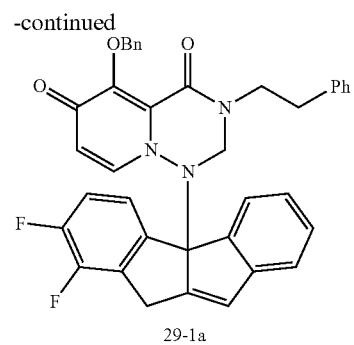

To a stirred solution of 5-(benzyloxy)-1-(2,3-difluoroindeno[1,2-a]inden-4b(9H)-yl)-3-phenethyl-2,3-dihydro-1H-pyrido[2,1-f][1,2,4]triazine-4,6-dione 28-2 5-(benzyloxy)-1-(6,7-difluoroindeno[1,2-a]inden-4b(9H)-yl)-3-phenethyl-2,3-dihydro-1H-pyrido[2,1-f][1,2,4]triazine-4,6-dione 28-2a (100 mg, 0.1631 mmol) in MeOH (3 mL) and EtOAc (3 mL) was treated with 10% w/w of 20% Pd(OH)$_2$ on carbon (10 mg) and stirred under balloon hydrogen pressure for 1 hr. Reaction mixture was filtered through Diatomaceous earth and washed the Diatomaceous earth bed with 10% MeOH in DCM (20 mL) and concentrated under reduced pressure. Crude compound was purified through Prep HPLC to afford 1-(2,3-difluoro-9a,10-dihydroindeno[1,2-a]inden-4b(9H)-yl)-5-hydroxy-3-phenethyl-2,3-dihydro-1H-pyrido[2,1-f][1,2,4]triazine-4,6-dione A22. TLC system: 10% MeOH in DCM Rf: 0.3, LCMS (ESI): m/z 526.10 (M+H)$^+$ Example 29: 1-(1,2-difluoro-9a,10-dihydroindeno[1,2-a]inden-4b(9H)-yl)-5-hydroxy-3-phenethyl-2,3-dihydro-1H-pyrido[2,1-f][1,2,4]triazine-4,6-dione (A25)

To a stirred solution of 5-(benzyloxy)-3-phenethyl-2,3-dihydro-1H-pyrido[2,1-f][1,2,4]triazine-4,6-dione 28-1 (500 mg, 1.3333 mmol) in DMF (5 mL) was added 60% of NaH (160 mg, 3.9999 mmol) at −15° C. and stirred for 15 minutes. Then added solution of 4b,9a-dichloro-1,2-difluoro-4b,9,9a,10-tetrahydroindeno[1,2-a]indene INT-4 (454 mg, 1.4666 mmol) in DMF (3 mL) at −15° C. and stirred for 2 hr. Reaction mixture was quenched with saturated NH$_4$Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 75% ACN in 0.1% formic acid in water to afford isomeric mixture of 5-(benzyloxy)-1-(1,2-difluoroindeno[1,2-a]inden-4b(9H)-yl)-3-phenethyl-2,3-dihydro-1H-pyrido [2,1-f][1,2,4]triazine-4,6-dione 29-1 and 5-(benzyloxy)-1-(7,8-difluoroindeno[1,2-a]inden-4b(9H)-yl)-3-phenethyl-2,3-dihydro-1H-pyrido[2,1-f][1,2,4]triazine-4,6-dione 29-1a. TLC system: 10% MeOH in DCM Rf: 0.6, LCMS (ESI): m/z 614.42 (M+H)$^+$

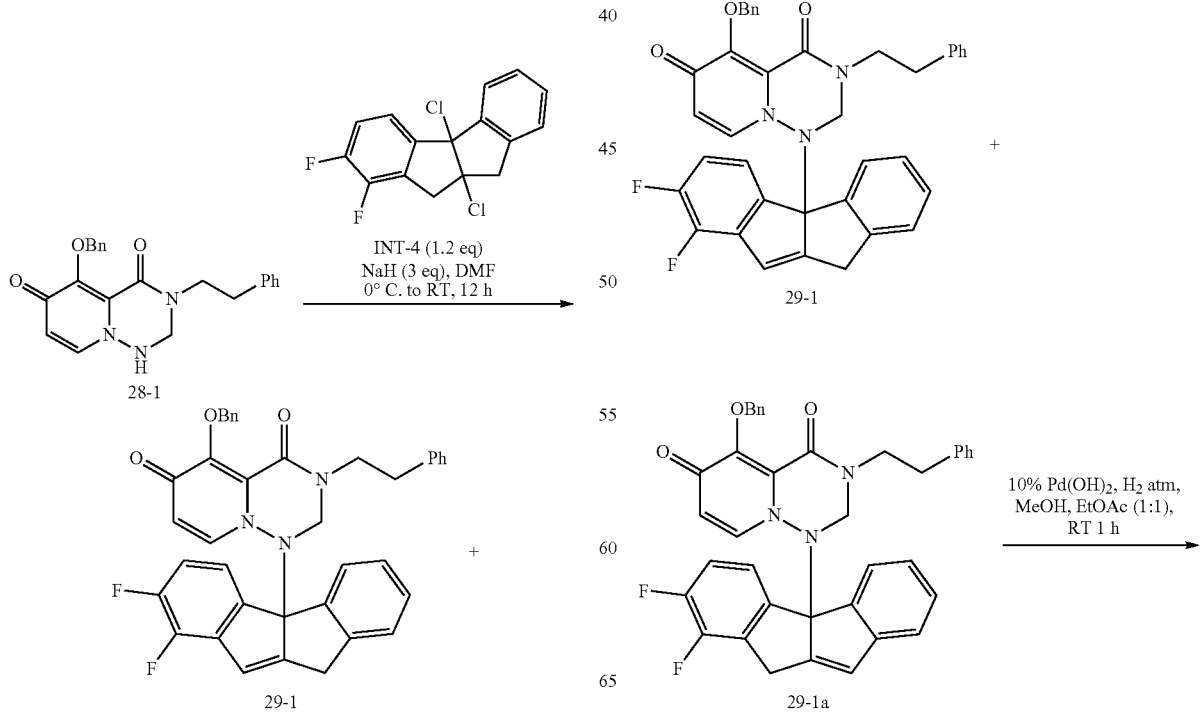

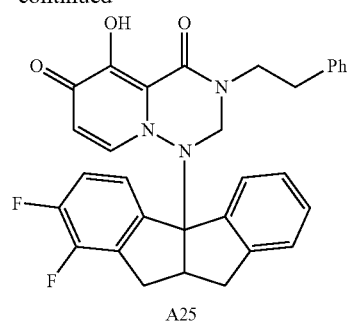

A25

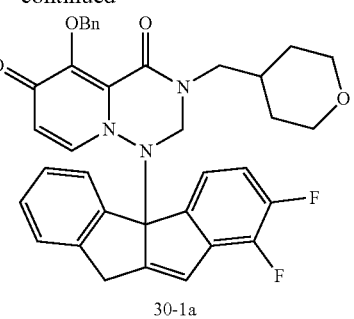

30-1a

To a stirred solution of 5-(benzyloxy)-1-(1,2-difluoroindeno[1,2-a]inden-4b(9H)-yl)-3-phenethyl-2,3-dihydro-1H-pyrido[2,1-f][1,2,4]triazine-4,6-dione 29-1 and 5-(benzyloxy)-1-(7,8-difluoroindeno[1,2-a]inden-4b(9H)-yl)-3-phenethyl-2,3-dihydro-1H-pyrido[2,1-f][1,2,4]triazine-4,6-dione 29-1a (180 mg, 0.2936 mmol) in MeOH (5 mL) and EtOAc (5 mL) was treated with 10% w/w of 20% Pd(OH)$_2$ on carbon (30 mg) and stirred under balloon hydrogen pressure for 1 hour. Reaction mixture was filtered through Diatomaceous earth and washed the Diatomaceous earth bed with 10% MeOH in DCM (20 mL) and concentrated under reduced pressure. Crude compound was purified through Prep HPLC method to afford 1-(1,2-difluoro-9a,10-dihydroindeno[1,2-a]inden-4b(9H)-yl)-5-hydroxy-3-phenethyl-2,3-dihydro-1H-pyrido[2,1-f][1,2,4]triazine-4,6-dione A25. TLC system: 10% MeOH in DCM Rf: 0.3, LCMS (ESI): m/z 526.10 (M+H)$^+$ Example 30: 1-(1,2-difluoro-9a,10-dihydroindeno[1,2-a]inden-4b(9H)-yl)-5-hydroxy-3-((tetrahydro-2H-pyran-4-yl)methyl)-2,3-dihydro-1H-pyrido[2,1-f][1,2,4]triazine-4,6-dione (A15)

To a stirred solution of 5-(benzyloxy)-3-((tetrahydro-2H-pyran-4-yl)methyl)-2,3-dihydro-1H-pyrido[2,1-f][1,2,4]triazine-4,6-dione 3 (600 mg, 1.626 mmol) in DMF (15 mL) was added 60% of NaH (162 mg, 4.065 mmol) at −15° C. and stirred for 15 minutes. Then added solution of 4b,9a-dichloro-1,2-difluoro-4b,9,9a,10-tetrahydroindeno[1,2-a]indene 8-3 (605 mg, 1.9512 mmol) in DMF (5 mL) at −15° C. then stirred 2 hr. Reaction mixture was quenched with saturated NH$_4$Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 65% ACN in 0.1% formic acid in water to afford isomeric mixture of 5-(benzyloxy)-1-(7,8-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 30-1 and 5-(benzyloxy)-1-(1,2-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 30-1a. TLC system: 10% MeOH in DCM Rf: 0.4, LCMS (ESI): m/z 608.14 (M+H)$^+$

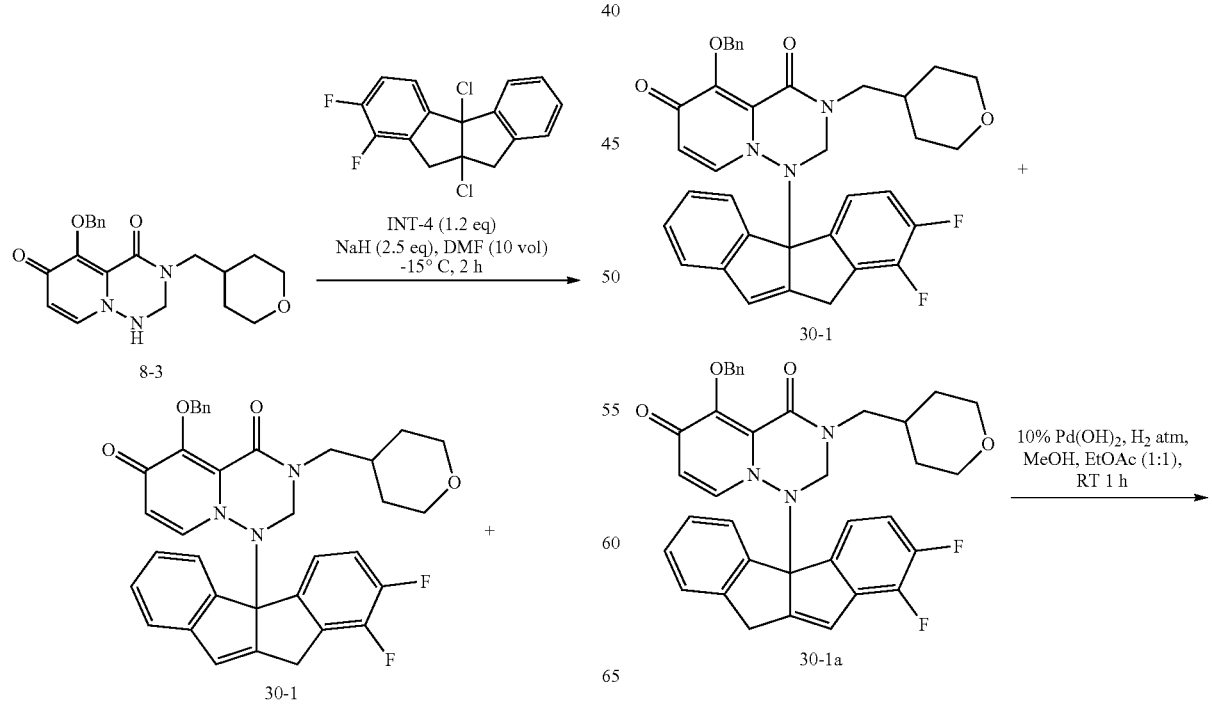

-continued

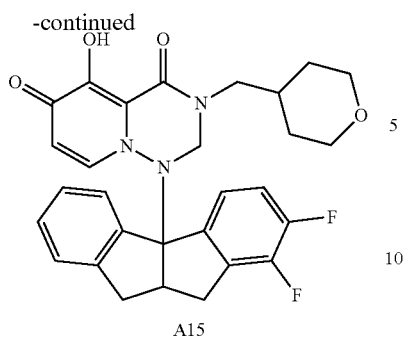

A15

To a stirred solution of 5-(benzyloxy)-1-(7,8-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 30-1 and 5-(benzyloxy)-1-(1,2-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 30-1a (80 mg, 0.13179 mmol) in MeOH (2 mL) and EtOAc (2 mL) was treated with 10% w/w of 20% Pd(OH)$_2$ on carbon (10 mg) and stirred under hydrogen atmosphere (balloon pressure) for 1 hour. Reaction mixture was filtered through Diatomaceous earth and washed the Diatomaceous earth bed with MeOH (20 mL) and concentrated under reduced pressure. Crude compound purified by prep-HPLC to afford 1-(1,2-difluoro-9a,10-dihydroindeno[1,2-a]inden-4b(9H)-yl)-5-hydroxy-3-(tetrahydro-2H-pyran-4-yl)methyl)-2,3-dihydro-1H-pyrido[2,1-f][1,2,4]triazine-4,6-dione A15. TLC system: 10% MeOH in DCM Rf: 0.3, LCMS (ESI): m/z 520.13 (M+H)$^+$ Example 31 1-(2,3-difluoro-9a,10-dihydroindeno[1,2-a]inden-4b(9H)-yl)-5-hydroxy-3-((tetrahydro-2H-pyran-4-yl)methyl)-2,3-dihydro-1H-pyrido[2,1-f][1,2,4]triazine-4,6-dione (A16)

-continued

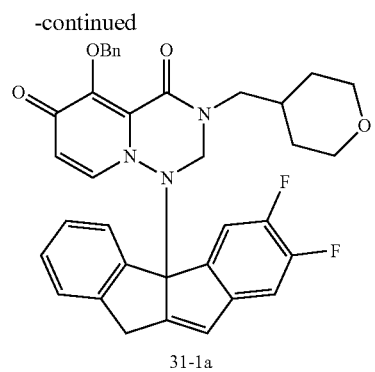

31-1a

To a stirred solution of 8-3 (600 mg, 1.626 mmol) in DMF (15 mL) was added 60% of NaH (162 mg, 4.065 mmol) at −15° C. and stirred for 15 minutes. To that mixture was added solution of 4b,9a-dichloro-2,3-difluoro-4b,9,9a,10-tetrahydroindeno[1,2-a]indene INT-3 (605 mg, 1.9512 mmol) in DMF (5 mL) at −15° C. then stirred 2 hr. Reaction mixture was quenched with saturated NH$_4$Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 65% ACN in 0.1% formic acid in water to afford 5-(benzyloxy)-1-(6,7-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 31-1 and 5-(benzyloxy)-1-(2,3-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 31-1a. TLC system: 10% MeOH in DCM Rf: 0.4, LCMS (ESI): m/z 608.52 (M+H)$^+$

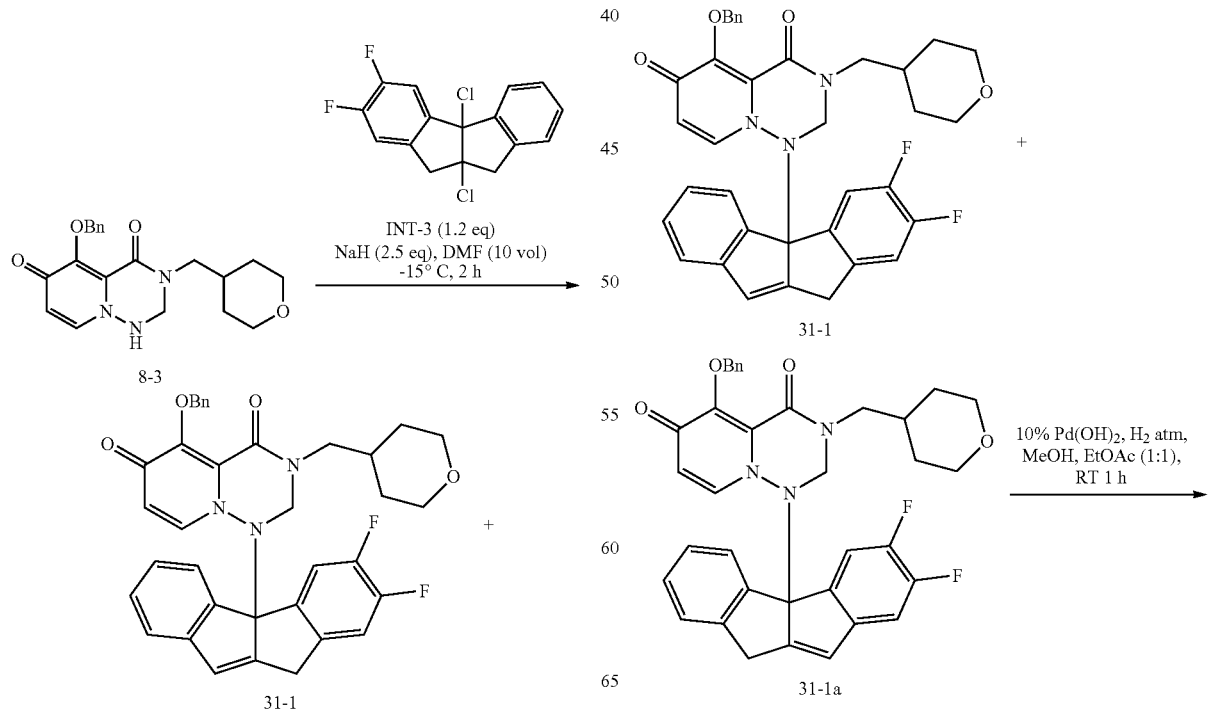

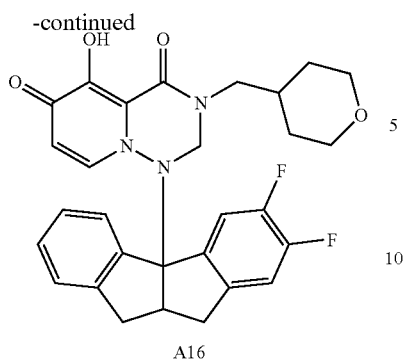

A16

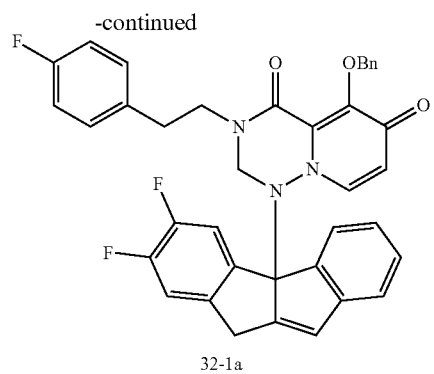

32-1a

A stirred solution of 5-(benzyloxy)-1-(6,7-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 31-1 and 5-(benzyloxy)-1-(2,3-difluoroindeno[1,2-a]inden-4b(9H)-yl)-3-((tetrahydro-2H-pyran-4-yl)methyl)-2,3-dihydro-1H-pyrido[2,1-f][1,2,4]triazine-4,6-dione 31-1a (60 mg, 0.0988 mmol) in MeOH (2 mL) and EtOAc (2 mL) was treated with 10% w/w of 20% Pd(OH)$_2$ on carbon (10 mg) and stirred under hydrogen atmosphere (balloon pressure) for 1 hour. Reaction mixture was filtered through Diatomaceous earth and washed the Diatomaceous earth bed with MeOH (20 mL) and concentrated under reduced pressure. Crude compound purified by prep-HPLC to afford compound 1-(2,3-difluoro-9a,10-dihydroindeno[1,2-a]inden-4b(9H)-yl)-5-hydroxy-3-(tetrahydro-2H-pyran-4-yl)methyl)-2,3-dihydro-1H-pyrido[2,1-f][1,2,4]triazine-4,6-dione A15. TLC system: 10% MeOH in DCM Rf: 0.3, LCMS (ESI): m/z 520.13 (M+H)$^+$ Example 32: 1-(2,3-difluoro-9a,10-dihydroindeno[1,2-a]inden-4b(9H)-yl)-3-(4-fluorophenethyl)-5-hydroxy-2,3-dihydro-1H-pyrido[2,1-f][1,2,4]triazine-4,6-dione (A29)

To a stirred solution of 5-(benzyloxy)-3-(4-fluorophenethyl)-2,3-dihydro-1H-pyrido[2,1-f][1,2,4]triazine-4,6-dione 19-2 (500 mg, 1.272 mmol) in DMF (8 mL) was added 60% of NaH (152 mg, 3.816 mmol) at −25° C. and stirred for 15 minutes. Then added solution of 4b,9a-dichloro-2,3-difluoro-4b,9,9a,10-tetrahydroindeno[1,2-a]indene INT-3 (591 mg, 1.908 mmol) in DMF (7 mL) at −25° C. and stirred for 2 hr. Reaction mixture was quenched with saturated NH$_4$Cl solution (50 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 82% ACN in 0.1% formic acid in water to afford compound with impurity. Again crude was purified through 60-120 silica gel column chromatography by eluting with 1% MeOH in DCM to afford 5-(benzyloxy)-1-(2,3-difluoroindeno[1,2-a]inden-4b(9H)-yl)-3-(4-fluorophenethyl)-2,3-dihydro-1H-pyrido[2,1-f][1,2,4]triazine-4,6-dione 32-1 and 5-(benzyloxy)-1-(6,7-difluoroindeno[1,2-a]inden-4b(9H)-yl)-3-(4-fluorophenethyl)-2,3-dihydro-1H-pyrido[2,1-f][1,2,4]triazine-4,6-dione 32-1a. TLC system: 10% MeOH in DCM R$_f$: 0.5, LCMS (ESI): m/z 632.15 (M+H)$^+$

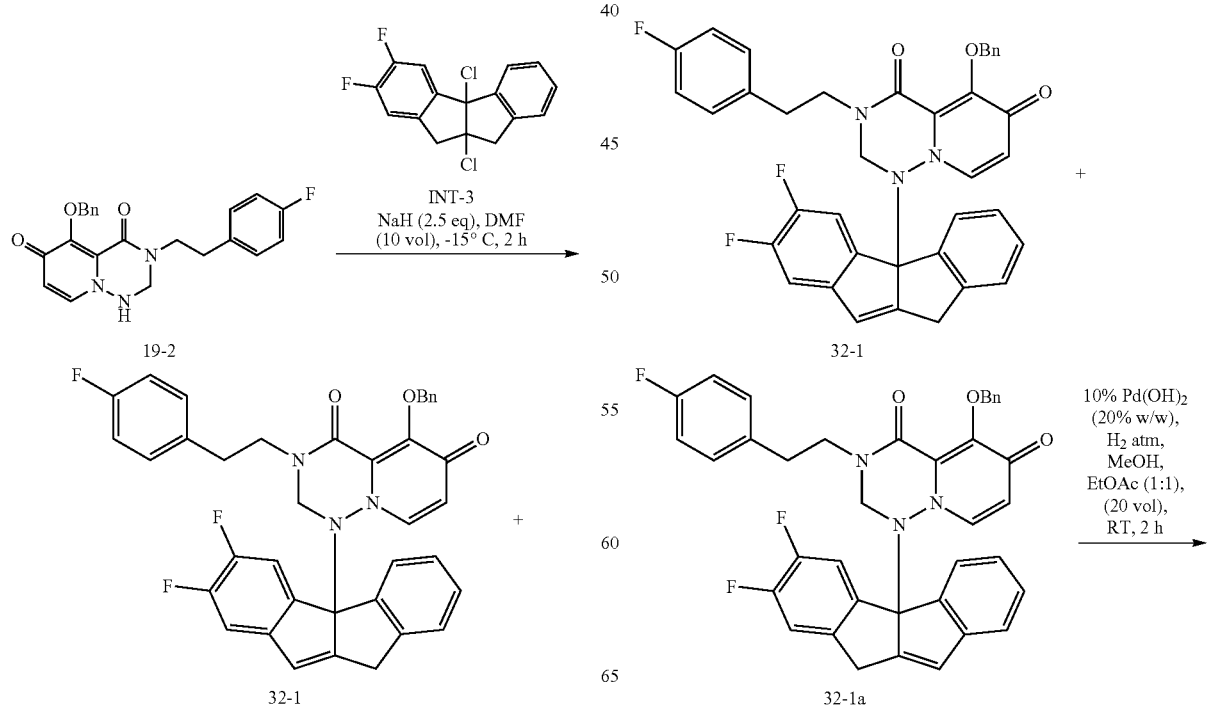

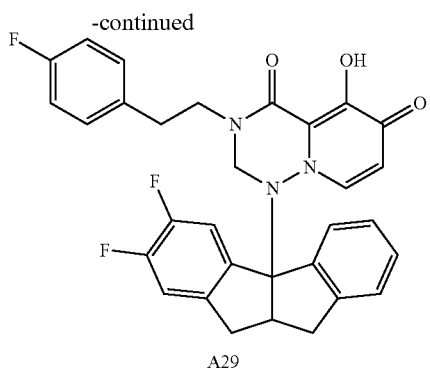

A29

A stirred solution of 5-(benzyloxy)-1-(2,3-difluoroindeno[1,2-a]inden-4b(9H)-yl)-3-(4-fluorophenethyl)-2,3-dihydro-1H-pyrido[2,1-f][1,2,4]triazine-4,6-dione 32-1 5-(benzyloxy)-1-(6,7-difluoroindeno[1,2-a]inden-4b(9H)-yl)-3-(4-fluorophenethyl)-2,3-dihydro-1H-pyrido[2,1-f][1,2,4]triazine-4,6-dione 32-1a (70 mg, 0.1109 mmol) in MeOH (2 mL) and EtOAc (2 mL) was treated with 10% w/w of 20% Pd(OH)$_2$ on carbon (10 mg) and stirred under balloon hydrogen pressure for 1 hour. Reaction mixture was filtered through Diatomaceous earth and washed the Diatomaceous earth bed with 10% MeOH in DCM (20 mL) and concentrated under reduced pressure. Crude compound was purified through Prep HPLC method to afford 1-(2,3-difluoro-9a,10-dihydroindeno[1,2-a]inden-4b(9H)-yl)-3-(4-fluorophenethyl)-5-hydroxy-2,3-dihydro-1H-pyrido[2,1-f][1,2,4]triazine-4,6-dione A29. TLC system: 10% MeOH in DCM R$_f$: 0.5, LCMS (ESI): m/z 544.11 (M+H)$^+$ Example 33: 1-(1,2-difluoro-9a,10-dihydroindeno[1,2-a]inden-4b(9H)-yl)-3-(3-fluorobenzyl)-5-hydroxy-2,3-dihydro-1H-pyrido[2,1-f][1,2,4]triazine-4,6-dione (A26)

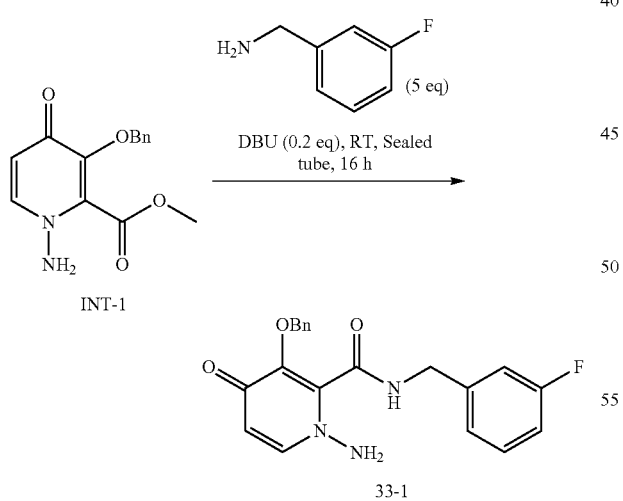

Methyl 1-amino-3-(benzyloxy)-4-oxo-1,4-dihydropyridine-2-carboxylate INT-1 (3.0 g, 10.9489 mmol) was added to (3-fluorophenyl)methanamine (6.8 mL, 54.7445 mmol) and DBU (0.47 mL, 2.1897 mmol) and then stirred at RT for 16 hr. Reaction mixture was distilled off under reduced pressure. Crude compound was purified through reverse phase chromatography by eluting with 60% ACN in 0.1% formic acid in water to afford 1-amino-3-(benzyloxy)-N-(3-fluorobenzyl)-4-oxo-1,4-dihydropyridine-2-carboxamide 33-1. TLC system: 10% MeOH in DCM Rf: 0.2, LCMS (ESI): m/z 368.34 (M+H)

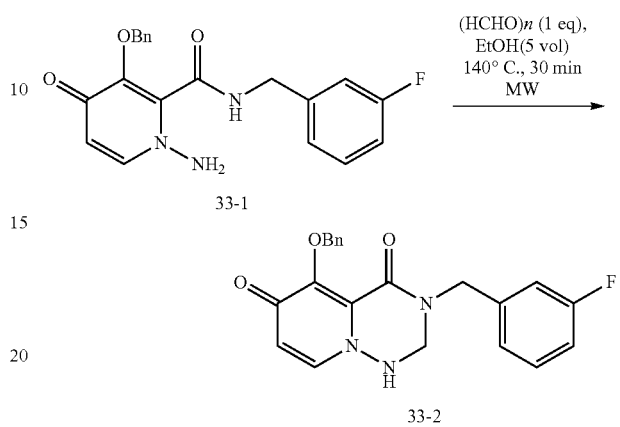

In a microwave vial, to a stirred solution of 1-amino-3-(benzyloxy)-N-(3-fluorobenzyl)-4-oxo-1,4-dihydropyridine-2-carboxamide 33-1 (500 mg, 1.3623 mmol) in ethanol (10 mL) was added paraformaldehyde (40.8 mg, 1.3623 mmol), then irradiated at 140° C. under microwave reactor for 30 minutes. After consumption of starting material, the reaction mixture was concentrated under reduced pressure. Crude compound was purified through reverse phase chromatography by eluting with 58% ACN in 0.1% formic acid in water to afford 5-(benzyloxy)-3-(3-fluorobenzyl)-2,3-dihydro-1H-pyrido[2,1-f][1,2,4]triazine-4,6-dione 33-2., TLC system: 10% MeOH in DCM Rf: 0.3, LCMS (ESI): m/z 380.09 (M+H)$^+$

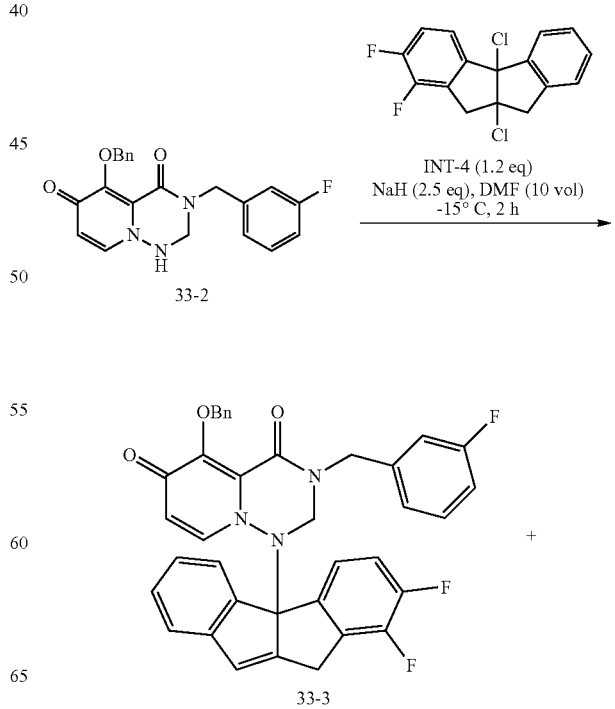

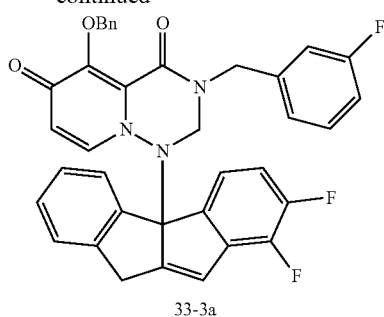

33-3a

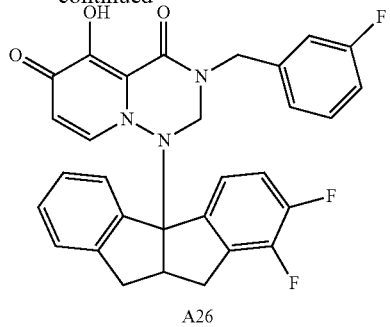

A26

To a stirred solution of 5-(benzyloxy)-3-(3-fluorobenzyl)-2,3-dihydro-1H-pyrido[2,1-f][1,2,4]triazine-4,6-dione 33-2 (550 mg, 1.4511 mmol) in DMF (15 mL) was added 60% of NaH (145 mg, 3.6277 mmol) at −15° C. and stirred for 15 minutes. Then added solution of 4b,9a-dichloro-1,2-difluoro-4b,9,9a,10-tetrahydroindeno[1,2-a]indene INT-4 (539 mg, 1.7413 mmol in DMF (5 mL) at −15° C. then stirred 2 hr. Reaction mixture was quenched with saturated NH4Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 90% ACN in 0.1% formic acid in water to afford 3-benzyl-5-(benzyloxy)-1-(7,8-difluoroindeno[1,2-a]inden-4b(9H)-yl)-2,3-dihydro-1H-pyrido[2,1-f][1,2,4]triazine-4,6-dione 33-3 and 3-benzyl-5-(benzyloxy)-1-(1,2-difluoroindeno[1,2-a]inden-4b(9H)-yl)-2,3-dihydro-1H-pyrido[2,1-f][1,2,4]triazine-4,6-dione 33-3a. TLC system: 10% MeOH in DCM Rf: 0.4, LCMS (ESI): m/z 618.39 (M+H)+

A stirred solution of 5-(benzyloxy)-1-(7,8-difluoroindeno[1,2-a]inden-4b(9H)-yl)-3-(3-fluorobenzyl)-2,3-dihydro-1H-pyrido[2,1-f][1,2,4]triazine-4,6-dione 33-3 and 3-benzyl-5-(benzyloxy)-1-(1,2-difluoroindeno[1,2-a]inden-4b (9H)-yl)-2,3-dihydro-1H-pyrido[2,1-f][1,2,4]triazine-4,6-dione 33-3a (200 mg, 0.3241 mmol) in MeOH (3 mL) and EtOAc (3 mL) was treated with 10% w/w of 20% Pd(OH)2 on carbon (20 mg) and stirred under balloon hydrogen pressure for 1 hour. Reaction mixture was filtered through Diatomaceous earth and washed the Diatomaceous earth bed with MeOH (20 mL) and concentrated under reduced pressure. Crude compound was purified by prep-HPLC to afford compound 1-(1,2-difluoro-9a,10-dihydroindeno[1,2-a]inden-4b(9H)-yl)-3-(3-fluorobenzyl)-5-hydroxy-2,3-dihydro-1H-pyrido[2,1-f][1,2,4]triazine-4,6-dione A26. TLC system: 10% MeOH in DCM Rf: 0.3, LCMS (ESI): m/z 530.09 (M+H)+

Example 34: 1-(2,3-difluoro-9a,10-dihydroindeno[1,2-a]inden-4b(9H)-yl)-3-(3-fluorobenzyl)-5-hydroxy-2,3-dihydro-1H-pyrido[2,1-f][1,2,4]triazine-4,6-dione (A24)

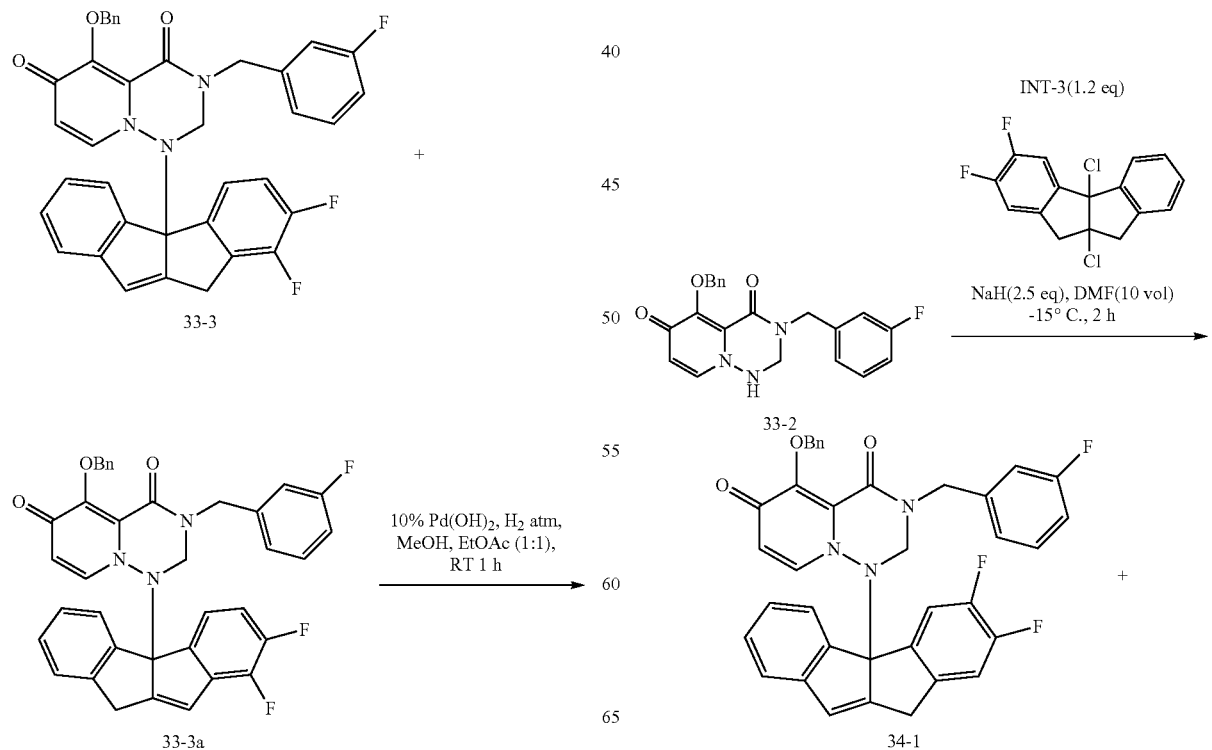

-continued

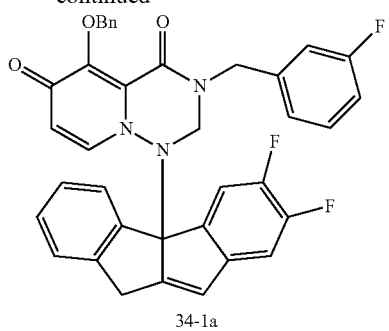

34-1a

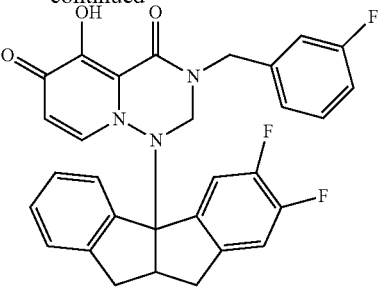

A24

To a stirred solution of 5-(benzyloxy)-3-(3-fluorobenzyl)-2,3-dihydro-1H-pyrido[2,1-f][1,2,4]triazine-4,6-dione 33-2 (550 mg, 1.4511 mmol) in DMF (15 mL) was added 60% of NaH (145 mg, 3.6277 mmol) at −15° C. and stirred for 15 minutes. Then added solution of 4b,9a-dichloro-2,3-difluoro-4b,9,9a,10-tetrahydroindeno[1,2-a]indene INT-3 (539 mg, 1.7413 mmol) in DMF (5 mL) at −15° C. then stirred 2 hr. Reaction mixture quenched with saturated NH₄Cl solution (40 mL) and extracted with EtOAc (2×30 mL). Combined organic layers were washed with brine solution (30 mL), dried over Na2SO4 and concentrated under reduced pressure. Crude compound was purified through reverse phase chromatography by eluting with 90% ACN in 0.1% formic acid in water to afford 3-benzyl-5-(benzyloxy)-1-(6,7-difluoroindeno[1,2-a]inden-4b(9H)-yl)-2,3-dihydro-1H-pyrido[2,1-f][1,2,4]triazine-4,6-dione 34-1 and 5-(benzyloxy)-1-(2,3-difluoroindeno[1,2-a]inden-4b(9H)-yl)-3-(3-fluorobenzyl)-2,3-dihydro-1H-pyrido[2,1-f][1,2,4]triazine-4,6-dione 34-1a. TLC system: 10% MeOH in DCM Rf: 0.4, LCMS (ESI): m/z 618.13 (M+H)⁺

To a stirred solution of 5-(benzyloxy)-1-(6,7-difluoroindeno[1,2-a]inden-4b(9H)-yl)-3-(3-fluorobenzyl)-2,3-dihydro-1H-pyrido[2,1-f][1,2,4]triazine-4,6-dione 34-1 5-(benzyloxy)-1-(2,3-difluoroindeno[1,2-a]inden-4b(9H)-yl)-3-(3-fluorobenzyl)-2,3-dihydro-1H-pyrido[2,1-f][1,2,4]triazine-4,6-dione 34-1a (140 mg, 0.2269 mmol) in MeOH (3 mL) and EtOAc (3 mL) was treated with 10% w/w of 20% Pd(OH)₂ on carbon (15 mg) and stirred under balloon hydrogen pressure for 1 hour. Reaction mixture was filtered through Diatomaceous earth and washed the Diatomaceous earth bed with MeOH (20 mL) and concentrated under reduced pressure. Crude compound was purified by prep-HPLC to afford compound 1-(2,3-difluoro-9a,10-dihydroindeno[1,2-a]inden-4b(9H)-yl)-3-(3-fluorobenzyl)-5-hydroxy-2,3-dihydro-1H-pyrido[2,1-f][1,2,4]triazine-4,6-dione A24. TLC system: 10% MeOH in DCM Rf: 0.3, LCMS (ESI): m/z 530.09 (M+H)⁺

Example 35: 1-(1,2-difluoro-9a,10-dihydroindeno[1,2-a]inden-4b(9H)-yl)-3-(3-fluorophenethyl)-5-hydroxy-2,3-dihydro-1H-pyrido[2,1-f][1,2,4]triazine-4,6-dione (A27)

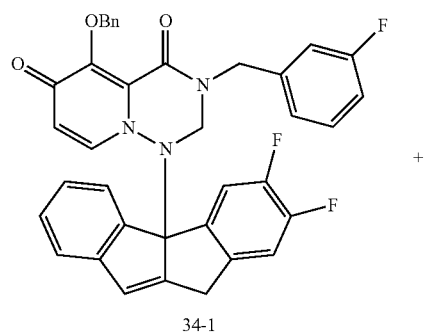

34-1

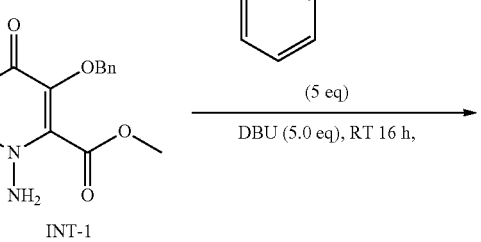

INT-1

35-1

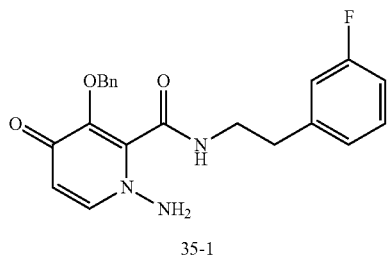

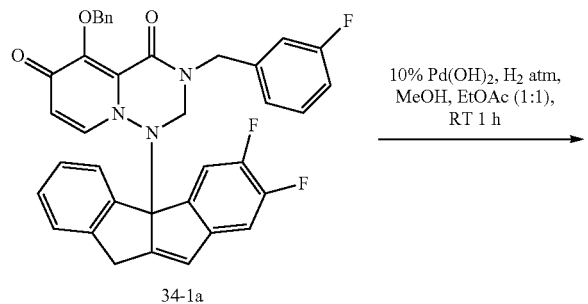

34-1a

To a stirred solution of methyl 1-amino-3-(benzyloxy)-4-oxo-1,4-dihydropyridine-2-carboxylate INT-1 (2 g, 7.0 mmol) was added DBU (2 vol) and 2-(3-fluorophenyl)ethan-1-amine (4.76 mL, 36 mmol) then stirred at RT for 16 hr. Reaction mixture was completely distilled off under reduced pressure. Crude compound was purified through reverse phase chromatography by eluting with 45% ACN in 0.1% formic acid in water to afford 1-amino-3-(benzyloxy)-N-(3-fluorophenethyl)-4-oxo-1, 4-dihydropyridine-2-carboxamide 35-1. TLC system: 10% MeOH in DCM Rf: 0.3, LCMS (ESI): m/z 382.35 (M+H)⁺

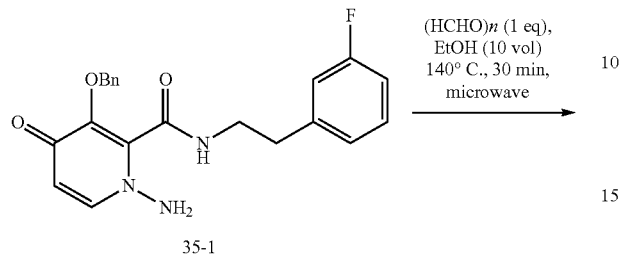

In a microwave vial, to a stirred solution of 1-amino-3-(benzyloxy)-N-(3-fluorophenethyl)-4-oxo-1, 4-dihydropyridine-2-carboxamide 35-1 (500 mg, 1.31 mmol) in ethanol (5 mL) was added paraformaldehyde (39 mg, 1.31 mmol), then stirred in microwave at 140° C. for 30 minutes. After consumption of starting material, the reaction mixture was concentrated under reduced pressure. Crude compound was purified through reverse phase chromatography by eluting with 45% ACN in 0.1% formic acid in water to afford 5-(benzyloxy)-3-(3-fluorophenethyl)-2, 3-dihydro-1H-pyrido [2, 1-f][1, 2, 4] triazine-4, 6-dione 35-2. TLC system: 10% MeOH in DCM Rf: 0.4, LCMS (ESI): m/z 394.1 (M+H)

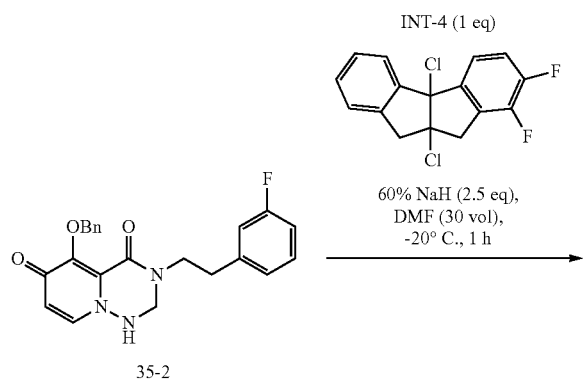

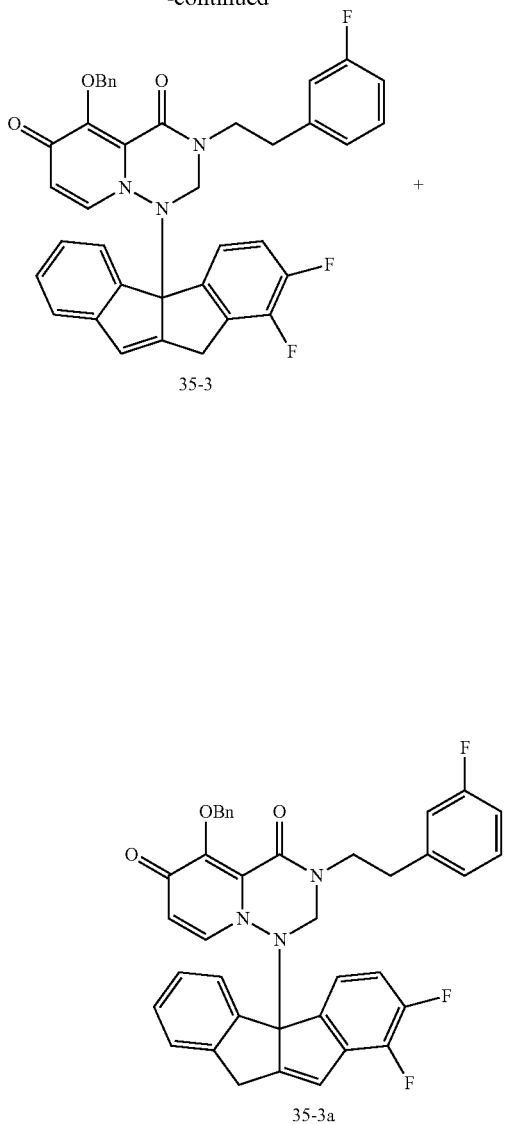

To a stirred solution of 5-(benzyloxy)-3-(3-fluorophenethyl)-2, 3-dihydro-1H-pyrido [2, 1-f][1, 2, 4] triazine-4, 6-dione 35-2 (200 mg, 0.508 mmol) in DMF (4 mL) was added 60% of NaH (61 mg, 1.526 mmol) at −20° C. and stirred for 30 minutes. Then added a solution of 4b,9a-dichloro-2,3-difluoro-4b,9,9a,10-tetrahydroindeno[1,2-a]indeneindene INT-4 (167 mg, 0.508 mmol) in DMF (4 mL) at −20° C. and stirred for 30 minutes. Reaction mixture was quenched with saturated NH₄Cl solution (20 mL) and extracted with EtOAc (2×20 mL). Combined organic layers were washed with brine solution (20 mL), dried over Na2SO4 and concentrated under reduced pressure. Crude compound was purified through reverse phase chromatography by eluting with 80% ACN in 0.1% formic acid in water to afford 5-(benzyloxy)-1-(7,8-difluoroindeno[1,2-a]inden-4b(9H)-yl)-3-(3-fluorophenethyl)-2,3-dihydro-1H-pyrido[2,1-f][1,2,4]triazine-4,6-dione 35-3 and 5-(benzyloxy)-1-(1,2-difluoroindeno[1,2-a]inden-4b(9H)-yl)-3-(3-fluorophenethyl)-2,3-dihydro-1H-pyrido[2,1-f][1,2,4]triazine-4,6-dione 35-3a. TLC system: 10% MeOH in DCM Rf: 0.5, LCMS (ESI): m/z 632.11 (M+H)⁺

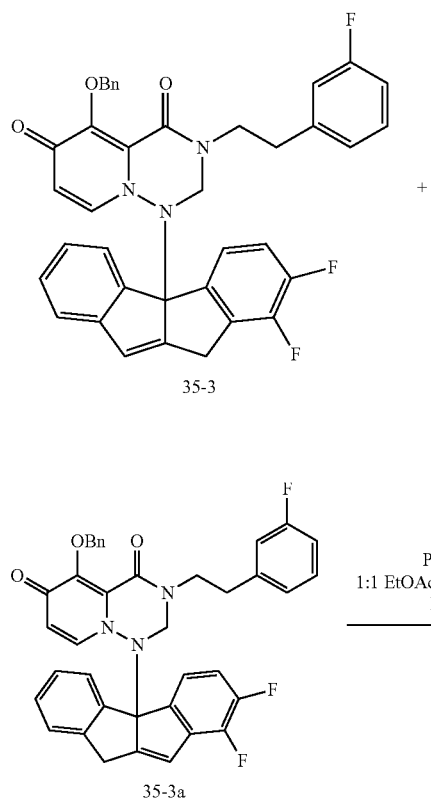

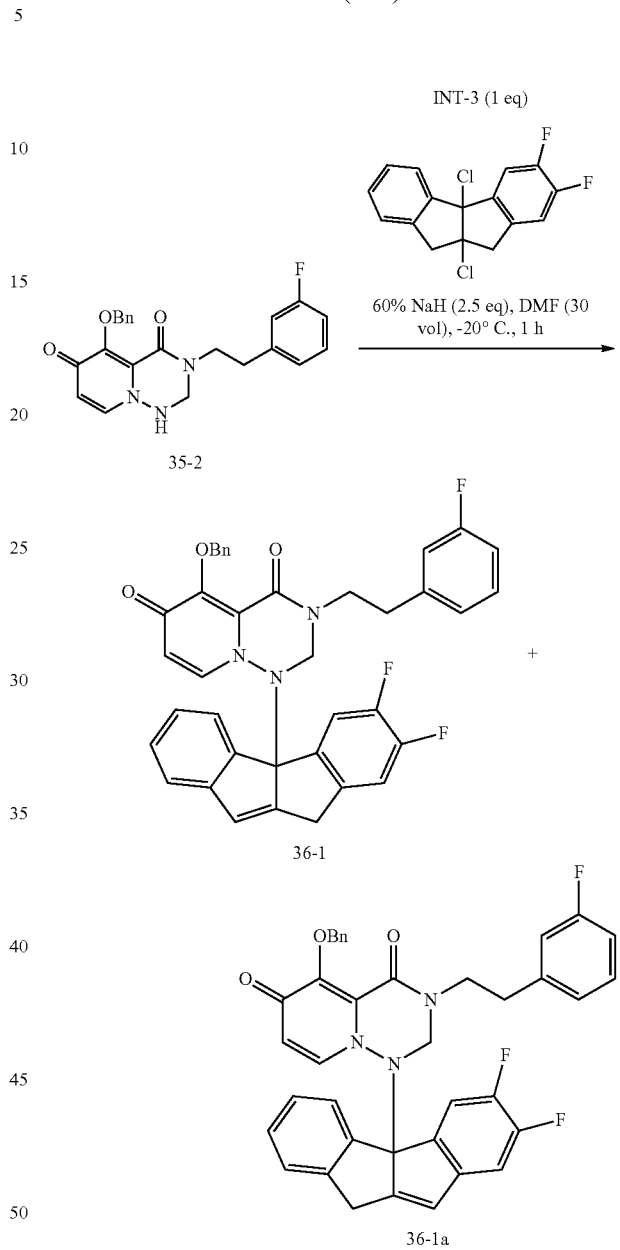

Example 36: 1-(2,3-difluoro-9a,10-dihydroindeno[1,2-a]inden-4b(9H)-yl)-3-(3-fluorophenethyl)-5-hydroxy-2,3-dihydro-1H-pyrido[2,1-f][1,2,4]triazine-4,6-dione (A28)

To a stirred solution of 5-(benzyloxy)-1-(7,8-difluoroindeno[1,2-a]inden-4b(9H)-yl)-3-(3-fluorophenethyl)-2,3-dihydro-1H-pyrido[2,1-f][1,2,4]triazine-4,6-dione 35-3 5-(benzyloxy)-1-(1,2-difluoroindeno[1,2-a]inden-4b(9H)-yl)-3-(3-fluorophenethyl)-2,3-dihydro-1H-pyrido[2,1-f][1,2,4]triazine-4,6-dione 35-3a (110 mg, 0.174 mmol) in MeOH (4 mL) and EtOAc (4 mL) was treated with 10% w/w of 20% Pd(OH)$_2$ on carbon (15 mg) and stirred under balloon hydrogen pressure for 2 hr. Reaction mixture was filtered through Diatomaceous earth and washed the Diatomaceous earth bed with 10% MeOH in DCM (20 mL) and concentrated under reduced pressure. Crude compound was purified through Prep HPLC method to afford 1-(1,2-difluoro-9a,10-dihydroindeno[1,2-a]inden-4b(9H)-yl)-3-(3-fluorophenethyl)-5-hydroxy-2,3-dihydro-1H-pyrido[2,1-f][1,2,4]triazine-4,6-dione A27. TLC system: 10% MeOH in DCM Rf: 0.5, LCMS (ESI): m/z 544.45 (M+H)$^+$ To a stirred solution of 5-(benzyloxy)-3-(3-fluorophenethyl)-2,3-dihydro-1H-pyrido [2,1-f][1, 2, 4] triazine-4,6-dione 35-2 (600 mg, 1.5 mmol) in DMF (12 mL) was added 60% of NaH (152 mg, 3.8 mmol) at −20° C. and stirred for 30 minutes. Then added solution of 4b,9a-dichloro-2,3-difluoro-4b,9,9a,10-tetrahydroindeno[1,2-a]indeneindene INT-3 (604 mg, 1.8 mmol) in DMF (6 mL) at −20° C. then stirred for 30 minutes. Reaction mixture was quenched with saturated NH$_4$Cl solution (20 mL) and extracted with EtOAc (2×20 mL). Combined organic layers were washed with brine solution (20 mL), dried over Na2SO4 and concentrated under reduced pressure. Crude compound was purified through reverse phase chromatography by eluting with 78% ACN in 0.1% formic acid in water to afford 5-(benzyloxy)-1-(6,7-difluoroindeno[1,2-a]inden-4b(9H)-yl)-3-(3-fluorophenethyl)-2,3-dihydro-1H-pyrido[2,1-f][1,2,4]triazine-4,6-dione 36-1 and 5-(benzyloxy)-1-(6,7-difluoroindeno[1,2-a]inden-4b(9H)-yl)-3-(3-fluorophenethyl)-2,3-dihydro-1H-pyrido[2,1-f][1,2,4]triazine-4,6-dione 36-1a. TLC system: 10% MeOH in DCM Rf: 0.5, LCMS (ESI): m/z 632.47 (M+H)+

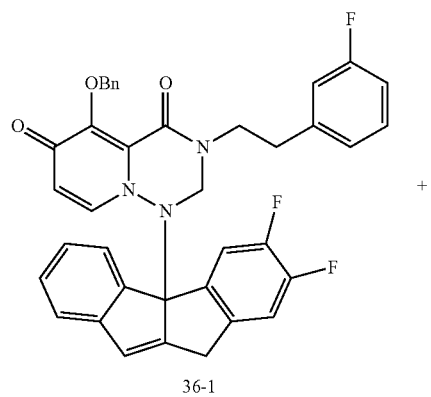

36-1

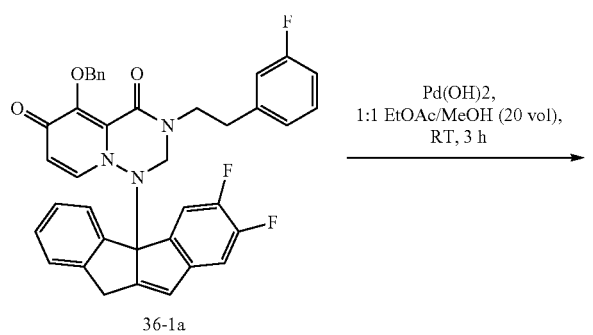

36-1a

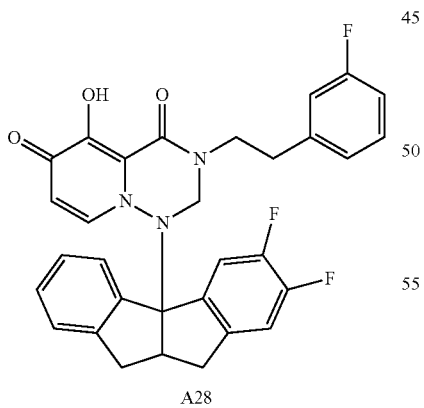

A28

To a stirred solution of 5-(benzyloxy)-1-(6,7-difluoroindeno[1,2-a]inden-4b(9H)-yl)-3-(3-fluorophenethyl)-2,3-dihydro-1H-pyrido[2,1-f][1,2,4]triazine-4,6-dione 36-1 5-(benzyloxy)-1-(6,7-difluoroindeno[1,2-a]inden-4b(9H)-yl)-3-(3-fluorophenethyl)-2,3-dihydro-1H-pyrido[2,1-f][1,2,4]triazine-4,6-dione 36-1a (125 mg, 0.198 mmol) in MeOH (3 mL) and EtOAc (3 mL) was treated with 10% w/w of 20% Pd(OH)$_2$ on carbon (15 mg) and stirred under balloon hydrogen pressure for 2 hr. Reaction mixture was filtered through Diatomaceous earth and washed the Diatomaceous earth bed with 10% MeOH in DCM (20 mL) and concentrated under reduced pressure. Crude compound was purified through Prep HPLC method to afford 1-(2,3-difluoro-9a,10-dihydroindeno[1,2-a]inden-4b(9H)-yl)-3-(3-fluorophenethyl)-5-hydroxy-2,3-dihydro-1H-pyrido[2,1-f][1,2,4]triazine-4,6-dione A28. TLC system: 10% MeOH in DCM Rf: 0.5, LCMS (ESI): m/z 544.38 (M+H)+

Example 37: 5-hydroxy-1-(indeno[1,2-a]inden-4b(9H)-yl)-3-methyl-2,3-dihydro-1H-pyrido[2,1-f][1,2,4]triazine-4,6-dione (A30)

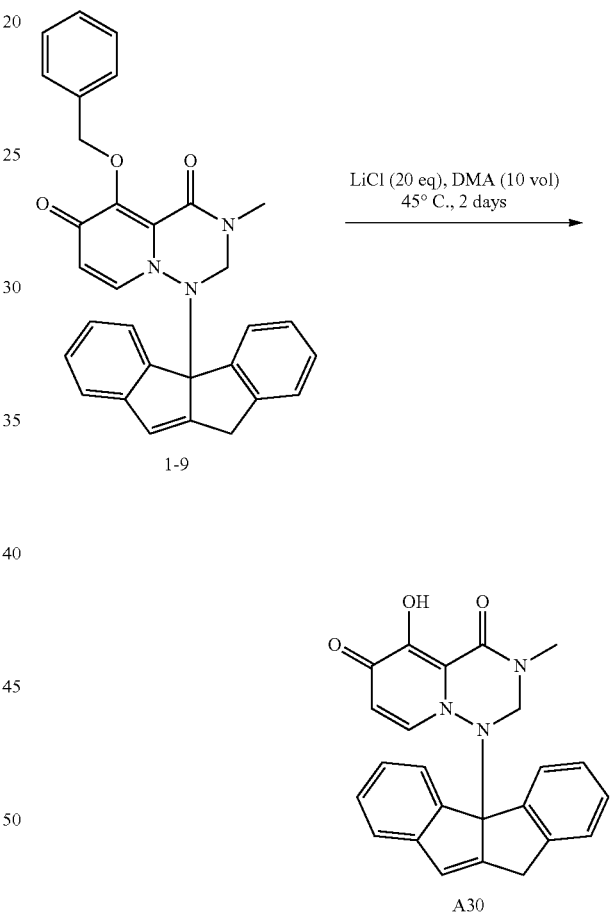

To a stirred solution of 5-(benzyloxy)-3-(cyclopropylmethyl)-1-(indeno[1,2-a]inden-4b(9H)-yl)-2,3-dihydro-1H-pyrido[2,1-f][1,2,4]triazine-4,6-dione 1-9 (105 mg, 0.215 mmol) in dimethylacetamide (DMA) (2 mL) was added LiCl (181 mg, 4.312) and heated to 45° C. stirred for 2 days. Reaction mixture was filtered through Diatomaceous earth and washed the Diatomaceous earth pad with ACN (20 mL) and concentrated under reduced pressure. Crude compound was purified over Prep HPLC to afford 5-hydroxy-1-(indeno[1,2-a]inden-4b(9H)-yl)-3-methyl-2,3-dihydro-1H-pyrido[2,1-f][1,2,4]triazine-4,6-dione A30. TLC system: 10% MeOH in DCM Rf: 0.2, LCMS (ESI): m/z 398.34 (M+H)+

Example 38: 1-(1-Chloro-2-fluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione (A46)

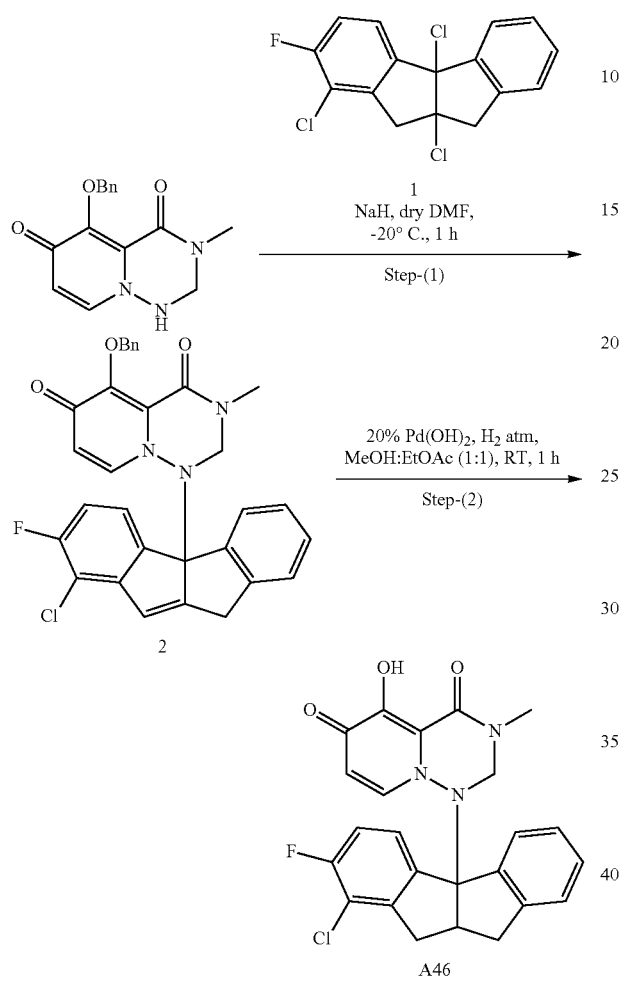

To a stirred solution of 5-(benzyloxy)-3-methyl-2,3-dihydro-1H-pyrido[2,1-f][1,2,4]triazine-4,6-dione (600 mg, 2.105 mmol) in dry DMF (15 mL) was added 60% NaH (252 mg, 6.31 mmol) at −20° C. and stirred for 30 minutes. Then, 1,4b,9a-trichloro-2-fluoro-4b,9,9a,10-tetrahydroindeno[1,2-a]indene 1 (892 mg, 2.73 mmol) was added at −20° C. and the solution was stirred for 1 h. The reaction mixture was quenched with saturated aq. NH₄Cl solution (100 mL) and extracted with ethyl acetate (2×100 mL). The combined organic layers were washed with brine solution (100 mL), dried over sodium sulfate, and concentrated under reduced pressure. The crude compound was purified via reverse phase chromatography by eluting with 90% acetonitrile in 0.1% formic acid in water to afford 5-(benzyloxy)-1-(1-chloro-2-fluoroindeno[1,2-a]inden-4b(9H)-yl)-3-methyl-2,3-dihydro-1H-pyrido[2,1-f][1,2,4]triazine-4,6-dione 2.

Next, a stirred solution of 2 (150 mg, 0.278 mmol) in methanol (5 mL) and ethyl acetate (5 mL) was treated with 20% Pd(OH)₂ on carbon (25 mg) and stirred under balloon hydrogen balloon pressure for 1 h. The reaction mixture was filtered through Diatomaceous earth and the Diatomaceous earth bed was washed with 10% methanol in dichloromethane (50 mL) and concentrated under reduced pressure. The crude compound was purified via Prep HPLC to afford 1-(1-chloro-2-fluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione (A46). TLC system: 10% MeOH in DCM Rf: 0.5, LCMS (ESI): m/z 452.14 (M+H)⁺.

Compounds A43, A44, A45, A47, A49, A52, A55, A58, A59, A60, A61, A64, A65, A66, A67, A68, A69, A70, A71, A72, A73, A74, A75, A76, A77, A78, A79, A80, A81, A82, A83, A84, A85, A86, A88, A90, A91, A94, A95, A96, A97, A98, A102, A105, A108, A110, A11, A112, A114, A115, A117, A118, A121, A122, A129, A131, A137, A138, A139, A141, and A142 were synthesized in the same manner as compound A46.

Example 39: 1-(9a-Ethoxy-9a,10-dihydroindeno[1,2-a]inden-4b(9H)-yl)-3-ethyl-5-hydroxy-2,3-dihydro-1H-pyrido[2,1-f][1,2,4]triazine-4,6-dione (A48)

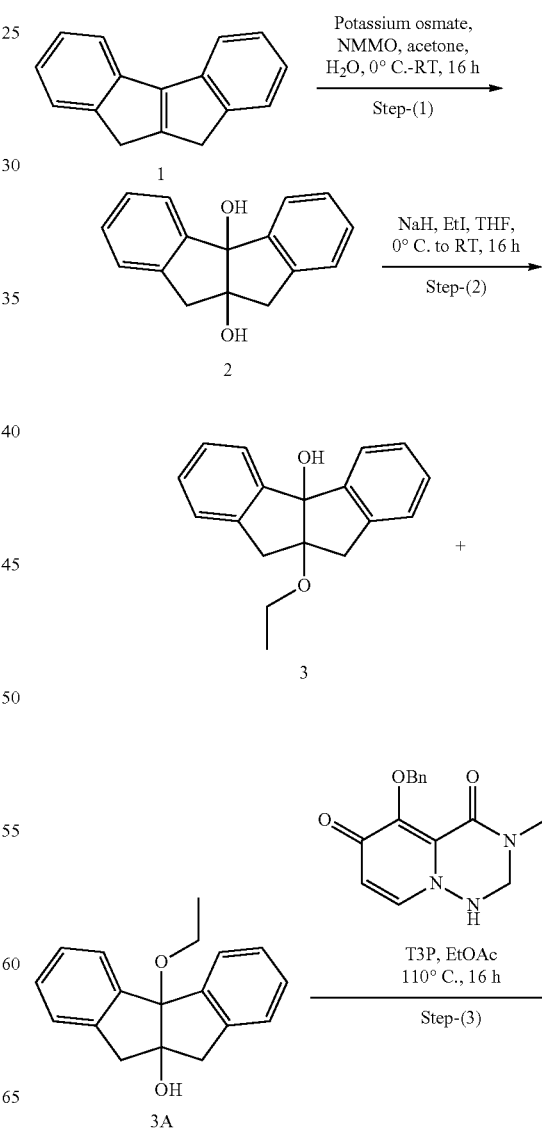

199

-continued

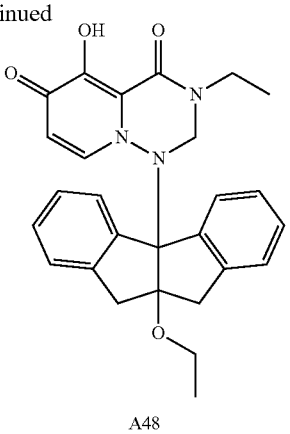

A48

To a stirred solution of 9,10-dihydroindeno[1,2-a]indene 1 (2.1 g, 10.29 mmol) in acetone, water (16:1.8) (10 vol) were added NMMO (4.1 mL, 30.88 mmol) and potassium osmate (378 mg, 1.02 mmol) at 0° C., and the solution was stirred at room temperature for 16 h. The reaction mixture was quenched with water and extracted with ethyl acetate (2×150 mL), the combined organic layer was washed with brine solution (1×150 mL), dried over sodium sulfate, and concentrated under reduced pressure to afford crude Indeno[1,2-a]indene-4b,9a(9H, 10H)-diol 2. This product was used for next step without any purification.

Next, to a stirred solution of indeno[1,2-a]indene-4b,9a (9H, 10H)-diol 2 (1.5 g, 6.78 mmol) in THF (75 mL) was added 60% NaH (271 mg, 6.78 mmol) followed by ethyl iodide (0.5 mL, 6.78 mmol) at 0° C., and the solution was stirred at room temperature for 16 h. The reaction mixture was quenched with water and extracted with ethyl acetate (2×150 mL), the combined organic layers were washed with brine solution (2×150 mL), dried over sodium sulfate, and concentrated under reduced pressure to afford a residue. The residue was purified through reverse phase chromatography by eluting with 50% acetonitrile in 0.1% formic acid in water to afford a mixture of compounds 9a-ethoxy-9a,10-dihydroindeno[1,2-a]inden-4b(9H)-ol 3 and 4b-ethoxy-4b,10-dihydroindeno[1,2-a]inden-9a(9H)-ol 3A. This product was used for next step.

To a stirred solution of mixture of 9a-ethoxy-9a,10-dihydroindeno[1,2-a]inden-4b(9H)-ol (3) & 4b-ethoxy-4b,10-dihydroindeno[1,2-a]inden-9a(9H)-ol 3A (380 mg, 1.27 mmol) was added 5-(benzyloxy)-3-ethyl-2,3-dihydro-1H-pyrido[2,1-f][1,2,4]triazine-4,6-dione (338 mg, 1.27 mmol) in ethyl acetate (5 mL) and 50% T3P in ethyl acetate (6 mL, 19.06 mmol) at room temperature. The solution was then heated to 110° C. for 16 h. The reaction mixture was quenched with ice cold water (40 mL) and extracted with ethyl acetate (2×40 mL). The combined organic layers were washed with brine solution (30 mL), dried over sodium sulfate, and concentrated under reduced pressure to yield a residue which was purified by prep HPLC to afford 1-(9a-ethoxy-9a,10-dihydroindeno[1,2-a]inden-4b(9H)-yl)-3-ethyl-5-hydroxy-2,3-dihydro-1H-pyrido[2,1-f][1,2,4]triazine-4,6-dione (A48). TLC system: 10% MeOH in DCM Rf: 0.1, LCMS (ESI): m/z 458.26 (M+H)+.

Compounds A54, A56, A57, A62, and A63 were synthesized in the same manner as compound A48.

200

Example 40: 1-(9a-Ethoxy-9a,10-dihydroindeno[1,2-a]inden-4b(9H)-yl)-3-ethyl-5-hydroxy-2,3-dihydro-1H-pyrido[2,1-f][1,2,4]triazine-4,6-dione (A50)

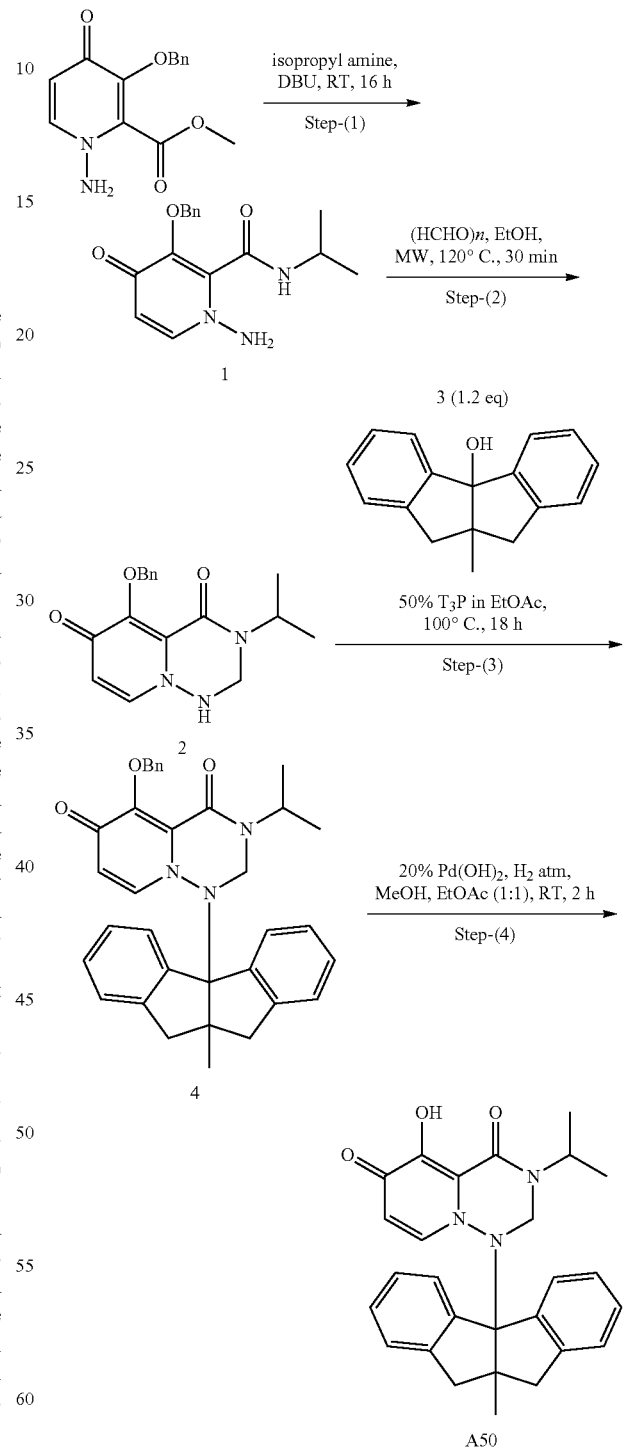

To a stirred solution of methyl-1-amino-3-(benzyloxy)-4-oxo-1,4-dihydropyridine-2-carboxylate in isopropyl amine (12.5 mL) in a sealed tube was added DBU (0.3 mL, 1.82 mmol), which was then stirred at room temperature for 16 h.

The reaction mixture was distilled under reduced pressure, and the residue was purified over reverse phase chromatography by eluting with 32% acetonitrile in 0.1% formic acid in water to afford pure 1-amino-3-(benzyloxy)-N-isopropyl-4-oxo-1,4-dihydropyridine-2-carboxamide 1.

Next, in a microwave vial, to a stirred solution of 1-amino-3-(benzyloxy)-N-isopropyl-4-oxo-1,4-dihydropyridine-2-carboxamide 1 (500 mg, 1.66 mmol) in ethanol (10 mL) was added paraformaldehyde (49 mg, 1.66 mmol), and the solution was treated with microwave irradiation at 140° C. for 30 minutes. After consumption of starting material, the reaction mixture was concentrated under reduced pressure. The residue was purified over reverse phase chromatography by eluting with 40% of acetonitrile in 0.1% formic acid in water to afford 5-(benzyloxy)-3-isopropyl-2,3-dihydro-1H-pyrido[2,1-f][1,2,4]triazine-4,6-dione (2).

Next, To a stirred solution of 5-(benzyloxy)-3-isopropyl-2,3-dihydro-1H-pyrido[2,1-f][1,2,4]triazine-4,6-dione 2 (300 mg, 0.958 mmol) was added 9a-methyl-9a,10-dihydroindeno[1,2-a]inden-4b(9H)-ol (271 mg, 1.149 mmol) in ethyl acetate (5 mL), and to this was added 50% T3P in ethyl acetate (6 mL, 9.58 mmol) at room temperature. The reaction mixture was then heated to 100° C. for 16 h. The reaction mixture was quenched with ice cold water (30 mL) and extracted with ethyl acetate (2×30 mL). The combined organic layers were washed with brine solution (30 mL), dried over sodium sulfate and concentrated under reduced pressure to afford crude 5-(benzyloxy)-3-isopropyl-1-(9a-methyl-9a,10-dihydroindeno[1,2-a]inden-4b(9H)-yl)-2,3-dihydro-1H-pyrido[2,1-f][1,2,4]triazine-4,6-dione 4.

Then, a stirred solution of crude 5-(benzyloxy)-3-isopropyl-1-(9a-methyl-9a,10-dihydroindeno[1,2-a]inden-4b(9H)-yl)-2,3-dihydro-1H-pyrido[2,1-f][1,2,4] triazine-4,6-dione 4 (550 mg, 1.03 mmol) in methanol (10 mL) and ethyl acetate (10 mL) was treated with 20% Pd(OH)$_2$ on carbon (100 mg) and stirred under balloon hydrogen atmosphere for 2 h. The reaction mixture was filtered through Diatomaceous earth and washed with methanol (30 mL), then concentrated under reduced pressure to afford a residue which was purified by prep-HPLC to afford 5-hydroxy-3-isopropyl-1-(9a-methyl-9a,10-dihydroindeno[1,2-a]inden-4b(9H)-yl)-2,3-dihydro-1H-pyrido[2,1-f] [1,2,4] triazine-4,6-dione (A50). TLC system: 10% MeOH in DCM Rf: 0.2, LCMS (ESI): m/z 442.36 (M+H)$^+$.

Compounds A51, A89, A116, and A126 were synthesized in the same manner as compound A50.

Example 41: 3-Cyclobutyl-1-(1,2-difluoro-9a,10-dihydroindeno[1,2-a]inden-4b(9H)-yl)-5-hydroxy-2,3-dihydro-1H-pyrido[2,1-f][1,2,4]triazine-4,6-dione (A92)

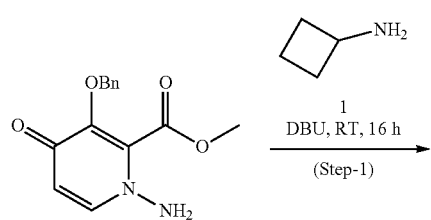

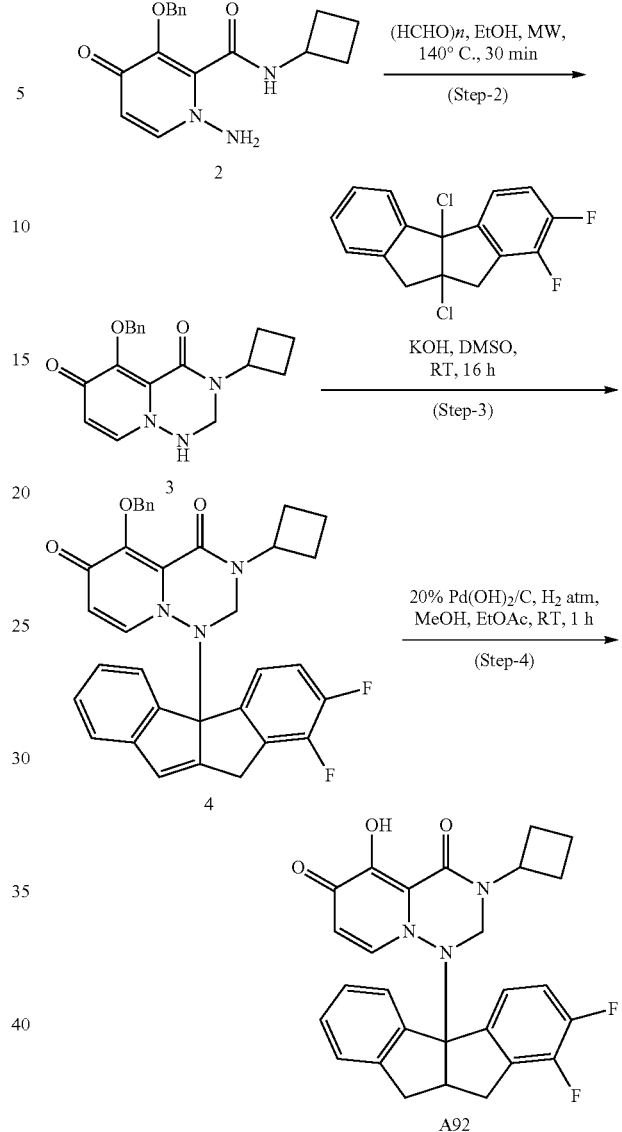

To a stirred solution of methyl 1-amino-3-(benzyloxy)-4-oxo-1,4-dihydropyridine-2-carboxylate (8 g, 29.19 mmol) in cyclobutanamine 1 (12.46 mL, 145.98 mmol) was added DBU (1.26 mL, 5.83 mmol) and the reaction mixture was stirred at room temperature for 16 h. The reaction mixture was completely distilled under reduced pressure, and the residue was purified through reverse phase chromatography by eluting with 30% acetonitrile in 0.1% formic acid in water to afford 1-amino-3-(benzyloxy)-N-cyclobutyl-4-oxo-1,4-dihydropyridine-2-carboxamide 2.

Next, in a microwave vial, to a stirred solution of 1-amino-3-(benzyloxy)-N-cyclobutyl-4-oxo-1,4-dihydropyridine-2-carboxamide 2 (1 g, 3.19 mmol) in ethanol (15 mL) was added paraformaldehyde (124 mg, 4.15 mmol), and the solution was irradiated at 140° C. under microwave conditions for 30 minutes. After consumption of starting material, the reaction mixture was concentrated under reduced pressure. The resulting residue was purified through reverse phase chromatography by eluting with 40% acetonitrile in 0.1% formic acid in water to afford 5-(benzyloxy)-3-cyclobutyl-2,3-dihydro-1H-pyrido[2,1-f][1,2,4]triazine-4,6-dione 3.

Next, to a stirred solution of 5-(benzyloxy)-3-cyclobutyl-2,3-dihydro-1H-pyrido[2,1-f][1,2,4]triazine-4,6-dione 3 (500 mg, 1.53 mmol) in DMSO (10 mL) were added 4b,9a-dichloro-1,2-difluoro-4b,9,9a,10-tetrahydroindeno[1,2-a]indene (572 mg, 1.84 mmol) and KOH (258 mg, 4.61 mmol) at room temperature, and this solution was stirred for 16 h. The reaction mixture was quenched with ice water (40 mL) and extracted with ethyl acetate (2×40 mL). The combined organic layers were washed with brine solution (30 mL), dried over sodium sulfate, and concentrated under reduced pressure. The residue thus obtained was purified through reverse phase chromatography by eluting with 80% acetonitrile in 0.1% formic acid in water to afford 5-(benzyloxy)-3-cyclobutyl-1-(1,2-difluoroindeno[1,2-a]inden-4b(9H)-yl)-2,3-dihydro-1H-pyrido[2,1-f][1,2,4]triazine-4,6-dione 4.

Then, a stirred solution of 5-(benzyloxy)-3-cyclobutyl-1-(1,2-difluoroindeno[1,2-a]inden-4b(9H)-yl)-2,3-dihydro-1H-pyrido[2,1-f][1,2,4]triazine-4,6-dione 4 (300 mg, 0.53 mmol) in methanol (5 mL) and ethyl acetate (5 mL) was treated with 10% w/w of 20% Pd(OH)$_2$ on carbon (100 mg) and stirred under hydrogen balloon atmosphere for 1 h. The reaction mixture was filtered through celite, washed with methanol (20 mL), and filtrate was concentrated under reduced pressure. The resulting residue was purified by prep-HPLC to afford 3-cyclobutyl-1-(1,2-difluoro-9a,10-dihydroindeno[1,2-a]inden-4b(9H)-yl)-5-hydroxy-2,3-dihydro-1H-pyrido[2,1-f][1,2,4]triazine-4,6-dione (A92). TLC system: 10% MeOH in DCM Rf: 0.2, LCMS (ESI): m/z 476.58 (M+H)$^+$.

Compounds A93, A99, A100, A103, A104, A113, A122, A123, A124, A125, A128, A130, A132, A133, and A140 were synthesized in the same manner as compound A92.

Example 42: 2-(aminomethyl)-1-(1,8-difluoroindeno[1,2-a]inden-4b(9H)-yl)-5-hydroxy-3-methyl-2,3-dihydro-1H-pyrido[2,1-f][1,2,4]triazine-4,6-dione (A106) and 2-(aminomethyl)-1-(1,8-difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione (A107)

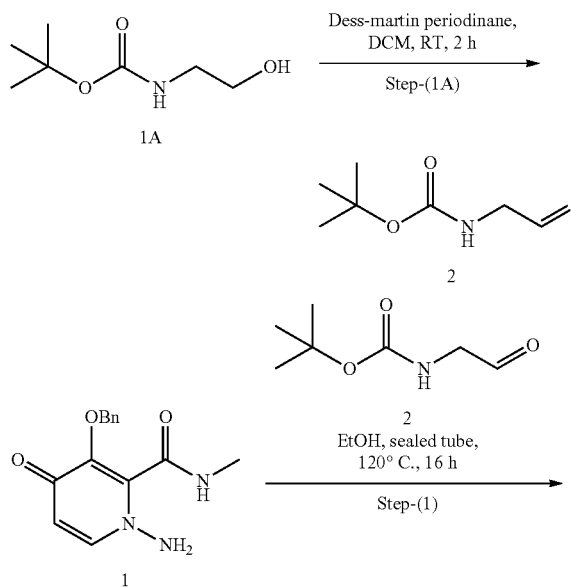

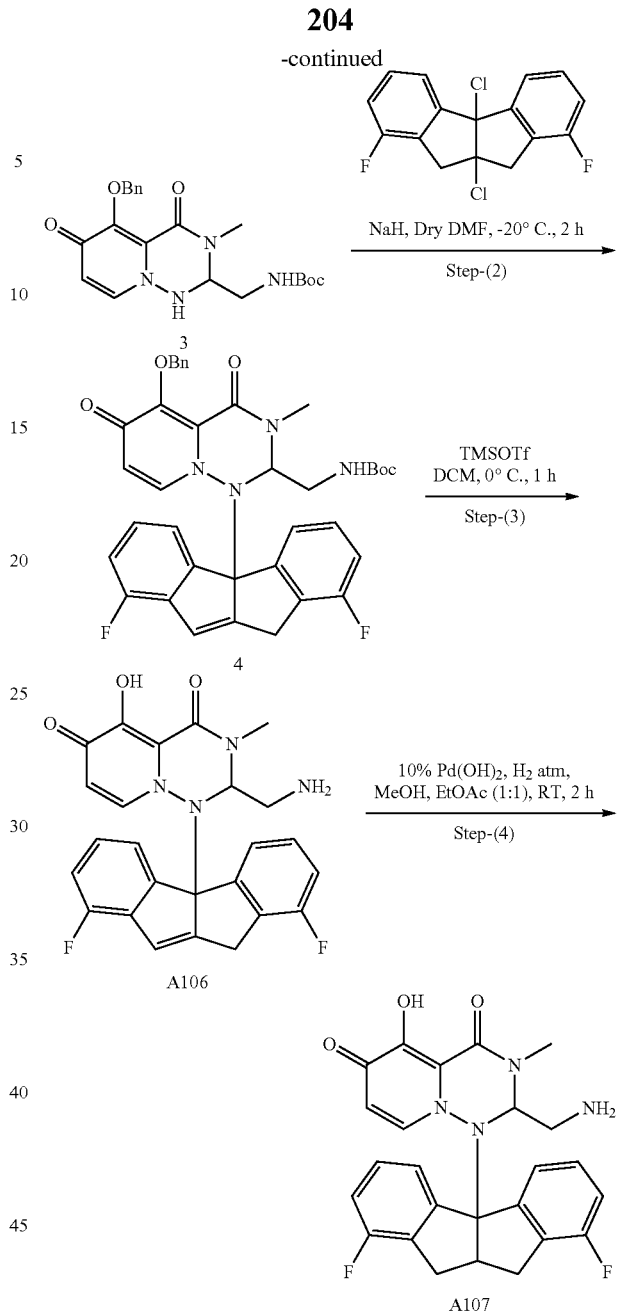

To a stirred solution of tert-butyl (2-hydroxyethyl) carbamate (5 g, 31.05 mmol) in dichloromethane (50 mL) was added dess-martinperiodinane (15.8 g, 37.26 mmol) at 0° C. and stirred at RT for 2 h. The reaction was mixture diluted with dichloromethane (150 mL) and quenched with 20% hypo solution (5×100 mL), dried over sodium sulfate and concentrated under reduced pressure to afford crude tert-butyl (2-oxoethyl) carbamate 2. This residue was used for next step without further purification.

Next, to a stirred solution of 1-amino-3-(benzyloxy)-N-methyl-4-oxo-1,4-dihydropyridine-2-carboxamide 1 (1.5 g, 5.49 mmol) was added tert-butyl (2-oxoethyl) carbamate 2 (3.05 g, 19.22 mmol) in ethanol (15 mL), and the solution was heated to 120° C. in a sealed tube for 16 h. The reaction mixture was evaporated under reduced pressure to afford a residue which was purified by reverse phase chromatography by eluting with 30% of acetonitrile in 0.1% formic acid in water to afford pure compound tert-butyl ((5-(benzyloxy)-3-methyl-4,6-dioxo-2,3,4,6-tetrahydro-1H-pyrido[2,1-f][1,2,4]triazin-2-yl)methyl)carbamate 3.

Next, to a stirred solution of tert-butyl ((5-(benzyloxy)-3-methyl-4,6-dioxo-2,3,4,6-tetrahydro-1H-pyrido[2,1-f][1,2,4]triazin-2-yl)methyl)carbamate 3 (500 mg, 1.20 mmol) and 4b,9a-dichloro-1,8-difluoro-4b,9,9a,10-tetrahydroindeno[1,2-a]indene (449 mg, 1.44 mmol) in dry DMF (10 mL) was added 60% NaH (145 mg, 3.62 mmol) at −20° C., and the solution was stirred for 2 h. The reaction mixture was quenched with ice cold water (40 mL) and the solids were filtered and dried under vaccum to obtain a residue. The residue was purified through reverse phase chromatography by eluting with 70% of acetonitrile in 0.1% formic acid in water to afford tert-butyl ((5-(benzyloxy)-1-(1,8-difluoroindeno[1,2-a]inden-4b(9H)-yl)-3-methyl-4,6-dioxo-2,3,4,6-tetrahydro-1H-pyrido[2,1-f][1,2,4]triazin-2-yl)methyl)carbamate 4.

Then, to a stirred solution of tert-butyl ((5-(benzyloxy)-1-(1,8-difluoroindeno[1,2-a]inden-4b(9H)-yl)-3-methyl-4,6-dioxo-2,3,4,6-tetrahydro-1H-pyrido[2,1-f][1,2,4]triazin-2-yl)methyl)carbamate 4 (180 mg, 0.27 mmol) in dichloromethane (5 mL) was added TMsOTf (0.38 mL, 1.65 mmol) at 0° C., and the solution was stirred for 1 h. The reaction mixture was basified with aqueous ammonia solution and evaporated under reduced pressure. The residue thus obtained was purified through prep HPLC to afford pure 2-(aminomethyl)-1-(1,8-difluoroindeno[1,2-a]inden-4b(9H)-yl)-5-hydroxy-3-methyl-2,3-dihydro-1H-pyrido[2,1-f][1,2,4]triazine-4,6-dione (A106). TLC system: 20% MeOH in DCM Rf: 0.1, LCMS (ESI): m/z 463.08 (M+H)$^+$.

Then, to a stirred solution of 2-(aminomethyl)-1-(1,8-difluoroindeno[1,2-a]inden-4b(9H)-yl)-5-hydroxy-3-methyl-2,3-dihydro-1H-pyrido[2,1-f][1,2,4]triazine-4,6-dione (A106) (65 mg, 0.14 mmol) in methanol (2 mL) and ethyl acetate (2 mL) was added 20% Pd(OH)$_2$ on carbon (20 mg), and the mixture was stirred under hydrogen balloon pressure for 5 h. The reaction mixture was filtered through celite, and the Diatomaceous earth bed was washed with 10% methanol in dichloromethane (10 mL), which was concentrated under reduced pressure. The residue thus obtained was purified through prep HPLC to afford 2-(aminomethyl)-1-(1,8-difluoro-9a,10-dihydroindeno[1,2-a]inden-4b(9H)-yl)-5-hydroxy-3-methyl-2,3-dihydro-1H-pyrido[2,1-f][1,2,4]triazine-4,6-dione (A107). TLC system: 20% MeOH in DCM Rf: 0.1, LCMS (ESI): m/z 465.10 (M+H)$^+$.

Other compounds disclosed herein can be prepared by analogous methods to the general methods and examples above.

Example 43: Data on Selected Compounds

In Vitro Antiviral Assays

Influenza antiviral assays: Inhibition of virus-induced cytopathic effects (CPE) and cell viability following Influenza type A (strain A/PR/8/34, ATCC VR-95) or Influenza type B (cell culture adapted strain B/Lee/40, ATCC VR-1535) replication in MDCK cells (Female cocker spaniel kidney epithelial, ATCC CCL-34) were measured by XTT dye reduction (Appleyard et al. *J Antimicrob Chemother.* 1(4 Suppl): 49-53, 1975 and Shigeta et al. *Antimicrob Agents Chemother.* 41(7): 1423-1427, 1997.). MDCK cells (1×10$^4$ cells per well) are grown to monolayers in 96-well flat-bottomed tissue culture plates using Dulbecco's Minimum Essential Medium (DMEM) supplemented with 10% heat-inactivated fetal bovine serum (FBS), 2 mM L-glutamine, 100 U/mL penicillin, 100 µg/ml streptomycin, 1 mM sodium pyruvate, and 0.1 mM NEAA in a 100 µL per well volume. On the day of assay set up, the cell monolayer was washed three times with DPBS. The viruses were obtained from ATCC and were grown in MDCK cells for the production of stock virus pools. Test compounds were diluted into assay medium (DMEM, 2 mM L-glutamine, 100 U/mL penicillin, 100 µg/mL streptomycin, 50 ng/mL TPCK-treated trypsin, 0.1 mM NEAA, and 1 mM sodium pyruvate) at 2× the desired starting concentration and serially diluted. Test compound was added at 100 µL per well volume in triplicate for efficacy, duplicate for cytotoxicity and a single well per concentration for colorimetric evaluation immediately prior to the addition of diluted virus. Ribavirin and oseltamivir carboxylate were evaluated in parallel as control compounds. A pretitered aliquot of virus was removed from the freezer (−80° C.) and was rapidly thawed in a biological safety cabinet. Virus was diluted in assay medium such that the amount of virus added to each well in a volume of 100 µL was the amount determined to yield 85 to 95% cell killing at 4 days post-infection. Cell controls containing medium alone, virus-infected controls containing medium and virus, cytotoxicity controls containing medium and each Following incubation at 37° C., 5% CO$_2$ for four days, inhibition of CPE (increased cell viability) was measured by reduction of the formazan dye XTT following a 4 hour incubation at 37° C. and measured spectrophotometrically at 450 nm, with 650 nm as the reference wavelength using Softmax Pro 4.6 software. Percent CPE reduction of the virus-infected wells and the percent cell viability of uninfected drug control wells are calculated by four parameter curve fit analysis using Microsoft Excel® XLfit4.

(Potency against Influenza A (H1N1) is reported in Table B and potency against Influenza B (Lee/B40) is reported in Table C as follows: +++++; EC50, <0.125 µM; ++++; EC50, 0.125-0.250 µM; +++: EC50, 0.250-0.375 µM; ++: EC50, 0.375-0.5 µM; and +: EC50, >0.5 µM

TABLE B

| Influenza A (H1N1) | |
|---|---|
| Compound No. | EC$_{50}$ |
| A1 | +++++ |
| A2 | ++++ |
| A3 | ++++ |
| A4 | + |
| A6 | +++++ |
| A7 | + |
| A8 | ++ |
| A9 | + |
| A10 | +++ |
| A11 | + |
| A12 | +++++ |
| A13 | +++++ |
| A14 | +++++ |
| A15 | +++++ |
| A16 | +++++ |
| A17 | ++++ |
| A19 | +++++ |
| A20 | +++++ |
| A21 | +++ |
| A22 | +++ |
| A23 | + |
| A24 | + |
| A25 | +++++ |
| A26 | ++ |
| A27 | ++++ |
| A28 | ++++ |

TABLE B-continued

Influenza A (H1N1)

| Compound No. | EC$_{50}$ |
|---|---|
| A29 | ++++ |
| A30 | +++++ |
| A31 | + |
| A32 | + |
| A33 | ++ |
| A34 | +++++ |
| A43 | +++++ |
| A45 | +++++ |
| A45 enantiomer | +++++ |
| A46 | +++++ |
| A47 | +++++ |
| A48 | +++++ |
| A49 | +++++ |
| A50 | +++++ |
| A51 | +++++ |
| A52 | +++++ |
| A53 | +++++ |
| A54 | +++++ |
| A55 | +++++ |
| A56 | +++++ |
| A57 | +++++ |
| A58 | +++++ |
| A59 | +++++ |
| A60 | +++++ |
| A61 | +++++ |
| A62 | ++++ |
| A63 | ++++ |
| A64 | +++++ |
| A65 | ++++ |
| A66 | ++++ |
| A67 | +++++ |
| A68 | +++++ |
| A69 | +++++ |
| A70 | +++++ |
| A71 | +++++ |
| A72 | +++++ |
| A73 | +++++ |
| A74 | ++++ |
| A75 | +++++ |
| A76 | +++++ |
| A77 | +++++ |
| A78 | +++++ |
| A79 | +++++ |
| A80 | +++++ |
| A81 | ++++ |
| A82 | +++++ |
| A83 | +++++ |
| A84 | +++++ |
| A85 | ++++ |
| A86 | ++++ |
| A87 | ++++ |
| A89 | ++++ |
| A90 | ++++ |
| A 90 enantiomer | +++++ |
| A91 | + |
| A92 | +++ |
| A93 | ++++ |
| A94 | +++ |
| A95 | ++++ |
| A96 | +++++ |
| A98 | +++ |
| A99 | + |
| A100 | + |
| A101 | ++++ |
| A102 | ++++ |
| A103 | +++ |
| A104 | + |
| A105 | +++++ |
| A106 | ++++ |
| A107 | ++++ |
| A108 | +++ |
| A110 | ++++ |
| A111 | ++++ |

TABLE B-continued

Influenza A (H1N1)

| Compound No. | EC$_{50}$ |
|---|---|
| A112 | ++ |
| A113 | ++++ |
| A114 | ++++ |
| A115 | ++ |
| A116 | +++++ |
| A117 | + |
| A118 | + |
| A121 | ++++ |
| A124 | ++ |
| A125 | +++ |
| A126 | ++++ |
| A127 | + |
| A128 | +++ |
| A129 | +++ |
| A130 | + |
| A131 | ++ |
| A132 | +++ |
| A133 | ++++ |
| A136 | ++ |
| A137 | ++++ |
| A138 | ++++ |
| A139 | ++++ |
| A140 | +++ |
| A141 | ++ |
| A144 | +++++ |
| A145 | +++++ |
| A146 | +++++ |
| A147 | +++++ |
| A148 | +++++ |
| A149 | +++++ |
| A150 | +++++ |
| A151 | +++++ |
| A152 | +++++ |
| A153 | +++++ |
| A156 | +++ |
| A157 | ++++ |
| A158 | ++++ |
| A160 | +++++ |
| A161 | +++++ |
| A162 | +++++ |
| A164 | +++++ |
| A165 | +++++ |
| A166 | +++++ |
| A167 | +++++ |

TABLE C

Influenza B

| Compound No. | EC$_{50}$ |
|---|---|
| A1 | +++ |
| A2 | + |
| A3 | + |
| A4 | + |
| A7 | +++++ |
| A8 | + |
| A9 | ++++ |
| A10 | + |
| A11 | ++ |
| A12 | + |
| A13 | +++++ |
| A14 | ++++ |
| A15 | +++++ |
| A16 | +++++ |
| A17 | ++++ |
| A19 | +++ |
| A21 | +++++ |
| A22 | +++++ |
| A23 | +++ |
| A24 | ++ |

TABLE C-continued

Influenza B

| Compound No. | EC$_{50}$ |
|---|---|
| A25 | ++ |
| A26 | +++ |
| A27 | +++ |
| A28 | +++ |
| A29 | +++ |
| A30 | ++ |
| A31 | ++ |
| A32 | +++++ |
| A33 | + |
| A34 | + |
| A43 | +++++ |
| A45 | +++++ |
| A45 enantiomer | +++++ |
| A46 | +++++ |
| A47 | ++++ |
| A48 | +++++ |
| A49 | +++++ |
| A50 | +++++ |
| A51 | +++++ |
| A52 | +++++ |
| A53 | +++++ |
| A54 | +++++ |
| A55 | +++++ |
| A56 | +++++ |
| A57 | +++++ |
| A58 | +++++ |
| A59 | +++++ |
| A60 | +++++ |
| A61 | +++++ |
| A62 | +++++ |
| A63 | +++++ |
| A64 | +++++ |
| A65 | +++++ |
| A66 | +++++ |
| A67 | +++++ |
| A68 | +++++ |
| A69 | +++++ |
| A70 | +++++ |
| A71 | +++++ |
| A72 | +++++ |
| A73 | +++++ |
| A74 | +++++ |
| A75 | +++++ |
| A76 | +++++ |
| A77 | ++++ |
| A78 | +++++ |
| A79 | +++++ |
| A80 | +++++ |
| A81 | ++++ |
| A82 | ++++ |
| A83 | +++++ |
| A84 | ++++ |
| A85 | +++ |
| A86 | +++++ |
| A87 | +++++ |
| A89 | ++ |
| A90 | +++++ |
| A90 enantiomer | +++++ |
| A91 | ++++ |
| A92 | +++ |
| A93 | ++++ |
| A94 | +++ |
| A95 | +++++ |
| A96 | +++++ |
| A98 | +++++ |
| A99 | +++ |
| A100 | +++ |
| A101 | +++++ |
| A102 | +++++ |
| A103 | ++++ |
| A104 | ++++ |
| A105 | +++++ |
| A106 | +++++ |
| A107 | ++++ |
| A108 | +++ |
| A110 | +++++ |
| A111 | ++++ |
| A112 | +++ |
| A113 | ++++ |
| A114 | ++++ |
| A115 | +++ |
| A116 | +++++ |
| A117 | +++ |
| A118 | +++ |
| A121 | ++++ |
| A124 | ++ |
| A125 | ++++ |
| A126 | +++++ |
| A127 | +++ |
| A128 | ++++ |
| A129 | ++++ |
| A130 | ++++ |
| A131 | ++++ |
| A133 | ++++ |
| A136 | +++ |
| A137 | ++++ |
| A138 | +++++ |
| A139 | ++++ |
| A132 | +++ |
| A140 | +++ |
| A141 | +++ |
| A144 | +++++ |
| A145 | +++++ |
| A146 | ++++ |
| A147 | ++++ |
| A148 | ++++ |
| A149 | +++++ |
| A150 | +++++ |
| A151 | ++++ |
| A152 | ++++ |
| A153 | ++++ |
| A156 | ++++ |
| A157 | ++++ |
| A158 | ++++ |
| A160 | +++++ |
| A161 | +++++ |
| A162 | +++++ |
| A164 | +++++ |
| A165 | +++++ |
| A166 | +++++ |
| A167 | +++++ |

What is claimed is:

1. A compound having a structure of Formula (I), or a pharmaceutically acceptable salt thereof:

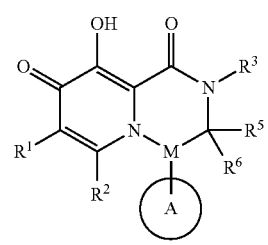

(I)

wherein
ring A is

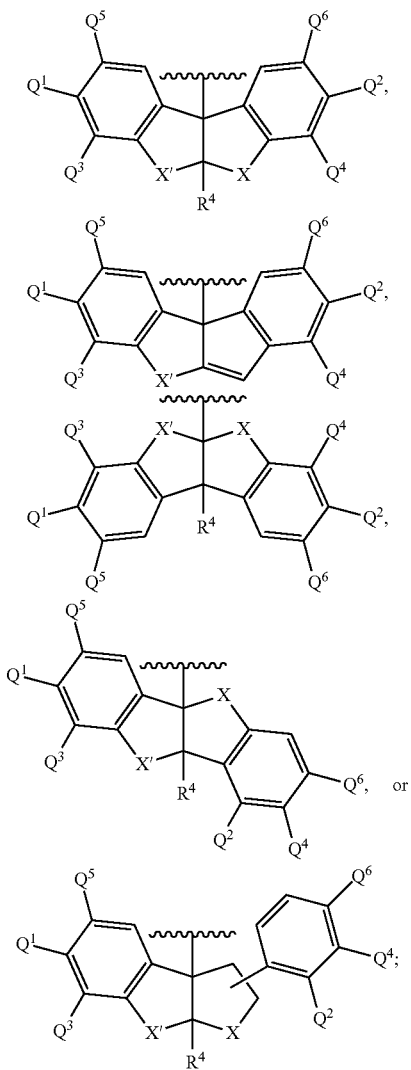

M is N or CH;
each of X and X' is independently $CH_2$, $CH_2CH_2$, $OCH_2$, or $CH_2O$;
each of $R^1$ and $R^2$ is independently H, halo, OH, $CO_2H$, CN, CHO, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{1-6}$alkoxy optionally substituted by 1-3 of substituent group A, $C_{1-6}$alkyl-C(O)— optionally substituted by 1-3 of substituent group A, $C_{1-6}$alkyl-OC(O)— optionally substituted by 1-3 of substituent group A, $C_{3-10}$ carbocyclyl-$C_{0-6}$ alkylene optionally substituted by 1-3 of substituent group A, $C_{3-10}$ carbocyclyl-C(O)— optionally substituted by 1-3 of substituent group A, $C_{3-10}$carbocyclyl-O-optionally substituted by 1-3 of substituent group A, $C_{3-10}$carbocyclyl-OC(O)— optionally substituted by 1-3 of substituent group A, 3-7 membered heterocyclyl-$C_{0-6}$alkylene optionally substituted by 1-3 of substituent group A, 3-7 membered heterocyclyl-C(O)— optionally substituted by 1-3 of substituent group A, 3-7 membered heterocyclyl-O— optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S;
$R^3$ is H, OH, $CO_2H$, CN, CHO, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{1-6}$alkoxy optionally substituted by 1-3 of substituent group A, $C_{1-6}$alkyl-C(O)— optionally substituted by 1-3 of substituent group A, $C_{1-6}$alkyl-OC(O)— optionally substituted by 1-3 of substituent group A, $C_{3-10}$carbocyclyl-$C_{0-6}$alkylene optionally substituted by 1-3 of substituent group A, $C_{3-10}$carbocyclyl-O—$C_{1-6}$alkylene optionally substituted by 1-3 of substituent group A, $C_{3-10}$carbocyclyl-C(O)— optionally substituted by 1-3 of substituent group A, $C_{3-10}$ carbocyclyl-OC(O)— optionally substituted by 1-3 of substituent group A, 3-7 membered heterocyclyl-$C_{0-6}$alkylene optionally substituted by 1-3 of substituent group A, 3-7 membered heterocyclyl-C(O)— optionally substituted by 1-3 of substituent group A, 3-7 membered heterocyclyl-OC(O)— optionally substituted by 1-3 of substituent group A, wherein the heterocyclyl comprises 1-4 ring heteroatoms independently selected from N, O, and S, or
$R^3$ and $R^5$ together with the atoms to which they are attached form a 5-7 heterocyclyl having 1-4 total ring heteroatoms selected from N, O, and S, and can be optionally substituted with 1-3 of substituent group A;
$R^4$, when present, is H, OH, $C_{1-3}$alkyl, $C_{1-3}$haloalkyl, or $C_{1-3}$alkoxy;
$R^5$ and $R^6$ are each independently H, OH, $CO_2H$, CN, CHO, $C_{1-6}$ alkyl optionally substituted by 1-3 of substituent group A, $C_{2-6}$ alkenyl optionally substituted by 1-3 of substituent group A, $C_{2-6}$ alkynyl optionally substituted by 1-3 of substituent group A, $C_{1-6}$alkyl carbonyl optionally substituted by 1-3 of substituent group A, $C_{1-6}$ alkyl-O—C(O)— optionally substituted by 1-3 of substituent group A, $C_{3-8}$carbocyclyl$C_{1-6}$ alkylene optionally substituted by 1-3 of substituent group A, $C_{3-8}$carbocyclyl-O—$C_{1-6}$alkylene optionally substituted by 1-3 of substituent group A, $C_{3-8}$carbocyclyl-C(O)— optionally substituted by 1-3 of substituent group A, $C_{3-8}$carbocyclyl-OC(O)— optionally substituted by 1-3 of substituent group A, 3-7 membered heterocyclyl-$C_{0-6}$alkylene optionally substituted by substituent group A, 3-7 membered heterocyclyl-O—$C_{1-6}$alkylene optionally substituted by 1-3 of substituent group A, 3-7 membered heterocyclyl-C(O)— optionally substituted by 1-3 of substituent group A, or 3-7 membered heterocyclyl-OC(O)— optionally substituted by 1-3 of substituent group A, wherein the heterocyclyl comprises 1-4 ring heteroatoms independently selected from N, O, and S, or
$R^5$ and $R^6$ together with the atom to which they are attached form a $C_{3-7}$carbocyclyl or 3-7 membered heterocyclyl having 1-3 ring heteroatoms selected N, O, and S, and is optionally substituted with 1-3 of substituent group A;
optionally one of $R^1$, $R^2$, $R^3$, $R^5$, and $R^6$ can be
—Z—N($R^N$)($R^N$),
—Z—N($R^N$)—$SO_2$—$R^{x2}$,
—Z—C(O)—N($R^N$)—$SO_2$—$R^{x2}$,
—Z—N($R^N$)—C(O)—$R^{x1}$, —Z—C(O)—N($R^N$)($R^N$),
—Z—S(O)$_{0-2}$—$R^{x2}$,
—Z—N($R^N$)—C(O)O—$R^{x1}$,
—Z—N($R^N$)—C(O)—N($R^N$)($R^N$),
—Z—C(O)—N($R^N$)—C(O)—N($R^N$)($R^N$), or
—Z—N($R^N$)—C(O)—C(O)—$R^{x1}$, in which:
- each $R^N$ and $R^{x1}$ independently is hydrogen, $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{3-10}$carbocyclyl-$C_{0-6}$alkylene optionally substituted by 1-3 of substituent group A, or 3-7 membered heterocyclyl-$C_{0-6}$alkylene optionally substituted by 1-3 of substituent group A, and the heterocyclyl group comprises 1-4 ring heteroatoms independently selected from N, O, and S, or
- two $R^N$ attached to the same nitrogen atom can together with the nitrogen atom to which they are attached form a 3-8 membered heterocyclyl having 0-2 additional ring heteroatoms selected from N, O, and S;
- each $R^{x2}$ is independently $C_{1-6}$alkyl optionally substituted by 1-3 of substituent group A, $C_{2-6}$alkenyl optionally substituted by 1-3 of substituent group A, $C_{2-6}$alkynyl optionally substituted by 1-3 of substituent group A, $C_{3-10}$carbocyclyl-$C_{0-6}$alkylene optionally substituted by 1-3 of substituent group A, or 3-7 membered heterocyclyl-$C_{0-6}$alkylene optionally substituted by 1-3 of substituent group A, and the heterocyclyl group comprises 1-4 ring heteroatoms independently selected from N, O, and S, and
- Z is a bond or $C_{1-6}$alkylene;
- substituent group A is halo, CN, OH, $CO_2H$, CHO, $NH_2$, oxo, $NO_2$, $C_{1-6}$alkyl, $C_{1-6}$haloalkyl, $C_{1-6}$alkoxy, $C_{1-6}$alkylthio, $C_{1-6}$ alkyl-OH, $C_{3-10}$carbocyclyl, 3-7 membered heterocyclyl, $C_{6-10}$ aryl, $C_{3-10}$carbocyclyl-$C_{1-6}$alkoxy, $C_{3-10}$carbocyclyl-O—$C_{1-6}$alkylene, $C_{3-10}$ carbocyclyl-$C_{1-6}$ alkoxy-$C_{1-6}$alkylene, 3-7 membered heterocyclyl-$C_{1-6}$ alkoxy, 3-7 membered heterocyclyl-O—$C_{1-6}$alkylene, 3-7 membered heterocyclyl-$C_{1-6}$alkoxy-$C_{1-6}$alkylene, $C_{1-6}$ haloalkoxy, $C_{1-6}$alkoxy-$C_{1-6}$alkylene, $C_{1-6}$alkoxy-$C_{1-6}$alkoxy, $C_{1-6}$alkyl-C(O)—, $C_{1-6}$alkyl-C(O)O—, NH$C_{1-6}$alkyl, $C_{1-6}$alkyl-C(O)NH—, $C_{1-6}$haloalkyl-C(O)NH, $C_{1-6}$alkyl-NHC(O)—, $C_{1-6}$alkyl-$SO_2$—, $C_{1-6}$alkyl-SO—, and $C_{1-6}$alkylSO$_2$NH—; and
- each of $Q^1$, $Q^2$, $Q^3$, $Q^4$, $Q^5$, and $Q^6$ is independently H, halo, CN, OH, $CO_2H$, CHO, $NH_2$, $NO_2$, $C_{1-6}$alkyl, $C_{1-6}$haloalkyl, $C_{1-6}$alkoxy, $C_{1-6}$alkylthio, or $C_{1-6}$ alkyl-OH.

2. The compound or salt of claim 1, wherein M is N.

3. The compound or salt of claim 1, having a structure of Formula (IIA) or (IIB).

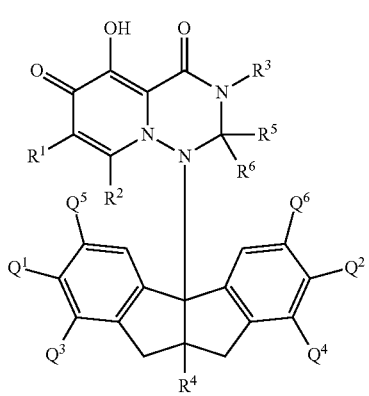

(IIA)

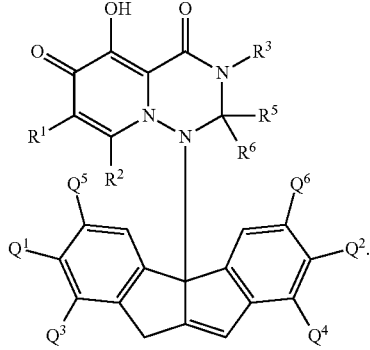

(IIB)

4. The compound or salt of claim 1, wherein at least one of $R^1$ and $R^2$ is H.

5. The compound or salt of claim 1, wherein $R^4$ is H, OH or OMe.

6. The compound or salt of claim 1, wherein at least one of $R^5$ and $R^6$ is H.

7. The compound or salt of claim 1, wherein $R^5$ and $R^6$ together with the atom to which they are attached form a $C_{3-7}$carbocyclyl or 3-7 membered heterocyclyl having 1-3 ring heteroatoms selected N, O, and S, and is optionally substituted with 1-3 of substituent group A.

8. The compound or salt of claim 1, wherein $R^3$ and $R^5$ together with the atoms to which they are attached form a 5-7 membered heterocyclyl having 1-4 total ring heteroatoms selected N, O, and S, and can be optionally substituted with 1-3 of substituent group A.

9. The compound or salt of claim 1, wherein $R^3$ is $C_{1-6}$alkyl, $C_{3-6}$carbocyclyl-$C_{1-6}$alkylene, $C_{3-6}$carbocyclyl-O—$C_{1-6}$alkylene, or 3-7 membered heterocyclyl-$C_{1-6}$alkylene.

10. The compound or salt of claim 1, wherein $R^3$ is
—Z—N($R^N$)($R^N$),
—Z—N($R^N$)—$SO_2$—$R^{x2}$,
—Z—C(O)—N($R^N$)—$SO_2$—$R^{x2}$,
—Z—N($R^N$)—C(O)—$R^{x1}$,
—Z—C(O)—N($R^N$)($R^N$),
—Z—S(O)$_{0-2}$—$R^{x2}$,
—Z—N($R^N$)—C(O)O—$R^{x1}$,
—Z—N($R^N$)—C(O)—N($R^N$)($R^N$),
—Z—C(O)—N($R^N$)—C(O)—N($R^N$)($R^N$), or
—Z—N($R^N$)—C(O)—C(O)—$R^{x1}$.

11. The compound or salt of claim 1, wherein at least two of $Q^1$, $Q^2$, $Q^3$, $Q^4$, $Q^5$, and $Q^6$ are H.

12. The compound or salt of claim 1, wherein at least two of $Q^1$, $Q^2$, $Q^3$, $Q^4$, $Q^5$, and $Q^6$ are halo.

13. The compound or salt of claim 12, wherein the halo is F.

14. The compound or salt of claim 1, wherein ring A is

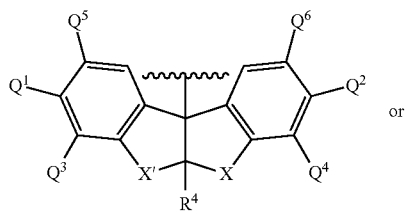

or

-continued

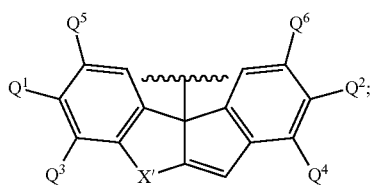

each of $R^1$, $R^2$, $R^4$, $R^5$, and $R^6$ is H;

M is N;

each of X and X' are $CH_2$;

$R^3$ is H, OH, $CO_2H$, CN, CHO, $C_{1-6}$alkyl optionally substituted by 1-3 of substituent group A, $C_{3-10}$carbocyclyl-$C_{0-6}$alkylene optionally substituted by 1-3 of substituent group A, $C_{3-10}$ carbocyclyl-O—$C_{1-6}$alkylene optionally substituted by 1-3 of substituent group A, 3-7 membered heterocyclyl-$C_{0-6}$alkylene optionally substituted by 1-3 of substituent group A, 3-7 membered heterocyclyl-C(O)— optionally substituted by 1-3 of substituent group A wherein the heterocyclyl comprises 1-4 ring heteroatoms independently selected from N, O, and S;

substituent group A is halo; and each of $Q^1$, $Q^2$, $Q^3$, $Q^4$, $Q^5$, and $Q^6$ is iH or halo, provided that at least two of $Q^1$, $Q^2$, $Q^3$, $Q^4$, $Q^5$, and $Q^6$ are H.

15. The compound or salt of claim 1 having a structure of

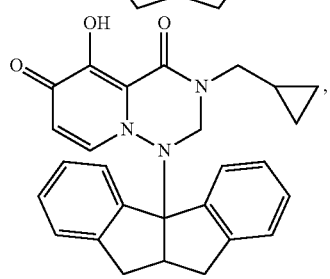

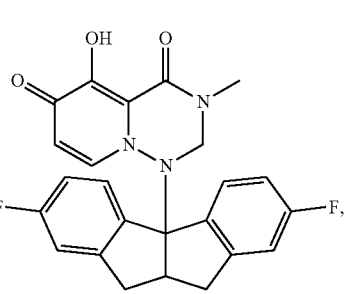

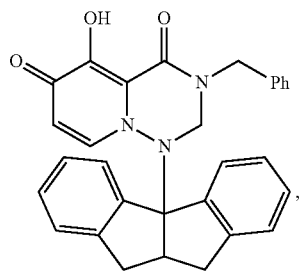 [SMILES: CN1CC(C23c4ccccc4CC2Cc2ccccc23)n2ccc(=O)c(O)c2C1=O]

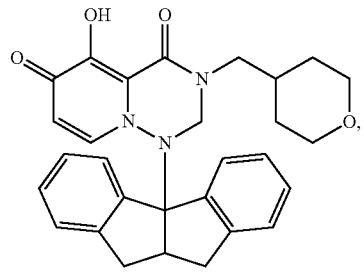

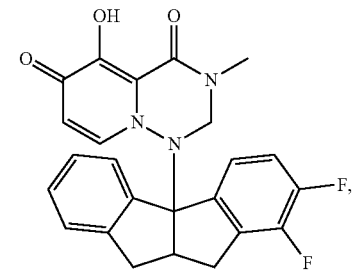

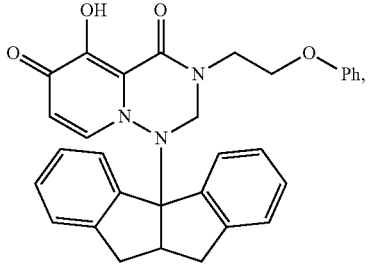

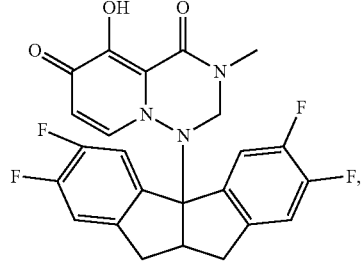

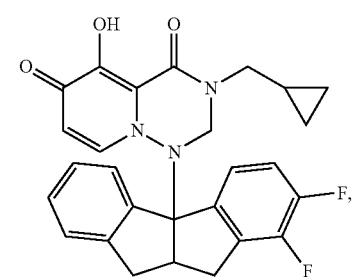

217
-continued
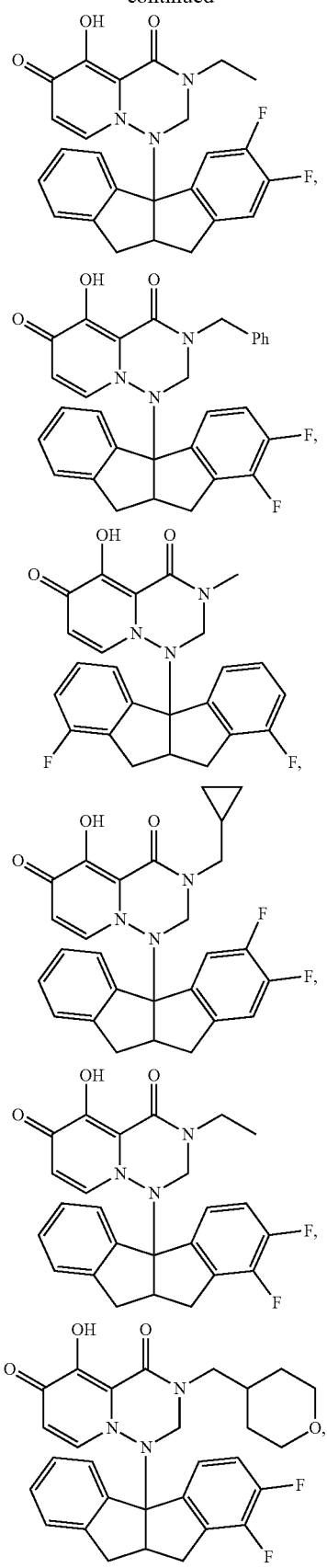
218
-continued
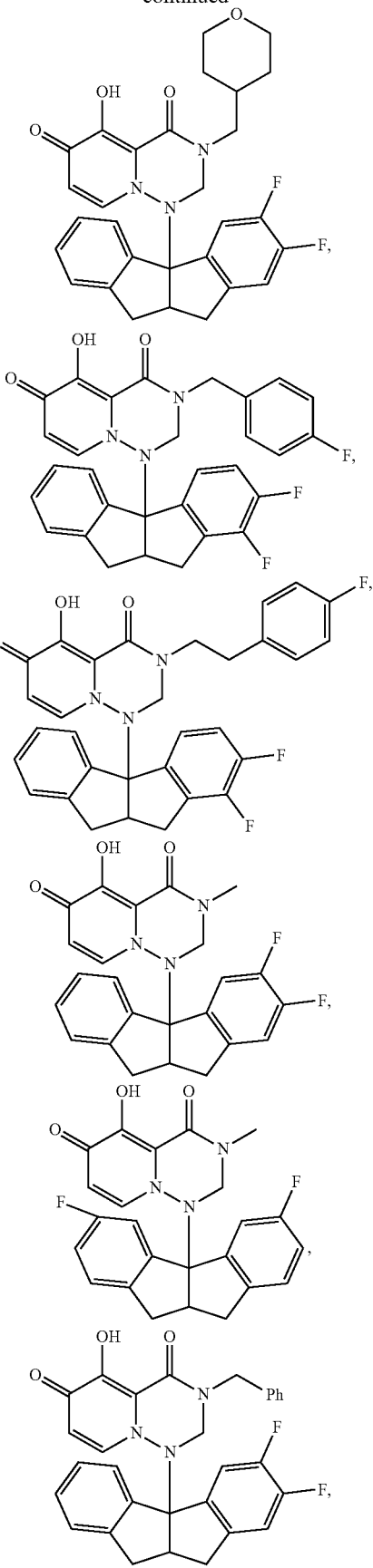

-continued
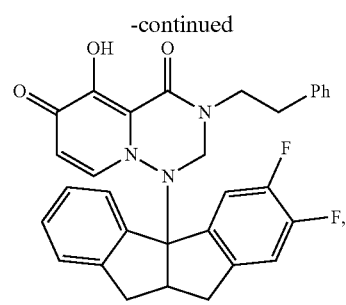
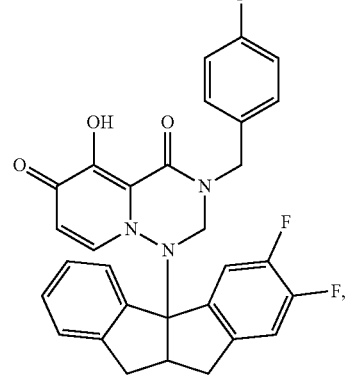
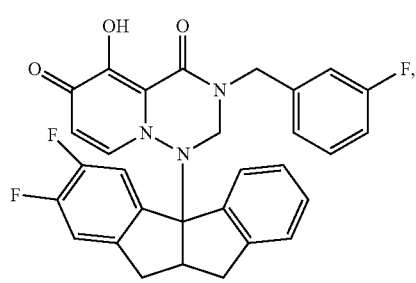
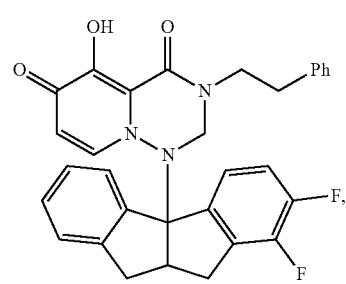
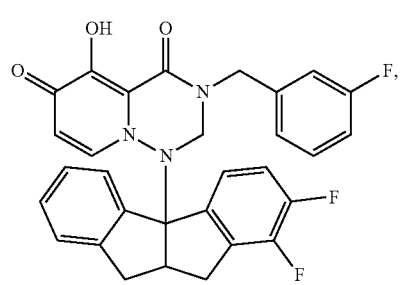
-continued
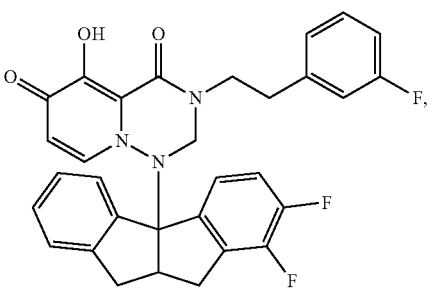
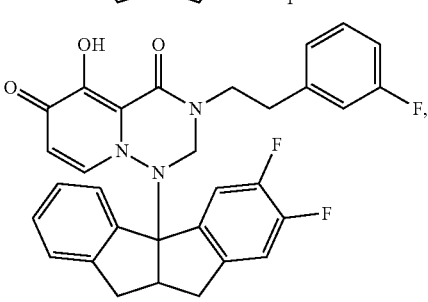
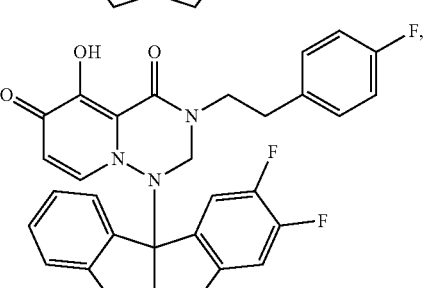
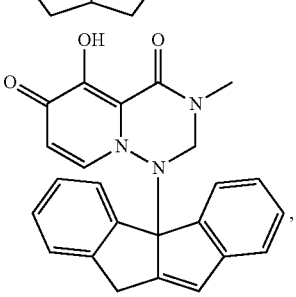
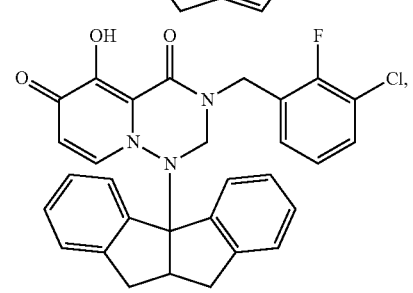
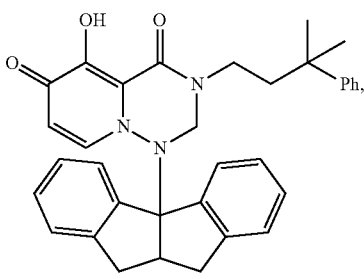

221
-continued

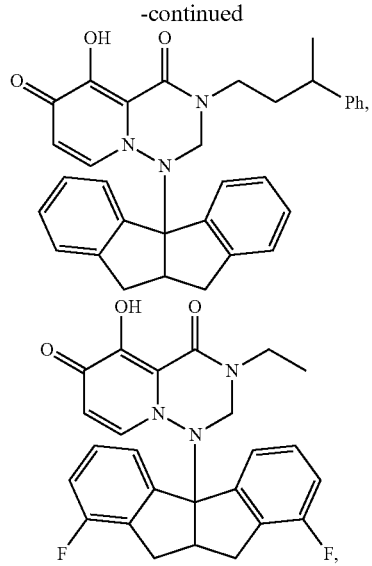

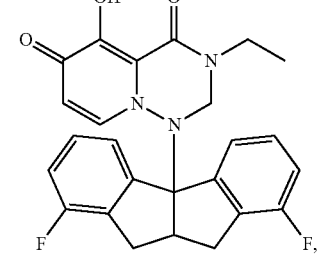

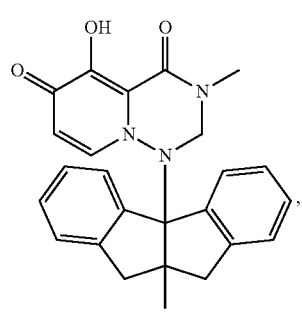

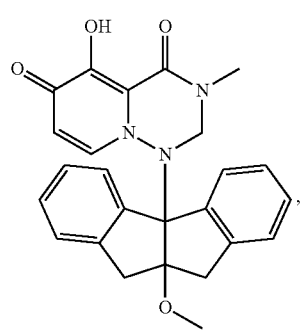

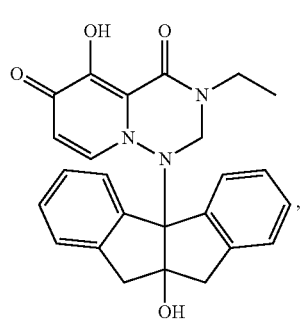

222
-continued

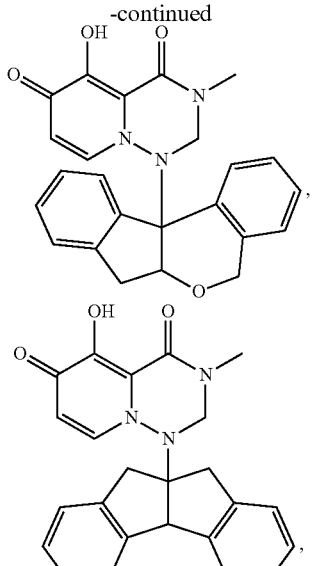

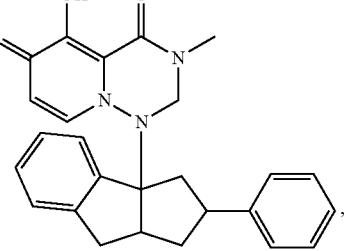

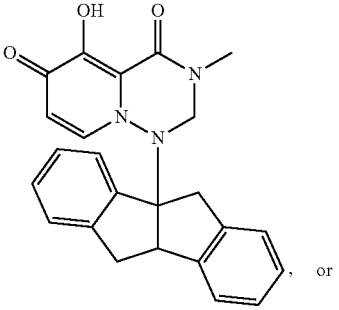

, or

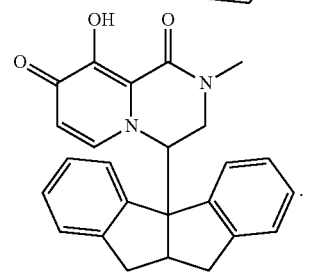

16. A pharmaceutical formulation comprising the compound or salt of claim 1 and a pharmaceutically acceptable excipient.

17. A method of inhibiting endonuclease activity of influenza polymerase PA in an influenza A or B virus, comprising contacting the virus with the compound or salt of claim 1.

18. A method for treating or preventing an Influenza A or Influenza B infection in a host, comprising administering to the host a therapeutic amount of the compound or salt of claim 1.

19. A method for reducing endonuclease activity of influenza polymerase PA in an influenza A or B virus in a host, comprising administering to the host a therapeutic amount of the compound or salt of claim 1.

20. A method for reducing influenza virus replication in a host, comprising administering to the host a therapeutic amount of the compound or salt of claim 1.

21. The method of claim 17, further comprising contacting the influenza A or B virus with or administering to the host a therapeutically effective amount of a second antiviral agent.

22. The method of claim 21, wherein the second antiviral agent is a pyrazinecarboxamide antiviral compound, an influenza neuraminidase inhibitor, an influenza PB1 polymerase domain inhibitor, or an influenza CAP-binding PB2 domain inhibitor.

* * * * *